US011813267B2

(12) United States Patent
Maxwell et al.

(10) Patent No.: US 11,813,267 B2
(45) Date of Patent: Nov. 14, 2023

(54) DNA-PK INHIBITORS

(71) Applicant: Vertex Pharmaceuticals Incorporated, Boston, MA (US)

(72) Inventors: John Patrick Maxwell, Hingham, MA (US); Paul S. Charifson, Framingham, MA (US); Qing Tang, Acton, MA (US); Steven M. Ronkin, Watertown, MA (US); Katrina Lee Jackson, Cambridge, MA (US); Albert Charles Pierce, Cambridge, MA (US); David J. Lauffer, Stow, MA (US); Pan Li, Lexington, MA (US); Simon Giroux, Cambridge, MA (US); Jinwang Xu, Framingham, MA (US); Kevin Michael Cottrell, Cambridge, MA (US); Mark A. Morris, Somerville, MA (US); Nathan D. Waal, Cambridge, MA (US); John J. Court, Littleton, MA (US); Wenxin Gu, Concord, MA (US); Hongbo Deng, Southborough, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 325 days.

(21) Appl. No.: 17/023,597

(22) Filed: Sep. 17, 2020

(65) Prior Publication Data

US 2021/0069203 A1 Mar. 11, 2021

Related U.S. Application Data

(60) Continuation of application No. 16/282,083, filed on Feb. 21, 2019, now Pat. No. 10,786,512, which is a (Continued)

(51) Int. Cl.

| | |
|---|---|
| *A61K 31/537* | (2006.01) |
| *A61K 31/506* | (2006.01) |
| *A61K 31/5386* | (2006.01) |
| *C07D 513/04* | (2006.01) |
| *C07D 241/40* | (2006.01) |
| *C07D 401/14* | (2006.01) |
| *C07D 403/12* | (2006.01) |
| *C07D 403/14* | (2006.01) |
| *C07D 405/12* | (2006.01) |
| *C07D 405/14* | (2006.01) |
| *C07D 413/12* | (2006.01) |
| *C07D 417/12* | (2006.01) |
| *C07D 471/04* | (2006.01) |

(Continued)

(52) U.S. Cl.

CPC ........ *A61K 31/5377* (2013.01); *A61K 31/506* (2013.01); *A61K 31/5386* (2013.01); *C07D 241/40* (2013.01); *C07D 241/42* (2013.01); *C07D 241/44* (2013.01); *C07D 271/12* (2013.01); *C07D 401/12* (2013.01); *C07D 401/14* (2013.01); *C07D 403/12* (2013.01); *C07D 403/14* (2013.01); *C07D 405/12* (2013.01); *C07D 405/14* (2013.01); *C07D 413/04* (2013.01); *C07D 413/12* (2013.01); *C07D 413/14* (2013.01); *C07D 417/12* (2013.01); *C07D 471/04* (2013.01); *C07D 473/40* (2013.01); *C07D 475/00* (2013.01); *C07D 487/04* (2013.01); *C07D 491/048* (2013.01); *C07D 491/052* (2013.01); *C07D 491/056* (2013.01); *C07D 491/08* (2013.01); *C07D 498/08* (2013.01); *C07D 513/04* (2013.01)

(58) Field of Classification Search

CPC .............. A61K 31/5377; A61K 31/506; A61K 31/5386; A61K 31/4245; C07D 241/40; C07D 241/42; C07D 241/44; C07D 271/12; C07D 401/12; C07D 401/14; C07D 403/12; C07D 403/14; C07D 405/12; C07D 405/14; C07D 413/04; C07D 413/12; C07D 413/14; C07D 417/12; C07D 471/04; C07D 473/40; C07D 475/00; C07D 487/04; C07D 491/048; C07D 491/052; C07D 491/056; C07D 491/08; C07D 498/08; C07D 513/04

See application file for complete search history.

(56) References Cited

U.S. PATENT DOCUMENTS

| | | |
|---|---|---|
| 5,478,938 A | 12/1995 | Clemence et al. |
| 5,571,506 A | 11/1996 | Regan et al. |

(Continued)

FOREIGN PATENT DOCUMENTS

| | | |
|---|---|---|
| CA | 2716898 A1 | 9/2009 |
| CN | 102137854 A | 7/2011 |

(Continued)

OTHER PUBLICATIONS

Extended European Search Report, dated Feb. 28, 2022, in connection with Application No. EP 21192836.1.

(Continued)

*Primary Examiner* — Erich A Leeser
(74) *Attorney, Agent, or Firm* — Wolf, Greenfield & Sacks, P.C.

(57) ABSTRACT

The present invention relates to compounds useful as inhibitors of DNA-PK. The invention also provides pharmaceutically acceptable compositions comprising said compounds and methods of using the compositions in the treatment of various disease, conditions, or disorders.

19 Claims, No Drawings

Related U.S. Application Data division of application No. 15/659,306, filed on Jul. 25, 2017, now Pat. No. 10,258,627, which is a continuation of application No. 15/148,229, filed on May 6, 2016, now abandoned, which is a division of application No. 14/205,508, filed on Mar. 12, 2014, now Pat. No. 9,359,380.

(60) Provisional application No. 61/777,816, filed on Mar. 12, 2013.

(51) Int. Cl.

| | |
|---|---|
| *C07D 473/40* | (2006.01) |
| *C07D 475/00* | (2006.01) |
| *C07D 487/04* | (2006.01) |
| *C07D 491/048* | (2006.01) |
| *C07D 498/08* | (2006.01) |
| *C07D 413/04* | (2006.01) |
| *C07D 241/44* | (2006.01) |
| *C07D 491/052* | (2006.01) |
| *C07D 241/42* | (2006.01) |
| *C07D 271/12* | (2006.01) |
| *C07D 401/12* | (2006.01) |
| *C07D 413/14* | (2006.01) |
| *C07D 491/056* | (2006.01) |
| *C07D 491/08* | (2006.01) |
| *A61K 31/5377* | (2006.01) |

(56) References Cited

U.S. PATENT DOCUMENTS

| | | | | |
|---|---|---|---|---|
| 5,571,815 | A | 11/1996 | Schaper et al. | |
| 5,595,756 | A | 1/1997 | Bally et al. | |
| 5,668,140 | A | 9/1997 | Schaper et al. | |
| 5,723,461 | A | 3/1998 | Rosner et al. | |
| 5,977,117 | A | 11/1999 | Chan et al. | |
| 6,004,979 | A | 12/1999 | Clemence et al. | |
| 6,057,371 | A | 5/2000 | Glennon | |
| 6,222,073 | B1 | 4/2001 | Herwig et al. | |
| 6,265,428 | B1 | 7/2001 | Chan et al. | |
| 6,610,677 | B2 | 8/2003 | Davies et al. | |
| 6,613,776 | B2 | 9/2003 | Knegtel et al. | |
| 6,638,926 | B2 | 10/2003 | Davies et al. | |
| 6,642,227 | B2 | 11/2003 | Cao et al. | |
| 6,653,300 | B2 | 11/2003 | Bebbington et al. | |
| 6,653,301 | B2 | 11/2003 | Bebbington et al. | |
| 6,656,939 | B2 | 12/2003 | Bebbington et al. | |
| 6,660,731 | B2 | 12/2003 | Bebbington et al. | |
| 6,664,247 | B2 | 12/2003 | Bebbington et al. | |
| 6,689,778 | B2 | 2/2004 | Bemis et al. | |
| 6,696,452 | B2 | 2/2004 | Davies et al. | |
| 6,727,251 | B2 | 4/2004 | Bebbington et al. | |
| 6,743,791 | B2 | 6/2004 | Cao et al. | |
| 6,762,179 | B2 | 7/2004 | Cochran et al. | |
| 6,777,413 | B2 | 8/2004 | Zhu et al. | |
| 6,825,190 | B2 | 11/2004 | Moon et al. | |
| 6,844,347 | B1 | 1/2005 | Schnidler et al. | |
| 6,875,781 | B2 | 4/2005 | Hong et al. | |
| 6,884,804 | B2 | 4/2005 | Choon-Moon | |
| 6,949,544 | B2 | 9/2005 | Bethiel et al. | |
| 6,989,385 | B2 | 1/2006 | Bebbington et al. | |
| 7,008,948 | B2 | 3/2006 | Bebbington et al. | |
| 7,084,159 | B2 | 8/2006 | Cao et al. | |
| 7,087,603 | B2 | 8/2006 | Bebbington et al. | |
| 7,098,330 | B2 | 8/2006 | Bebbington et al. | |
| 7,115,739 | B2 | 10/2006 | Bebbington et al. | |
| 7,122,552 | B2 | 10/2006 | Ledford | |
| 7,144,911 | B2 | 12/2006 | Flynn et al. | |
| 7,179,912 | B2 | 2/2007 | Halbrook et al. | |
| 7,189,724 | B2 | 3/2007 | An et al. | |
| 7,208,507 | B2 | 4/2007 | Hong et al. | |
| 7,226,919 | B2 | 6/2007 | Ledeboer et al. | |
| 7,244,735 | B2 | 7/2007 | Straub et al. | |
| 7,253,187 | B2 | 8/2007 | Cao et al. | |
| 7,256,190 | B2 | 8/2007 | Cochran et al. | |
| 7,259,161 | B2 | 8/2007 | Bethiel et al. | |
| 7,271,179 | B2 | 9/2007 | Bemis et al. | |
| 7,300,929 | B2 | 11/2007 | Baxter et al. | |
| 7,304,061 | B2 | 12/2007 | Hale et al. | |
| 7,304,071 | B2 | 12/2007 | Cochran et al. | |
| 7,312,227 | B2 | 12/2007 | Ledeboer et al. | |
| 7,329,652 | B2 | 2/2008 | Salituro et al. | |
| 7,345,054 | B2 | 3/2008 | Hale et al. | |
| 7,358,258 | B2 | 4/2008 | Hale et al. | |
| 7,361,665 | B2 | 4/2008 | Ledeboer et al. | |
| 7,390,815 | B2 | 6/2008 | Davies et al. | |
| 7,407,962 | B2 | 8/2008 | Aronov et al. | |
| 7,419,984 | B2 | 9/2008 | Bhatt et al. | |
| 7,427,681 | B2 | 9/2008 | Bebbington et al. | |
| 7,456,190 | B2 | 11/2008 | Maltais et al. | |
| 7,473,691 | B2 | 1/2009 | Davies et al. | |
| 7,488,727 | B2 | 2/2009 | Cochran et al. | |
| 7,501,415 | B2 | 3/2009 | Aronov et al. | |
| 7,517,870 | B2 | 4/2009 | Auricchio et al. | |
| 7,528,142 | B2 | 5/2009 | Binch et al. | |
| 7,531,536 | B2 | 5/2009 | Bebbington et al. | |
| 7,557,106 | B2 | 7/2009 | Charrier et al. | |
| 7,592,340 | B2 | 9/2009 | Bernis et al. | |
| 7,625,913 | B2 | 12/2009 | Bebbington et al. | |
| 7,635,683 | B2 | 12/2009 | Gai et al. | |
| 7,666,895 | B2 | 2/2010 | Flynn et al. | |
| 7,691,853 | B2 | 4/2010 | Bebbington et al. | |
| 7,696,204 | B2 | 4/2010 | McDonald et al. | |
| 7,732,444 | B2 | 6/2010 | Fleming et al. | |
| 7,767,672 | B2 | 8/2010 | Binch et al. | |
| 7,820,685 | B2 | 10/2010 | Binch et al. | |
| 7,951,820 | B2 | 5/2011 | Bebbington et al. | |
| 7,968,565 | B2 | 6/2011 | Arkin et al. | |
| 7,982,037 | B2 | 7/2011 | Bebbington et al. | |
| 8,026,359 | B2 | 9/2011 | Chen | |
| 8,084,457 | B2 | 12/2011 | Choidas et al. | |
| 8,129,399 | B2 | 3/2012 | Binch et al. | |
| 8,268,811 | B2 | 9/2012 | Mortimore et al. | |
| 8,268,829 | B2 | 9/2012 | Charrier et al. | |
| 8,304,414 | B2 | 11/2012 | Bebbington et al. | |
| 8,372,850 | B2 | 2/2013 | Jimenez et al. | |
| 8,383,633 | B2 | 2/2013 | Mortimore et al. | |
| 8,410,133 | B2 | 4/2013 | Jimenez et al. | |
| 8,426,425 | B2 | 4/2013 | Jimenez et al. | |
| 8,455,500 | B2 | 6/2013 | Okano et al. | |
| 8,455,507 | B2 | 6/2013 | Studley et al. | |
| 8,476,287 | B2 | 7/2013 | Okano et al. | |
| 8,518,953 | B2 | 8/2013 | Pierce et al. | |
| 8,524,720 | B2 | 9/2013 | Bebbington et al. | |
| 8,541,428 | B2 | 9/2013 | Gavish et al. | |
| 8,546,392 | B2 | 10/2013 | Hartmann et al. | |
| 8,557,833 | B2 | 10/2013 | Binch et al. | |
| 8,563,549 | B2 | 10/2013 | Burger et al. | |
| 8,633,210 | B2 | 1/2014 | Charrier et al. | |
| 8,637,511 | B2 | 1/2014 | Binch et al. | |
| 8,664,219 | B2 | 3/2014 | Jimenez et al. | |
| 8,691,847 | B2 | 4/2014 | Zhu et al. | |
| 8,697,685 | B2 | 4/2014 | Axten et al. | |
| 8,697,698 | B2 | 4/2014 | Bebbington et al. | |
| 8,735,593 | B2 | 5/2014 | Jimenez et al. | |
| 8,779,127 | B2 | 7/2014 | Charrier et al. | |
| 8,784,782 | B2 | 7/2014 | Tachdjian et al. | |
| 8,785,444 | B2 | 7/2014 | Mortimore et al. | |
| 8,841,308 | B2 | 9/2014 | Charrier et al. | |
| 9,062,076 | B2 | 6/2015 | Williams et al. | |
| 9,296,701 | B2 | 3/2016 | Charifson et al. | |
| 9,340,557 | B2 | 5/2016 | Maxwell et al. | |
| 9,359,380 | B2 | 6/2016 | Maxwell et al. | |
| 9,376,448 | B2 | 6/2016 | Charifson et al. | |
| 9,592,232 | B2 | 3/2017 | Charifson et al. | |
| 9,987,284 | B2 | 6/2018 | Maxwell et al. | |
| 10,258,627 | B2 | 4/2019 | Maxwell et al. | |
| 10,786,512 | B2 | 9/2020 | Maxwell et al. | |
| 10,973,830 | B2 * | 4/2021 | Maxwell .............. | C07D 401/14 |
| 2002/0111353 | A1 | 8/2002 | Ledeboer et al. | |
| 2003/0096813 | A1 | 5/2003 | Cao et al. | |

(56) References Cited

U.S. PATENT DOCUMENTS

| | | | |
|---|---|---|---|
| 2003/0199525 A1 | 10/2003 | Hirst et al. | |
| 2003/0199526 A1 | 10/2003 | Choquette et al. | |
| 2003/0207873 A1 | 11/2003 | Harrington | |
| 2003/0207886 A1 | 11/2003 | Plucker et al. | |
| 2004/0097502 A1 | 5/2004 | Gellibert | |
| 2004/0192687 A1 | 9/2004 | Martin et al. | |
| 2004/0235834 A1 | 11/2004 | Farmer et al. | |
| 2005/0054568 A1 | 3/2005 | Ling et al. | |
| 2006/0142572 A1 | 6/2006 | Martinez-Botella et al. | |
| 2006/0166936 A1 | 7/2006 | Binch et al. | |
| 2006/0264427 A1 | 11/2006 | Smith et al. | |
| 2007/0179125 A1 | 8/2007 | Fraysse et al. | |
| 2007/0265263 A1 | 11/2007 | Cao et al. | |
| 2007/0270420 A1 | 11/2007 | Harbeson et al. | |
| 2008/0139585 A1 | 6/2008 | Rathinavelu et al. | |
| 2008/0207616 A1 | 8/2008 | Aquila et al. | |
| 2008/0267918 A1 | 10/2008 | Gai et al. | |
| 2008/0280891 A1 | 11/2008 | Kelly et al. | |
| 2009/0023729 A1 | 1/2009 | Nakamura et al. | |
| 2009/0042865 A1 | 2/2009 | Frigerio et al. | |
| 2009/0053192 A1 | 2/2009 | Millan et al. | |
| 2009/0124612 A1 | 5/2009 | Albrecht et al. | |
| 2009/0221581 A1 | 9/2009 | Wabnitz et al. | |
| 2009/0298844 A1 | 12/2009 | Pollard | |
| 2010/0137305 A1 | 6/2010 | Binch et al. | |
| 2010/0197674 A1 | 8/2010 | Tamai et al. | |
| 2011/0046104 A1 | 2/2011 | Mortimore et al. | |
| 2011/0060013 A1 | 3/2011 | Mortimore et al. | |
| 2011/0065739 A1 | 3/2011 | Ishikawa et al. | |
| 2011/0144114 A1 | 6/2011 | Lochead et al. | |
| 2011/0275643 A1 | 11/2011 | Liou et al. | |
| 2011/0319618 A1 | 12/2011 | Nishio | |
| 2012/0009151 A1 | 1/2012 | Han et al. | |
| 2012/0202806 A1 | 8/2012 | Durrenberger et al. | |
| 2013/0012489 A1 | 1/2013 | Mederski et al. | |
| 2013/0150359 A1 | 6/2013 | Fuchss et al. | |
| 2013/0172337 A1 | 7/2013 | Fuchss et al. | |
| 2013/0209400 A1 | 8/2013 | Bach Tana et al. | |
| 2013/0281431 A1 | 10/2013 | Charifson et al. | |
| 2014/0045869 A1 | 2/2014 | Charifson et al. | |
| 2014/0113012 A1 | 4/2014 | Schultz et al. | |
| 2014/0148434 A1 | 5/2014 | Boyall et al. | |
| 2014/0187772 A1 | 7/2014 | Bebbington et al. | |
| 2014/0194444 A1 | 7/2014 | Jimenez et al. | |
| 2014/0256703 A1 | 9/2014 | Jimenez et al. | |
| 2014/0275024 A1 | 9/2014 | Maxwell et al. | |
| 2014/0275059 A1 | 9/2014 | Maxwell et al. | |
| 2014/0275072 A1 | 9/2014 | Mederski et al. | |
| 2015/0111871 A1 | 4/2015 | Charifson et al. | |
| 2016/0250212 A1 | 9/2016 | Charifson et al. | |
| 2016/0339024 A1 | 11/2016 | Nti-Addae et al. | |
| 2016/0340341 A1 | 11/2016 | Maxwell et al. | |
| 2016/0354381 A1 | 12/2016 | Maxwell et al. | |
| 2016/0368899 A1 | 12/2016 | Charifson et al. | |
| 2018/0161336 A1 | 6/2018 | Maxwell et al. | |
| 2018/0311254 A1 | 11/2018 | Maxwell et al. | |
| 2019/0255062 A1 | 8/2019 | Maxwell et al. | |
| 2019/0290654 A1 | 9/2019 | Maxwell et al. | |
| 2021/0236505 A1* | 8/2021 | Maxwell | C07D 491/056 |

FOREIGN PATENT DOCUMENTS

| | | |
|---|---|---|
| DE | 102006050512 A1 | 4/2008 |
| DE | 102007044032 A | 3/2009 |
| EA | 16028 B1 | 1/2012 |
| EP | 1 678 147 B1 | 7/2006 |
| EP | 1 701 944 B1 | 7/2009 |
| JP | H10-251255 A | 9/1998 |
| JP | 2003-511378 A | 3/2003 |
| JP | 2005-336138 A | 12/2005 |
| JP | 2007-008045 A | 1/2007 |
| JP | 2011-246389 A | 12/2011 |
| WO | WO 93/22291 A1 | 11/1993 |
| WO | WO 98/37079 A1 | 8/1998 |
| WO | WO 98/54158 A1 | 12/1998 |
| WO | WO 00/09496 A1 | 2/2000 |
| WO | WO 00/42026 A1 | 7/2000 |
| WO | WO 01/25220 A1 | 4/2001 |
| WO | WO 01/27089 A1 | 4/2001 |
| WO | WO 01/64646 A2 | 9/2001 |
| WO | WO 2004/085418 A2 | 10/2004 |
| WO | WO 2005/026129 A1 | 3/2005 |
| WO | WO 2005/066139 A2 | 7/2005 |
| WO | WO 2005/089730 A2 | 9/2005 |
| WO | WO 2005/121121 A2 | 12/2005 |
| WO | WO 2006/044503 A2 | 4/2006 |
| WO | WO 2006/044732 A2 | 4/2006 |
| WO | WO 2006/108107 A1 | 10/2006 |
| WO | WO 2006/138418 A2 | 12/2006 |
| WO | WO 2007/056143 A2 | 5/2007 |
| WO | WO 2007/082899 A1 | 7/2007 |
| WO | WO 2007/109783 A2 | 9/2007 |
| WO | WO 2008/006583 A1 | 1/2008 |
| WO | WO 2008/008747 A1 | 1/2008 |
| WO | WO 2008/008852 A2 | 1/2008 |
| WO | WO 2008/028691 A1 | 3/2008 |
| WO | WO 2008/042639 A1 | 4/2008 |
| WO | WO 2008/070661 A1 | 6/2008 |
| WO | WO 2008/083346 A1 | 7/2008 |
| WO | WO 2008/092199 A1 | 8/2008 |
| WO | WO 2008/106202 A1 | 9/2008 |
| WO | WO 2008/115973 A2 | 9/2008 |
| WO | WO 2008/141065 A1 | 11/2008 |
| WO | WO 2008/144253 A1 | 11/2008 |
| WO | WO 2008/145616 A1 | 12/2008 |
| WO | WO 2009/004621 A1 | 1/2009 |
| WO | WO 2009/008991 A2 | 1/2009 |
| WO | WO 2009/016841 A1 | 2/2009 |
| WO | WO 2009/047359 A1 | 4/2009 |
| WO | WO 2009/105220 A1 | 8/2009 |
| WO | WO 2009/107391 A1 | 9/2009 |
| WO | WO 2009/109258 A1 | 9/2009 |
| WO | WO 2009/115517 A2 | 9/2009 |
| WO | WO 2009/152909 A1 | 12/2009 |
| WO | WO 2010/048149 A2 | 4/2010 |
| WO | WO 2010/064737 A1 | 6/2010 |
| WO | WO 2010/065899 A2 | 6/2010 |
| WO | WO 2010/093808 A1 | 8/2010 |
| WO | WO 2011/022348 A1 | 2/2011 |
| WO | WO 2011/051535 A1 | 5/2011 |
| WO | WO 2011/113512 A1 | 9/2011 |
| WO | WO 2012/000632 A1 | 1/2012 |
| WO | WO 2012/028233 A1 | 3/2012 |
| WO | WO 2013/024282 A2 | 2/2013 |
| WO | WO 2013/032951 A1 | 3/2013 |
| WO | WO 2013/040515 A1 | 3/2013 |
| WO | WO 2013/043935 A1 | 3/2013 |
| WO | WO 2013/049701 A1 | 4/2013 |
| WO | WO 2013/072015 A1 | 5/2013 |
| WO | WO 2013/083991 A1 | 6/2013 |
| WO | WO 2013/112950 A2 | 8/2013 |
| WO | WO 2013/163190 A1 | 10/2013 |
| WO | WO 2014/075077 A1 | 5/2014 |

OTHER PUBLICATIONS

International Search Report and Written Opinion dated May 27, 2014 in connection with Application No. PCT/US2014/024767.

International Search Report and Written Opinion dated Dec. 22, 2014 in connection with Application No. PCT/US2014/061102.

International Search Report and Written Opinion dated Aug. 29, 2013 in connection with Application No. PCT/US2013/037811.

International Search Report and Written Opinion dated Dec. 22, 2014 in connection with Application No. PCT/US2014/061033.

Davis et al., Dynamics of the P13K-like protein kinase members ATM and DNA-PKcs at DNA double strand breaks. Cell Cycle. Jul. 2010; 9(13):2529-36.

Edelman et al., Targeted readiopharmaceutical therapy for advanced lung cancer: phase 1 trial of rhenium Rel88 P2045, a somatostatin analog. J Thorac Oncol. 2009; 4(12):1550-4.

Goodwin et al., Beyond DNA repair: DNA-PK function in cancer. Cancer discovery. Oct. 1, 2014;4(10):1126-39. Published online Aug. 28, 2014. doi: 10.1158/2159-8290.CD-14-0358.

(56) References Cited

OTHER PUBLICATIONS

Gura, Systems for identifying new drugs are often faulty. Science. Nov. 7, 1997;278(5340):1041-2.
Hackam et al., Translation of research evidence from animals to humans. JAMA. Oct. 11, 2006;296(14):1731-2.
Jordan, Tamoxifen: a most unlikely pioneering medicine. Nature Reviews Drug Discovery. Mar. 1, 2003;2(3):205-13.
Kashishian et al., DNA-dependent protein kinas inhibitors as drug candidates for the treatment of cancer. Mol Cancer Ther. 2003; 2(12):1257-64.
Kuntzinger et al., Protein phosphatase 1 regulators in DNA damage signaling. Cell Cycle. May 2011; 10(9): 1-7.
Sporn et al., Chemoprevention of cancer. Carcinogenesis. Mar. 1, 2000;21(3):525-30.
Veuger et al., Radiosensitization and DNA repair inhibition by combined use of novel inhibitors of DNA-dependent protein kinase and poly(ADP-ribose) polymerase-1. Cancer Res. 2003; 63;6008-15.
Davidson et al., Small Molecules, Inhibitors of DNA-PK, Targeting DNA Repair, and Beyond. Front Pharmacol. Jan. 31, 2013;4:5(1-7). doi: 10.3389/fphar.2013.00005.

* cited by examiner

DNA-PK INHIBITORS

RELATED APPLICATIONS

This application is a continuation of and claims priority under 35 U.S.C. § 120 to U.S. application Ser. No. 16/282,083, filed Feb. 21, 2019, which is a divisional of U.S. application Ser. No. 15/659,306, filed Jul. 25, 2017, now U.S. Pat. No. 10,258,627, which is a continuation of U.S. application Ser. No. 15/148,229, filed on May 6, 2016, which is a divisional of U.S. application Ser. No. 14/205,508, filed on Mar. 12, 2014, now U.S. Pat. No. 9,359,380, which claims the benefit to U.S. Provisional Application No. 61/777,816, filed on Mar. 12, 2013, all of which are incorporated herein by reference in their entireties.

TECHNICAL FIELD OF THE INVENTION

The present invention relates to compounds useful as inhibitors of DNA-dependent protein kinase (DNA-PK). The invention also provides pharmaceutically acceptable compositions comprising the compounds of the invention and methods of using the compositions in the treatment of cancer,

BACKGROUND OF THE INVENTION

Ionizing radiation (IR) induces a variety of DNA damage of which double strand breaks (DSBs) are the most cytotoxic. These DSBs can lead to cell death via apoptosis and/or mitotic catastrophe if not rapidly and completely repaired. In addition to IR, certain chemotherapeutic agents including topoisomerase II inhibitors, bleomycin, and doxorubicin also cause DSBs. These DNA lesions trigger a complex set of signals through the DNA damage response network that function to repair the damaged DNA and maintain cell viability and genomic stability. In mammalian cells, the predominant repair pathway for DSBs is the Non-Homologous End Joining Pathway (NHEJ). This pathway functions regardless of the phase of the cell cycle and does not require a template to re-ligate the broken DNA ends. NHEJ requires coordination of many proteins and signaling pathways. The core NHEJ machinery consists of the Ku70/80 heterodimer and the catalytic subunit of DNA-dependent protein kinase (DNA-PKcs), which together comprise the active DNA-PK enzyme complex. DNA-PKcs is a member of the phosphatidylinositol 3-kinase-related kinase (PIKK) family of serine/threonine protein kinases that also includes ataxia telangiectasia mutated (ATM), ataxia telangiectasia and Rad3-related (ATR), mTOR, and four PI3K isoforms. However, while DNA-PKcs is in the same protein kinase family as ATM and ATR, these latter kinases function to repair DNA damage through the Homologous Recombination (HR) pathway and are restricted to the S and $G_2$ phases of the cell cycle. While ATM is also recruited to sites of DSBs, ATR is recruited to sites of single stranded DNA breaks.

NHEJ is thought to proceed through three key steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-PKcs to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. In some cases DNA polymerase may be required to synthesize new ends prior to the ligation step. The auto-phosphorylation of DNA-PKcs is believed to induce a conformational change that opens the central DNA binding cavity, releases DNA-PKcs from DNA, and facilitates the ultimate relegation of the DNA ends.

It has been known for some time that DNA-PK mice are hypersensitive to the effects of IR and that some non-selective small molecule inhibitors of DNA-PKcs can radiosensitize a variety of tumor cell types across a broad set of genetic backgrounds. While it is expected that inhibition of DNA-PK will radiosensitize normal cells to some extent, this has been observed to a lesser degree than with tumor cells likely due to the fact that tumor cells possess higher basal levels of endogenous replication stress and DNA damage (oncogene-induced replication stress) and DNA repair mechanisms are less efficient in tumor cells. Most importantly, an improved therapeutic window with greater sparing of normal tissue will be imparted from the combination of a DNA-PK inhibitor with recent advances in precision delivery of focused IR, including image-guide RT (IGRT) and intensity-modulated RT (IMRT).

Inhibition of DNA-PK activity induces effects in both cycling and non-cycling cells. This is highly significant since the majority of cells in a solid tumor are not actively replicating at any given moment, which limits the efficacy of many agents targeting the cell cycle. Equally intriguing are recent reports that suggest a strong connection between inhibition of the NHEJ pathway and the ability to kill traditionally radioresistant cancer stem cells (CSCs). It has been shown in some tumor cells that DSBs in dormant CSCs predominantly activate DNA repair through the NHEJ pathway; it is believed that CSCs are usually in the quiescent phase of the cell cycle. This may explain why half of cancer patients may experience local or distant tumor relapse despite treatment as current strategies are not able to effectively target CSCs. A DNA-PK inhibitor may have the ability to sensitize these potential metastatic progenitor cells to the effects of IR and select DSB-inducing chemotherapeutic agents.

Given the involvement of DNA-PK in DNA repair processes, an application of specific DNA-PK inhibitory drugs would be to act as agents that will enhance the efficacy of both cancer chemotherapy and radiotherapy. Accordingly, it would be desirable to develop compounds useful as inhibitors of DNA-PK.

SUMMARY OF THE INVENTION

It has been found that compounds of this invention, and pharmaceutically acceptable compositions thereof, are effective as inhibitors of DNA-PK. Accordingly, the invention features compounds having the general formula:

(I)

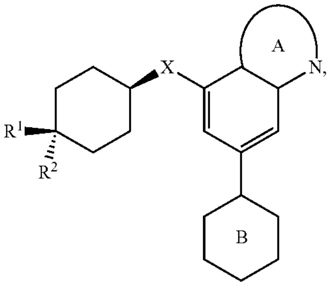

or a pharmaceutically acceptable salt thereof, where each of $R^1$, $R^2$, X, Ring A, and Ring B is as defined elsewhere herein.

The invention also provides pharmaceutical compositions that include a compound of formula I and a pharmaceutically acceptable carrier, adjuvant, or vehicle. These compounds and pharmaceutical compositions are useful for treating or lessening the severity of cancer.

The compounds and compositions provided by this invention are also useful for the study of DNA-PK in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, $75^{th}$ Ed. 1994. Additionally, general principles of organic chemistry are described in "Organic Chemistry," Thomas Sorrell, University Science Books, Sausalito: 1999, and "March's Advanced Organic Chemistry," $5^{th}$ Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. As is also apparent to a skilled person, a heteroaryl or heterocyclic ring containing an NH group can be optionally substituted by replacing the hydrogen atom with the substituent. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" or "alkyl group," as used herein, means a straight-chain (i.e., unbranched) or branched, substituted or unsubstituted hydrocarbon chain that is completely saturated. Unless otherwise specified, alkyl groups contain 1-8 carbon atoms. In some embodiments, alkyl groups contain 1-6 carbon atoms, and in yet other embodiments, alkyl groups contain 1-4 carbon atoms (represented as "$C_{1-4}$ alkyl"). In other embodiments, alkyl groups are characterized as "$C_{0-4}$ alkyl" representing either a covalent bond or a $C_{1-4}$ alkyl chain. Examples of alkyl groups include methyl, ethyl, propyl, butyl, isopropyl, isobutyl, sec-butyl, and tert-butyl. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloalkyl" (or "carbocycle") refers to a monocyclic $C_3$-$C_8$ hydrocarbon or bicyclic $C_8$-$C_{12}$ hydrocarbon that is completely saturated and has a single point of attachment to the rest of the molecule, and wherein any individual ring in said bicyclic ring system has 3-7 members. Suitable cycloalkyl groups include, but are not limited to, cyclopropyl, cyclobutyl, cyclopentyl, cyclohexyl, and cycloheptyl.

The term "heterocycle," "heterocyclyl," "heterocycloalkyl," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloalkyl," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, or phosphorus, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 4 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

Structure a

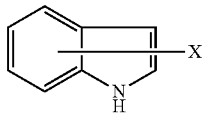

Structure b

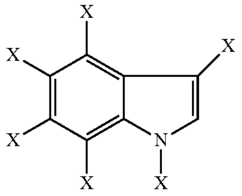

This also applies to multiple ring systems fused to optional ring systems (which would be represented by dotted lines). For example, in Structure c, X is an optional substituent both for ring A and ring B.

Structure c

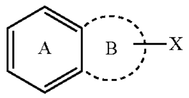

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

Structure d

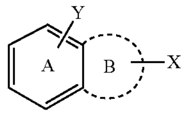

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis,* 3*rd* *Edition* (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz). Examples of hydroxyl protecting groups include ethers, such as tetrahydropyranyl, tert butyl, benzyl, allyl, and the like; silyl ethers such as trimethyl silyl, triethyl silyl, triisopropylsilyl, tert-butyl diphenyl silyl, and the like; esters such as acetyl, trifluoroacetyl, and the like; and carbonates. Hydroxyl protecting groups also include those appropriate for the protection of phenols.

Unless otherwise depicted or stated, structures recited herein are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Compounds that have been drawn with stereochemical centers defined, usually through the use of a hatched (''''') or bolded (▬) bond, are stereochemically pure, but with the absolute stereochemistry still undefined. Such compounds can have either the R or S configuration. In those cases where the absolute configuration has been determined, the chiral center(s) are labeled (R) or (S) in the drawing.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools, probes in biological assays, or as DNA-PK inhibitors with an improved therapeutic profile.

Description of Compounds of the Invention

In one aspect, the invention features compounds having the formula:

(I)

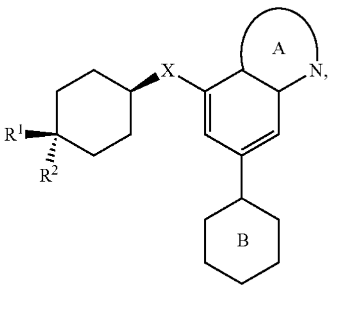

wherein

Ring A is a ring system selected from

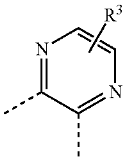 , 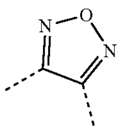 , 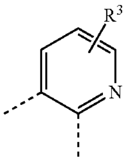 , 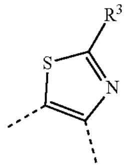 , or 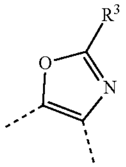 ;

Ring B is a ring system selected from

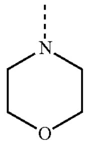 , 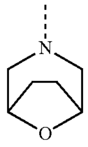 , 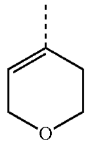 , or 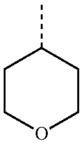 , wherein Ring B is optionally substituted with up to 4 fluorine atoms or up to two $C_{1-4}$alkyl optionally substituted with up to 3 fluorine atoms, up to two OH, or up to two $OC_{1-2}$alkyl groups;

X is NH or O;

each of $R^1$ and $R^2$ is, independently, hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, or —OR$^4$, wherein $R^1$ and $R^2$ cannot simultaneously be hydrogen, and wherein $R^1$ and $R^2$ and the intervening carbon atom can form a dioxane or dioxolane ring;

$R^3$ is hydrogen, $C_{1-4}$alkyl, fluoro, chloro, $OC_{1-2}$alkyl, C(O)OH, C(O)$OC_{1-2}$alkyl, CN, C(O)$NHC_{1-2}$alkyl, or C(O)$NH_2$, wherein each of said $R^3$ alkyl is optionally substituted with up to 3 fluorine atoms, up to two OH, or up to two $OC_{1-2}$alkyl groups;

$R^4$ is hydrogen, $C_{1-4}$alkyl, $C_{2-4}$alkenyl, $C_{2-4}$alkynyl, $C_{3-5}$cycloalkyl, phenyl, a 5-10-membered monocyclic or bicyclic heteroaryl ring selected from pyrrole, imidazole, pyrazole, triazole, thiazole, isothiazole, oxazole, pyridine, pyrimidine, pyrimidinone, pyrazine, pyridazine, or quinoline, or a 4-10-membered monocyclic or bicyclic heterocyclyl ring selected from oxetane, tetrahydrofuran, tetrahydropyran, dihydroisoxazole, pyrimidine-2,4(1H,3H)-dione, dihydrofuropyrimidine, dihydropyranopyrimidine, dihydropyrrolopyrimidine, tetrahydropteridine, or tetrahydropyridopyrimidine, wherein each of said $R^4$ groups is optionally substituted with Br, Cl, up to three fluorine atoms, up to three $C_{1-4}$alkyl, $C_{2-4}$alkenyl, $C_{2-4}$alkynyl, $C_{3-6}$cycloalkyl, an oxetane ring, a tetrahydrofuran ring, a dihydropyran ring, a tetrahydropyran ring, a pyrrolidine ring, a pyrazole ring, a triazole ring, a tetrazole ring, an oxadiazole ring, CN, $CH_2OR^5$, C(O)R$^5$, C(O)N(R$^5$)$_2$, C(O)OR$^5$, $NO_2$, NHC(O)R$^5$, N(R$^5$)$_2$, or up to two OR$^5$, wherein each of said optional $R^4$ substituents is optionally substituted with up to 3 fluorine atoms, up to two $C_{1-4}$alkyl groups, up to two OH groups, up to two $OC_{1-4}$alkyl groups, or up to two $SC_{1-4}$alkyl groups; and each $R^5$ is, independently, hydrogen, $C_{1-4}$alkyl, a 5-6-membered heteroaryl selected from imidazole, triazole, thiazole, pyridine, or pyrimidine, a 4-6-membered heterocyclyl selected from oxetane, tetrahydrofuran, or tetrahydropyran, and each $R^5$ group is optionally substituted with chloro, up to three fluorine atoms, up to two $C_{1-2}$alkyl, $CH_2OH$, CN, up to two OH, up to two $OC_{1-2}$alkyl, a spirooxetane, pyrrolidine, or triazole, or two $R^5$ groups together with the intervening nitrogen atom form a morpholine ring, azetidine ring, pyrrolidine ring, piperidine ring, or piperazine ring, wherein each of said rings is optionally substituted with up to 3 fluorine atoms, up to two OH, or up to two $OC_{1-2}$alkyl groups.

In one embodiment, X is NH.

In another embodiment, the invention features compounds having the formula:

(I-A)

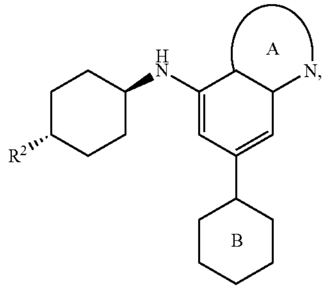

wherein $R^2$ is as defined for compounds of formula I.

In a further embodiment, the invention features compounds having formulae:

(I-A-1)

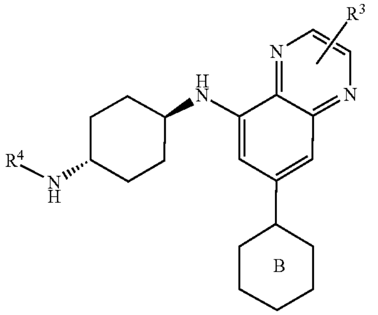

or (I-A-2)

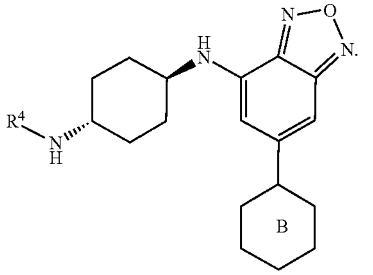

In another embodiment, the invention features compounds having the formula:

(I-B)

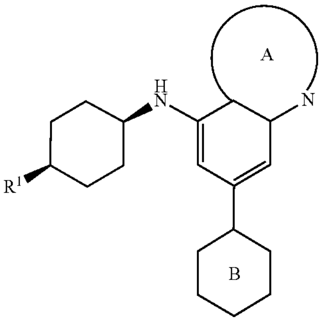

, wherein $R^1$ is as defined for compounds of formula I.

In a further embodiment, the invention features compounds having formulae:

(I-B-1)

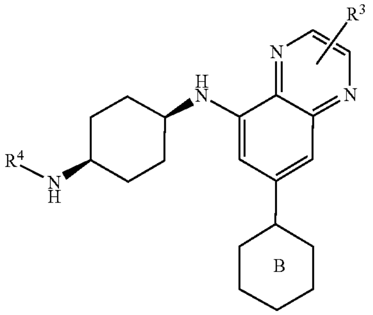

or (I-B-2)

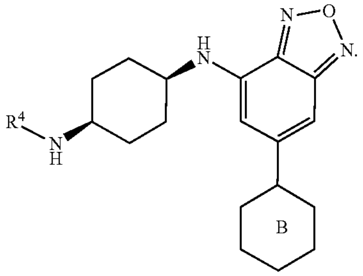

In another further embodiment, the invention features compounds having the formulae (I-B-1) or (I-B-2), wherein $R^3$ is hydrogen, $C_{1-4}$alkyl, fluoro, chloro, $OC_{1-2}$alkyl, C(O)OH, C(O)$OC_{1-2}$alkyl, CN, C(O)$NHC_{1-2}$alkyl, or C(O)$NH_2$, wherein each of said $R^3$ alkyl is optionally substituted with up to 3 fluorine atoms, up to two OH, or up to two $OC_{1-2}$alkyl groups;

$R^4$ is hydrogen, $C_{1-4}$alkyl, $C_{2-4}$alkenyl, $C_{2-4}$alkynyl, $C_{3-5}$cycloalkyl, phenyl, a 5-10-membered monocyclic or bicyclic heteroaryl ring selected from pyrrole, imidazole, pyrazole, triazole, thiazole, isothiazole, oxazole, pyridine, pyrimidine, pyrimidinone, pyrazine, pyridazine, or quinoline, or a 4-10-membered monocyclic or bicyclic heterocyclyl ring selected from oxetane, tetrahydrofuran, tetrahydropyran, dihydroisoxazole, pyrimidine-2,4(1H,3H)-dione, dihydrofuropyrimidine, dihydropyranopyrimidine, dihydropyrrolopyrimidine, tetrahydropteridine, or tetrahydropyridopyrimidine;

each of said $R^4$ groups is optionally substituted with Br, Cl, up to three fluorine atoms, up to three $C_{1-4}$alkyl, $C_{2-4}$alkenyl, $C_{2-4}$alkynyl, $C_{3-6}$cycloalkyl, an oxetane ring, a tetrahydrofuran ring, a dihydropyran ring, a tetrahydropyran ring, a pyrrolidine ring, a pyrazole ring, a triazole ring, a tetrazole ring, an oxadiazole ring, CN, $CH_2OR^5$, $C(O)R^5$, $C(O)N(R^5)_2$, $C(O)OR^5$, $NO_2$, $NHC(O)R^5$, $N(R^5)_2$, or up to two $OR^5$, wherein each of said optional $R^4$ substituents is optionally substituted with up to 3 fluorine atoms, up to two $C_{1-4}$alkyl groups, up to two OH groups, up to two $OC_{1-4}$alkyl groups, or up to two $SC_{1-4}$alkyl groups; and each $R^5$ is, independently, hydrogen, $C_{1-4}$alkyl, a 5-6-membered heteroaryl selected from imidazole, triazole, thiazole, pyridine, or pyrimidine, a 4-6-membered heterocyclyl selected from oxetane, tetrahydrofuran, or tetrahydropyran, and each $R^5$ group is optionally substituted with chloro, up to three fluorine atoms, up to two $C_{1-2}$alkyl, $CH_2OH$, CN, up to two OH, up to two $OC_{1-2}$alkyl, pyrrolidine, or triazole, or two $R^5$ groups together with the intervening nitrogen atom form a morpholine ring, azetidine ring, pyrrolidine ring, piperidine ring, or piperazine ring, wherein each of said rings is optionally substituted with up to 3 fluorine atoms, up to two OH, or up to two $OC_{1-2}$alkyl groups.

In another aspect, the invention features compounds having the formula (II)

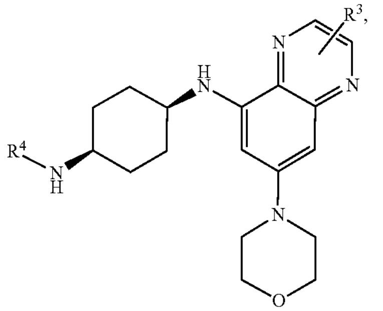

wherein $R^3$ is hydrogen, $C_{1-4}$alkyl, fluoro, chloro, $OC_{1-2}$alkyl, C(O)OH, $C(O)OC_{1-2}$alkyl, CN, $C(O)NHC_{1-2}$alkyl, or $C(O)NH_2$, wherein each of said $R^3$ alkyl is optionally substituted with up to 3 fluorine atoms, up to two OH, or up to two $OC_{1-2}$alkyl groups;

$R^4$ is a 5-10-membered monocyclic or bicyclic heteroaryl ring selected from pyrrole, imidazole, pyrazole, triazole, thiazole, isothiazole, oxazole, pyridine, pyrimidine, pyrimidinone, pyrazine, pyridazine, or quinoline, or a 4-10-membered monocyclic or bicyclic heterocyclyl ring selected from oxetane, tetrahydrofuran, tetrahydropyran, dihydroisoxazole, dihydrofuropyrimidine, dihydropyranopyrimidine, dihydropyrrolopyrimidine, tetrahydropteridine, or tetrahydropyridopyrimidine;

each of said $R^4$ groups is optionally substituted with Br, Cl, up to three fluorine atoms, up to three $C_{1-4}$alkyl, $C_{2-4}$alkenyl, $C_{2-4}$alkynyl, $C_{3-6}$cycloalkyl, an oxetane ring, a tetrahydrofuran ring, a dihydropyran ring, a tetrahydropyran ring, a pyrrolidine ring, a triazole ring, a tetrazole ring, an oxadiazole ring, CN, $CH_2OR^5$, $C(O)R^5$, $C(O)N(R^5)_2$, $C(O)OR^5$, $NO_2$, $NHC(O)R^5$, $N(R^5)_2$, or up to two $OR^5$, wherein each of said optional $R^4$ substituents is optionally substituted with up to 3 fluorine atoms, up to two $C_{1-2}$alkyl groups, up to two OH, or up to two $OC_{1-2}$alkyl groups; and each $R^5$ is, independently, hydrogen, $C_{1-4}$alkyl, a 5-6-membered heteroaryl selected from imidazole, triazole, thiazole, pyridine, or pyrimidine, a 4-6-membered heterocyclyl selected from oxetane, tetrahydrofuran, or tetrahydropyran, and each $R^5$ group is optionally substituted with chloro, up to three fluorine atoms, up to two $C_{1-2}$alkyl, $CH_2OH$, CN, up to two OH, up to two $OC_{1-2}$alkyl, pyrrolidine, or triazole, or two $R^5$ groups together with the intervening nitrogen atom form a morpholine ring, azetidine ring, pyrrolidine ring, piperidine ring, or piperazine ring, wherein each of said rings is optionally substituted with up to 3 fluorine atoms, up to two OH, or up to two $OC_{1-2}$alkyl groups.

In one embodiment of a compound of formula I, X is O.

In another embodiment, the invention features compounds having the formula:

(I-C)

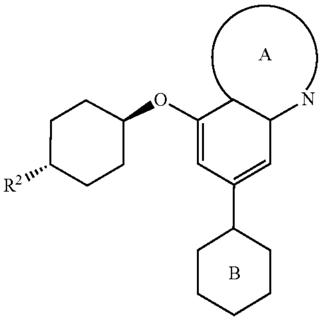

, wherein $R^2$ is as defined for compounds of formula I.

In a further embodiment, the invention features compounds having formulae:

(I-C-1)

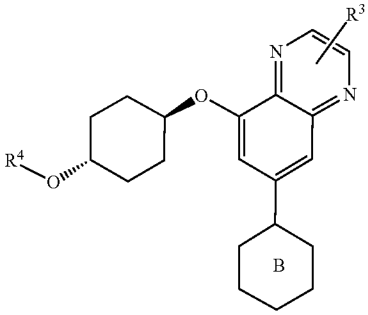

or (I-C-2)

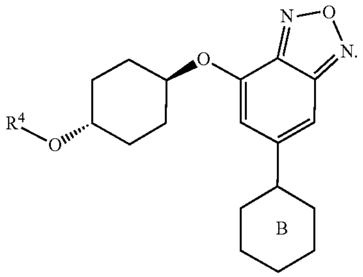

In another further embodiment, the invention features compounds having formulae:

(I-C-3)

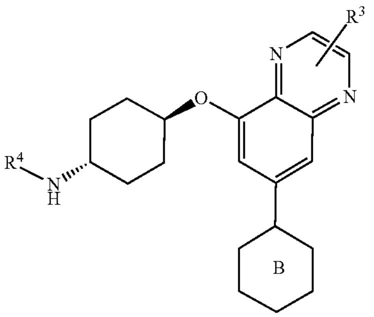

or (I-C-4)

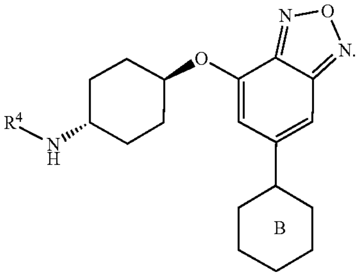

In another embodiment, the invention features compounds having the formula:

(I-D)

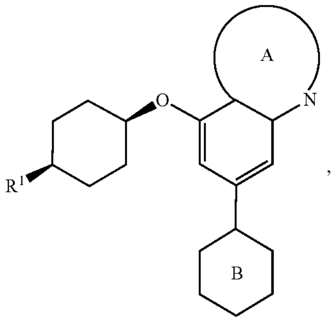

wherein $R^1$ is as defined for compounds of formula I.

In a further embodiment, the invention features compounds having formulae:

(I-D-1)

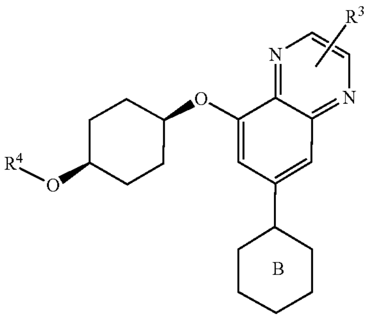

or

-continued (I-D-2)

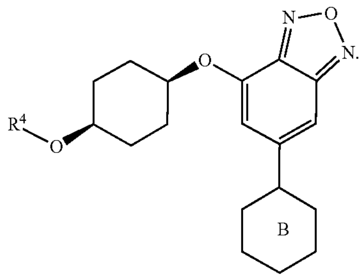

In another further embodiment, the invention features compounds having formula:

(I-D-3)

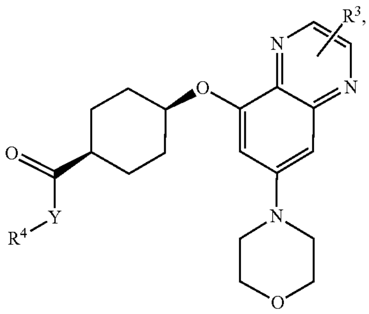

wherein

Y is O or NH.

In another further embodiment, the invention features compounds having formulae:

(I-D-4)

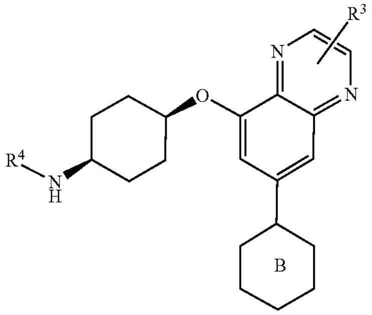

or (I-D-5)

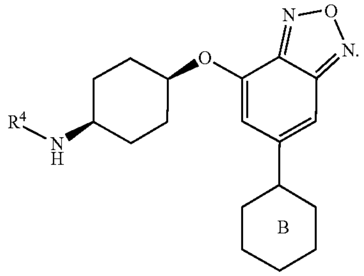

In another aspect, the invention features compounds having the formula:

(III)

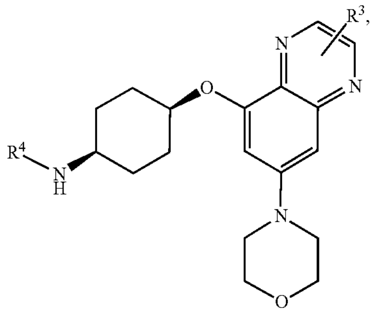

wherein $R^3$ is hydrogen, $C_{1-4}$alkyl, fluoro, chloro, $OC_{1-2}$alkyl, or CN, wherein each of said $R^3$ alkyl is optionally substituted with up to 3 fluorine atoms;

$R^4$ is

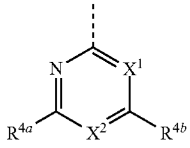

$X^1$ is N, CH, CF, CCl, or $CC_{1-2}$ alkyl optionally substituted with up to 3 fluorine atoms;

$X^2$ is N, $CR^{4c}$ each of $R^{4a}$, $R^{4b}$, and $R^{4c}$ is, independently, hydrogen, F, Cl, Br, CN, $NO_2$, $C_{1-4}$ alkyl, $C_{0-4}$ alkyl-$C_{3-5}$ cycloalkyl, $C_{0-4}$ alkyl-O—$C_{1-4}$ alkyl, $C_{0-4}$ alkyl-O—$C_{0-4}$ alkyl-$C_{3-5}$ cycloalkyl, $C_{2-4}$ alkenyl, $C_{2-4}$ alkynyl, C(O)$OC_{1-4}$ alkyl, C(O)$OC_{0-4}$ alkyl-$C_{3-5}$ cycloalkyl, C(O)$NH_2$, C(O)$NHC_{1-4}$ alkyl, C(O)N($C_{1-4}$ alkyl)$_2$, C(O)NH($C_{0-4}$ alkyl-$C_{3-5}$ cycloalkyl), a heterocyclic ring system selected from oxetane, azetidine, tetrahydrofuran, dihydropyran, tetrahydropyran, morpholine, piperidine, or piperazine, or a heteroaryl ring system selected from furan, oxazole, oxadiazole, pyrrole, pyrazole, triazole, or tetrazole, or $R^{4c}$, $R^{4a}$, and the intervening atoms form a dihydrofuran, a dihydropyran, or a tetrahydropiperidine heterocyclic ring system;

wherein each of said $R^{4a}$, $R^{4b}$ or $R^{4c}$ heterocyclic or heteroaryl ring systems is optionally substituted with up to four fluorine atoms, up to two $C_{1-4}$ alkyl, a C(O)$C_{1-4}$ alkyl, a C(O)$OC_{1-4}$ alkyl, or a C(O)$OC_{0-4}$ alkyl-$C_{3-5}$ cycloalkyl; and wherein each of said $R^{4a}$, $R^{4b}$ or $R^{4c}$ alkyl or cycloalkyl is optionally substituted with up to 2 non-geminal OH groups or up to 3 fluorine atoms.

In yet another embodiment for compounds of formulae I-A, I-A-1, I-A-2, I-B, I-B-1, I-B-2, I-C, I-C-1, I-C-2, I-C-3, I-C-4, I-D, I-D-1, I-D-2, I-D-3, I-D-4, or I-D-5,

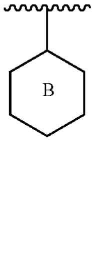

is

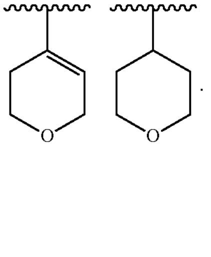

In another embodiment, the invention features a compound selected from the group of compounds listed in Table 1.

Compositions, Formulations, and Administration of Compounds of the Invention

In another embodiment, the invention provides a pharmaceutical composition comprising a compound of any of the formulae described herein and a pharmaceutically acceptable excipient. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a DNA-PK in a biological sample or in a patient. In another embodiment, the amount of compound in the compositions of this invention is such that is effective to measurably inhibit DNA-PK. In one embodiment, the composition of this invention is formulated for administration to a patient in need of such composition. In a further embodiment, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of DNA-PK.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences,* 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^{+}(C_{1-4}\ alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular proliferative condition or cancer to be treated, additional therapeutic agents, which are normally administered to treat or prevent that condition, may also be present in the compositions of this invention. As used herein, additional therapeutic agents which are normally administered to treat or prevent a particular proliferative condition or cancer are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one embodiment, the invention provides a method of sensitizing a cell to an agent that induces a DNA lesion comprising the step of contacting the cell with one or more DNA-PK inhibitors of formulae I, II, or III, or subformula thereof (e.g., formulae I-A, I-A-1, I-A-2, I-B, I-B-1, I-B-2, I-C, I-C-1, I-C-2, I-C-3, I-C-4, I-D, I-D-1, I-D-2, I-D-3, I-D-4, or I-D-5).

The invention further provides methods of potentiating a therapeutic regimen for treatment of cancer comprising the step of administering to an individual in need thereof an effective amount of a DNA-PK inhibitor of formula I, II, or III, or a subformula thereof. In one aspect, the therapeutic regimen for treatment of cancer includes radiation therapy. Compounds of the invention are useful in instances where radiation therapy is indicated to enhance the therapeutic benefit of such treatment. In addition, radiation therapy frequently is indicated as an adjuvent to surgery in the treatment of cancer. The goal of radiation therapy in the adjuvant setting is to reduce the risk of recurrence and enhance disease-free survival when the primary tumor has been controlled. Adjuvant radiation therapy is indicated in several diseases including colon, rectal, lung, gastroesophageal, and breast cancers as described below.

The invention also can be practiced by including another anti-cancer chemotherapeutic agent with a compound of the invention in a therapeutic regimen for the treatment of cancer, with or without radiation therapy. The combination of a DNA-PK inhibitor compound of the invention with such other agents can potentiate the chemotherapeutic protocol. For example, the inhibitor compound of the invention can be administered with etoposide or bleomycin, agents known to cause DNA strand breakage.

The invention further relates to radiosensitizing tumor cells utilizing a compound of formula I, II, or III, or a subformula thereof. The preferred compounds are those as described for the pharmaceutical compositions of the invention. A compound that can "radiosensitize" a cell, as used herein, is defined as a molecule, preferably a low molecular weight molecule, administered to animals in therapeutically effective amount to increase the sensitivity of cells to electromagnetic radiation and/or to promote the treatment of diseases that are treatable with electromagnetic radiation (e.g., X-rays). Diseases that are treatable with electromagnetic radiation include neoplastic diseases, benign and malignant tumors, and cancerous cells.

The present invention also provides methods of treating cancer in an animal that includes administering to the animal an effective amount of a DNA-PK inhibitor such as, for example, a compound of the invention. The invention further is directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention also are readily adaptable for use in assay systems, e.g., assaying cancer cell growth and properties thereof, as well as identifying compounds that affect cancer cell growth.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells which infiltrate (invade) the surrounding tissues and give rise to metastases. Adenocarcinomas are carcinomas derived from glandular tissue, or from tissues which form recognizable glandular structures. Another broad category of cancers includes sarcomas, which are tumors whose cells are embedded in a fibrillar or homogeneous substance like embryonic connective tissue. The invention also enables treatment of cancers of the myeloid or lymphoid systems, including leukemias, lymphomas, and other cancers that typically do not present as a tumor mass, but are distributed in the vascular or lymphoreticular systems.

DNA-PK activity can be associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell lung carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Methods to potentiate treatment of these and other forms of cancer are embraced by the invention.

The invention provides a method of inhibiting DNA-PK activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly DNA-PK activity, in a biological sample is useful for a variety of purposes known to one of skill in the art. Examples of such purposes include, but are not limited to, biological specimen storage and biological assays. In one embodiment, the method of inhibiting DNA-PK activity in a biological sample is limited to non-therapeutic methods.

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:

BPin pinacol boronate ester
Brine a saturated NaCl solution in water
DCM dichloromethane
DIAD diisopropylazodicarboxylate
DIEA diisopropylethylamine
DMA dimethylacetamide
DMF dimethylformamide
DMSO dimethylsulfoxide
DTT dithiothreitol
ESMS electrospray mass spectrometry
$Et_2O$ ethyl ether
EtOAc ethyl acetate
EtOH ethyl alcohol
HEPES 4-(2-hydroxyethyl)-1-piperazineethanesulfonic acid
HPLC high performance liquid chromatography
IPA isopropanol
LAH lithium aluminum hydride
LC-MS liquid chromatography-mass spectrometry
LDA lithium diisoproylethylamide
Me methyl
MeOH methanol
MsCl methanesulfonyl chloride
MTBE methyl t-butyl ether
NMP N-methylpyrrolidine
$Pd_2(dba)_3$ tris(dibenzylideneacetone)dipalladium(O)
$Pd(dppf)Cl_2$ 1,1' bis(diphenylphosphino)-ferrocene dichloro-palladium PG protecting group
Ph phenyl
(rac)-BINAP racemic 2,2'-bis(diphenylphosphino)-1,1'-binaphthyl
RockPhos di-tert-butyl(2',4',6'-triisopropyl-3,6-dimethoxy-[1,1'-biphenyl]-2-yl)phosphine
RT or rt room temperature
SFC supercritical fluid chromatography
SPhos 2-dicyclohexylphosphino-2',6'-dimethoxybiphenyl
TBAI tetrabutylammonium iodide
tBu tertiary butyl
THF tetrahydrofuran
TEA triethylamine
TMEDA tetramethylethylenediamine
VPhos [3-(2-dicyclohexylphosphanylphenyl)-2,4-dimethoxy-phenyl]sulfonyloxysodium General Synthetic Procedures In general, the compounds of this invention may be prepared by methods described herein or by other methods known to those skilled in the art.

Example 1. General Preparation of the Compounds of Formula G

Scheme 1

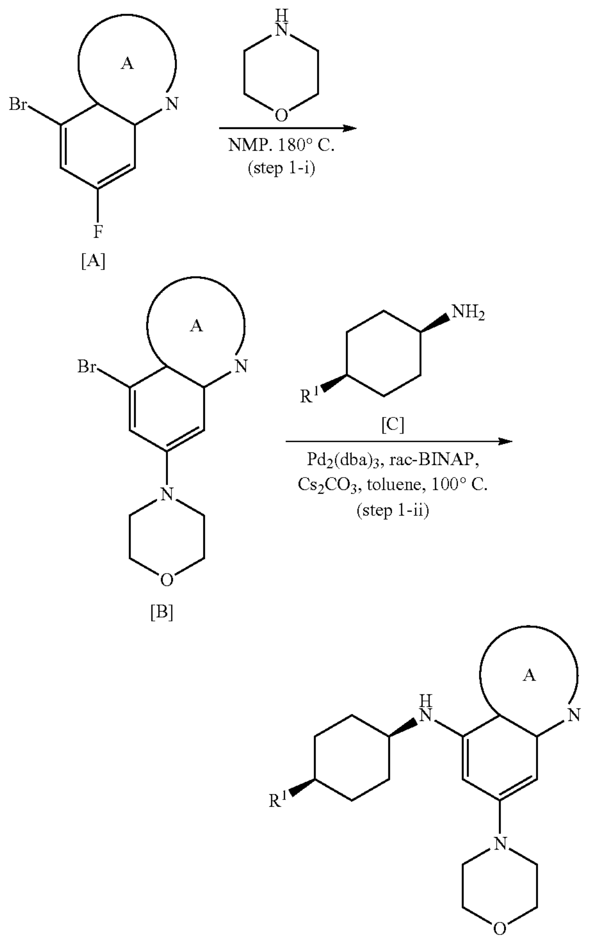

[A] [B] [C] [D]

-continued

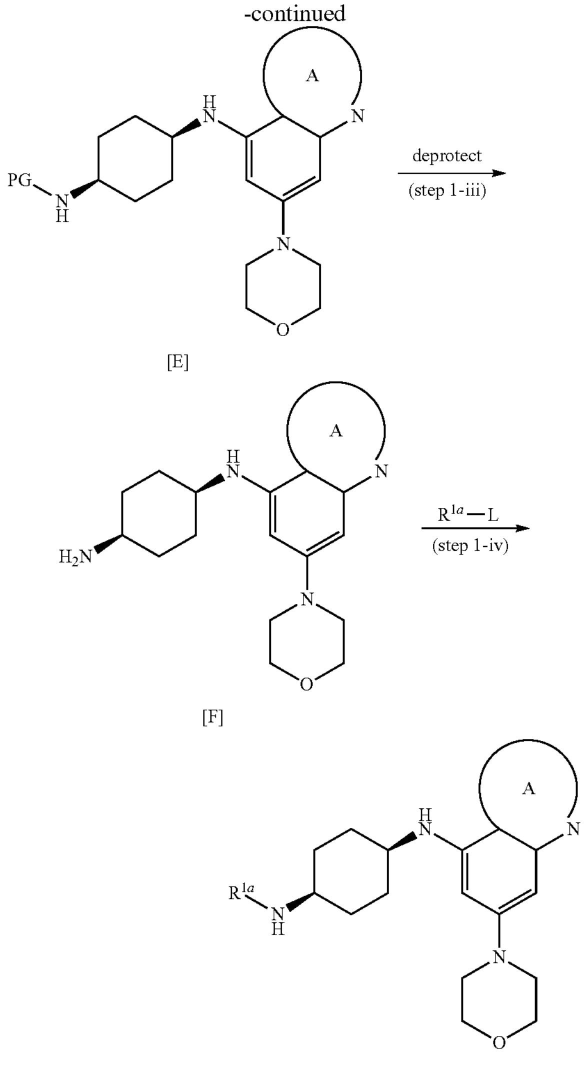

[E] [F] [G]

Compounds of formula I, wherein $X^1$ is NH (i.e., compounds of formula I-A), can be prepared as outlined below in Scheme 1. Accordingly, as shown in step 1-i of Scheme 1, heteroaryl compounds of formula A can be reacted with morpholine or a morpholine analog by heating the mixture in a polar, non-protic solvent to produce compounds of formula B. Utilizing a palladium-catalyzed, phosphine ligand-assisted Buchwald/Hartwig-type coupling, as shown in step 1-ii of Scheme 1, a compound of formula B can be reacted with aminocyclohexanes of formula C to produce compounds of formula D, wherein $R^1$ and $R^2$ are as described elsewhere herein. In one example, when mono-protected meso cyclohexane-1,4-diamines of formula E are prepared, removal of the protecting group forms compounds of formula F, as shown in step 1-iii of Scheme 1. The resulting free amine can then be reacted with various moieties having groups reactive towards amines (e.g., $R^{1a}$-L, where L is a leaving group such as chloro, bromo, iodo, toluenesulfonate, methanesulfonate, or trifluoromethanesulfonate; or where L is a reactive carbonyl-containing moiety such as an active ester or an isocyanato group) to produce a compound of formula G, as shown in step 1-iv of Scheme 1.

Example 2. General Preparation of the Compounds of Formula M, N, R, and S

Scheme 2a

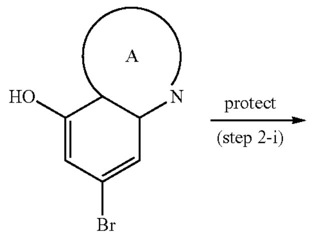

[H]

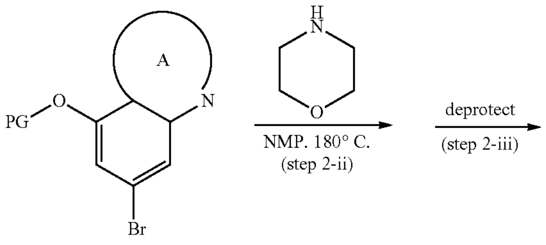

[J]

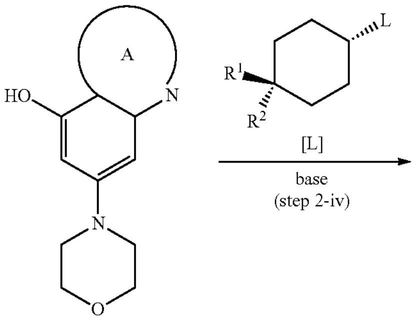

[K]

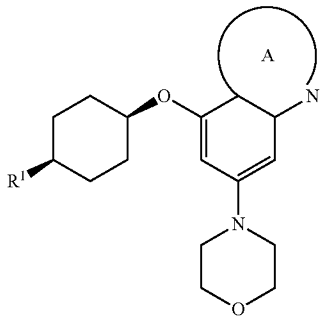

[M]

or

-continued

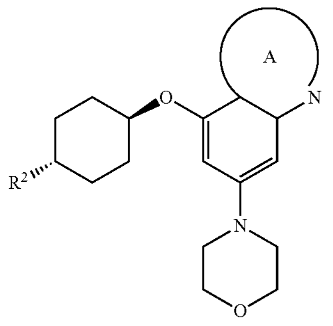

[N]

Compounds of formula I, wherein $X^1$ is O can be prepared as outlined below in Schemes 2a and 2b. Accordingly, as shown in step 2-i of Scheme 2a, the hydroxyl group of heteroaryl compounds of formula H can be protected to produce compounds of formula J, which can then be reacted with morpholine or a morpholine analog by heating the mixture in a polar, non-protic solvent to produce compounds of formula K after removal of the protecting group, as shown in steps 2-ii and 2-iii of Scheme 2a. Subsequently, as shown in step 2-iv of Scheme 2a, a compound of formula K can be reacted with a compound of formula L under conditions sufficient to affect the SN2 displacement of its leaving group (e.g., where L is a leaving group such as chloro, bromo, iodo, toluenesulfonate, methanesulfonate, or trifluoromethanesulfonate) to produce a compound of formula M or formula M, depending on whether $R^1$ or $R^2$ is hydrogen. In those instances when $R^1$ or $R^2$ are protected nitrogen or oxygen moieties, compounds of the invention can be produced by removal of the protecting group and subsequent synthetic manipulation of the resulting free amine/alcohol.

Alternatively, as shown in Scheme 2b, the hydroxyl group of a compound of formula O can be reacted with a compound of formula L to produce a fused bicycloheteroaryl bromide of formula P, which can subsequently be reacted with morpholine or a morpholine analog to produce a compound of formula M or formula N.

Scheme 2b

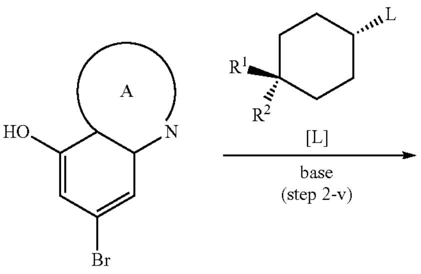

[O]

-continued

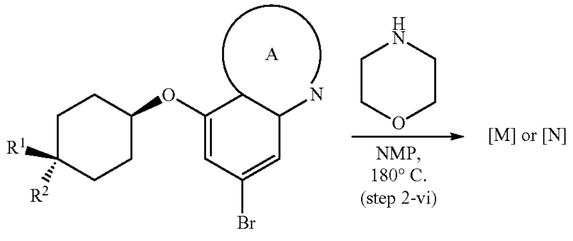

[P]

Alternatively, as shown in Scheme 2c, compounds of the invention in which Ring B is a dihydropyran ring can be prepared by reacting compounds of formula Q with dialkyl (3,6-dihydro-2H-pyran-4-yl)boronates to produce compounds of formula R. Compounds of formula R can then be subsequently reduced to form compounds of formula S.

Scheme 2c

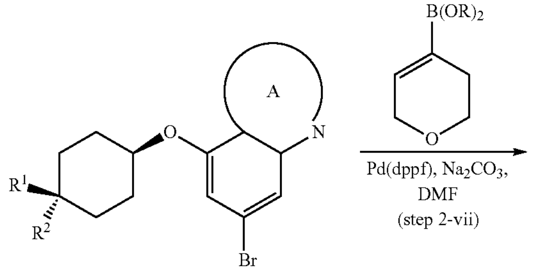

[Q]

-continued

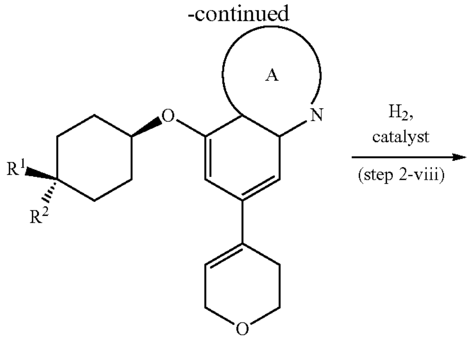

[R]

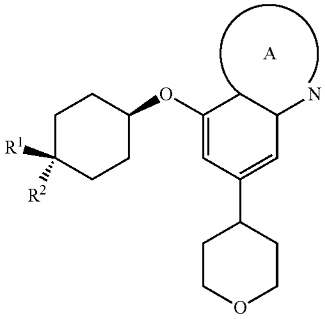

[S]

Example 3. Preparation of ethyl (4-((7-morpholinoquinoxalin-5-yl)amino)cyclohexyl)carbamate (Compound 6) and $N^1$-(7-morpholinoquinoxalin-5-yl)-$N^4$-(pyrimidin-2-yl)cyclohexane-1,4-diamine (Compound 18)

Scheme 3

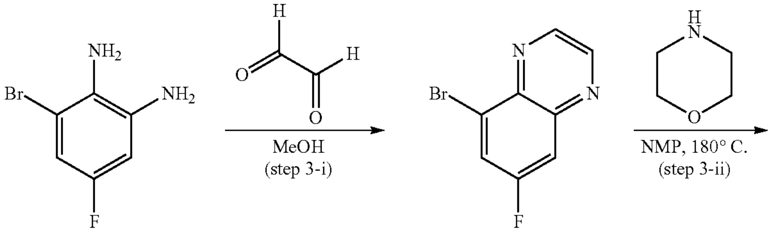

[1001]

[1002]

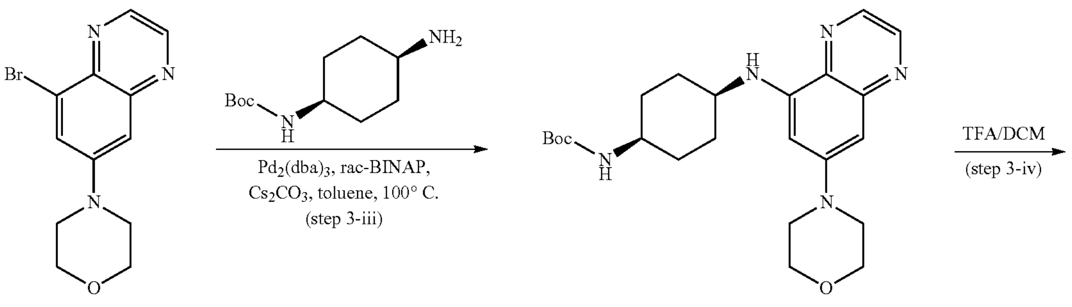

[1003]

[1004]

-continued

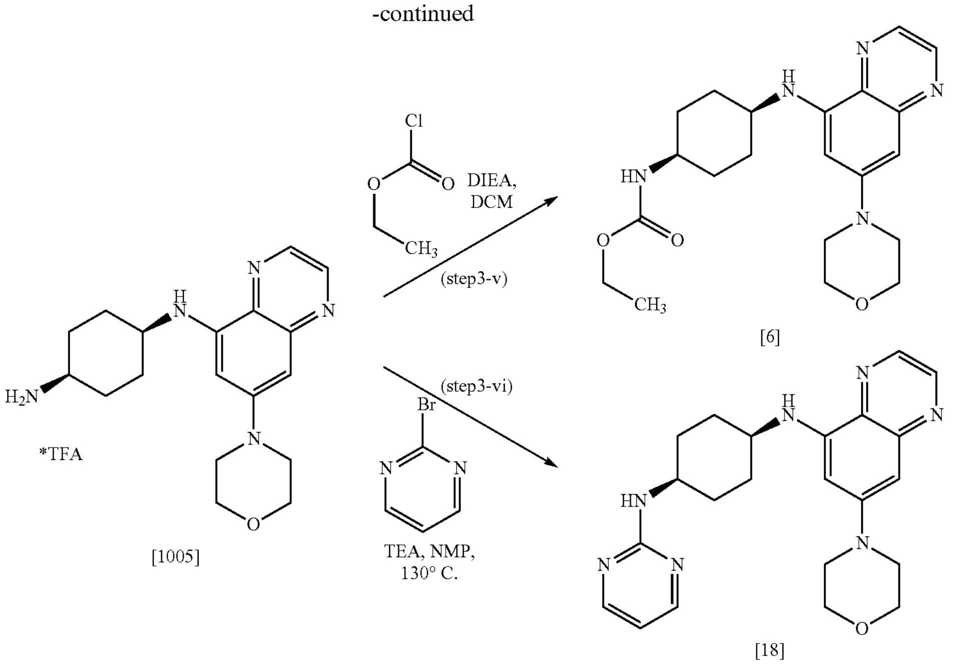

*TFA

[1005]

[6]

[18]

As shown in step 3-i of Scheme 3, to a solution of 3-bromo-5-fluoro-benzene-1,2-diamine (compound 1001, 1.11 g, 5.41 mmol) in methanol (11 mL) was added oxaldehyde (1.57 mL of 40% w/v, 10.8 mmol). The reaction mixture was stirred at room temperature under nitrogen. After 2 hours a yellow solid precipitated. The reaction mixture was diluted with water (20 mL), stirred an additional 5 minutes, filtered, and the collected solid dried under high vacuum to produce 5-bromo-7-fluoroquinoxaline (compound 1002, 868 mg, 70.6% yield): $^1$H-NMR (300 MHz, DMSO-$d_6$) δ 9.06 (s, 2H), 8.36 (dd, J=8.5, 2.7 Hz, 1H), 8.00 (dd, J=9.2, 2.7 Hz, 1H); ESMS (M+H$^+$)=227.14.

As shown in step 3-ii of Scheme 3, to a solution of 5-bromo-7-fluoroquinoxaline (4.5 g, 19.8 mmol) in NMP (67.5 mL) was added morpholine (3.1 mL, 35.6 mmol). The reaction mixture was heated to 140° C. and stirred for 15 hours. After cooling, the mixture was poured into water (200 mL), extracted with ethyl acetate (2×100 mL), dried over magnesium sulfate, filtered, evaporated under reduced pressure, and purified by medium pressure silica gel chromatography (10 to 80% EtOAc/hexanes gradient) to provide 4-(8-bromoquinoxalin-6-yl)morpholine (compound 1003, 3.86 g, 66% yield) as a yellow solid: $^1$H-NMR (400 MHz, DMSO-$d_6$) δ 8.82 (d, J=1.6 Hz, 1H), 8.73 (d, J=1.6 Hz, 1H), 8.12 (d, J=2.5 Hz, 1H), 7.27 (d, J=2.4 Hz, 1H), 3.87-3.69 (m, 4H), 3.44-3.34 (m, 4H); ESMS (M+H$^+$)=227.14.

As shown in step 3-iii of Scheme 3, a mixture of 4-(8-bromoquinoxalin-6-yl)morpholine (1.57 g, 5.34 mmol), tert-butyl-N-(4-aminocyclohexyl)carbamate (1.37 g, 6.40 mmol), (rac)-BINAP (664 mg, 1.07 mmol), cesium carbonate (5.22 g, 16.0 mmol), and $Pd_2(dba)_3$ (489 mg, 0.534 mmol) in toluene (50 mL) was heated at 100° C. for 12 hours. After cooling, the mixture was diluted with ethyl acetate (150 mL) and water (25 mL), then filtered through diatomaceous earth which was subsequently washed with ethyl acetate. The combined organics were washed with brine, dried over sodium sulfate, concentrated under reduced pressure, and purified by medium pressure silica gel chromatography (0 to 60% EtOAc/hexanes gradient) to provide tert-butyl(-4-((7-morpholinoquinoxalin-5-yl)amino)cyclohexyl)carbamate (compound 1004, 1.83 g, 83.2% yield): $^1$H-NMR (300 MHz, $CDCl_3$) δ 8.65 (d, J=2.0 Hz, 1H), 8.35 (d, J=2.0 Hz, 1H), 6.60 (d, J=2.4 Hz, 1H), 6.34 (d, J=2.4 Hz, 1H), 6.11 (d, J=7.8 Hz, 1H), 4.60 (s, 1H), 3.97-3.86 (m, 4H), 3.67 (s, 2H), 3.41-3.25 (m, 4H), 1.85 (d, J=3.0 Hz, 5H), 1.74-1.57 (m, 3H), 1.45 (s, 9H).

As shown in step 3-iv of Scheme 3, to a solution of tert-butyl (-4-((7-morpholinoquinoxalin-5-yl)amino)cyclohexyl)carbamate (900 mg, 2.00 mmol) in dichloromethane (16 mL) was added trifluoroacetic acid (3 mL, 38.9 mmol). The resulting black reaction mixture was stirred under an atmosphere of nitrogen at room temperature for 2 hours. Saturated aqueous sodium bicarbonate (150 mL) was added slowly until the color turned from black to orange. The mixture was extracted with dichloromethane (2×100 mL) and the combined organics washed with brine (50 mL), dried over sodium sulfate, and concentrated under reduced pressure to provide-N$^1$-(7-morpholinoquinoxalin-5-yl)cyclohexane-1,4-diamine, trifluoroacetate (compound 1005): $^1$H NMR (300 MHz, $CDCl_3$) δ 8.64 (d, J=1.9 Hz, 1H), 8.36 (d, J=1.9 Hz, 1H), 6.59 (d, J=2.3 Hz, 1H), 6.34 (d, J=2.3 Hz, 1H), 6.20 (d, J=7.9 Hz, 1H), 3.95-3.84 (m, 4H), 3.69 (s, 1H), 3.41-3.25 (m, 4H), 2.93 (d, J=8.9 Hz, 1H), 2.09-1.87 (m, 2H), 1.90-1.68 (m, 6H), 1.58 (dd, J=11.2, 8.7 Hz, 2H); ESMS (M+H$^+$)=328.34. This compound was used as is without further purification.

As shown in step 3-v of Scheme 3, to solution of N$^1$-(7-morpholinoquinoxalin-5-yl)cyclohexane-1,4-diamine (25 mg, 0.07 mmol) and diisopropylethylamine (18.0 mg, 24.3 μL, 0.14 mmol) in dichloromethane (750 μL) was added ethyl chloroformate (11.4 mg, 10.0 μL, 0.105 mmol). The reaction mixture was stirred for 12 hours, diluted with dichloromethane (10 mL), washed with saturated aqueous sodium bicarbonate (5 mL), dried over sodium sulfate, and concentrated under reduced pressure. The resulting residue was purified by HPLC preparative chromatography using a 10-90% acetonitrile/water (0.1% TFA) gradient as eluant to provide ethyl (4-((7-morpholinoquinoxalin-5-yl)amino)cyclohexyl)carbamate (compound 6, 14 mg, 50% yield): $^1$H-NMR (300 MHz, $CDCl_3$) δ 8.65 (d, J=2.0 Hz, 1H), 8.36 (d, J=2.0 Hz, 1H), 6.61 (d, J=2.4 Hz, 1H), 6.35 (d, J=2.4 Hz, 1H), 6.10 (d, J=7.6 Hz, 1H), 4.72 (s, 1H), 4.12 (q, J=7.0 Hz, 2H), 3.96-3.82 (m, 4H), 3.68 (s, 2H), 3.42-3.23 (m, 4H), 1.93-1.78 (m, 6H), 1.69 (dd, J=15.0, 6.3 Hz, 2H), 1.25 (t, J=7.1 Hz, 3H); ESMS (M+H$^+$)=400.17.

As shown in step 3-vi of Scheme 3, A mixture of N$^1$-(7-morpholinoquinoxalin-5-yl)cyclohexane-1,4-diamine (185 mg, 0.56 mmol), 2-bromopyrimidine (93 mg, 0.58 mmol), and triethylamine (143 mg, 197 μL, 1.41 mmol) in 1-methylpyrrolidin-2-one (3 mL) was heated to 130° C. and stirred for 15 hours. After cooling to room temperature, the mixture was diluted with ethyl acetate (70 mL) and methyl tert-butyl ether (20 mL), washed with water (3x20 mL), washed with brine (15 mL), dried over sodium sulfate, concentrated under reduced pressure, and purified by medium pressure silica gel chromatography (10 to 100% EtOAc/hexanes gradient) to provide N$^1$-(7-morpholinoquinoxalin-5-yl)-N$^4$-(pyrimidin-2-yl)cyclohexane-1,4-diamine (compound 18, 102 mg, 45% yield): $^1$H-NMR (300 MHz, $CDCl_3$) δ 8.65 (d, J=2.0 Hz, 1H), 8.37 (d, J=2.0 Hz, 1H), 8.27 (d, J=4.8 Hz, 2H), 6.60 (d, J=2.4 Hz, 1H), 6.51 (t, J=4.8 Hz, 1H), 6.36 (d, J=2.4 Hz, 1H), 6.15 (d, J=7.8 Hz, 1H), 5.20 (d, J=7.7 Hz, 1H), 4.04 (d, J=7.9 Hz, 1H), 3.96-3.82 (m, 4H), 3.70 (s, 1H), 3.39-3.24 (m, 4H), 1.94 (dd, J=13.7, 4.4 Hz, 6H), 1.78 (dt, J=28.8, 16.1 Hz, 2H); ESMS (M+H$^+$)=328.34.

Example 4. Preparation of 1-(4-((7-(8-oxa-3-azabicyclo[3.2.1]octan-3-yl)quinoxalin-5-yl)amino)cyclohexyl)-3-ethylurea (Compound 22)

Scheme 4

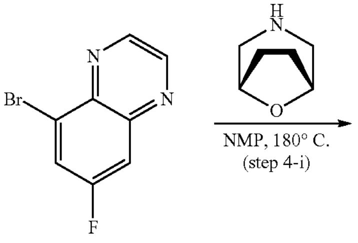

[1002]

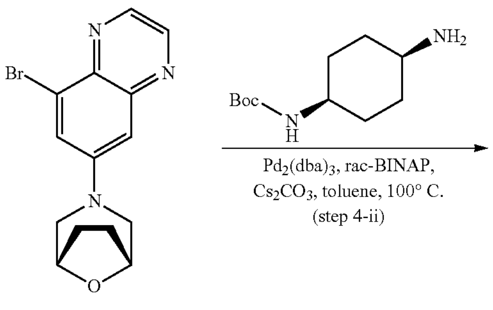

[1006]

-continued

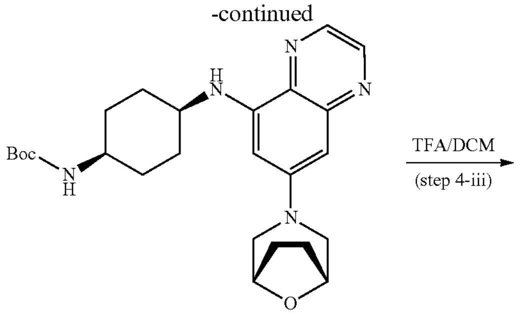

[1007]

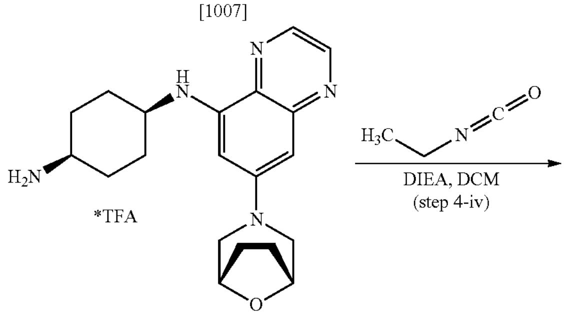

[1008]

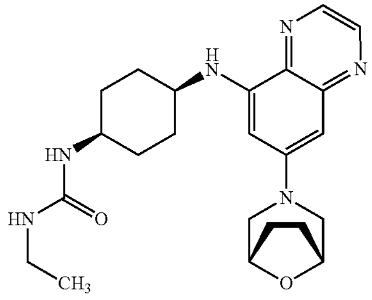

[22]

As shown in step 4-i of Scheme 4, to a solution of 5-bromo-7-fluoroquinoxaline (compound 1002, 150 mg, 0.66 mmol) in NMP (2.3 mL) was added 8-oxa-3-azabicyclo[3.2.1]octane (178 mg, 1.2 mmol) at RT. The reaction mixture was sealed in a microwave vial and heated at 180° C. for 20 minutes. After cooling to RT and pouring into water, the aqueous phase was extracted with EtOAc (3x). The combined extracts were dried over $MgSO_4$, filtered, concentrated under reduced pressure, and purified by medium pressure silica gel chromatography (0 to 100% EtOAc/hexanes gradient) to provide 3-(8-bromoquinoxalin-6-yl)-8-oxa-3-azabicyclo[3.2.1]octane (compound 1006, 87 mg, 41% yield) as a dark orange oil: ESMS (M+H$^+$)=320.07.

As shown in step 4-ii of Scheme 4, a degassed solution of 3-(8-bromoquinoxalin-6-yl)-8-oxa-3-azabicyclo[3.2.1]octane (261 mg, 0.815 mmol), tert-butyl N-(4-aminocyclohexyl)carbamate (210 mg, 0.98 mmol), rac-BINAP (102 mg, 0.163 mmol), $Cs_2CO_3$ (797 mg, 2.45 mmol), and $Pd_2(dba)_3$ (75 mg, 0.0815 mmol) in toluene (10.5 mL) was heated at 100° C. (oil bath temp) in a sealed microwave tube for 15 hours. After cooling, the mixture was applied directly to a chromatography column and purified by medium pressure silica gel chromatography (0 to 100% EtOAc/hexanes gradient) to afford tert-butyl (4-((7-(8-oxa-3-azabicyclo[3.2.1]octan-3-yl)quinoxalin-5-yl)amino)cyclohexyl)carbamate (compound 1007, 141 mg, 36% yield) as a white solid: $^1$H-NMR (400 MHz, $CDCl_3$) δ 8.49 (s, 1H), 8.23 (d, J=1.5

Hz, 1H), 6.48 (s, 1H), 6.18 (d, J=1.9 Hz, 1H), 6.06 (s, 1H), 4.52 (s, 1H), 4.47 (s, 2H), 3.60 (s, 2H), 3.45 (d, J=11.6 Hz, 2H), 3.14-3.12 (m, 2H), 1.96-1.84 (m, 4H), 1.79 (s, 5H), 1.54 (s, 3H) and 1.38 (s, 9H) ppm; ESMS $(M+H^+)$=453.96.

As shown in step 4-iii of Scheme 4, to a solution of compound 1007 (141 mg, 0.295 mmol) in $CH_2Cl_2$ (2.5 mL) was added TFA (656 mg, 443 µL, 5.75 mmol) at RT. The resulting black solution was stirred for 2 hours and then the reaction was quenched by the addition of saturated $NaHCO_3$ until the black color gradually turned into an orange color. The reaction mixture was extracted with $CH_2Cl_2$ (3×) and the combined organic extracts were dried over $Na_2SO_4$ and evaporated to dryness to provide $N^1$-(7-(8-oxa-3-azabicyclo[3.2.1]octan-3-yl)quinoxalin-5-yl)cyclohexane-1,4-diamine, trifluoroacetate (compound 1008): ESMS $(M+H^+)$=354.20. This material was used in subsequent reactions without any further purification.

As shown in step 4-iv of Scheme 4, to a solution of compound 1008 (45 mg, 0.071 mmol) and DIEA (36.5 mg, 49.0 µL, 0.28 mmol) in $CH_2Cl_2$ (1.4 mL) was added ethyl isocyanate (20 mg, 0.28 mmol) at RT. The solution was stirred at this temperature for 15 hours and then applied directly to a chromatography column and purified by medium pressure silica gel chromatograph (0 to 100% EtOAc/hexanes gradient) to afford 1-(4-((7-(8-oxa-3-azabicyclo[3.2.1]octan-3-yl)quinoxalin-5-yl)amino)cyclohexyl)-3-ethylurea (compound 22, 8 mg, 27% yield) as a white solid: $^1$H-NMR (400 MHz, $CDCl_3$) δ 8.54 (s, 1H), 8.22 (s, 1H), 6.43 (s, 1H), 6.19 (s, 1H), 6.02 (s, 1H), 4.47 (s, 2H), 4.38 (d, J=5.2 Hz, 1H), 4.28 (s, 1H), 3.74 (s, 1H), 3.60 (s, 1H), 3.42 (s, 4H), 3.14-3.09 (m, 4H), 2.05-1.87 (m, 3H), 1.79 (s, 3H), 1.55 (d, J=7.1 Hz, 2H) and 1.21-1.05 (m, 5H) ppm; ESMS $(M+H^+)$=425.35.

Example 5. Preparation of $N^1$-(6-morpholinobenzo[c][1,2,5]oxadiazol-4-yl)-$N^4$-(pyrimidin-2-yl)cyclohexane-1,4-diamine (Compound 23)

Scheme 5

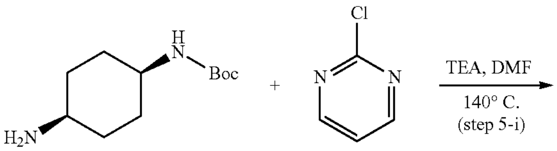

[1009]

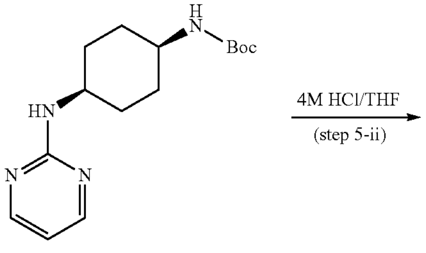

[1010]

-continued

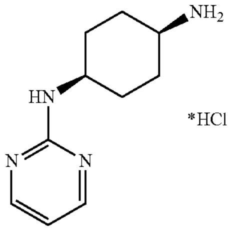

[1011]

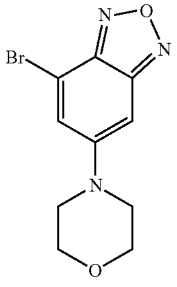

[1012]

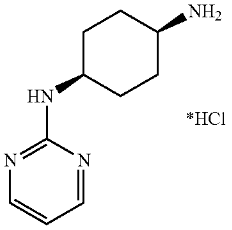

[1011]

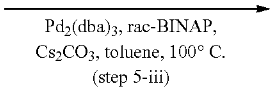

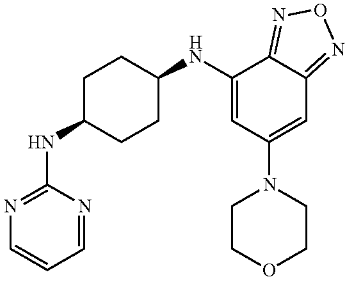

[23]

As shown in step 5-i of Scheme 5, a mixture of tert-butyl ((cis)-4-aminocyclohexyl)carbamate (compound 1009, 490 mg, 2.3 mmol), 2-chloropyrimidine (262 mg, 2.3 mmol) and TEA (463 mg, 637 µL, 4.6 mmol) in DMF (10 mL) was subjected to microwave irradiation for 20 minutes at 150° C. The reaction mixture was diluted with EtOAc, washed with $H_2O$, dried over $Na_2SO_4$, concentrated under reduced pressure, and purified by medium pressure silica gel chromatography (0 to 50% EtOAc/hexanes gradient) to provide tert-butyl ((cis)-4-(pyrimidin-2-ylamino)cyclohexyl)carbamate (compound 1010) as a white solid: $^1$H-NMR (300 MHz, $CDCl_3$) δ 8.28 (d, J=4.8 Hz, 2H), 6.53 (t, J=4.8 Hz, 1H), 5.12 (s, 1H), 4.56 (s, 1H), 3.99 (dq, J=7.0, 3.5 Hz, 1H), 3.65 (s, 1H), 1.83 (tq, J=10.2, 3.6 Hz, 5H), 1.66 (s, 8H), 8.13-7.91 (m, 3H), 1.47 (s, 9H).

As shown in step 5-ii of Scheme 5, HCl (3 mL, 4M in THF, 12 mmol) was added to compound 1010. The mixture was stirred for 30 min and concentrated under reduced pressure to produce (cis)-$N^1$-(pyrimidin-2-yl)cyclohexane-1,4-diamine hydrochloride (compound 1011). This material was used in subsequent reactions as is without further purification.

As shown in step 5-iii of Scheme 5, a mixture of 4-bromo-6-morpholinobenzo[c][1,2,5]oxadiazole (compound 1012, 147 mg, 0.5 mmol), (cis)-$N^1$-(pyrimidin-2-yl)cyclohexane- 1,4-diamine hydrochloride (120 mg, 0.6 mmol), (rac)-BINAP (32 mg, 0.05 mmol), $Pd_2(dba)_3$ (24 mg, 0.026 mmol), and cesium carbonate (506 mg, 1.55 mmol) in toluene (5 mL) was flushed with nitrogen gas and stirred overnight at 90° C. under an atmosphere of nitrogen. The mixture was filtered though a layer of diatomaceous earth, concentrated under reduced pressure, and purified by medium pressure silica gel chromatography (0 to 80% EtOAc/hexanes gradient) to provide (cis)-$N^1$-(6-morpholinobenzo[c][1,2,5]oxadiazol-4-yl)-$N^4$-(pyrimidin-2-yl)cyclohexane-1,4-diamine (compound 23) as an orange solid: $^1$H-NMR (300 MHz, $CDCl_3$) δ 8.20 (d, J=4.9 Hz, 2H), 6.46 (t, J=4.8 Hz, 1H), 6.05 (d, J=1.6 Hz, 1H), 5.82 (s, 1H), 5.24 (s, 1H), 4.82 (d, J=7.0 Hz, 1H), 3.98 (s, 1H), 3.85-3.72 (m, 4H), 3.60 (s, 1H), 3.23-3.06 (m, 4H), 1.95-1.62 (m, 8H).

Example 6. Preparation of 5-methoxy-N-((cis)-4-((7-morpholinoquinoxalin-5-yl)oxy)cyclohexyl)pyrimidin-2-amine (Compound 134)

Scheme 6

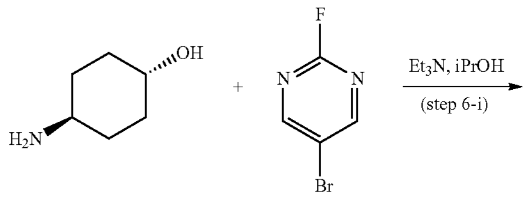

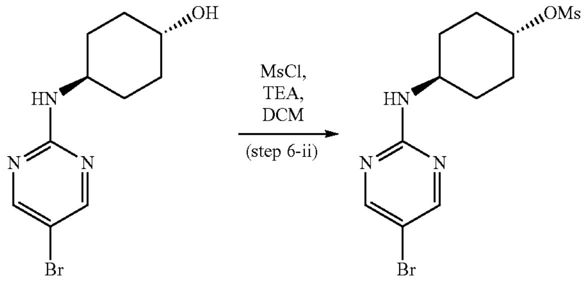

[1013] [1014]

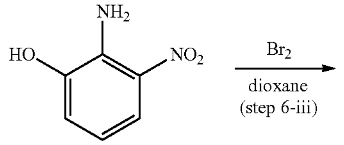

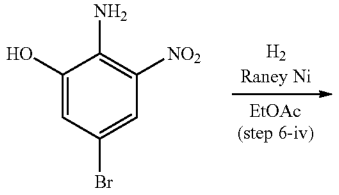

[1015]

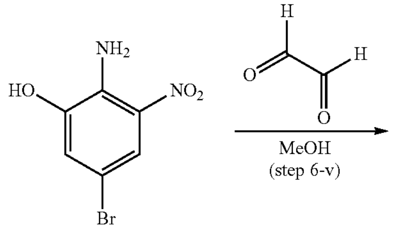

[1016]

-continued

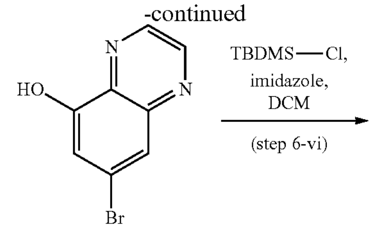

[1017]

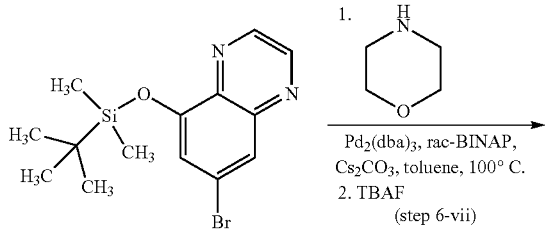

[1018]

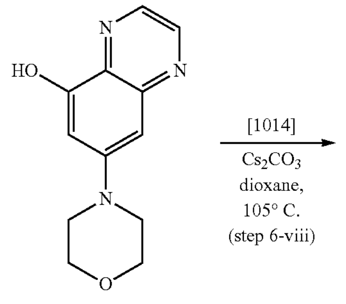

[1019]

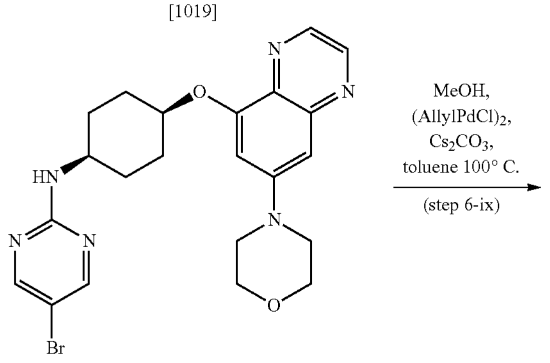

[1020]

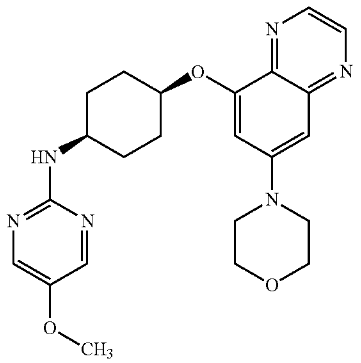

[134]

As shown in step 6-i of Scheme 6, to a mixture of 5-bromo-2-fluoro-pyrimidine (1 g, 5.651 mmol) in iPrOH (10 mL) was added TEA (1.143 g, 1.574 mL, 11.30 mmol) and trans-4-aminocyclohexan-1-ol (650.8 mg, 5.651 mmol). The mixture was microwaved for 20 min at 150° C., concentrated under reduced pressure, diluted with EtOAc, washed with water, and dried over $Na_2SO_4$. After removal of the volatiles under reduced pressure, the residue was purified by medium pressure silica gel chromatography (0-80% EtOAc/hexanes gradient) to provide (trans)-4-((5-bromopyrimidin-2-yl)amino)cyclohexanol (compound 1013, 1.2 g): $^1$H-NMR (300 MHz, $CDCl_3$) δ 8.28 (s, 2H), 5.03 (d, J=8.1 Hz, 1H), 3.91-3.49 (m, 2H), 2.31-1.90 (m, 4H), 1.56-1.19 (m, 4H).

As shown in step 6-ii of Scheme 6, to compound 1013 (1.2 g, 4.41 mmol) in DCM (20 mL) was added TEA (1.134 g, 1.84 mL, 13.2 mmol) and MsCl (505 mg, 341 μL, 4.41 mmol). The reaction mixture was stirred for 1 hour, concentrated under reduced pressure, and purified by medium pressure silica gel chromatography (0 to 80% EtOAc/hexanes gradient) to provide trans-4-((5-bromopyrimidin-2-yl)amino)cyclohexyl methanesulfonate (compound 1014): $^1$H-NMR (300 MHz, $CDCl_3$) δ 8.29 (s, 2H), 5.03 (d, J=7.8 Hz, 1H), 4.70 (tt, J=10.6, 3.9 Hz, 1H), 3.80 (dtt, J=11.2, 7.6, 3.7 Hz, 1H), 3.04 (s, 3H), 2.30-2.12 (m, 4H), 1.93-1.69 (m, 2H), 1.51-1.33 (m, 2H).

As shown in step 6-iii of Scheme 6, to a solution of 2-amino-3-nitrophenol (5.00 g, 32.4 mmol) in dioxane (50 mL) was added bromine (6.22 g, 2.01 mL, 38.9 mmol). The mixture was stirred for 2 hours and a precipitate formed, which was collected and washed with dioxane and ether. The resulting yellow solid treated with a saturated $NaHCO_3$ solution, which was extracted with EtOAc (3×). The combined organics were dried over $Na_2SO_4$, filtered, and concentrated under reduced pressure to yield 2-amino-5-bromo-3-nitrophenol (compound 1015) as a brown solid. This material was carried on as is in subsequent reactions without further purification.

As shown in step 6-iv of Scheme 6, to a solution of 2-amino-5-bromo-3-nitrophenol (7.5 g, 31.8 mmol) in ethyl acetate (60 mL) was added Raney Nickel™ (1.90 g, 214 μL, 32.4 mmol) and the reaction mixture was shaken for 2 hours under an atmosphere of $H_2$ at 30 p.s.i. After filtering and drying over $Na_2SO_4$, the mixture was concentrated under reduced pressure to provide 2,3-diamino-5-bromophenol (compound 1016), which was used as is in subsequent reactions without further purification.

As shown in step 6-v of Scheme 6, 2,3-diamino-5-bromophenol (6.0 g, 29.5 mmol) was dissolved in methanol and to this solution was added glyoxal (3.77 g, 2.98 mL, 64.9 mmol) and stirred overnight. The reaction mixture was concentrated under reduced pressure to a minimum volume and the resulting tan solid collected by filtration and dried under high vacuum to produce 7-bromoquinoxalin-5-ol (compound 1017), which was used as is in subsequent reactions without further purification.

As shown in step 6-vi of Scheme 6, a solution of 7-bromoquinoxalin-5-ol (2.0 g, 8.89 mmol) in DCM (20 mL) was added imidazole (1.82 g, 26.7 mmol) and tert-butyldimethylsilyl chloride (1.34 g, 1.65 mL, 8.89 mmol). The reaction mixture was stirred overnight at RT, concentrated under reduced pressure, and purified by medium pressure silica gel chromatography (0 to 20% EtOAc/hexanes gradient) to provide 7-bromo-5-((tert-butyldimethylsilyl)oxy)quinoxaline (compound 1018) as a colorless oil: $^1$H-NMR (300 MHz, $CDCL_3$) δ 8.69 (q, J=1.8 Hz, 2H), 7.80 (d, J=2.1 Hz, 1H), 7.22 (d, J=2.1 Hz, 1H), 0.96 (s, 9H), 0.81 (s, 7H).

As shown in step 6-vii of Scheme 6, a mixture of 7-bromo-5-((tert-butyldimethylsilyl)oxy)quinoxaline (700 mg, 2.06 mmol), morpholine (270 mg, 270 μL, 3.09 mmol), $Pd_2(dba)_3$ (94.50 mg, 0.1032 mmol), (rac)-BINAP (129 mg, 0.206 mmol), cesium carbonate (2.02 g, 6.19 mmol) in toluene (7 mL) was flushed with nitrogen for 10 minutes. The mixture was then heated overnight at 100° C. After cooling, the reaction mixture was diluted with EtOAc, filtered through a layer of diatomaceous earth, concentrated under reduced pressure, and purified by medium pressure silica gel chromatography (0 to 30% EtOAc/hexanes gradient) to provide 7-morpholinoquinoxalin-5-ol. This compound (450 mg, 1.3 mmol) was dissolved in THE (20 mL) and tetra-n-butylammonium fluoride (539 mg, 2.06 mmol) was added. The reaction mixture was stirred for 0.5 hour, concentrated under reduced pressure, and purified by medium pressure silica gel chromatography (0 to 100% EtOAc/hexanes gradient) to provide 7-morpholinoquinoxalin-5-ol (compound 1019) as a yellow solid: $^1$H-NMR (300 MHz, $CDCl_3$) δ 8.75 (d, J=2.0 Hz, 1H), 8.46 (d, J=2.0 Hz, 1H), 7.70 (d, J=41.8 Hz, 1H), 7.01 (d, J=2.6 Hz, 1H), 6.89 (d, J=2.5 Hz, 1H), 4.12-3.78 (m, 4H), 3.51-3.24 (m, 4H).

As shown in step 6-viii of Scheme 6, a solution of 7-morpholinoquinoxalin-5-ol (100 mg, 0.432 mmol), (trans)-4-((5-bromopyrimidin-2-yl)amino)cyclohexyl methanesulfonate (compound 1014, 303 mg, 0.865 mmol), and $CsCO_3$ (282 mg, 0.865 mmol) in dioxane (1.0 mL was stirred for 16 hours at 105° C. After cooling, the reaction mixture was diluted with EtOAc, filtered through diatomaceous earth, concentrated under reduced pressure, and purified by medium pressure silica gel chromatography (0 to 5% MeOH/DCM gradient) to produce 5-bromo-N-((cis)-4-((7-morpholinoquinoxalin-5-yl)oxy)cyclohexyl)pyrimidin-2-amine (compound 1020, 110 mg) as a yellow foam: $^1$H-NMR (400 MHz, $CDCl_3$) δ 8.70 (d, J=2.0 Hz, 1H), 8.64 (d, J=1.9 Hz, 1H), 8.29 (s, 2H), 6.98 (d, J=2.5 Hz, 1H), 6.92 (d, J=2.5 Hz, 1H), 5.29 (d, J=8.3 Hz, 1H), 4.81 (s, 1H), 4.04-3.84 (m, 4H), 3.42-3.31 (m, 4H), 2.22 (s, 2H), 1.92 (d, J=4.9 Hz, 6H).

As shown in step 6-ix of Scheme 6, to a mixture 5-bromo-N-((cis)-4-((7-morpholinoquinoxalin-5-yl)oxy)cyclohexyl) pyrimidin-2-amine (75 mg, 0.155 mmol), cesium carbonate (101 mg, 0.309 mmol), allylpalladium(II) chloride dimer (0.28 mg, 0.0015 mmol), RockPhos (2.17 mg, 0.0046 mmol) and MeOH (9.9 mg, 12.5 μL, 0.31 mmol) in toluene (2 mL) was flushed with nitrogen gas and heated to 100° C. for 18 hours. The reaction mixture was diluted with EtOAc, filtered though a layer of diatomaceous earth, and concentrated under reduced pressure. Purification by medium pressure silica gel chromatography (0-8% MeOH/DCM gradient) yielded 5-methoxy-N-((cis)-4-((7-morpholinoquinoxalin-5-yl)oxy)cyclohexyl)pyrimidin-2-amine (compound 134, 43 mg): $^1$H-NMR (300 MHz, $CDCl_3$) δ 8.70 (d, J=1.9 Hz, 1H), 8.63 (d, J=1.9 Hz, 1H), 8.07 (s, 2H), 6.96 (d, J=2.5 Hz, 1H), 6.92 (d, J=2.5 Hz, 1H), 5.01 (d, J=8.1 Hz, 1H), 4.80 (q, J=5.6, 4.2 Hz, 1H), 4.03-3.87 (m, 5H), 3.80 (s, 3H), 3.42-3.27 (m, 4H), 2.29-2.10 (m, 2H), 1.99-1.82 (m, 6H).

Example 7. Preparation of 4-(8-(((trans)-4-(pyrimidin-2-yloxy)cyclohexyl)oxy)quinoxalin-6-yl)morpholine (Compound 34) and 4-(8-(((cis)-4-(pyrimidin-2-yloxy)cyclohexyl)oxy)-quinoxalin-6-yl) morpholine (Compound 42)

Scheme 7

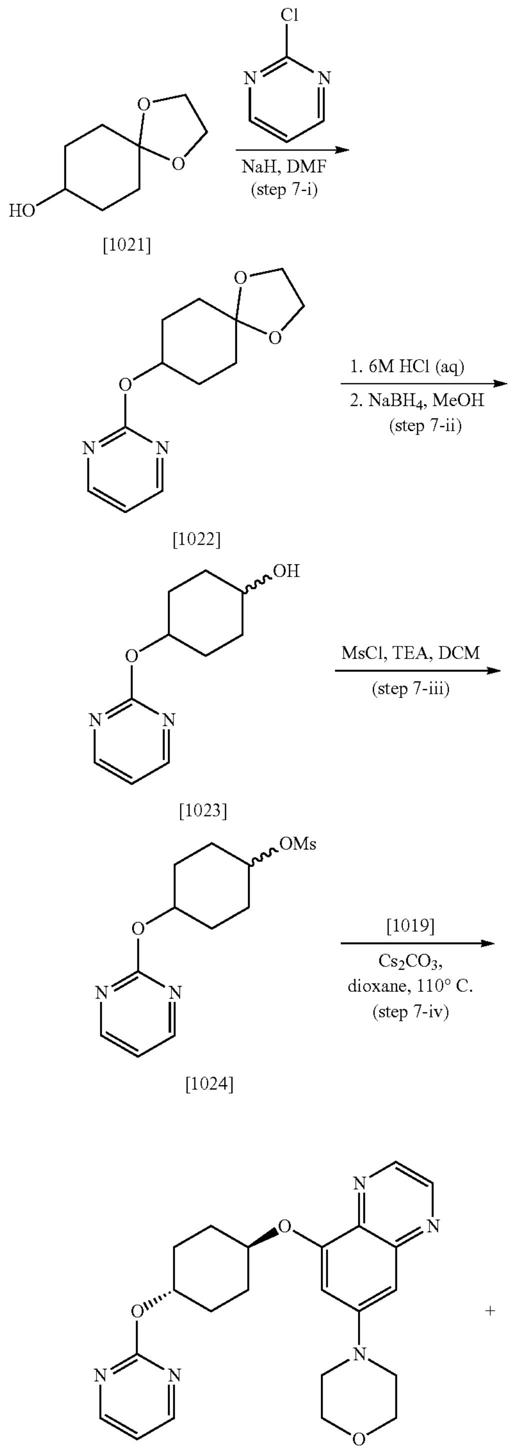

[1021]

[1022]

[1023]

[1024]

[34]

-continued

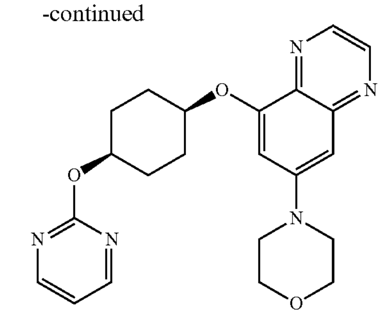

[42]

As shown in step 7-i of Scheme 7, to a solution of 1,4-dioxaspiro[4.5]decan-8-ol (compound 1021, 1.0 g, 6.32 mmol) in DMF (10 mL) was added NaH (370 mg, 9.25 mmol). The reaction mixture was stirred for 20 minutes before the addition of 2-chloropyrimidine (869 mg, 7.59 mmol). The mixture was stirred for 30 minute at RT and then heated to 100° C. for 9 hours. After cooling, the mixture was diluted with EtOAc, washed with $H_2O$, dried over $Na_2SO_4$, concentrated under reduced pressure, and purified by medium pressure silica gel chromatography (0-40% EtOAc/hexanes) to produce 2-(1,4-dioxaspiro[4.5]decan-8-yloxy)pyrimidine (compound 1022) as a colorless oil: $^1H$ NMR (300 MHz, Chloroform-d) δ 8.52 (d, J=4.8 Hz, 2H), 6.92 (t, J=4.8 Hz, 1H), 5.15 (ddd, J=10.7, 6.5, 4.2 Hz, 1H), 4.05-3.87 (m, 4H), 2.14-1.85 (m, 6H), 1.79-1.65 (m, 2H); ESMS $(M+H^+)$=237.12.

As shown in step 7-ii of Scheme 7, to 2-(1,4-dioxaspiro[4.5]decan-8-yloxy)pyrimidine (620 mg, 2.624 mmol) was added HCl (4.0 mL of 6 M, 8.86 mmol) and the reaction mixture was stirred for 2 hours. The pH of the mixture was neutralized with with sat. $NaHCO_3$(aq) and the mixture was concentrated under reduced pressure as a methanol azeotrope. To the residue was added DCM (30 mL) to produce a precipitate, followed by stirring for an additional 20 minutes. The solids were filtered off and the mother liquor was concentrated under reduced pressure. The resulting residue was dissolved in methanol and sodium borohydride (151 mg, 3.99 mmol) was added as a solid. The mixture was stirred for 1 hour and the reaction quenched with HCl (6M, 0.70 mL). Stirring was continued until gas evolution ceased. The pH of the mixture was adjusted to about 8 with 1N sodium hydroxide and extracted with EtOAc (20 mL). The organics were dried over sodium sulfate and concentrated under reduced pressure to produce 4-(pyrimidin-2-yloxy)cyclohexanol (compound 1023, 248 mg, 64% yield) as a mixture of (cis)- and (trans)-isomers. A 12 mg aliquot of the sample was purified via HPLC preparative reversed-phase chromatography (10-90% $CH_3CN$/water gradient containing 0.1% TFA) to separate the isomers: (trans)-4-pyrimidin-2-yloxycyclohexanol-$^1H$ NMR (300 MHz, Chloroform-d) δ 8.54 (d, J=4.8 Hz, 2H), 6.95 (t, J=4.8 Hz, 1H), 5.05 (tt, J=9.4, 4.0 Hz, 1H), 3.91-3.75 (m, 1H), 2.26-1.99 (m, 4H), 1.76-1.41 (m, 4H); ESMS $(M+H^+)$=195.07, (cis)-4-pyrimidin-2-yloxycyclohexanol-$^1H$ NMR (300 MHz, Chloroform-d) δ 8.62 (d, J=4.9 Hz, 2H), 7.04 (t, J=4.9 Hz, 1H), 5.21 (tt, J=5.3, 2.6 Hz, 1H), 4.56 (s, 1H), 3.85 (p, J=5.9 Hz, 1H), 2.17-2.02 (m, 2H), 1.88-1.67 (m, 6H); ESMS $(M+H^+)$=195.07. The remaining material was used in subsequent reactions as the cis/trans mixture.

As shown in step 7-iii of Scheme 7, to a solution of a cis/trans mixture of 4-pyrimidin-2-yloxycyclohexanol (244 mg, 1.256 mmol) and triethylamine (350 μL, 2.51 mmol) in dichloromethane (5 mL) was added methane sulfonyl chloride (145 μL, 1.87 mmol). The reaction mixture was stirred for 2 hours, concentrated under reduced pressure, and purified by medium pressure silica gel chromatography (0-20% EtOAc/dichloromethane gradient) to provide 4-pyrimidin-2-yloxycyclohexyl) methanesulfonate (compound 1024, 239 mg, 70% yield) as a mixture of cis/trans isomers: $^1$H NMR (300 MHz, Chloroform-d) δ 8.51 (d, J=4.8 Hz, 2H), 6.93 (t, J=4.8 Hz, 1H), 5.13 (dq, J=9.9, 3.0 Hz, 1H), 4.87 (p, J=3.8 Hz, 1H), 3.04 (d, J=2.4 Hz, 3H), 2.28-1.99 (m, 4H), 1.99-1.74 (m, 4H); ESMS (M+H$^+$)=273.52.

As shown in step 7-iv of Scheme 7, a mixture of (4-pyrimidin-2-yloxycyclohexyl) methanesulfonate (105 mg, 0.386 mmol), 7-morpholinoquinoxalin-5-ol (178.3 mg, 0.7712 mmol), and $Cs_2CO_3$ (125.6 mg, 0.3856 mmol) in dioxane (1.5 mL) was sealed in a 5 mL microwave tube and heated to 110° C. for 14 hours using an oil bath. The reaction mixture was cooled to room temperature, diluted with EtOAc, and filtered through diatomaceous earth which was subsequently washed with ethyl acetate. The filtrate was concentrated under reduced pressure and the residue purified via preparative reversed-phase HPLC (10-90% $CH_3CN$/water gradient containing 0.1% TFA). Fractions containing a mixture of cis and trans isomers were further purified via SFC using a chiral OJ column and eluting with 40% MeOH in $CO_2$ to provide 21 mg of 4-(8-(((trans)-4-(pyrimidin-2-yloxy)cyclohexyl)oxy)quinoxalin-6-yl)morpholine (compound 34): $^1$H NMR (300 MHz, Chloroform-d) δ 8.69 (dd, J=3.4, 1.9 Hz, 1H), 8.62 (dd, J=3.6, 1.9 Hz, 1H), 8.51 (dd, J=4.8, 2.2 Hz, 2H), 7.01-6.83 (m, 3H), 5.18 (tt, J=7.0, 3.4 Hz, 1H), 4.79 (tt, J=6.9, 3.1 Hz, 1H), 4.00-3.85 (m, 4H), 3.34 (dq, J=4.8, 2.6 Hz, 4H), 2.44-2.16 (m, 4H), 1.92 (tdd, J=16.4, 7.7, 2.8 Hz, 4H); ESMS (M+H$^+$)=408.56, and 22 mg of 4-(8-(((cis)-4-(pyrimidin-2-yloxy)cyclohexyl)oxy)-quinoxalin-6-yl)morpholine (compound 42): $^1$H NMR (300 MHz, Chloroform-d) δ 8.70 (d, J=1.9 Hz, 1H), 8.63 (d, J=1.9 Hz, 1H), 8.52 (d, J=4.8 Hz, 2H), 7.01-6.87 (m, 3H), 5.17 (ddt, J=8.7, 6.7, 3.4 Hz, 1H), 4.76-4.58 (m, 1H), 4.00-3.87 (m, 4H), 3.40-3.27 (m, 4H), 2.43-2.22 (m, 4H), 2.05-1.87 (m, 2H), 1.86-1.71 (m, 2H); ESMS (M+H$^+$)=408.56.

Example 8. N-[(cis)-4-[7-(3,6-dihydro-2H-pyran-4-yl)quinoxalin-5-yl]oxycyclohexyl]pyrimidin-2-amine (Compound 36)

Scheme 8

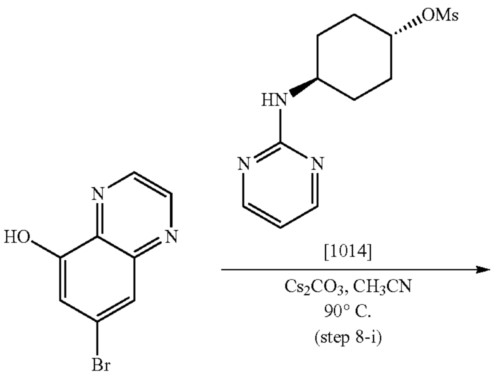

[1018]

-continued

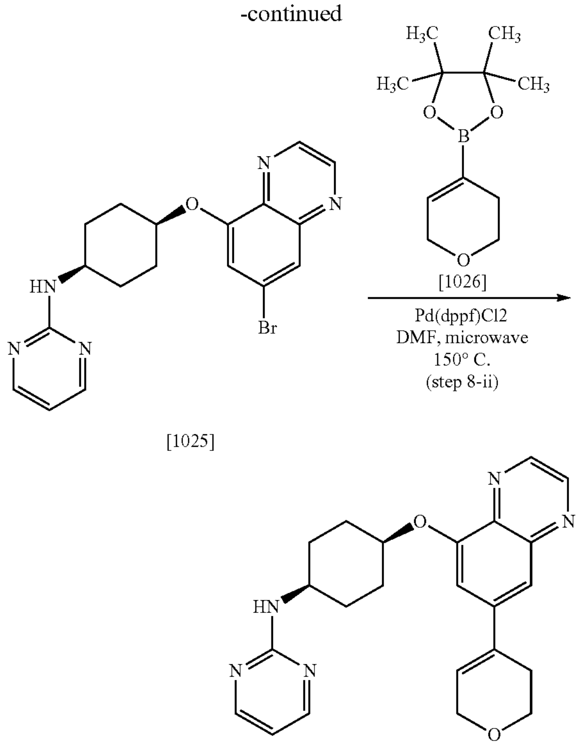

As shown in step 8-i of Scheme 8, to a mixture of 7-bromoquinoxalin-5-ol (compound 1018, 200 mg, 0.89 mmol) and cesium carbonate (579 mg, 1.78 mmol) in NMP (4.0 mL) was added (trans)-4-(pyrimidin-2-ylamino)cyclohexyl methanesulfonate (compound 1014, 241.1 mg, 0.8887 mmol). The mixture was stirred for 18 hours at 90° C., at which time an additional 0.5 eq of compound 1014 (241 mg, 0.89 mmol) was added. After stirring at 90° C. for an additional 6 hours, the reaction mixture was diluted with EtOAc, washed with $H_2O$, dried over $Na_2SO_4$, concentrated, and purified by medium pressure silica gel chromatography (0-5% MeOH/DCM) to provide N-((cis)-4-((7-bromoquinoxalin-5-yl)oxy)cyclohexyl)pyrimidin-2-amine (compound 1025): $^1$H-NMR (300 MHz, $CDCl_3$) δ 9.01-8.77 (m, 2H), 8.29 (d, J=4.8 Hz, 2H), 7.89 (d, J=1.9 Hz, 1H), 7.25 (d, J=2.0 Hz, 1H), 6.53 (t, J=4.8 Hz, 1H), 5.43-5.22 (m, 1H), 4.79 (td, J=5.2, 2.5 Hz, 1H), 4.18-3.95 (m, 1H), 3.51 (s, 1H), 2.22 (td, J=10.2, 9.6, 5.4 Hz, 2H), 2.09-1.86 (m, 6H).

As shown in step 8-ii of Scheme 8, a mixture of N-((cis)-4-((7-bromoquinoxalin-5-yl)oxy)cyclohexyl)pyrimidin-2-amine (compound 1025, 52 mg, 0.1299 mmol), $Pd(dppf)Cl_2$ (10.61 mg, 0.01299 mmol), 2-(3,6-dihydro-2H-pyran-4-yl)-4,4,5,5-tetramethyl-1,3,2-dioxaborolane (compound 1026, 27.3 mg, 0.13 mmol), $Na_2CO_3$ (195 μL of 2M (aq) solution, 0.39 mmol) in DMF (1 mL) was flushed with nitrogen gas for 10 minutes. The mixture was subjected to microwave radiation for 20 min at 150° C. After cooling, the mixture was diluted with EtOAc, washed with $H_2O$, dried over $Na_2SO_4$, concentrated under reduced pressure and purified by medium pressure silica gel chromatography (0-5% MeOH/DCM) to provide N-[(cis)-4-[7-(3,6-dihydro-2H-pyran-4-yl)quinoxalin-5-yl]oxycyclohexyl]pyrimidin-2-amine (compound 36) as an off-white solid: $^1$H-NMR (300 MHz, $CDCl_3$) δ 8.94-8.76 (m, 2H), 8.29 (d, J=4.8 Hz, 2H), 7.67 (d, J=1.7 Hz, 1H), 6.53 (t, J=4.8 Hz, 1H), 6.37 (tt, J=3.1, 1.5 Hz, 1H), 5.30 (d, J=7.9 Hz, 1H), 4.87 (dt, J=7.5, 3.6 Hz, 1H), 4.43 (q, J=2.8 Hz, 2H), 4.02 (t, J=5.5 Hz, 3H), 2.68 (dqd, J=6.0, 3.4, 3.0, 1.8 Hz, 2H), 2.35-2.11 (m, 2H), 2.07-1.84 (m, 6H); ESMS $(M+H^+)$=404.2.

Example 9. N-((cis)-4-((7-morpholinoquinoxalin-5-yl)oxy)cyclohexyl)pyrimidin-2-amine (Compound 28)

Scheme 9

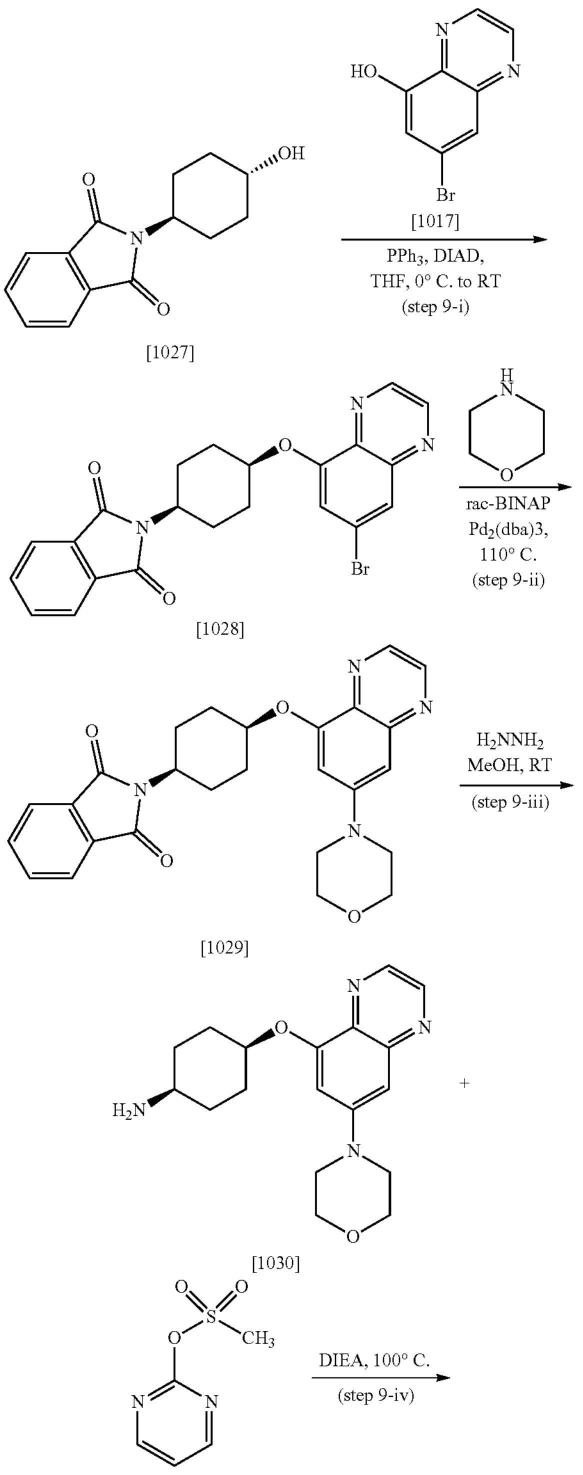

[1017] [1027] [1028] [1029] [1030]

-continued

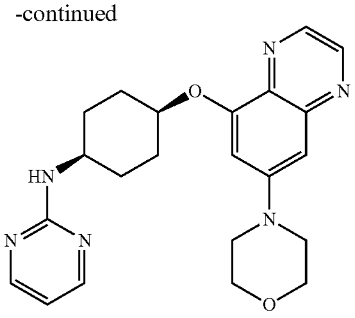

[28]

As shown in step 9-i of Scheme 9, 7-bromoquinoxalin-5-ol (compound 1017, 5.4 g, 24.0 mmol), 2-((trans)-4-hydroxycyclohexyl)isoindoline-1,3-dione (5.607 g, 22.86 mmol), and triphenylphosphine (8.994 g, 7.945 mL, 34.29 mmol) were dissolved in anhydrous THF and the flask was cooled in an ice bath. DIAD (6.93 g, 6.64 mL, 34.3 mmol) was added dropwise and the reaction was stirred at 0° C. for 5 minutes, then warmed to room temperature and stirred for 18 hours. The reaction mixture was concentrated under reduced pressure, the residue was treated with $Et_2O$ and stirred for 0.5 hour at RT, the precipitates filtered off, the filtrate concentrated under reduced pressure, and the residue purified by medium pressure silica gel chromatography (0-50% EtOAc/hexanes gradient) to produce 2-[(cis)-4-(7-bromoquinoxalin-5-yl)oxycyclohexyl]isoindoline-1,3-dione (compound 1028, 6.2 g, 60% yield): $^1$H-NMR (300 MHz, $CDCl_3$) δ 8.95 (d, J=1.8 Hz, 1H), 8.86 (d, J=1.8 Hz, 1H), 7.91 (d, J=2.0 Hz, 1H), 7.88-7.80 (m, 2H), 7.77-7.68 (m, 2H), 7.31 (d, J=2.0 Hz, 1H), 4.96 (t, J=2.9 Hz, 1H), 4.29 (tt, J=12.5, 3.8 Hz, 1H), 2.88 (qd, J=12.9, 3.6 Hz, 2H), 2.54-2.32 (m, 2H), 1.94-1.61 (m, 4H).

As shown in step 9-ii of Scheme 9, In a round bottom flask fitted with a condenser, a mixture of 2-[4-(7-bromoquinoxalin-5-yl)oxycyclohexyl]isoindoline-1,3-dione (6.2 g, 12.34 mmol), morpholine (1.61 g, 1.62 mL, 18.5 mmol), and $Cs_2CO_3$ (12.06 g, 37.0 mmol) in anhydrous toluene (73 mL) was treated with rac-BINAP (768.4 mg, 1.234 mmol) and $Pd_2(dba)_3$ (565 mg, 0.617 mmol). The reaction mixture was heated at 110° C. for 18 hours. After cooling to room temperature, the mixture was filtered through diatomaceous earth and concentrated under reduced pressure. The residue was triturated with $Et_2O$ and the solids collected by filtration and washed with $Et_2O$ to produce 2-((cis)-4-((7-morpholinoquinoxalin-5-yl)oxy)cyclohexyl)isoindoline-1,3-dione (compound 1029, 4.2 g) as yellow solid. The filterate was concentrated under reduced pressure and purified by medium pressure silica gel chromatography (0-100% EtOAc/hexanes gradient) to produce an additional 300 mg of compound 1029: $^1$H-NMR (300 MHz, $CDCl_3$) δ 8.76-8.63 (m, 2H), 7.85 (dd, J=5.4, 3.1 Hz, 2H), 7.79-7.60 (m, 2H), 7.09 (d, J=2.6 Hz, 1H), 6.99 (d, J=2.5 Hz, 1H), 5.06 (t, J=2.8 Hz, 1H), 4.27 (tt, J=12.3, 3.8 Hz, 1H), 4.02-3.85 (m, 4H), 3.49-3.27 (m, 4H), 3.03-2.75 (m, 2H), 2.37 (d, J=14.0 Hz, 2H), 1.83-1.56 (m, 4H).

As shown in step 9-iii of Scheme 9, to a suspension of 2-[(cis)-4-(7-morpholinoquinoxalin-5-yl)oxycyclohexyl] isoindoline-1,3-dione (2.3 g, 5.02 mmol) in MeOH (25 mL) was added hydrazine (321 mg, 315 µL, 10.0 mmol) and the reaction mixture stirred for 18 hours at RT, over which time the initial suspension became homogenous followed by the appearance of a precipitate. $Et_2O$ (30 mL) was added and the reaction mixture stirred an additional 30 minutes. The precipitates were filtered off, the filtrate concentrated under reduced pressure, the residue treated with DCM (30 mL), and any remaining solids removed by filtration. The filtrate was concentrated under reduced pressure to provide (cis)-4-((7-morpholinoquinoxalin-5-yl)oxy)cyclohexanamine (compound 1030), which was used as is in subsequent reactions: $^1$H-NMR (300 MHz, $CDCl_3$) δ 8.69 (d, J=1.9 Hz, 1H), 8.62 (d, J=1.9 Hz, 1H), 6.95 (d, J=2.5 Hz, 1H), 6.90 (d, J=2.5 Hz, 1H), 5.00-4.67 (m, 3H), 4.03-3.81 (m, 4H), 3.49 (s, 1H), 3.43-3.25 (m, 4H), 2.88 (q, J=6.2 Hz, 2H), 2.36-1.96 (m, 6H).

As shown in step 9-iv of Scheme 9, to a solution so (cis) 4-(7-morpholinoquinoxalin-5-yl)oxycyclohexanamine (415 mg, 1.264 mmol) and 2-methylsulfonylpyrimidine (400 mg, 2.53 mmol) was added DIEA (490 mg, 661 μL, 3.79 mmol) and the reaction mixture was sealed in a vessel and heated to 100° C. for 16 hours. After this time, the volatiles were removed under a stream of nitrogen gas and the crude residue dissolved in minimal amount of DCM. Purification by medium pressure silica gel chromatography (0-10% MeOH/DCM, 1% $Et_3N$] produced N-((cis)-4-((7-morpholinoquinoxalin-5-yl)oxy)cyclohexyl)pyrimidin-2-amine containing triethylamine hydrochloride as an impurity. Dissolved product in DCM and stirred with a silica-supported amine (Silabond Amine® 40-63 μm). The scavenger mixture was filtered, concentrated under reduced pressure, and dried under high vacuum to provide N-((cis)-4-((7-morpholinoquinoxalin-5-yl)oxy)cyclohexyl)pyrimidin-2-amine (Compound 28, 435 mg): $^1$H-NMR (400 MHz, $CDCl_3$) δ 8.68 (d, J=1.9 Hz, 1H), 8.61 (d, J=1.9 Hz, 1H), 8.27 (s, 1H), 8.26 (s, 1H), 6.94 (d, J=2.4 Hz, 1H), 6.90 (d, J=2.4 Hz, 1H), 6.50 (t, J=4.8 Hz, 1H), 4.78 (s, 1H), 4.08-3.97 (m, 1H), 3.94-3.86 (m, 4H), 3.37-3.28 (m, 4H), 2.20 (d, J=9.1 Hz, 2H), 1.95-1.85 (m, 6H).

Table 1 provides analytical characterization data for certain compounds of formula I (blank cells indicate that the test was not performed).

TABLE 1

| Cmpd. No. | Compound | ESMS (M + H) | $^1$H NMR (300 MHz, unless indicated otherwise) NMR peaks given as δ values |
|---|---|---|---|
| 1 | 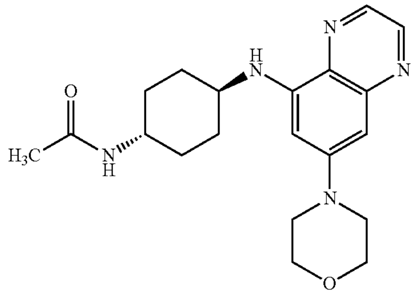 [SMILES: CC(=O)N[C@H]1CC[C@H](Nc2cc(N3CCOCC3)cc3nccnc23)CC1] | 370.52 | ($CDCl_3$) δ 8.64 (d, J = 2.0 Hz, 1H), 8.36 (d, J = 2.0 Hz, 1H), 6.61 (d, J = 2.4 Hz, 1H), 6.34 (d, J = 2.4 Hz, 1H), 5.90 (s, 1H), 5.40 (d, J = 7.7 Hz, 1H), 3.98-3.76 (m, 5H), 3.51-3.24 (m, 5H), 2.33-2.08 (m, 4H), 1.99 (s, 3H), 1.58-1.31 (m, 4H) |
| 2 | 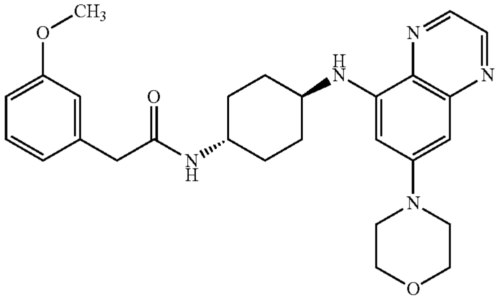 [SMILES: COc1cccc(CC(=O)N[C@H]2CC[C@H](Nc3cc(N4CCOCC4)cc4nccnc34)CC2)c1] | 476.61 | ($CDCl_3$) δ 8.63 (d, J = 1.9 Hz, 1H), 8.34 (d, J = 1.9 Hz, 1H), 7.17 (d, J = 8.6 Hz, 2H), 6.90 (d, J = 8.5 Hz, 2H), 6.59 (d, J = 2.2 Hz, 1H), 6.29 (d, J = 2.2 Hz, 1H), 5.86 (d, J = 7.6 Hz, 1H), 5.29 (d, J = 8.0 Hz, 1H), 3.96-3.75 (m, 8H), 3.52 (s, 2H), 3.39-3.32 (m, 5H), 2.19 (d, J = 11.7 Hz, 2H), 2.12-1.89 (m, 2H), 1.43 (td, J = 13.0, 2.4 Hz, 2H), 1.32-1.15 (m, 2H) |
| 3 | 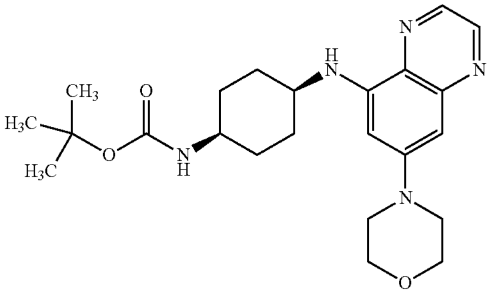 [SMILES: CC(C)(C)OC(=O)N[C@H]1CC[C@@H](Nc2cc(N3CCOCC3)cc3nccnc23)CC1] | 428.49 | ($CDCl_3$) δ 8.65 (d, J = 2.0 Hz, 1H), 8.35 (d, J = 2.0 Hz, 1H), 6.60 (d, J = 2.4 Hz, 1H), 6.34 (d, J = 2.4 Hz, 1H), 6.11 (d, J = 7.8 Hz, 1H), 4.60 (s, 1H), 3.97-3.86 (m, 4H), 3.67 (s, 2H), 3.41-3.25 (m, 4H), 1.85 (d, J = 3.0 Hz, 5H), 1.74-1.57 (m, 3H), 1.45 (s, 9H) |

TABLE 1-continued

| Cmpd. No. | Compound | ESMS (M + H) | $^1$H NMR (300 MHz, unless indicated otherwise) NMR peaks given as δ values |
|---|---|---|---|
| 4 | 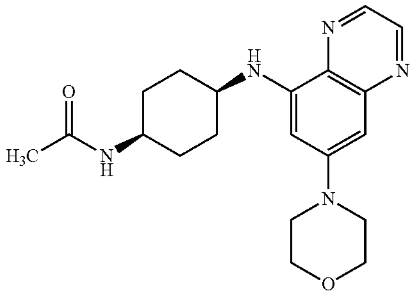 [SMILES: CC(=O)N[C@H]1CC[C@@H](Nc2cc(N3CCOCC3)cc3nccnc23)CC1] | 370.46 | ($CDCl_3$) δ 8.64 (d, J = 1.9 Hz, 1H), 8.34 (d, J = 1.9 Hz, 1H), 6.61 (d, J = 2.2 Hz, 1H), 6.35 (d, J = 2.3 Hz, 1H), 6.12 (br s, 1H), 5.56 (d, J = 7.5 Hz, 1H), 4.11-3.81 (m, 5H), 3.70 (m, 1H), 3.42-3.24 (m, 4H), 1.99 (s, 3H), 1.86 (m, 6H), 1.75-1.51 (m, 2H) |
| 5 | 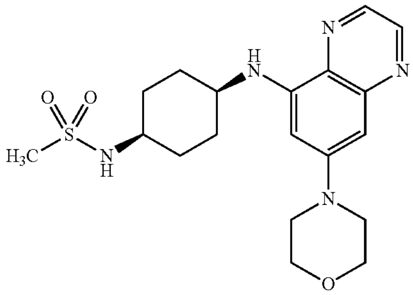 [SMILES: CS(=O)(=O)N[C@H]1CC[C@@H](Nc2cc(N3CCOCC3)cc3nccnc23)CC1] | 406.12 | ($CDCl_3$) δ 8.65 (d, J = 2.0 Hz, 1H), 8.36 (d, J = 2.0 Hz, 1H), 6.62 (d, J = 2.4 Hz, 1H), 6.34 (d, J = 2.3 Hz, 1H), 6.09 (d, J = 7.6 Hz, 1H), 4.68 (d, J = 7.2 Hz, 1H), 3.97-3.82 (m, 4H), 3.76-3.47 (m, 2H), 3.40-3.23 (m, 4H), 3.01 (s, 3H), 2.04-1.65 (m, 8H) |
| 6 | 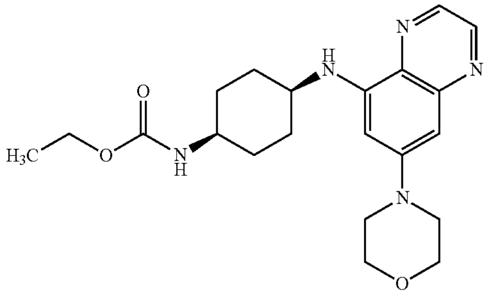 [SMILES: CCOC(=O)N[C@H]1CC[C@@H](Nc2cc(N3CCOCC3)cc3nccnc23)CC1] | 400.17 | ($CDCl_3$) δ 8.65 (d, J = 2.0 Hz, 1H), 8.36 (d, J = 2.0 Hz, 1H), 6.61 (d, J = 2.4 Hz, 1H), 6.35 (d, J = 2.4 Hz, 1H), 6.10 (d, J = 7.6 Hz, 1H), 4.72 (s, 1H), 4.12 (q, J = 7.0 Hz, 2H), 3.96-3.82 (m, 4H), 3.68 (s, 2H), 3.42-3.23 (m, 4H), 1.93-1.78 (m, 6H), 1.69 (dd, J = 15.0, 6.3 Hz, 2H), 1.25 (t, J = 7.1 Hz, 3H) |
| 7 | 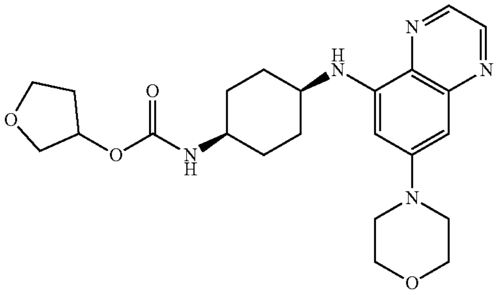 [SMILES: O=C(N[C@H]1CC[C@@H](Nc2cc(N3CCOCC3)cc3nccnc23)CC1)OC1CCOC1] | 442.14 | ($CDCl_3$) δ 8.65 (d, J = 2.0 Hz, 1H), 8.35 (d, J = 2.0 Hz, 1H), 6.61 (d, J = 2.4 Hz, 1H), 6.35 (d, J = 2.3 Hz, 1H), 6.10 (d, J = 7.7 Hz, 1H), 5.26 (s, 1H), 4.85 (d, J = 7.4 Hz, 1H), 4.03-3.79 (m, 8H), 3.68 (s, 2H), 3.41-3.24 (m, 4H), 2.16 (dd, J = 13.9, 6.0 Hz, 1H), 2.08-1.93 (m, 1H), 1.86 (d, J = 3.5 Hz, 6H), 1.76-1.54 (m, 2H) |
| 8 | 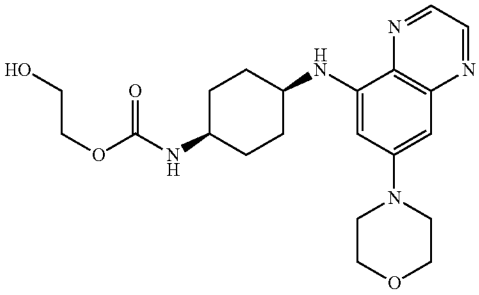 [SMILES: O=C(N[C@H]1CC[C@@H](Nc2cc(N3CCOCC3)cc3nccnc23)CC1)OCCO] | 416.42 | ($CDCl_3$) δ 8.65 (d, J = 2.0 Hz, 1H), 8.36 (d, J = 2.0 Hz, 1H), 6.61 (d, J = 2.4 Hz, 1H), 6.35 (d, J = 2.4 Hz, 1H), 6.10 (d, J = 7.6 Hz, 1H), 4.88 (d, J = 6.3 Hz, 1H), 4.21 (d, J = 4.1 Hz, 2H), 3.95-3.88 (m, 4H), 3.87-3.59 (m, 4H), 3.40-3.26 (m, 4H), 1.95-1.52 (m, 9H) |

TABLE 1-continued

| Cmpd. No. | Compound | ESMS (M + H) | $^1$H NMR (300 MHz, unless indicated otherwise) NMR peaks given as δ values |
|---|---|---|---|
| 9 | 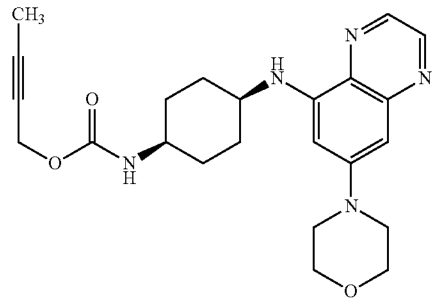 [SMILES: CC#CCOC(=O)N[C@H]1CC[C@@H](Nc2cc(N3CCOCC3)cc3nccnc23)CC1] | 424.42 | ($CDCl_3$) δ 8.65 (d, J = 1.9 Hz, 1H), 8.37 (d, J = 2.0 Hz, 1H), 6.61 (d, J = 2.3 Hz, 1H), 6.34 (d, J = 2.3 Hz, 1H), 6.09 (d, J = 7.4 Hz, 1H), 4.81 (s, 1H), 4.66 (s, 2H), 4.01-3.86 (m, 4H), 3.65 (s, 2H), 3.42-3.24 (m, 4H), 1.87 (t, J = 2.3 Hz, 5H), 1.64 (d, J = 26.9 Hz, 6H) |
| 10 | 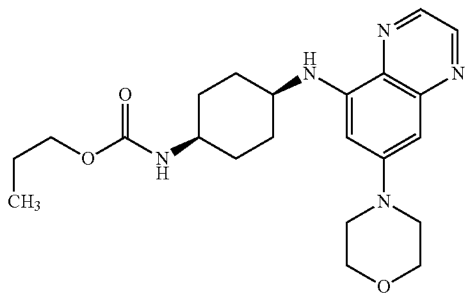 [SMILES: CCCOC(=O)N[C@H]1CC[C@@H](Nc2cc(N3CCOCC3)cc3nccnc23)CC1] | 414.44 | ($CDCl_3$) δ 8.65 (d, J = 1.9 Hz, 1H), 8.36 (d, J = 1.9 Hz, 1H), 6.61 (d, J = 2.3 Hz, 1H), 6.35 (d, J = 2.3 Hz, 1H), 6.10 (d, J = 7.7 Hz, 1H), 4.72 (s, 1H), 4.02 (t, J = 6.6 Hz, 2H), 3.95-3.82 (m, 4H), 3.68 (s, 2H), 3.43-3.26 (m, 4H), 1.87 (d, J = 3.7 Hz, 6H), 1.78-1.50 (m, 4H), 0.94 (t, J = 7.4 Hz, 3H) |
| 11 | 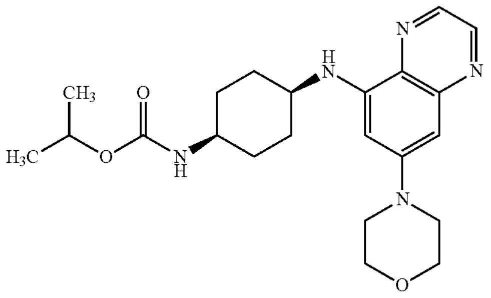 [SMILES: CC(C)OC(=O)N[C@H]1CC[C@@H](Nc2cc(N3CCOCC3)cc3nccnc23)CC1] | 414.44 | ($CDCl_3$) δ 8.65 (d, J = 2.0 Hz, 1H), 8.35 (d, J = 2.0 Hz, 1H), 6.60 (d, J = 2.4 Hz, 1H), 6.35 (d, J = 2.4 Hz, 1H), 6.10 (d, J = 7.7 Hz, 1H), 4.91 (dt, J = 12.5, 6.2 Hz, 1H), 4.69 (s, 1H), 4.01-3.81 (m, 4H), 3.68 (s, 2H), 3.46-3.24 (m, 4H), 1.93-1.76 (m, 6H), 1.78-1.56 (m, 2H), 1.25 (t, J = 9.6 Hz, 6H) |
| 12 | 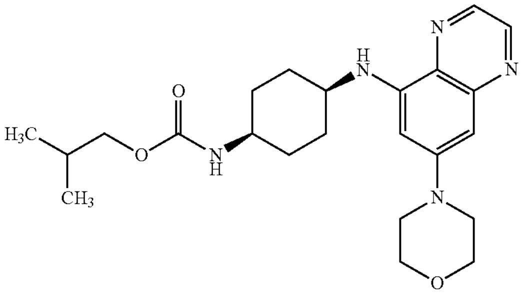 [SMILES: CC(C)COC(=O)N[C@H]1CC[C@@H](Nc2cc(N3CCOCC3)cc3nccnc23)CC1] | 428.2 | ($CDCl_3$) δ 8.65 (d, J = 1.9 Hz, 1H), 8.35 (d, J = 1.9 Hz, 1H), 6.61 (d, J = 2.3 Hz, 1H), 6.35 (d, J = 2.3 Hz, 1H), 6.11 (d, J = 7.6 Hz, 1H), 4.74 (s, 1H), 3.99-3.79 (m, 6H), 3.68 (s, 2H), 3.40-3.24 (m, 4H), 1.87 (d, J = 3.5 Hz, 7H), 1.78-1.52 (m, 2H), 0.93 (d, J = 6.7 Hz, 6H) |
| 13 | 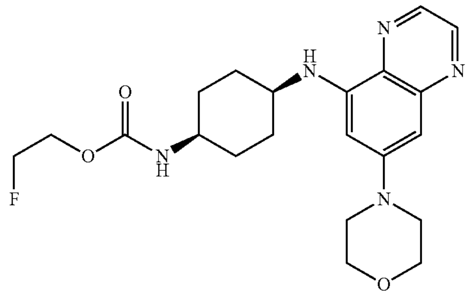 [SMILES: O=C(N[C@H]1CC[C@@H](Nc2cc(N3CCOCC3)cc3nccnc23)CC1)OCCF] | 418.44 | ($CDCl_3$) δ 8.65 (t, J = 1.6 Hz, 1H), 8.36 (t, J = 1.6 Hz, 1H), 6.61 (d, J = 2.3 Hz, 1H), 6.35 (d, J = 2.0 Hz, 1H), 6.11 (d, J = 7.6 Hz, 1H), 4.91 (d, J = 7.2 Hz, 1H), 4.80-4.18 (m, 4H), 4.00-3.84 (m, 4H), 3.81-3.56 (m, 2H), 3.46-3.21 (m, 4H), 1.87 (d, J = 3.5 Hz, 6H), 1.71 (dd, J = 16.0, 8.2 Hz, 2H) |

TABLE 1-continued

| Cmpd. No. | Compound | ESMS (M + H) | $^1$H NMR (300 MHz, unless indicated otherwise) NMR peaks given as δ values |
|---|---|---|---|
| 14 | 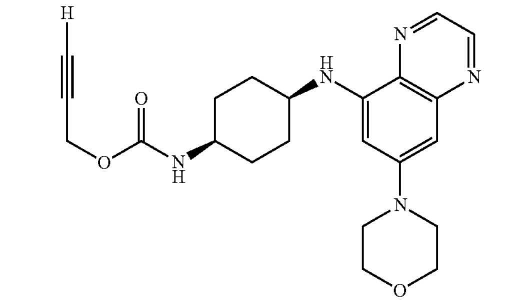 [SMILES: C#CCOC(=O)N[C@H]1CC[C@@H](Nc2cc(N3CCOCC3)cc3nccnc23)CC1] | 410.44 | ($CDCl_3$) δ 8.65 (d, J = 2.0 Hz, 1H), 8.36 (d, J = 2.0 Hz, 1H), 6.61 (d, J = 2.4 Hz, 1H), 6.34 (d, J = 2.3 Hz, 1H), 6.10 (d, J = 7.1 Hz, 1H), 4.83 (s, 1H), 4.69 (s, 2H), 3.96-3.83 (m, 4H), 3.68 (s, 2H), 3.40-3.23 (m, 4H), 2.48 (t, J = 2.4 Hz, 1H), 1.87 (d, J = 4.2 Hz, 6H), 1.71 (dd, J = 15.7, 7.4 Hz, 2H) |
| 15 | 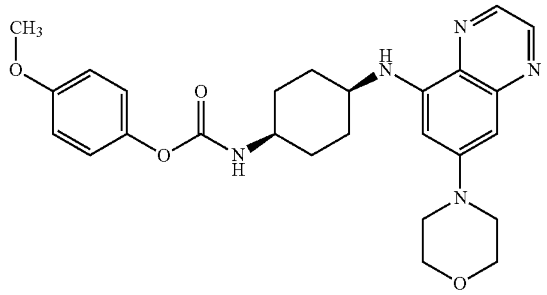 [SMILES: COc1ccc(OC(=O)N[C@H]2CC[C@@H](Nc3cc(N4CCOCC4)cc4nccnc34)CC2)cc1] | 478.44 | ($CDCl_3$) δ 8.66 (d, J = 2.0 Hz, 1H), 8.37 (d, J = 2.0 Hz, 1H), 7.10-6.98 (m, 2H), 6.87 (d, J = 9.0 Hz, 2H), 6.62 (d, J = 2.4 Hz, 1H), 6.36 (d, J = 2.4 Hz, 1H), 6.13 (d, J = 7.3 Hz, 1H), 5.06 (d, J = 7.9 Hz, 1H), 3.97-3.84 (m, 4H), 3.84-3.61 (m, 5H), 3.42-3.25 (m, 4H), 1.91 (d, J = 4.2 Hz, 6H), 1.85-1.68 (m, 2H) |
| 16 | 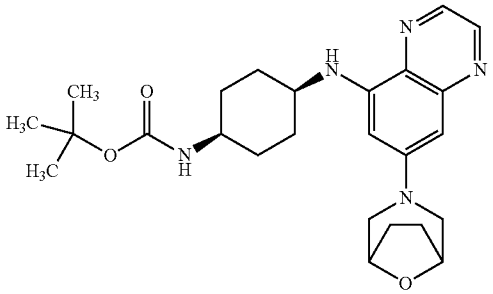 [SMILES: CC(C)(C)OC(=O)N[C@H]1CC[C@@H](Nc2cc(N3CC4CCC(C3)O4)cc3nccnc23)CC1] | 453.96 | ($CDCl_3$) δ 8.49 (s, 1H), 8.23 (d, J = 1.5 Hz, 1H), 6.48 (s, 1H), 6.18 (d, J = 1.9 Hz, 1H), 6.06 (s, 1H), 4.52 (s, 1H), 4.47 (s, 2H), 3.60 (s, 2H), 3.45 (d, J = 11.6 Hz, 2H), 3.14-3.12 (m, 2H), 1.96-1.84 (m, 4H), 1.79 (s, 5H), 1.54 (s, 3H) and 1.38 (s, 9H) ppm |
| 17 | 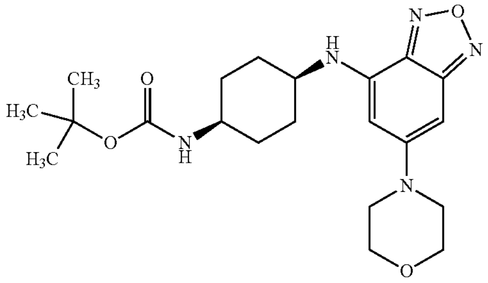 [SMILES: CC(C)(C)OC(=O)N[C@H]1CC[C@@H](Nc2cc(N3CCOCC3)cc3nonc23)CC1] | 418.4 | ($CDCl_3$) δ 6.13 (d, J = 1.6 Hz, 1H), 5.89 (d, J = 1.4 Hz, 1H), 4.87 (d, J = 7.0 Hz, 1H), 4.59 (s, 1H), 3.26 (dd, J = 9.2, 4.3 Hz, 4H), 1.98-1.74 (m, 6H), 1.65 (dd, J = 15.9, 7.3 Hz, 3H), 1.47 (s, 9H) |
| 18 | 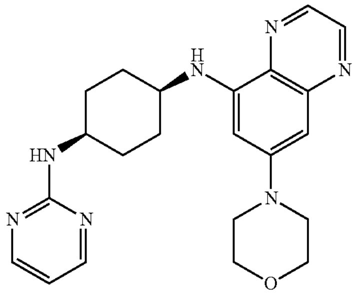 [SMILES: c1cnc(N[C@H]2CC[C@@H](Nc3cc(N4CCOCC4)cc4nccnc34)CC2)nc1] | 406.48 | ($CDCl_3$) δ 8.65 (d, J = 2.0 Hz, 1H), 8.37 (d, J = 2.0 Hz, 1H), 8.27 (d, J = 4.8 Hz, 2H), 6.60 (d, J = 2.4 Hz, 1H), 6.51 (t, J = 4.8 Hz, 1H), 6.36 (d, J = 2.4 Hz, 1H), 6.15 (d, J = 7.8 Hz, 1H), 5.20 (d, J = 7.7 Hz, 1H), 4.04 (d, J = 7.9 Hz, 1H), 3.96-3.82 (m, 4H), 3.70 (s, 1H), 3.39-3.24 (m, 4H), 1.94 (dd, J = 13.7, 4.4 Hz, 6H), 1.78 (dt, J = 28.8, 16.1 Hz, 2H) |

TABLE 1-continued

| Cmpd. No. | Compound | ESMS (M + H) | $^1H$ NMR (300 MHz, unless indicated otherwise) NMR peaks given as δ values |
|---|---|---|---|
| 19 | 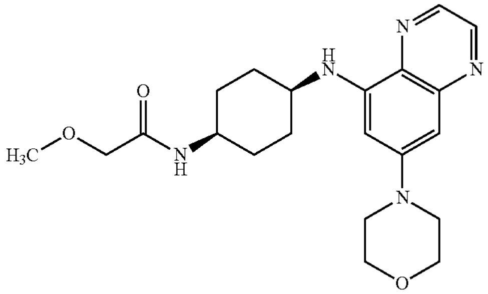 [SMILES: COCC(=O)N[C@H]1CC[C@@H](Nc2cc(N3CCOCC3)cc3nccnc23)CC1] | 400.46 | ($CDCl_3$) δ 8.64 (d, J = 1.9 Hz, 1H), 8.35 (d, J = 1.9 Hz, 1H), 6.58 (t, J = 5.1 Hz, 2H), 6.34 (d, J = 2.3 Hz, 1H), 6.10 (d, J = 7.3 Hz, 1H), 4.03 (d, J = 8.3 Hz, 1H), 3.88 (t, J = 4.7 Hz, 6H), 3.68 (s, 1H), 3.42 (s, 3H), 3.37-3.23 (m, 4H), 1.98-1.78 (m, 6H), 1.69 (dd, J = 15.8, 7.5 Hz, 2H) |
| 20 | 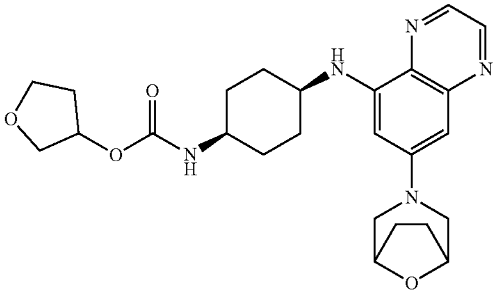 [SMILES: O=C(N[C@H]1CC[C@@H](Nc2cc(N3CC4CCC(C3)O4)cc3nccnc23)CC1)OC1CCOC1] | 468.23 | (400.0 MHz, $CDCl_3$) δ 8.52 (d, J = 1.7 Hz, 1H), 8.23 (d, J = 1.6 Hz, 1H), 6.47 (d, J = 1.9 Hz, 1H), 6.19 (s, 1H), 6.03 (s, 1H), 5.19 (s, 1H), 4.76 (d, J = 7.6 Hz, 1H), 4.47 (s, 2H), 3.87-3.76 (m, 4H), 3.60 (s, 2H), 3.45 (d, J = 11.6 Hz, 2H), 3.13-3.10 (m, 2H), 2.61 (s, 1H), 2.13-2.04 (m, 1H), 1.95-1.85 (m, 5H), 1.79 (s, 5H) and 1.62-1.58 (m, 2H) |
| 21 | 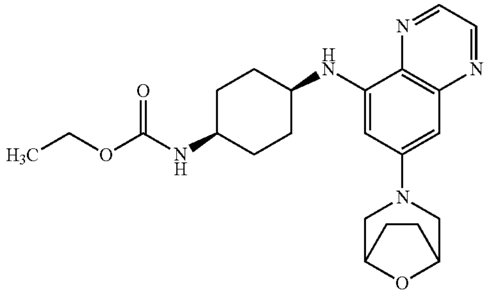 [SMILES: CCOC(=O)N[C@H]1CC[C@@H](Nc2cc(N3CC4CCC(C3)O4)cc3nccnc23)CC1] | 426.31 | |
| 22 | 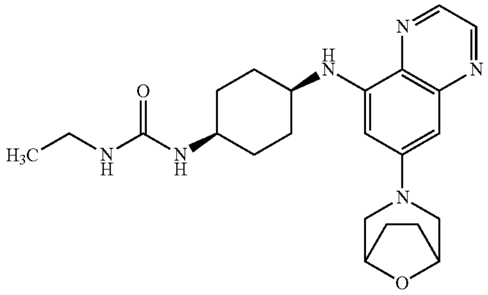 [SMILES: CCNC(=O)N[C@H]1CC[C@@H](Nc2cc(N3CC4CCC(C3)O4)cc3nccnc23)CC1] | 425.35 | (400.0 MHz, $CDCl_3$) δ 8.54 (s, 1H), 8.22 (s, 1H), 6.43 (s, 1H), 6.19 (s, 1H), 6.02 (s, 1H), 4.47 (s, 2H), 4.38 (d, J = 5.2 Hz, 1H), 4.28 (s, 1H), 3.74 (s, 1H), 3.60 (s, 1H), 3.42 (s, 4H), 3.14-3.09 (m, 4H), 2.05-1.87 (m, 3H), 1.79 (s, 3H), 1.55 (d, J = 7.1 Hz, 2H) and 1.21-1.05 (m, 5H) |
| 23 | 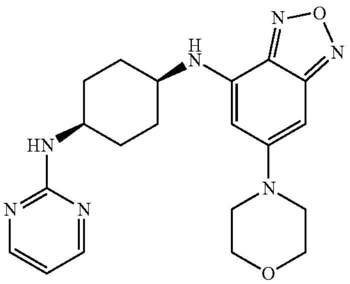 [SMILES: c1cnc(N[C@H]2CC[C@@H](Nc3cc(N4CCOCC4)cc4nonc34)CC2)nc1] | 396.2 | ($CDCl_3$) δ 8.20 (d, J = 4.9 Hz, 2H), 6.46 (t, J = 4.8 Hz, 1H), 6.05 (d, J = 1.6 Hz, 1H), 5.82 (s, 1H), 5.24 (s, 1H), 4.82 (d, J = 7.0 Hz, 1H), 3.98 (s, 1H), 3.85-3.72 (m, 4H), 3.60 (s, 1H), 3.23-3.06 (m, 4H), 1.95-1.62 (m, 8H). [2] |

TABLE 1-continued

| Cmpd. No. | Compound | ESMS (M + H) | $^1$H NMR (300 MHz, unless indicated otherwise) NMR peaks given as δ values |
|---|---|---|---|
| 24 | 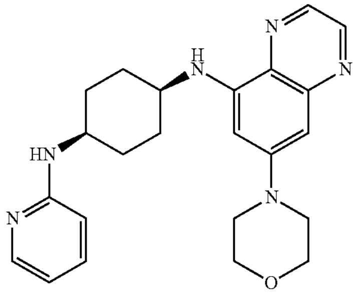 [SMILES: c1ccc(N[C@H]2CC[C@@H](Nc3cc(N4CCOCC4)cc4nccnc34)CC2)nc1] | 405.59 | (400 MHz, $CDCl_3$) δ 8.65 (s, 1H), 8.37 (d, J = 1.8 Hz, 1H), 8.08 (d, J = 4.9 Hz, 1H), 7.41 (t, J = 7.7 Hz, 1H), 6.61 (s, 1H), 6.58-6.53 (m, 1H), 6.46-6.30 (m, 2H), 6.15 (d, J = 7.3 Hz, 1H), 4.56 (s, 1H), 3.98-3.78 (m, 5H), 3.76-3.61 (m, 1H), 3.42-3.24 (m, 4H), 1.97 (d, J = 29.6 Hz, 6H), 1.86-1.66 (m, 2H) |
| 25 | 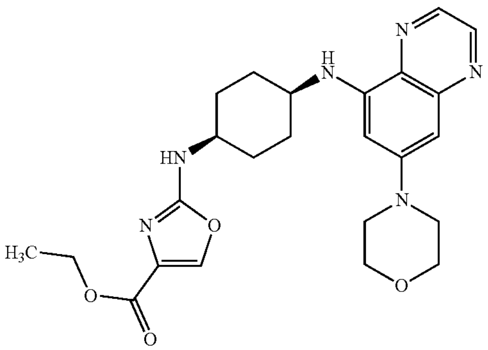 [SMILES: CCOC(=O)c1coc(N[C@H]2CC[C@@H](Nc3cc(N4CCOCC4)cc4nccnc34)CC2)n1] | 467.57 | ($CDCl_3$) δ 8.69 (d, J = 2.0 Hz, 1H), 8.42 (d, J = 2.0 Hz, 1H), 8.26 (s, 1H), 7.14 (d, J = 2.1 Hz, 1H), 6.64 (d, J = 2.4 Hz, 1H), 6.38 (d, J = 2.3 Hz, 1H), 6.24 (d, J = 6.8 Hz, 1H), 4.31 (q, J = 7.1 Hz, 2H), 3.97-3.81 (m, 5H), 3.41-3.24 (m, 4H), 2.22 (d, J = 7.5 Hz, 2H), 1.90 (dd, J = 22.4, 10.3 Hz, 6H), 1.35 (t, J = 7.1 Hz, 3H) |
| 26 | 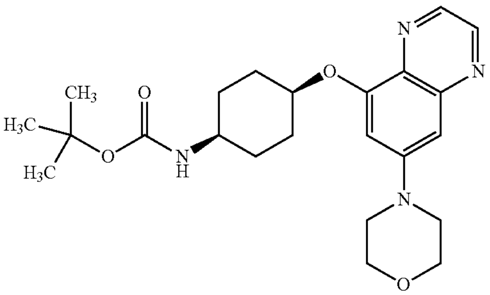 [SMILES: CC(C)(C)OC(=O)N[C@H]1CC[C@@H](Oc2cc(N3CCOCC3)cc3nccnc23)CC1] | 429.62 | ($CDCl_3$) δ 8.70 (d, J = 1.9 Hz, 1H), 8.62 (d, J = 1.9 Hz, 1H), 6.95 (d, J = 2.5 Hz, 1H), 6.88 (d, J = 2.5 Hz, 1H), 4.82 ? 4.60 (m, 2H), 4.00 ? 3.88 (m, 4H), 3.69 (d, J = 6.8 Hz, 1H), 3.42 ? 3.28 (m, 4H), 2.15 (p, J = 6.7, 5.6 Hz, 2H), 1.94 ? 1.75 (m, 6H), 1.46 (s, 9H) |
| 27 | 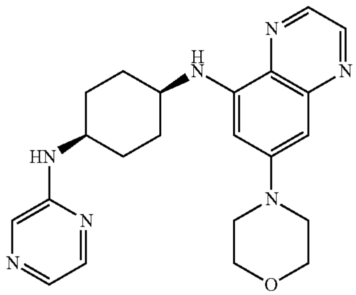 [SMILES: c1cnc(N[C@H]2CC[C@@H](Nc3cc(N4CCOCC4)cc4nccnc34)CC2)cn1] | 406.58 | ($CDCl_3$) δ 8.65 (d, J = 2.0 Hz, 1H), 8.36 (d, J = 2.0 Hz, 1H), 7.98 (dd, J = 2.8, 1.5 Hz, 1H), 7.88 (d, J = 1.5 Hz, 1H), 7.79 (d, J = 2.8 Hz, 1H), 6.62 (d, J = 2.4 Hz, 1H), 6.37 (d, J = 2.4 Hz, 1H), 6.17 (s, 1H), 8.69-8.61 (m, 1H), 4.60 (d, J = 7.7 Hz, 1H), 4.08-3.83 (m, 5H), 8.71-8.57 (m, 1H), 3.73 (t, J = 6.9 Hz, 1H), 3.40-3.25 (m, 4H), 1.96 (h, J = 4.9 Hz, 6H), 1.77 (q, J = 7.4, 6.1 Hz, 2H) |
| 28 | 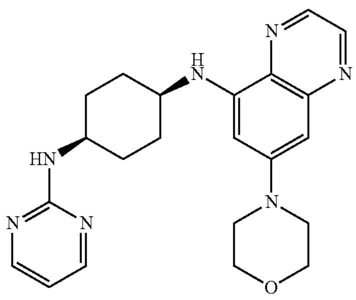 [SMILES: c1cnc(N[C@H]2CC[C@@H](Nc3cc(N4CCOCC4)cc4nccnc34)CC2)nc1] | 407.3 | (400 MHz, $CDCl_3$) δ 8.77-8.59 (m, 2H), 8.29 (d, J = 4.9 Hz, 2H), 7.01-6.87 (m, 2H), 6.61-6.48 (m, 1H), 4.82 (s, 1H), 4.05 (s, 1H), 3.93 (t, J = 4.8 Hz, 4H), 3.35 (t, J = 4.8 Hz, 4H), 2.23 (d, J = 13.1 Hz, 2H), 2.05-1.82 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 29 | 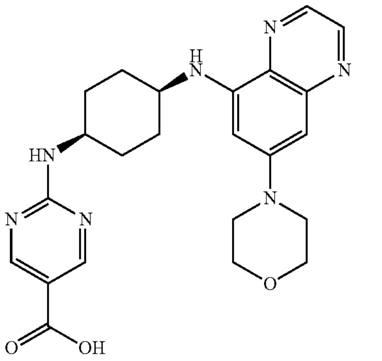 [SMILES: O=C(O)c1cnc(N[C@H]2CC[C@@H](Nc3cc(N4CCOCC4)cc4nccnc34)CC2)nc1] | 450.61 | (DMSO-$d_6$) δ 12.65 (s, 1H), 8.69 (d, J = 2.0 Hz, 2H), 8.43 (d, J = 2.0 Hz, 1H), 8.00 (d, J = 7.9 Hz, 1H), 6.54 (d, J = 2.5 Hz, 1H), 6.48 (d, J = 2.3 Hz, 1H), 6.17 (d, J = 8.2 Hz, 1H), 4.06 (s, 1H), 3.77 (dd, J = 5.9, 3.8 Hz, 4H), 3.29 (s, 5H), 2.04-1.46 (m, 8H) |
| 30 | 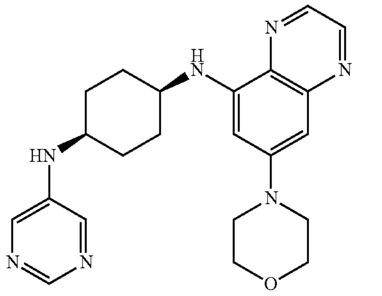 [SMILES: c1ncc(N[C@H]2CC[C@@H](Nc3cc(N4CCOCC4)cc4nccnc34)CC2)cn1] | 406.52 | ($CDCl_3$) δ 8.66 (d, J = 2.0 Hz, 1H), 8.58 (s, 1H), 8.37 (d, J = 2.0 Hz, 1H), 8.13 (s, 2H), 6.63 (d, J = 2.4 Hz, 1H), 6.37 (d, J = 2.4 Hz, 1H), 6.14 (d, J = 7.6 Hz, 1H), 3.96-3.86 (m, 4H), 3.76 (d, J = 7.7 Hz, 2H), 3.54 (d, J = 8.3 Hz, 1H), 3.39-3.29 (m, 4H), 2.02-1.86 (m, 6H), 1.76 (q, J = 8.9, 8.3 Hz, 2H) |
| 31 | 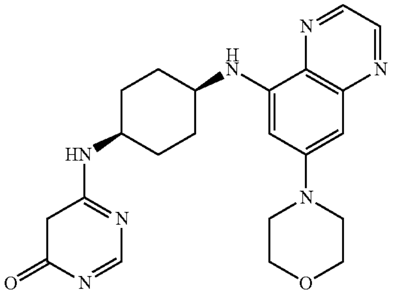 [SMILES: O=C1CC(N[C@H]2CC[C@@H](Nc3cc(N4CCOCC4)cc4nccnc34)CC2)=NC=N1] | 422.49 | ($CDCl_3$) δ 12.88-12.45 (m, 1H), 8.66 (d, J = 2.0 Hz, 1H), 8.37 (d, J = 2.0 Hz, 1H), 7.81 (s, 1H), 6.62 (d, J = 2.3 Hz, 1H), 6.36 (d, J = 2.4 Hz, 1H), 6.12 (d, J = 7.7 Hz, 1H), 5.27 (s, 1H), 5.05 (d, J = 7.6 Hz, 1H), 4.02-3.83 (m, 4H), 3.63 (d, J = 47.6 Hz, 2H), 3.44-3.22 (m, 4H), 1.91 (q, J = 4.8, 4.3 Hz, 6H), 1.82-1.69 (m, 2H) |
| 32 | 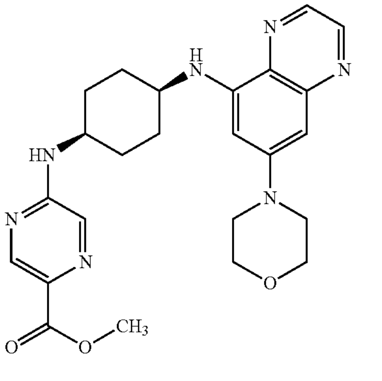 [SMILES: COC(=O)c1cnc(N[C@H]2CC[C@@H](Nc3cc(N4CCOCC4)cc4nccnc34)CC2)cn1] | 464.6 | ($CDCl_3$) δ 8.78 (d, J = 1.3 Hz, 1H), 8.66 (d, J = 2.0 Hz, 1H), 8.37 (d, J = 2.0 Hz, 1H), 7.91 (d, J = 1.3 Hz, 1H), 6.62 (d, J = 2.4 Hz, 1H), 6.37 (d, J = 2.4 Hz, 1H), 6.16 (d, J = 7.6 Hz, 1H), 5.13 (d, J = 7.6 Hz, 1H), 4.10 (s, 1H), 3.99-3.86 (m, 7H), 3.76 (s, 1H), 3.39-3.28 (m, 4H), 1.98 (h, J = 4.8 Hz, 6H), 1.80 (t, J = 87 Hz, 2H) |

TABLE 1-continued

| Cmpd. No. | Compound | ESMS (M + H) | $^{1}$H NMR (300 MHz, unless indicated otherwise) NMR peaks given as δ values |
|---|---|---|---|
| 33 | 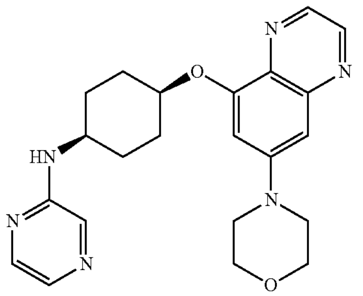 [SMILES: c1cnc(N[C@H]2CC[C@@H](Oc3cc(N4CCOCC4)cc4nccnc34)CC2)cn1] | 407.3 | ($CDCl_3$) δ 8.63 (d, J = 1.9 Hz, 1H), 7.99 (dd, J = 2.8, 1.5 Hz, 1H), 7.94-7.85 (m, 1H), 7.79 (d, J = 2.8 Hz, 1H), 7.14 (d, J = 1.0 Hz, 1H), 7.03-6.87 (m, 2H), 4.82 (d, J = 5.7 Hz, 1H), 4.70 (d, J = 8.0 Hz, 1H), 4.03-3.86 (m, 4H), 3.51 (s, 1H), 3.43-3.30 (m, 4H), 2.35-1.81 (m, 8H |
| 34 | 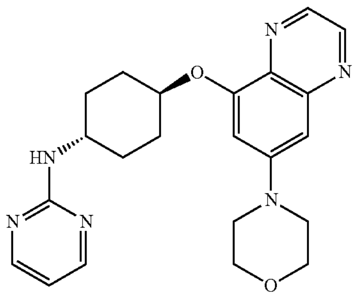 [SMILES: c1cnc(N[C@H]2CC[C@H](Oc3cc(N4CCOCC4)cc4nccnc34)CC2)nc1] | 408.5 | ($CDCl_3$) δ 8.69 (dd, J = 3.4, 1.9 Hz, 1H), 8.62 (dd, J = 3.6, 1.9 Hz, 1H), 8.51 (dd, J = 4.8, 2.2 Hz, 2H), 7.01-6.83 (m, 3H), 5.18 (tt, J = 7.0, 3.4 Hz, 1H), 4.79 (tt, J = 6.9, 3.1 Hz, 1H), 4.00-3.85 (m, 4H), 3.34 (dq, J = 4.8, 2.6 Hz, 4H), 2.44-2.16 (m, 4H), 1.92 (tdd, J = 16.4, 7.7, 2.8 Hz, 4H) |
| 35 | 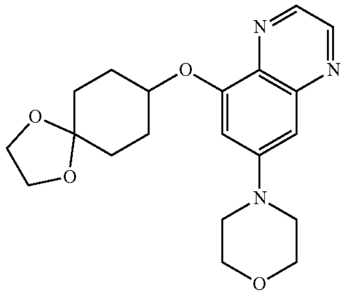 [SMILES: c1cnc2c(OC3CCC4(CC3)OCCO4)cc(N3CCOCC3)cc2n1] | 372.23 | ($CDCl_3$) δ 8.68 (d, J = 1.9 Hz, 1H), 8.61 (d, J = 1.9 Hz, 1H), 6.99-6.85 (m, 2H), 4.70 (dq, J = 7.3, 3.5 Hz, 1H), 4.05-3.84 (m, 8H), 3.40-3.25 (m, 4H), 2.19-1.93 (m, 6H), 1.77-1.64 (m, 2H) |
| 36 | 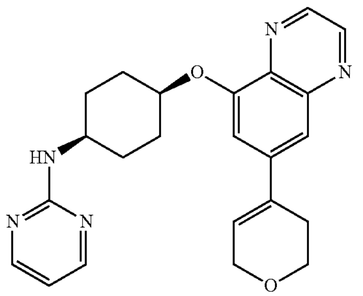 [SMILES: C1=C(c2cc(O[C@H]3CC[C@@H](Nc4ncccn4)CC3)c3nccnc3c2)CCOC1] | 404.2 | ($CDCl_3$) δ 8.94-8.76 (m, 2H), 8.29 (d, J = 4.8 Hz, 2H), 7.67 (d, J = 1.7 Hz, 1H), 6.53 (t, J = 4.8 Hz, 1H), 6.37 (tt, J = 3.1, 1.5 Hz, 1H), 5.30 (d, J = 7.9 Hz, 1H), 4.87 (dt, J = 7.5, 3.6 Hz, 1H), 4.43 (q, J = 2.8 Hz, 2H), 4.02 (t, J = 5.5 Hz, 3H), 2.68 (dqd, J = 6.0, 3.4, 3.0, 1.8 Hz, 2H), 2.35-2.11 (m, 2H), 2.07-1.84 (m, 6H) |
| 37 | 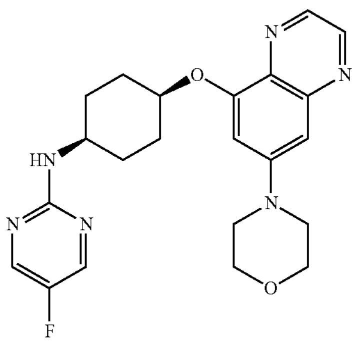 [SMILES: Fc1cnc(N[C@H]2CC[C@@H](Oc3cc(N4CCOCC4)cc4nccnc34)CC2)nc1] | 425.25 | ($CDCl_3$) δ 8.71 (d, J = 1.9 Hz, 1H), 8.63 (d, J = 1.9 Hz, 1H), 8.18 (dd, J = 3.7, 0.8 Hz, 2H), 7.01-6.85 (m, 2H), 5.37-5.20 (m, 1H), 4.79 (d, J = 5.5 Hz, 1H), 4.02-3.85 (m, 4H), 3.43-3.29 (m, 4H), 2.31-2.15 (m, 2H), 2.02-1.85 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 38 | 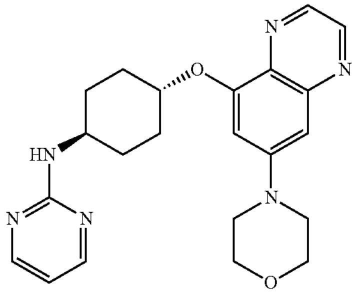 [SMILES: c1cnc(N[C@H]2CC[C@H](Oc3cc(N4CCOCC4)cc4nccnc34)CC2)nc1] | 407.25 | ($CDCl_3$) δ 8.61 (d, J = 2.0 Hz, 1H), 8.55 (d, J = 1.9 Hz, 1H), 8.20 (d, J = 5.8 Hz, 2H), 6.87 (d, J = 2.5 Hz, 1H), 6.81 (d, J = 2.5 Hz, 1H), 6.46 (t, J = 4.8 Hz, 1H), 4.95 (s, 1H), 4.45 (tt, J = 10.7, 3.6 Hz, 1H), 3.95-3.77 (m, 5H), 3.32-3.19 (m, 4H), 2.34-2.10 (m, 4H), 1.82 (dt, J = 12.9, 10.0 Hz, 2H), 1.45-1.20 (m, 2H) |
| 39 | 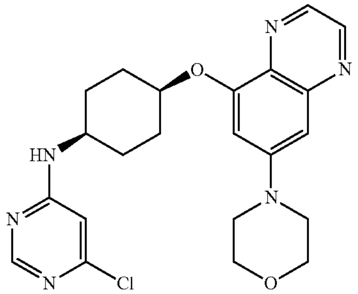 [SMILES: Clc1cc(N[C@H]2CC[C@@H](Oc3cc(N4CCOCC4)cc4nccnc34)CC2)ncn1] | 441.28 | ($CDCl_3$) δ 8.72 (d, J = 1.9 Hz, 1H), 8.62 (d, J = 1.9 Hz, 1H), 8.37 (s, 1H), 6.98 (d, J = 2.5 Hz, 1H), 6.92 (d, J = 2.5 Hz, 1H), 6.36 (d, J = 1.0 Hz, 1H), 4.91-4.76 (m, 1H), 4.00-3.88 (m, 4H), 3.45-3.24 (m, 4H), 2.34-2.17 (m, 2H), 2.03-1.84 (m, 6H) |
| 40 | 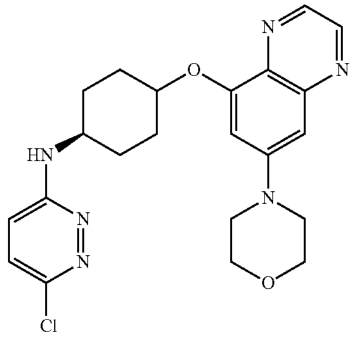 | 441.3 | ($CDCl_3$) δ 8.71 (d, J = 1.9 Hz, 1H), 8.61 (d, J = 1.9 Hz, 1H), 7.15 (d, J = 9.3 Hz, 1H), 7.00-6.87 (m, 2H), 6.64 (d, J = 9.3 Hz, 1H), 4.89-4.76 (m, 2H), 4.11-4.03 (m, 1H), 4.00-3.83 (m, 4H), 3.40-3.24 (m, 4H), 2.23 (dq, J = 12.9, 6.3, 5.6 Hz, 2H), 2.02-1.79 (m, 6H) |
| 41 | 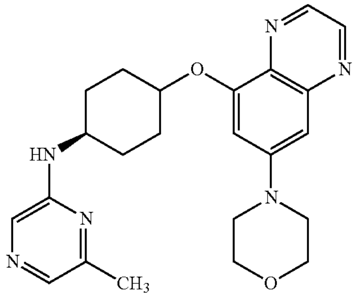 | 421.43 | ($CDCl_3$) δ 8.63 (d, J = 1.9 Hz, 1H), 8.55 (d, J = 1.9 Hz, 1H), 7.58 (d, J = 23.6 Hz, 2H), 6.89 (d, J = 2.4 Hz, 1H), 6.84 (d, J = 2.5 Hz, 1H), 4.73 (s, 2H), 3.93-3.72 (m, 5H), 3.34-3.18 (m, 4H), 2.29 (s, 3H), 2.15 (m, 2H), 1.84 (m, 6H) |
| 42 | 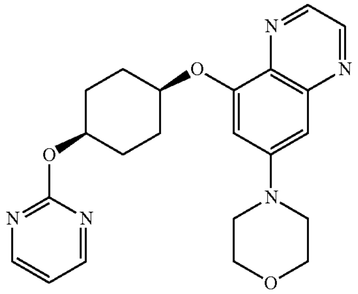 [SMILES: c1cnc(O[C@H]2CC[C@@H](Oc3cc(N4CCOCC4)cc4nccnc34)CC2)nc1] | 408.56 | ($CDCl_3$) δ 8.70 (d, J = 1.9 Hz, 1H), 8.63 (d, J = 1.9 Hz, 1H), 8.52 (d, J = 4.8 Hz, 2H), 7.01-6.87 (m, 3H), 5.17 (ddt, J = 8.7, 6.7, 3.4 Hz, 1H), 4.76-4.58 (m, 1H), 4.00-3.87 (m, 4H), 3.40-3.27 (m, 4H), 2.43-2.22 (m, 4H), 2.05-1.87 (m, 2H), 1.86-1.71 (m, 2H) |

TABLE 1-continued

| Cmpd. No. | Compound | ESMS (M + H) | $^{1}$H NMR (300 MHz, unless indicated otherwise) NMR peaks given as δ values |
|---|---|---|---|
| 43 | 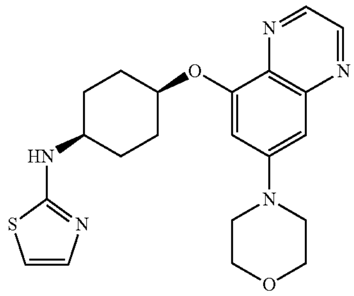 [SMILES: c1csc(N[C@H]2CC[C@@H](Oc3cc(N4CCOCC4)cc4nccnc34)CC2)n1] | 412.48 | ($CDCl_3$) δ 8.70 (d, J = 1.9 Hz, 1H), 8.61 (d, J = 1.9 Hz, 1H), 7.36 (s, 1H), 7.12 (d, J = 3.6 Hz, 1H), 6.95 (d, J = 2.5 Hz, 1H), 6.90 (d, J = 2.5 Hz, 1H), 6.48 (d, J = 3.6 Hz, 1H), 5.18 (d, J = 8.0 Hz, 1H), 4.79 (td, J = 5.4, 2.7 Hz, 1H), 3.97-3.85 (m, 4H), 3.70 (q, J = 6.8 Hz, 1H), 3.39-3.25 (m, 4H), 2.29-2.12 (m, 2H), 2.07-1.77 (m, 6H) |
| 44 | 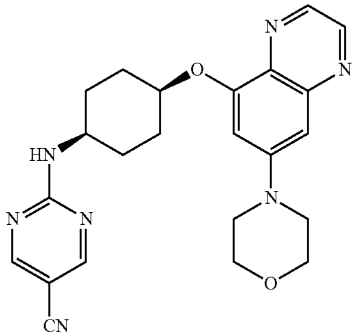 [SMILES: N#Cc1cnc(N[C@H]2CC[C@@H](Oc3cc(N4CCOCC4)cc4nccnc34)CC2)nc1] | 432.6 | ($CDCl_3$) δ 8.71 (d, J = 2.0 Hz, 1H), 8.64 (d, J = 2.0 Hz, 1H), 8.54 (d, J = 2.9 Hz, 1H), 8.47 (d, J = 3.0 Hz, 1H), 6.99 (d, J = 2.4 Hz, 1H), 6.92 (d, J = 2.5 Hz, 1H), 5.81 (d, J = 8.3 Hz, 1H), 4.84 (dt, J = 5.3, 2.8 Hz, 1H), 4.13-4.05 (m, 1H), 4.00-3.84 (m, 4H), 3.43-3.30 (m, 4H), 2.32-2.17 (m, 2H), 2.02-1.85 (m, 6H) |
| 45 | 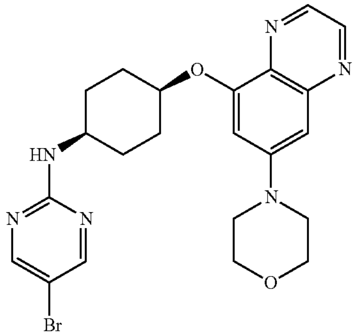 | 485.26 | ($CDCl_3$) δ 8.70 (d, J = 2.0 Hz, 1H), 8.64 (d, J = 1.9 Hz, 1H), 8.29 (s, 2H), 6.98 (d, J = 2.5 Hz, 1H), 6.92 (d, J = 2.5 Hz, 1H), 5.29 (d, J = 8.3 Hz, 1H), 4.81 (s, 1H), 4.04-3.84 (m, 4H), 3.42-3.31 (m, 4H), 2.22 (s, 2H), 1.92 (d, J = 4.9 Hz, 6H) |
| 46 | 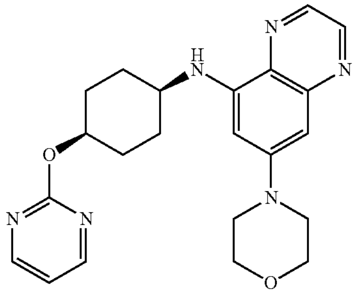 [SMILES: c1cnc(O[C@H]2CC[C@@H](Nc3cc(N4CCOCC4)cc4nccnc34)CC2)nc1] | 407.57 | ($CDCl_3$) δ 8.63 (d, J = 2.0 Hz, 1H), 8.52 (d, J = 4.8 Hz, 2H), 8.37 (d, J = 2.0 Hz, 1H), 6.92 (t, J = 4.8 Hz, 1H), 6.62 (d, J = 2.4 Hz, 1H), 6.38 (d, J = 2.4 Hz, 1H), 6.16 (s, 1H), 5.27 (s, 1H), 4.06-3.78 (m, 4H), 3.64 (s, 1H), 3.48-3.20 (m, 4H), 2.14 (s, 2H), 2.04-1.80 (m, 4H) |

TABLE 1-continued

| Cmpd. No. | Compound | ESMS (M + H) | $^1$H NMR (300 MHz, unless indicated otherwise) NMR peaks given as δ values |
|---|---|---|---|
| 47 | 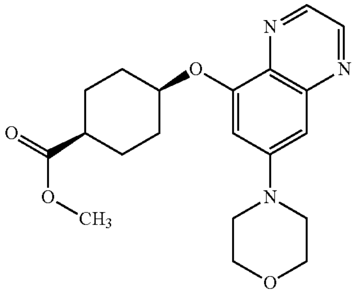 [SMILES: COC(=O)[C@H]1CC[C@@H](Oc2cc(N3CCOCC3)cc3nccnc23)CC1] | 372.16 | ($CDCl_3$) δ 8.66 (dd, J = 20.5, 1.9 Hz, 2H), 6.93 (dd, J = 17.3, 2.5 Hz, 2H), 4.87-4.65 (m, 1H), 4.04-3.83 (m, 4H), 3.72 (s, 3H), 3.46-3.22 (m, 4H), 2.72-2.40 (m, 1H), 2.35-1.99 (m, 4H), 1.99-1.51 (m, 4H) |
| 48 | 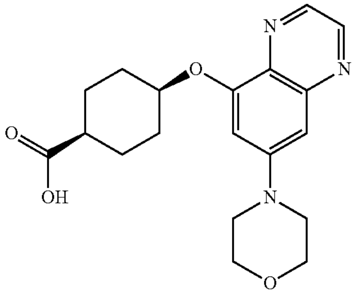 [SMILES: O=C(O)[C@H]1CC[C@@H](Oc2cc(N3CCOCC3)cc3nccnc23)CC1] | 358.64 | (DMSO-$d_6$) δ 12.13 (s, 1H), 8.72 (d, J = 1.7 Hz, 1H), 8.58 (d, J = 1.8 Hz, 1H), 7.13 (d, J = 2.1 Hz, 1H), 6.83 (d, J = 2.0 Hz, 1H), 4.94-4.84 (m, 1H), 3.91-3.68 (m, 4H), 3.51-3.19 (m, 4H), 2.47-2.33 (m, 1H), 2.04-1.82 (m, 4H), 1.82-1.60 (m, 4H) |
| 49 | 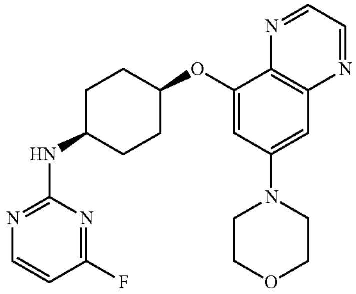 [SMILES: Fc1ccnc(N[C@H]2CC[C@@H](Oc3cc(N4CCOCC4)cc4nccnc34)CC2)n1] | 425.39 | (400 MHz, $CDCl_3$) δ 8.70 (d, J = 1.9 Hz, 1H), 8.60 (d, J = 1.9 Hz, 1H), 7.99 (s, 1H), 6.96 (d, J = 2.4 Hz, 1H), 6.89 (d, J = 2.3 Hz, 1H), 6.20 (s, 1H), 5.19 (bs, 1H), 4.81 (bs, 1H), 3.96-3.84 (m, 4H), 3.40-3.27 (m, 4H), 2.29-2.14 (m, 2H), 1.99-1.81 (m, 6H) |
| 50 | 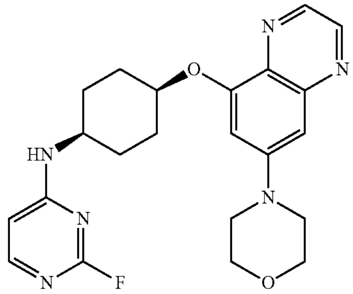 [SMILES: Fc1nccc(N[C@H]2CC[C@@H](Oc3cc(N4CCOCC4)cc4nccnc34)CC2)n1] | 425.39 | (400 MHz, $CDCl_3$) δ 8.69 (d, J = 1.9 Hz, 1H), 8.60 (d, J = 1.9 Hz, 1H), 8.30 (d, J = 2.1 Hz, 1H), 6.95 (d, J = 2.4 Hz, 1H), 6.89 (d, J = 2.4 Hz, 1H), 5.84 (s, 1H), 5.42 (s, 1H), 4.81 (s, 1H), 3.99-3.82 (m, 4H), 3.39-3.24 (m, 4H), 2.31-2.19 (m, 2H), 2.08-1.72 (m, 8H) |
| 51 | 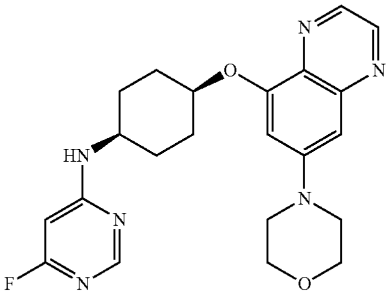 [SMILES: Fc1cc(N[C@H]2CC[C@@H](Oc3cc(N4CCOCC4)cc4nccnc34)CC2)ncn1] | 425.33 | (400 MHz, $CDCl_3$) δ 8.69 (d, J = 1.9 Hz, 1H), 8.60 (d, J = 1.9 Hz, 1H), 8.30 (d, J = 2.1 Hz, 1H), 6.95 (d, J = 2.4 Hz, 1H), 6.89 (d, J = 2.4 Hz, 1H), 5.84 (s, 1H), 5.42 (s, 1H), 4.81 (s, 1H), 3.99-3.82 (m, 4H), 3.39-3.24 (m, 4H), 2.31-2.19 (m, 2H), 2.08-1.72 (m, 8H) |

TABLE 1-continued

| Cmpd. No. | Compound | ESMS (M + H) | $^1$H NMR (300 MHz, unless indicated otherwise) NMR peaks given as δ values |
|---|---|---|---|
| 52 | 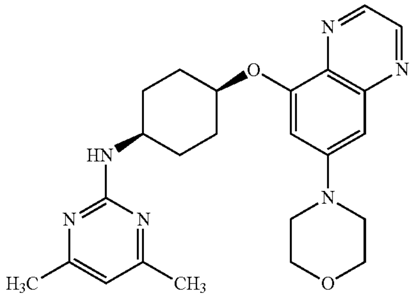 [SMILES: Cc1cc(C)nc(N[C@H]2CC[C@@H](Oc3cc(N4CCOCC4)cc4nccnc34)CC2)n1] | 435.19 | (400 MHz, $CDCl_3$) δ 8.68 (d, J = 1.4 Hz, 1H), 8.60 (d, J = 1.5 Hz, 1H), 6.93 (s, 1H), 6.90 (s, 1H), 6.28 (s, 1H), 5.06 (d, J = 7.9 Hz, 1H), 4.77 (s, 1H), 4.06 (bs, 1H), 3.97-3.84 (m, 4H), 3.38-3.25 (m, 4H), 2.27 (s, 6H), 2.18-2.09 (m, 2H), 1.94-1.83 (m, 7H) |
| 53 | 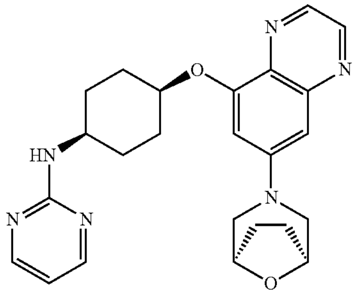 [SMILES: c1cnc(N[C@H]2CC[C@@H](Oc3cc(N4C[C@H]5CC[C@@H](C4)O5)cc4nccnc34)CC2)nc1] | 433.25 | ($CDCl_3$) δ .9 Hz, 1H), 8.28 (d, J = 4.8 Hz, 2H), 6.85 (t, J = 1.9 Hz, 2H), 6.51 (t, J = 4.8 Hz, 1H), 5.29 (d, J = 6.3 Hz, 1H), 4.80 (dq, J = 5.5, 2.8 Hz, 1H), 4.57 (d, J = 3.9 Hz, 2H), 4.02 (t, J = 6.2 Hz, 1H), 3.54-3.43 (m, 2H), 3.19 (dd, J = 11.6, 2.6 Hz, 2H), 2.27-2.14 (m, 2H), 2.08-1.85 (m, 10H) |
| 54 | 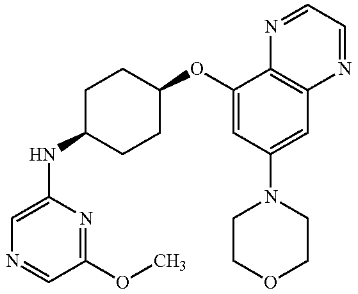 [SMILES: COc1cncc(N[C@H]2CC[C@@H](Oc3cc(N4CCOCC4)cc4nccnc34)CC2)n1] | 437.27 | ($CDCl_3$) δ 8.70 (d, J = 1.9 Hz, 1H), 8.62 (d, J = 1.9 Hz, 1H), 7.45 (d, J = 7.8 Hz, 2H), 7.02-6.81 (m, 2H), 4.78 (ddd, J = 7.3, 5.6, 3.1 Hz, 1H), 4.66 (d, J = 7.9 Hz, 1H), 4.01-3.78 (m, 7H), 3.41-3.25 (m, 4H), 2.30-2.08 (m, 2H), 1.94 (h, J = 8.8, 8.2 Hz, 6H) |
| 55 | 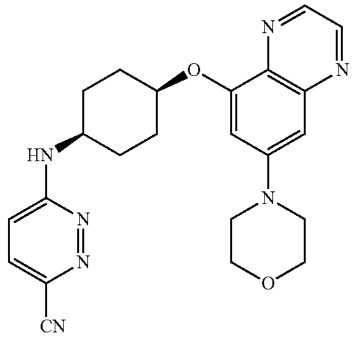 [SMILES: N#Cc1ccc(N[C@H]2CC[C@@H](Oc3cc(N4CCOCC4)cc4nccnc34)CC2)nn1] | 432.3 | ($CDCl_3$) δ 8.73 (d, J = 2.0 Hz, 1H), 8.63 (d, J = 2.0 Hz, 1H), 7.42 (d, J = 9.3 Hz, 1H), 6.96 (dd, J = 19.6, 2.5 Hz, 2H), 6.65 (d, J = 9.3 Hz, 1H), 5.40 (s, 1H), 4.86 (s, 1H), 3.94 (dd, J = 5.9, 3.8 Hz, 4H), 3.37 (dd, J = 6.0, 3.7 Hz, 4H), 2.27 (d, J = 12.7 Hz, 2H), 2.05-1.80 (m, 6H) |
| 56 | 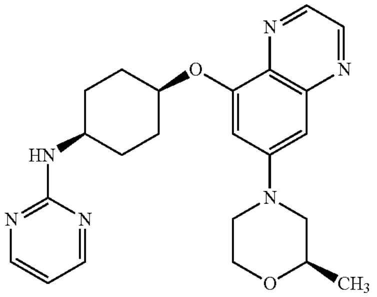 [SMILES: C[C@@H]1CN(c2cc(O[C@H]3CC[C@@H](Nc4ncccn4)CC3)c3nccnc3c2)CCO1] | 421.47 | ($CDCl_3$) δ 8.69 (d, J = 1.9 Hz, 1H), 8.61 (d, J = 1.9 Hz, 1H), 8.28 (d, J = 4.8 Hz, 2H), 6.98-6.86 (m, 2H), 6.53 (t, J = 4.8 Hz, 1H), 5.39 (s, 1H), 4.89-4.75 (m, 1H), 4.18-3.93 (m, 2H), 3.93-3.72 (m, 2H), 3.70-3.52 (m, 2H), 3.00 (td, J = 12.0, 3.5 Hz, 1H), 2.66 (dd, J = 12.1, 10.3 Hz, 1H), 2.21 (d, J = 8.9 Hz, 2H), 1.93 (d, J = 6.7 Hz, 6H), 1.30 (d, J = 6.2 Hz, 3H) |

TABLE 1-continued

| Cmpd. No. | Compound | ESMS (M + H) | $^1$H NMR (300 MHz, unless indicated otherwise) NMR peaks given as δ values |
|---|---|---|---|
| 57 | 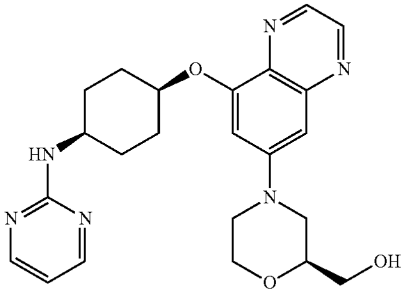 [SMILES: OC[C@@H]1CN(c2cc(O[C@H]3CC[C@@H](Nc4ncccn4)CC3)c3nccnc3c2)CCO1] | 437.49 | ($CDCl_3$) δ 8.69 (d, J = 1.9 Hz, 1H), 8.62 (d, J = 1.9 Hz, 1H), 8.28 (d, J = 4.8 Hz, 2H), 7.02-6.86 (m, 2H), 6.53 (t, J = 4.8 Hz, 1H), 5.40 (s, 1H), 4.82 (d, J = 5.8 Hz, 1H), 4.20-3.95 (m, 2H), 3.94-3.53 (m, 6H), 3.03 (td, J = 12.0, 3.5 Hz, 1H), 2.86 (dd, J = 12.1, 10.4 Hz, 1H), 2.20 (d, J = 9.2 Hz, 2H), 2.11-1.80 (m, 7H) |
| 58 | 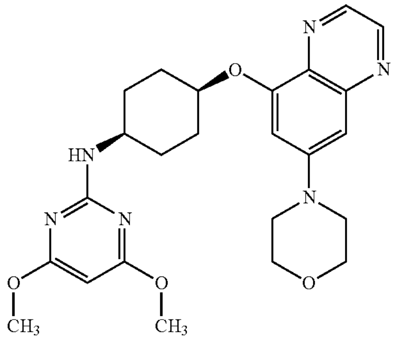 [SMILES: COc1cc(OC)nc(N[C@H]2CC[C@@H](Oc3cc(N4CCOCC4)cc4nccnc34)CC2)n1] | 467.16 | (400 MHz, methanol-$d_4$) δ 8.69 (d, J = 2.0 Hz, 1H), 8.56 (d, J = 2.0 Hz, 1H), 7.12 (d, J = 2.3 Hz, 1H), 6.89 (d, J = 2.4 Hz, 1H), 5.36 (s, 1H), 3.97 (s, 1H), 3.91-3.86 (m, 4H), 3.84 (s, 6H), 3.43-3.35 (m, 4H), 2.23-2.10 (m, 2H), 2.00-1.81 (m, 6H) |
| 59 | 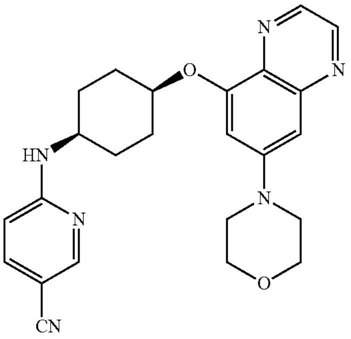 [SMILES: N#Cc1ccc(N[C@H]2CC[C@@H](Oc3cc(N4CCOCC4)cc4nccnc34)CC2)nc1] | 431.19 | (400 MHz, $CDCl_3$) δ 8.70 (d, J = 1.9 Hz, 1H), 8.61 (d, J = 1.9 Hz, 1H), 8.36 (d, J = 1.8 Hz, 1H), 7.54 (dd, J = 8.8, 2.2 Hz, 1H), 6.96 (d, J = 2.4 Hz, 1H), 6.90 (d, J = 2.4 Hz, 1H), 6.37 (d, J = 8.7 Hz, 1H), 5.11 (s, 1H), 4.80 (s, 1H), 3.94 (s, 1H), 3.94-3.79 (m, 4H), 3.38-3.25 (m, 4H), 2.32-2.12 (m, 2H), 2.02-1.78 (m, 6H) |
| 60 | 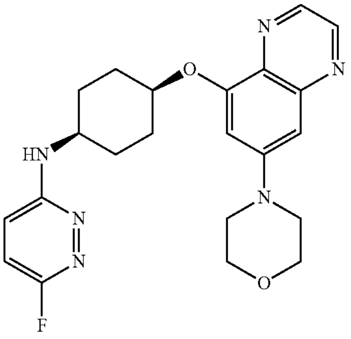 [SMILES: Fc1ccc(N[C@H]2CC[C@@H](Oc3cc(N4CCOCC4)cc4nccnc34)CC2)nn1] | 425.23 | ($CDCl_3$) δ 8.71 (d, J = 1.9 Hz, 1H), 8.62 (d, J = 1.9 Hz, 1H), 7.06-6.88 (m, 3H), 6.80 (dd, J = 9.4, 6.3 Hz, 1H), 4.97-4.71 (m, 2H), 4.14 (q, J = 7.1 Hz, 1H), 4.01-3.85 (m, 4H), 3.44-3.24 (m, 4H), 2.23 (d, J = 10.7 Hz, 2H), 1.96 (dt, J = 11.0, 7.6 Hz, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 61 | 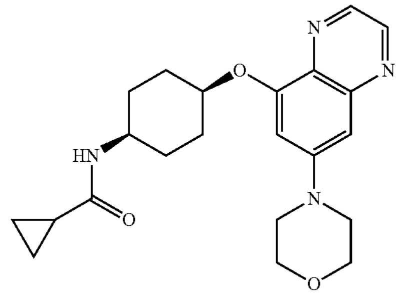 [SMILES: O=C(N[C@H]1CC[C@@H](Oc2cc(N3CCOCC3)cc3nccnc23)CC1)C1CC1] | 397.15 | (400 MHz, $CDCl_3$) δ 8.69 (d, J = 1.8 Hz, 1H), 8.61 (d, J = 1.9 Hz, 1H), 6.94 (d, J = 2.3 Hz, 1H), 6.87 (s, 1H), 5.78-5.64 (m, 1H), 4.73 (s, 1H), 4.01 (s, 1H), 3.97-3.78 (m, 4H), 3.43-3.18 (m, 4H), 2.26-2.05 (m, 2H), 1.98-1.73 (m, 6H), 1.36-1.26 (m, 1H), 1.01-0.92 (m, 2H), 0.78-0.67 (m, 2H) |
| 62 | 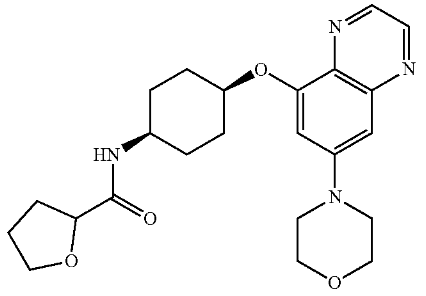 [SMILES: O=C(N[C@H]1CC[C@@H](Oc2cc(N3CCOCC3)cc3nccnc23)CC1)C1CCCO1] | 427.23 | (400 MHz, $CDCl_3$) δ 8.69 (d, J = 1.9 Hz, 1H), 8.62 (d, J = 1.9 Hz, 1H), 6.95 (d, J = 2.3 Hz, 1H), 6.87 (d, J = 2.2 Hz, 1H), 6.79 (d, J = 8.1 Hz, 1H), 4.73 (s, 1H), 4.34 (dd, J = 8.3, 5.9 Hz, 1H), 4.04-3.84 (m, 7H), 3.40-3.28 (m, 4H), 2.35-2.24 (m, 1H), 2.23-2.11 (m, 2H), 2.09-1.08 (m, 1H), 1.97-1.76 (m, 8H) |
| 63 | 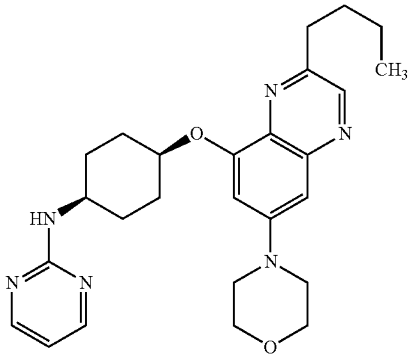 [SMILES: CCCCc1cnc2cc(N3CCOCC3)cc(O[C@H]3CC[C@@H](Nc4ncccn4)CC3)c2n1] | 463.54 | ($CDCl_3$) δ 8.53 (s, 1H), 8.29 (d, J = 4.8 Hz, 2H), 6.92 (d, J = 2.5 Hz, 1H), 6.85 (d, J = 2.5 Hz, 1H), 6.52 (t, J = 4.8 Hz, 1H), 5.25 (d, J = 8.3 Hz, 1H), 4.79 (s, 1H), 4.07 (d, J = 20.4 Hz, 1H), 3.98-3.85 (m, 4H), 3.43-3.21 (m, 4H), 3.05-2.83 (m, 2H), 2.30-2.14 (m, 1H), 2.03-1.71 (m, 7H), 1.45 (dq, J = 14.5, 7.3 Hz, 2H), 0.98 (t, J = 7.3 Hz, 3H) |
| 64 | 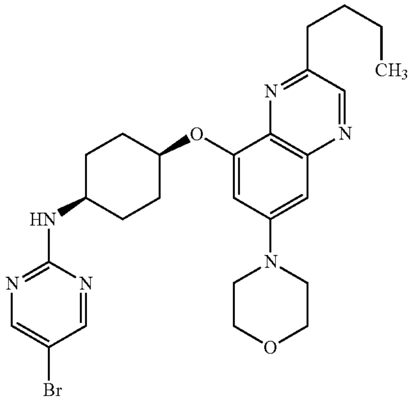 [SMILES: CCCCc1cnc2cc(N3CCOCC3)cc(O[C@H]3CC[C@@H](Nc4ncc(Br)cn4)CC3)c2n1] | 541.26 | ($CDCl_3$) δ 8.55 (s, 1H), 8.29 (d, J = 1.5 Hz, 2H), 7.05-6.93 (m, 1H), 6.85 (d, J = 2.5 Hz, 1H), 5.49 (d, J = 8.0 Hz, 1H), 4.80 (d, J = 5.8 Hz, 1H), 4.03-3.81 (m, 5H), 3.45-3.27 (m, 4H), 2.98 (dd, J = 8.5, 7.0 Hz, 2H), 2.32-2.09 (m, 2H), 2.00-1.71 (m, 8H), 1.56-1.34 (m, 2H), 0.98 (td, J = 7.3, 3.3 Hz, 3H) |

TABLE 1-continued

| Cmpd. No. | Compound | ESMS (M + H) | $^1$H NMR (300 MHz, unless indicated otherwise) NMR peaks given as δ values |
|---|---|---|---|
| 65 | 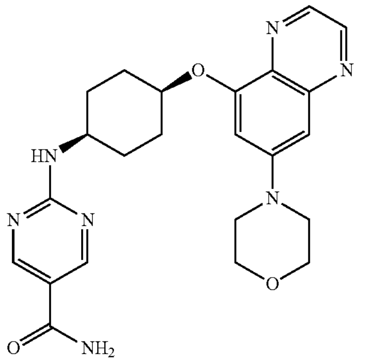 [SMILES: NC(=O)c1cnc(N[C@H]2CC[C@@H](Oc3cc(N4CCOCC4)cc4nccnc34)CC2)nc1] | 450.49 | ($CDCl_3$) δ 8.76-8.66 (m, 3H), 8.61 (d, J = 1.9 Hz, 1H), 6.99-6.87 (m, 2H), 5.71 (d, J = 8.1 Hz, 1H), 4.81 (s, 1H), 4.11 (s, 1H), 3.92 (t, J = 4.9 Hz, 4H), 3.34 (t, J = 4.9 Hz, 4H), 2.22 (d, J = 10.2 Hz, 2H), 2.02-1.85 (m, 6H) |
| 66 | 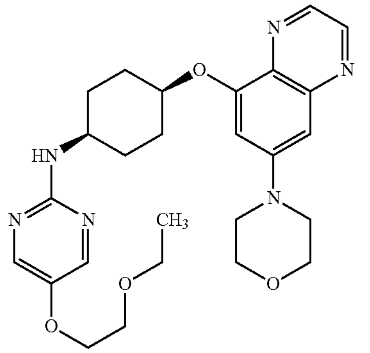 [SMILES: CCOCCOc1cnc(N[C@H]2CC[C@@H](Oc3cc(N4CCOCC4)cc4nccnc34)CC2)nc1] | 495.23 | ($CDCl_3$) δ 8.77 (d, J = 2.3 Hz, 1H), 8.72 (d, J = 2.3 Hz, 1H), 7.12 (d, J = 2.4 Hz, 1H), 7.02 (d, J = 24. Hz, 1H), 4.92 (s, 1H), 4.18-4.08 (m, 2H), 3.93 (t, J = 4.9 Hz, 4H), 3.85-3.76 (m, 2H), 3.60 (q, J = 7.0 Hz, 2H), 3.47 (t, J = 4.9 Hz, 4H), 2.26 (d, J = 13.3 Hz, 2H), 2.07 (t, J = 10.5 Hz, 2H), 2.01-1.72 (m, 2H), 1.26 (t, J = 7.0 Hz, 4H) |
| 67 | 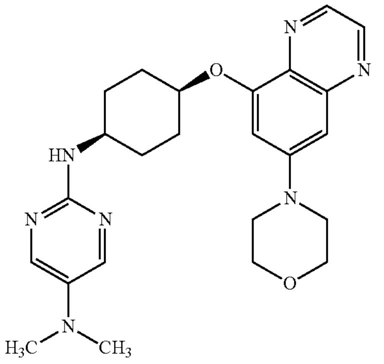 [SMILES: CN(C)c1cnc(N[C@H]2CC[C@@H](Oc3cc(N4CCOCC4)cc4nccnc34)CC2)nc1] | 450.3 | ($CDCl_3$) δ 8.71 (d, J = 2.0 Hz, 1H), 8.64 (d, J = 1.9 Hz, 1H), 8.02 (s, 1H), 6.94 (dd, J = 12.2, 2.5 Hz, 2H), 5.32 (s, 2H), 4.87 (d, J = 8.1 Hz, 1H), 4.79 (s, 1H), 4.01-3.86 (m, 4H), 3.36 (q, J = 5.4, 4.7 Hz, 4H), 2.83 (s, 6H), 2.19 (s, 2H), 1.92 (d, J = 4.8 Hz, 6H) |
| 68 | 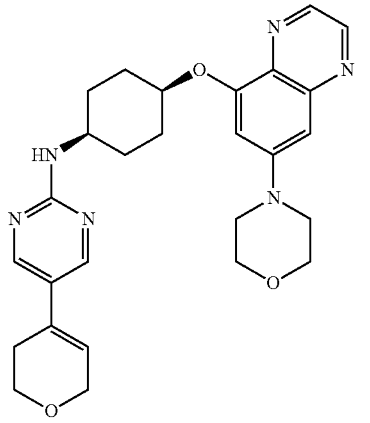 [SMILES: C1=C(c2cnc(N[C@H]3CC[C@@H](Oc4cc(N5CCOCC5)cc5nccnc45)CC3)nc2)CCOC1] | 489.24 | ($CDCl_3$) δ 8.70 (d, J = 1.9 Hz, 1H), 8.63 (d, J = 1.9 Hz, 1H), 8.34 (s, 2H), 7.02-6.86 (m, 2H), 6.00 (tt, J = 3.0, 1.5 Hz, 1H), 5.41-5.21 (m, 1H), 4.81 (dt, J = 7.2, 3.6 Hz, 1H), 4.31 (q, J = 2.8 Hz, 2H), 4.03 (dd, J = 7.8, 4.4 Hz, 1H), 4.00-3.82 (m, 6H), 3.42-3.25 (m, 4H), 2.44 (tdd, J = 5.7, 2.9, 1.7 Hz, 2H), 2.22 (dq, J = 11.2, 6.6, 6.0 Hz, 2H), 2.02-1.83 (m, 6H) |

TABLE 1-continued
| Cmpd. No. | Compound | ESMS (M + H) | $^1H$ NMR (300 MHz, unless indicated otherwise) NMR peaks given as δ values |
|---|---|---|---|
| 69 | 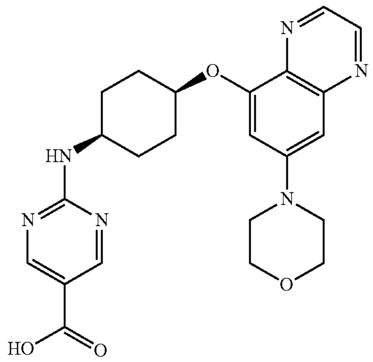 [SMILES: O=C(O)c1cnc(N[C@H]2CC[C@@H](Oc3cc(N4CCOCC4)cc4nccnc34)CC2)nc1] | 451.21 | ($CDCl_3$) δ 9.05 (s, 1H), 8.88-8.71 (m, 3H), 8.49 (s, 1H), 7.06 (d, J = 2.3 Hz, 1H), 6.96 (d, J = 2.3 Hz, 1H), 4.85 (s, 1H), 4.17 (s, 1H), 3.93 (t, J = 4.8 Hz, 4H), 3.42 (t, J = 4.9 Hz, 4H), 2.25-2.10 (m, 2H), 1.95 (d, J = 11.9 Hz, 4H) |
| 70 | 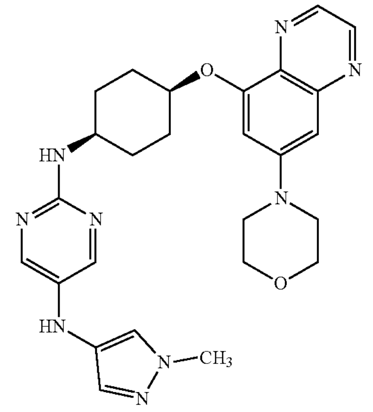 [SMILES: Cn1cc(Nc2cnc(N[C@H]3CC[C@@H](Oc4cc(N5CCOCC5)cc5nccnc45)CC3)nc2)cn1] | 409.45 | (methanol-$d_4$) δ 8.69 (s, 1H), 8.56 (s, 1H), 7.20 (s, 1H), 7.10 (d, J = 2.2 Hz, 1H), 6.88 (d, J = 2.4 Hz, 1H), 4.93 (d, J = 14.3 Hz, 2H), 3.95-3.76 (m, 7H), 3.42-3.32 (m, 4H), 3.09 (d, J = 7.3 Hz, 1H), 2.21-2.09 (m, 2H), 1.85 (dd, J = 10.8, 5.6 Hz, 6H) |
| 71 | 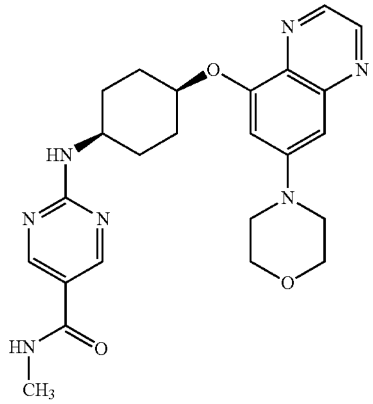 [SMILES: CNC(=O)c1cnc(N[C@H]2CC[C@@H](Oc3cc(N4CCOCC4)cc4nccnc34)CC2)nc1] | 464.4 | ($CDCl_3$) δ 8.79-8.64 (m, 3H), 8.59 (d, J = 1.9 Hz, 1H), 6.99-6.88 (m, 2H), 6.19 (q, J = 4.7 Hz, 1H), 5.90 (d, J = 8.2 Hz, 1H), 4.81 (dq, J = 5.3, 2.7 Hz, 1H), 4.08 (qd, J = 8.2, 6.5, 2.3 Hz, 1H), 3.97-3.87 (m, 4H), 3.39-3.29 (m, 4H), 2.93 (d, J = 4.8 Hz, 3H), 2.27-2.14 (m, 2H), 2.06-1.79 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 72 | 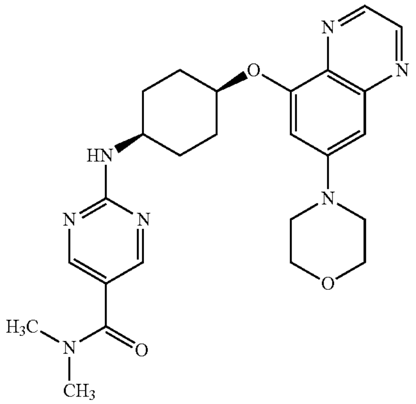 [SMILES: CN(C)C(=O)c1cnc(N[C@H]2CC[C@@H](Oc3cc(N4CCOCC4)cc4nccnc34)CC2)nc1] | 478.39 | ($CDCl_3$) δ 3.97-3.87 (m, 4H), 3.39-3.29 (m, 4H), 3.10 (s, 6H), 2.22 (dt, J = 11.3, 5.1 Hz, 2H), 1.94 (dd, J = 8.3, 3.9 Hz, 6H), 4.12-4.01 (m, 1H), 8.70 (d, J = 1.9 Hz, 1H), 8.62 (d, J = 1.9 Hz, 1H), 8.46 (s, 2H), 7.00-6.87 (m, 2H), 5.57 (d, J = 8.1 Hz, 1H), 4.81 (dq, J = 5.1, 2.4 Hz, 1H) |
| 73 | 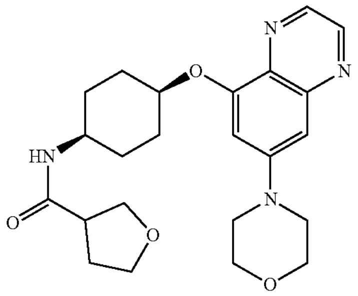 [SMILES: O=C(N[C@H]1CC[C@@H](Oc2cc(N3CCOCC3)cc3nccnc23)CC1)C1CCOC1] | 427.2 | (400 MHz, $CDCl_3$) δ 8.69 (d, J = 1.2 Hz, 1H), 8.57 (d, J = 21.7 Hz, 1H), 6.93 (d, J = 1.7 Hz, 1H), 6.86 (s, 1H), 5.75 (d, J = 7.4 Hz, 1H), 4.74 (s, 1H), 4.03-3.87 (m, 8H), 3.81 (dd, J = 15.2, 7.5 Hz, 1H), 3.37-3.25 (m, 4H), 2.96-2.76 (m, 1H), 2.23-2.07 (m, 4H), 1.84-1.78 (m, 6H) |
| 74 | 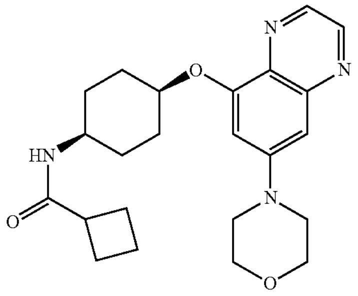 [SMILES: O=C(N[C@H]1CC[C@@H](Oc2cc(N3CCOCC3)cc3nccnc23)CC1)C1CCC1] | 411.25 | (400 MHz, $CDCl_3$) δ 8.69 (d, J = 1.9 Hz, 1H), 8.60 (d, J = 1.9 Hz, 1H), 6.94 (d, J = 2.4 Hz, 1H), 6.86 (d, J = 2.4 Hz, 1H), 5.42 (d, J = 7.9 Hz, 1H), 4.72 (s, 1H), 3.98 (s, 1H), 3.95-3.86 (m, 4H), 3.40-3.26 (m, 4H), 3.05-2.87 (m, 1H), 2.32-2.21 (m, 2H), 2.21-2.07 (m, 4H), 2.03-1.90 (m, 1H), 1.90-1.77 (m, 7H) |
| 75 | 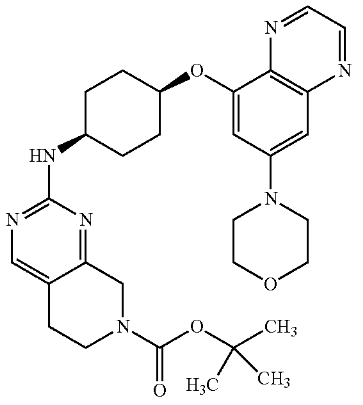 [SMILES: CC(C)(C)OC(=O)N1CCc2cnc(N[C@H]3CC[C@@H](Oc4cc(N5CCOCC5)cc5nccnc45)CC3)nc2C1] | 562.34 | ($CDCl_3$) δ 8.72-8.51 (m, 2H), 7.01 (d, J = 2.5 Hz, 1H), 6.93 (d, J = 2.5 Hz, 1H), 4.84 (s, 1H), 4.40 (s, 2H), 3.99 (s, 1H), 3.83 (dd, J = 5.9, 3.8 Hz, 4H), 3.65 (s, 2H), 3.35 (t, J = 4.9 Hz, 4H), 2.87 (s, 2H), 2.27-1.91 (m, 4H), 1.90-1.59 (m, 2H), 1.41 (s, 9H) |

TABLE 1-continued

| Cmpd. No. | Compound | ESMS (M + H) | $^1$H NMR (300 MHz, unless indicated otherwise) NMR peaks given as δ values |
|---|---|---|---|
| 76 | 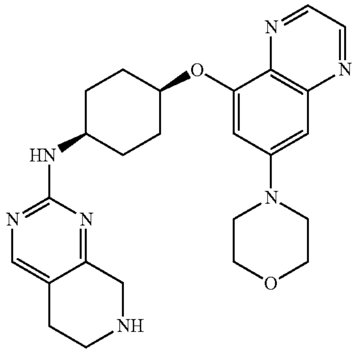 [SMILES: c1cnc2c(O[C@H]3CC[C@@H](Nc4ncc5c(n4)CNCC5)CC3)cc(N3CCOCC3)cc2n1] | 462.23 | ($CDCl_3$) δ 8.70 (t, J = 2.2 Hz, 1H), 8.63 (dd, J = 2.7, 1.9 Hz, 1H), 7.97 (s, 1H), 7.00-6.86 (m, 2H), 5.05 (d, J = 8.2 Hz, 1H), 4.77 (s, 1H), 4.02 (s, 1H), 3.93 (t, J = 4.7 Hz, 4H), 3.86 (s, 1H), 3.35 (t, J = 4.8 Hz, 4H), 3.17 (t, J = 6.0 Hz, 1H), 2.89 (d, J = 5.5 Hz, 1H), 2.17 (t, J = 6.0 Hz, 1H), 2.21 (dd, J = 9.2, 4.9 Hz, 2H), 1.91 (d, J = 5.5 Hz, 3H), 1.75 (d, J = 5.6 Hz, 4H) |
| 77 | 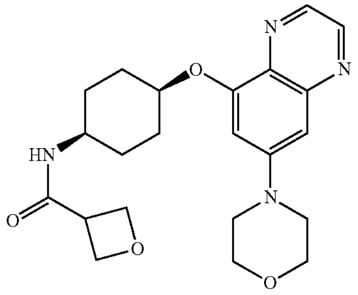 [SMILES: O=C(N[C@H]1CC[C@@H](Oc2cc(N3CCOCC3)cc3nccnc23)CC1)C1COC1] | 413.19 | (400 MHz, $CDCl_3$) δ 8.68 (d, J = 1.9 Hz, 1H), 8.63-8.54 (m, 1H), 6.93 (d, J = 2.4 Hz, 1H), 6.86 (d, J = 2.3 Hz, 1H), 5.76-5.55 (m, 1H), 4.93-4.67 (m, 4H), 3.99 (d, J = 26.0 Hz, 1H), 3.95-3.81 (m, 4H), 3.77-3.55 (m, 2H), 3.39-3.28 (m, 4H), 2.21-2.09 (m, 2H), 1.90-1.75 (m, 6H) |
| 78 | 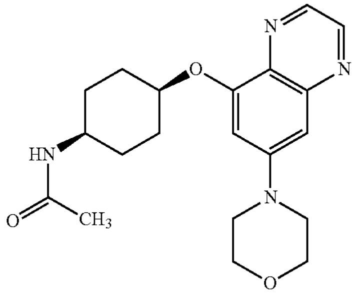 [SMILES: CC(=O)N[C@H]1CC[C@@H](Oc2cc(N3CCOCC3)cc3nccnc23)CC1] | 371.18 | (400 MHz, $CDCl_3$) δ 8.69 (s, 1H), 8.60 (s, 1H), 6.94 (s, 1H), 6.86 (s, 1H), 5.59 (s, 1H), 4.74 (s, 1H), 4.11-3.81 (m, 5H), 3.42-3.23 (m, 4H), 2.28-2.09 (m, 2H), 1.98 (s, 3H), 1.90-1.78 (m, 6H) |
| 79 | 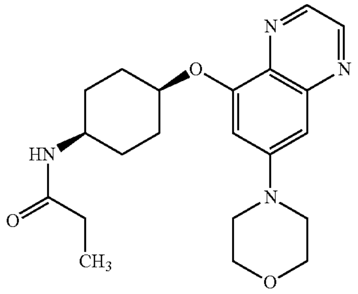 [SMILES: CCC(=O)N[C@H]1CC[C@@H](Oc2cc(N3CCOCC3)cc3nccnc23)CC1] | 385.18 | (400 MHz, $CDCl_3$) δ 8.69 (d, J = 1.9 Hz, 1H), 8.60 (d, J = 1.9 Hz, 1H), 6.93 (d, J = 2.4 Hz, 1H), 6.86 (d, J = 2.3 Hz, 1H), 5.52 (d, J = 7.3 Hz, 1H), 4.73 (s, 1H), 3.99 (s, 1H), 3.96-3.87 (m, 4H), 3.38-3.30 (m, 4H), 2.24-2.08 (m, 4H), 1.88-1.79 (m, 6H), 1.16 (t, J = 7.6 Hz, 3H) |
| 80 | 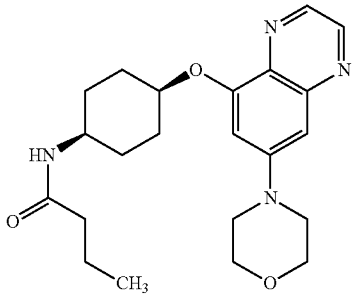 [SMILES: CCCC(=O)N[C@H]1CC[C@@H](Oc2cc(N3CCOCC3)cc3nccnc23)CC1] | 399.23 | (400 MHz, $CDCl_3$) δ 8.69 (d, J = 1.9 Hz, 1H), 8.60 (d, J = 1.9 Hz, 1H), 6.93 (d, J = 2.4 Hz, 1H), 6.86 (d, J = 2.3 Hz, 1H), 5.53 (d, J = 7.7 Hz, 1H), 4.73 (s, 1H), 4.00 (s, 1H), 3.95-3.84 (m, 4H), 3.39-3.25 (m, 4H), 2.22-2.06 (m, 4H), 1.88-1.76 (m, 6H), 1.70-1.61 (m, 2H), 0.94 (t, J = 7.4 Hz, 3H) |

TABLE 1-continued

| Cmpd. No. | Compound | ESMS (M + H) | $^1H$ NMR (300 MHz, unless indicated otherwise) NMR peaks given as δ values |
|---|---|---|---|
| 81 | 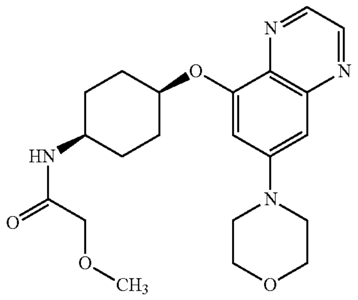 [SMILES: COCC(=O)N[C@H]1CC[C@@H](Oc2cc(N3CCOCC3)cc3nccnc23)CC1] | 401.21 | (400 MHz, $CDCl_3$) δ 8.69 (d, J = 1.9 Hz, 1H), 8.62 (d, J = 1.9 Hz, 1H), 6.94 (d, J = 2.4 Hz, 1H), 6.87 (d, J = 2.2 Hz, 1H), 6.65 (d, J = 8.5 Hz, 1H), 4.72 (s, 1H), 4.06 (s, 1H), 3.96-3.85 (m, 6H), 3.43 (s, 3H), 3.38-3.28 (m, 4H), 2.24-2.09 (m, 2H), 1.95-1.76 (m, 6H) |
| 82 | 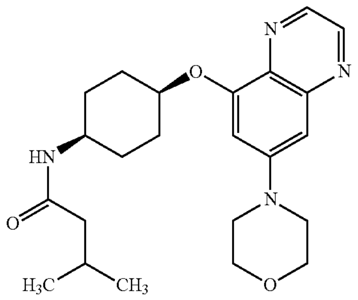 [SMILES: CC(C)CC(=O)N[C@H]1CC[C@@H](Oc2cc(N3CCOCC3)cc3nccnc23)CC1] | 413.27 | (400 MHz, $CDCl_3$) δ 8.68 (d, J = 1.8 Hz, 1H), 8.59 (d, J = 1.8 Hz, 1H), 6.93 (d, J = 2.3 Hz, 1H), 6.86 (d, J = 2.0 Hz, 1H), 5.53 (d, J = 7.8 Hz, 1H), 4.72 (s, 1H), 4.01 (s, 1H), 3.96-3.81 (m, 4H), 3.37-3.24 (m, 4H), 2.24-2.06 (m, 3H), 2.01 (d, J = 7.0 Hz, 2H), 1.87-1.76 (m, 6H), 0.94 (d, J = 6.5 Hz, 6H) |
| 83 | 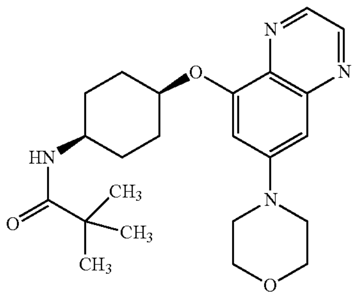 [SMILES: CC(C)(C)C(=O)N[C@H]1CC[C@@H](Oc2cc(N3CCOCC3)cc3nccnc23)CC1] | 413.23 | (400 MHz, $CDCl_3$) δ 8.62 (d, J = 1.9 Hz, 1H), 8.55 (d, J = 1.9 Hz, 1H), 6.87 (d, J = 2.4 Hz, 1H), 6.80 (d, J = 2.3 Hz, 1H), 5.62 (d, J = 7.7 Hz, 1H), 4.64 (s, 1H), 3.99-3.76 (m, 5H), 3.37-3.14 (m, 4H), 2.21-1.95 (m, 2H), 1.87-1.63 (m, 6H), 1.13 (s, 9H) |
| 84 | 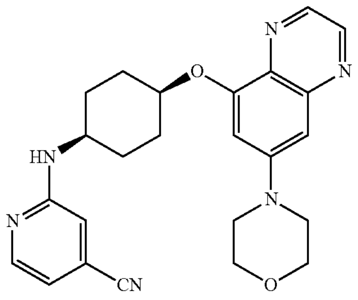 | 431.19 | (400 MHz, $CDCl_3$) δ 8.69 (d, J = 1.9 Hz, 1H), 8.61 (d, J = 1.9 Hz, 1H), 8.19 (d, J = 4.8 Hz, 1H), 6.95 (d, J = 2.3 Hz, 1H), 6.90 (d, J = 2.4 Hz, 1H), 6.70 (dd, J = 5.1, 1.2 Hz, 1H), 6.56 (s, 1H), 4.87 (d, J = 7.6 Hz, 1H), 4.80 (s, 1H), 3.96-3.88 (m, 4H), 3.85 (s, 1H), 3.38-3.28 (m, 4H), 2.28-2.14 (m, 2H), 2.00-1.85 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 85 | 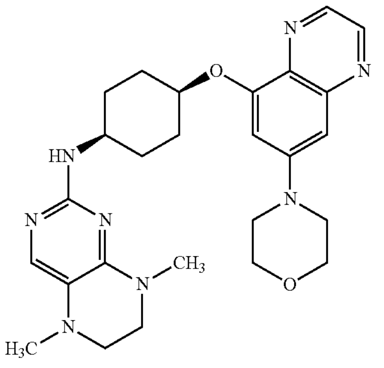 [SMILES: CN1CCN(C)c2nc(N[C@H]3CC[C@@H](Oc4cc(N5CCOCC5)cc5nccnc45)CC3)ncc21] | 491.3 | ($CDCl_3$) δ 8.67 (d, J = 2.0 Hz, 1H), 8.62 (d, J = 2.0 Hz, 1H), 7.05-6.95 (m, 2H), 6.72 (s, 1H), 4.88 (s, 1H), 3.98-3.82 (m, 4H), 3.64 (t, J = 5.1 Hz, 2H), 3.41-3.31 (m, 4H), 3.24 (s, 3H), 3.09 (t, J = 5.2 Hz, 2H), 2.68 (s, 3H), 2.30-1.99 (m, 4H), 1.86 (d, J = 9.0 Hz, 4H) |
| 86 | 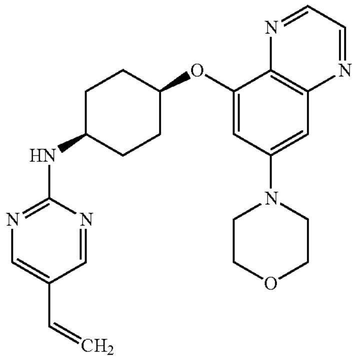 [SMILES: C=Cc1cnc(N[C@H]2CC[C@@H](Oc3cc(N4CCOCC4)cc4nccnc34)CC2)nc1] | 433.2 | ($CDCl_3$) δ 9.68 (s, 1H), 8.76-8.58 (m, 2H), 7.00 (d, J = 2.5 Hz, 1H), 6.92 (d, J = 2.5 Hz, 1H), 6.41 (dd, J = 17.7, 11.1 Hz, 1H), 5.65 (d, J = 17.7 Hz, 1H), 5.33 (d, J = 11.1 Hz, 1H), 4.85 (q, J = 3.6 Hz, 1H), 4.01 (s, 1H), 3.94-3.70 (m, 4H), 3.47-3.19 (m, 4H), 2.27-1.94 (m, 4H), 1.93-1.63 (m, 4H) |
| 87 | 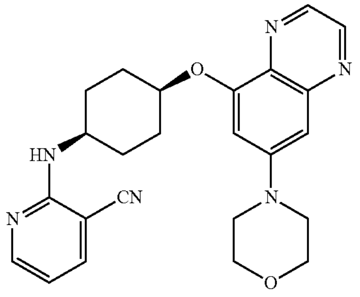 [SMILES: N#Cc1cccnc1N[C@H]1CC[C@@H](Oc2cc(N3CCOCC3)cc3nccnc23)CC1] | 431.2 | ($CDCl_3$) δ 8.63 (d, J = 1.9 Hz, 1H), 8.57 (d, J = 1.9 Hz, 1H), 8.20 (dd, J = 5.0, 1.9 Hz, 1H), 7.57 (dd, J = 7.6, 1.9 Hz, 1H), 6.89 (d, J = 2.5 Hz, 1H), 6.85 (d, J = 2.5 Hz, 1H), 6.51 (dd, J = 7.6, 4.9 Hz, 1H), 5.12 (d, J = 7.7 Hz, 1H), 4.83-4.71 (m, 0H), 4.24-4.03 (m, 1H), 3.92-3.77 (m, 4H), 3.35-3.19 (m, 4H), 2.28-2.10 (m, 2H), 1.88 (td, J = 8.3, 6.8, 3.9 Hz, 6H) |
| 88 | 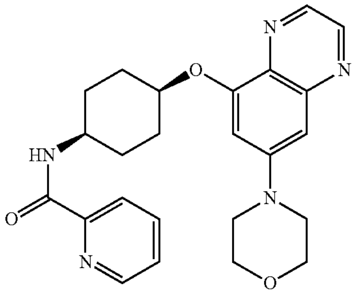 [SMILES: O=C(N[C@H]1CC[C@@H](Oc2cc(N3CCOCC3)cc3nccnc23)CC1)c1ccccn1] | 434.25 | (400 MHz, $CDCl_3$) δ 8.69 (s, 1H), 8.63 (s, 1H), 8.57 (s, 1H), 8.30-8.12 (m, 2H), 7.85 (t, J = 7.1 Hz, 1H), 7.50-7.37 (m, 1H), 6.94 (s, 1H), 6.89 (s, 1H), 4.89-4.63 (m, 1H), 4.35-4.13 (m, 1H), 4.01-3.78 (m, 4H), 3.43-3.19 (m, 4H), 2.37-2.15 (m, 2H), 2.12-1.82 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 89 | 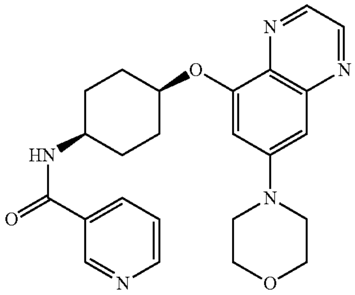 [SMILES: O=C(N[C@H]1CC[C@@H](Oc2cc(N3CCOCC3)cc3nccnc23)CC1)c1cccnc1] | 434.22 | (400 MHz, $CDCl_3$) δ 8.99 (s, 1H), 8.73 (d, J = 3.4 Hz, 1H), 8.70 (d, J = 1.6 Hz, 1H), 8.60 (d, J = 1.7 Hz, 1H), 8.11 (d, J = 7.8 Hz, 1H), 7.40 (dd, J = 7.6, 4.8 Hz, 1H), 6.95 (d, J = 2.1 Hz, 1H), 6.90 (s, 1H), 6.30 (d, J = 7.6 Hz, 1H), 4.81 (s, 1H), 4.22 (s, 1H), 3.97-3.85 (m, 4H), 3.41-3.23 (m, 4H), 2.32-2.17 (m, 2H), 2.01-1.84 (m, 6H) |
| 90 | 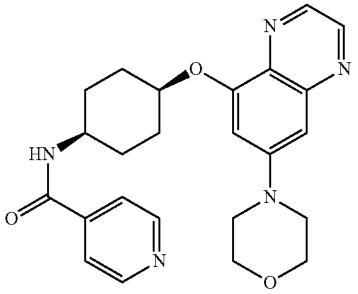 [SMILES: O=C(N[C@H]1CC[C@@H](Oc2cc(N3CCOCC3)cc3nccnc23)CC1)c1ccncc1] | 434.22 | (400 MHz, $CDCl_3$) δ 8.75 (dd, J = 4.4, 1.7 Hz, 2H), 8.70 (d, J = 1.9 Hz, 1H), 8.60 (d, J = 1.9 Hz, 1H), 7.62 (dd, J = 4.4, 1.7 Hz, 2H), 6.95 (d, J = 2.4 Hz, 1H), 6.89 (d, J = 2.5 Hz, 1H), 6.33 (d, J = 8.2 Hz, 1H), 4.81 (s, 1H), 4.27-4.16 (m, 1H), 3.96-3.87 (m, 4H), 3.38-3.31 (m, 4H), 2.30-2.16 (m, 2H), 2.00-1.86 (m, 6H) |
| 91 | 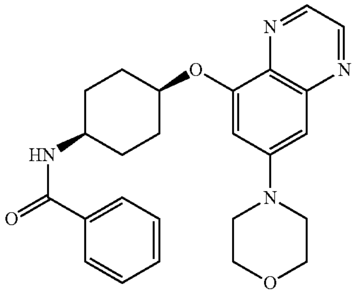 [SMILES: O=C(N[C@H]1CC[C@@H](Oc2cc(N3CCOCC3)cc3nccnc23)CC1)c1ccccc1] | 433.21 | (400 MHz, $CDCl_3$) δ 8.69 (d, J = 1.9 Hz, 1H), 8.63-8.58 (m, 1H), 7.77 (dd, J = 5.2, 3.2 Hz, 2H), 7.54-7.40 (m, 3H), 6.95 (d, J = 2.4 Hz, 1H), 6.89 (d, J = 2.4 Hz, 1H), 6.23 (d, J = 8.0 Hz, 1H), 4.78 (s, 1H), 4.31-4.13 (m, 1H), 3.95-3.87 (m, 4H), 3.38-3.27 (m, 4H), 2.31-2.17 (m, 2H), 1.97-1.85 (m, 6H) |
| 92 | 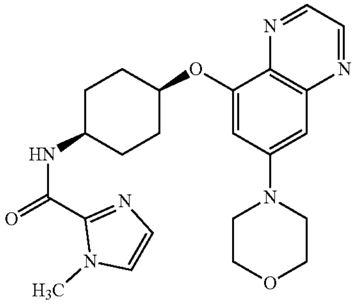 | 437.24 | (400 MHz, $CDCl_3$) δ 8.69 (d, J = 1.9 Hz, 1H), 8.62 (d, J = 1.9 Hz, 1H), 7.47 (d, J = 8.9 Hz, 1H), 7.00 (d, J = 1.0 Hz, 1H), 6.95 (d, J = 0.7 Hz, 1H), 6.94 (d, J = 2.5 Hz, 1H), 6.89 (d, J = 2.4 Hz, 1H), 4.81 (s, 1H), 4.07 (d, J = 12.3 Hz, 4H), 3.98-3.85 (m, 4H), 3.41-3.24 (m, 4H), 2.34-2.12 (m, 2H), 2.06-1.83 (m, 6H) |
| 93 | 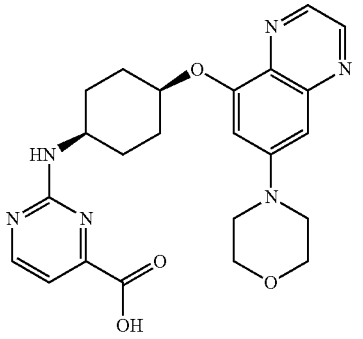 [SMILES: O=C(O)c1ccnc(N[C@H]2CC[C@@H](Oc3cc(N4CCOCC4)cc4nccnc34)CC2)n1] | 451.21 | (methanol-$d_4$) δ 8.69 (d, J = 2.2 Hz, 1H), 8.59 (d, J = 2.2 Hz, 1H), 8.53 (d, J = 4.9 Hz, 1H), 7.19 (d, J = 5.0 Hz, 1H), 7.15 (d, J = 2.3 Hz, 1H), 6.87 (d, J = 2.4 Hz, 1H), 4.95 (d, J = 7.7 Hz, 1H), 4.10 (s, 1H), 3.95-3.82 (m, 4H), 3.47-3.37 (m, 4H), 2.20 (d, J = 10.1 Hz, 2H), 2.04-1.81 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 94 | 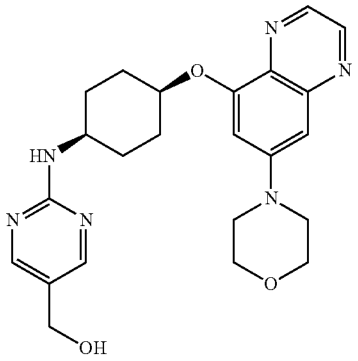 [SMILES: OCc1cnc(N[C@H]2CC[C@@H](Oc3cc(N4CCOCC4)cc4nccnc34)CC2)nc1] | 437.44 | ($CDCl_3$) δ 8.68 (d, J = 2.0 Hz, 1H), 8.60 (d, J = 1.9 Hz, 1H), 8.29 (s, 2H), 6.98-6.87 (m, 2H), 5.36 (d, J = 8.1 Hz, 1H), 4.79 (q, J = 5.2, 4.0 Hz, 1H), 4.52 (s, 2H), 4.01 (dd, J = 8.1, 4.3 Hz, 1H), 3.95-3.84 (m, 4H), 3.39-3.28 (m, 4H), 2.25-2.12 (m, 2H), 1.99-1.82 (m, 6H) |
| 95 | 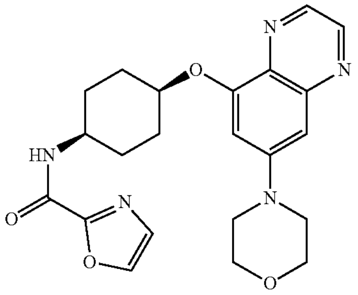 [SMILES: O=C(N[C@H]1CC[C@@H](Oc2cc(N3CCOCC3)cc3nccnc23)CC1)c1ncco1] | 424.21 | (400 MHz, $CDCl_3$) δ 8.70 (d, J = 1.7 Hz, 1H), 8.65-8.58 (m, 1H), 7.80 (s, 1H), 7.22 (d, J = 9.6 Hz, 1H), 7.15 (d, J = 7.6 Hz, 1H), 6.95 (d, J = 2.4 Hz, 1H), 6.89 (d, J = 2.4 Hz, 1H), 4.80 (s, 1H), 4.24-4.09 (m, 1H), 3.98-3.85 (m, 4H), 3.40-3.29 (m, 4H), 2.29-2.15 (m, 2H), 2.02-1.86 (m, 6H) |
| 96 | 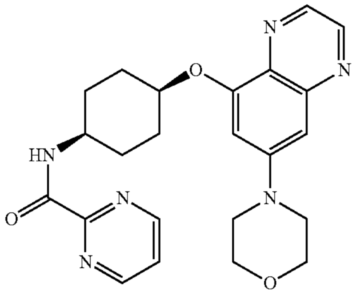 [SMILES: O=C(N[C@H]1CC[C@@H](Oc2cc(N3CCOCC3)cc3nccnc23)CC1)c1ncccn1] | 435.19 | (400 MHz, $CDCl_3$) δ 8.89 (d, J = 4.9 Hz, 2H), 8.69 (d, J = 1.9 Hz, 1H), 8.62 (d, J = 1.9 Hz, 1H), 8.20 (d, J = 8.3 Hz, 1H), 7.45 (t, J = 4.9 Hz, 1H), 6.94 (d, J = 2.4 Hz, 1H), 6.89 (d, J = 2.4 Hz, 1H), 4.75 (s, 1H), 4.39-4.21 (m, 1H), 4.00-3.84 (m, 4H), 3.41-3.21 (m, 4H), 2.29-2.13 (m, 2H), 2.12-1.87 (m, 6H) |
| 97 | 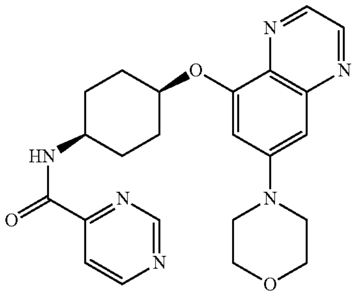 [SMILES: O=C(N[C@H]1CC[C@@H](Oc2cc(N3CCOCC3)cc3nccnc23)CC1)c1ccncn1] | 435.19 | (400 MHz, $CDCl_3$) δ 9.25 (d, J = 1.4 Hz, 1H), 8.97 (d, J = 5.0 Hz, 1H), 8.70 (d, J = 1.9 Hz, 1H), 8.63 (d, J = 1.9 Hz, 1H), 8.22-8.04 (m, 2H), 6.95 (d, J = 2.4 Hz, 1H), 6.89 (d, J = 2.4 Hz, 1H), 4.81-4.72 (m, 1H), 4.26-4.15 (m, 1H), 3.96-3.86 (m, 4H), 3.38-3.29 (m, 4H), 2.28-2.17 (m, 2H), 2.06-1.86 (m, 6H) |
| 98 | 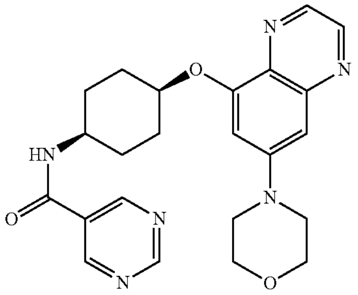 [SMILES: O=C(N[C@H]1CC[C@@H](Oc2cc(N3CCOCC3)cc3nccnc23)CC1)c1cncnc1] | 435.19 | (400 MHz, $CDCl_3$) δ 9.33 (s, 1H), 9.12 (s, 2H), 8.70 (d, J = 1.9 Hz, 1H), 8.57 (d, J = 1.9 Hz, 1H), 6.95 (d, J = 2.4 Hz, 1H), 6.89 (d, J = 2.4 Hz, 1H), 6.44 (d, J = 7.8 Hz, 1H) 4.83 (s, 1H), 4.23 (qd, J = 9.2, 4.7 Hz, 1H), 3.96-3.87 (m, 4H), 3.38-3.03 (m, 4H), 2.32-2.18 (m, 2H), 2.01-1.88 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 99 | 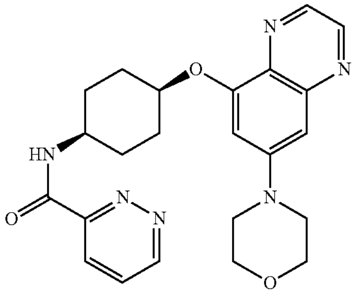 [SMILES: O=C(N[C@H]1CC[C@@H](Oc2cc(N3CCOCC3)cc3nccnc23)CC1)c1cccnn1] | 435.19 | (400 MHz, $CDCl_3$) δ 9.29 (dd, J = 5.0, 1.7 Hz, 1H), 8.70 (d, J = 1.9 Hz, 1H), 8.64 (d, J = 1.9 Hz, 1H), 8.33 (dd, J = 8.4, 1.7 Hz, 2H), 7.67 (dd, J = 8.4, 5.0 Hz, 1H), 6.95 (d, J = 2.5 Hz, 1H), 6.91 (d, J = 2.5 Hz, 1H), 4.85 (s, 1H), 4.29-4.13 (m, 1H), 3.98-3.85 (m, 4H), 3.40-3.26 (m, 4H), 2.32-2.16 (m, 2H), 2.12-1.98 (m, 2H), 1.99-1.87 (m, 4H) |
| 100 | 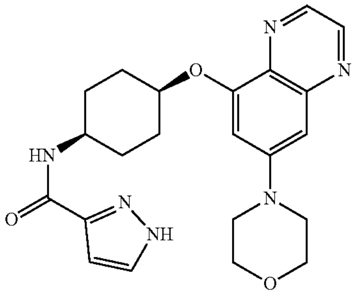 [SMILES: O=C(N[C@H]1CC[C@@H](Oc2cc(N3CCOCC3)cc3nccnc23)CC1)c1cc[nH]n1] | 423.13 | (400 MHz, $CDCl_3$) δ 11.83 (s, 1H), 8.71 (d, J = 1.9 Hz, 1H), 8.59 (d, J = 1.9 Hz, 1H), 7.55 (d, J = 2.4 Hz, 1H), 7.05 (d, J = 8.5 Hz, 1H), 6.94 (d, J = 2.4 Hz, 1H), 6.87 (dd, J = 4.7, 2.3 Hz, 1H), 6.84 (d, J = 2.4 Hz, 1H), 4.74 (s, 1H), 4.18 (s, 1H), 3.96-3.88 (m, 4H), 3.38-3.29 (m, 4H), 2.17-2.09 (m, 2H), 1.94-1.81 (m, 6H) |
| 101 | 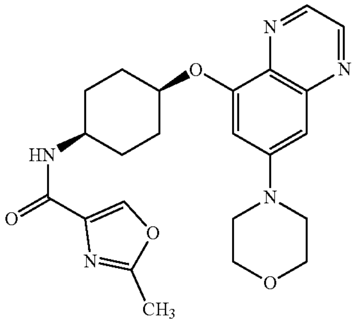 [SMILES: Cc1nc(C(=O)N[C@H]2CC[C@@H](Oc3cc(N4CCOCC4)cc4nccnc34)CC2)co1] | 438.18 | (400 MHz, $CDCl_3$) δ 8.70 (d, J = 1.9 Hz, 1H), 8.63 (d, J = 1.9 Hz, 1H), 8.07 (s, 1H), 7.01 (d, J = 8.3 Hz, 1H), 6.94 (d, J = 2.4 Hz, 1H), 6.88 (d, J = 2.4 Hz, 1H), 4.76 (s, 1H), 4.23-4.09 (m, 1H), 3.98-3.84 (m, 4H), 3.40-3.26 (m, 4H), 2.48 (s, 3H), 2.28-2.12 (m, 2H), 1.99-1.82 (m, 6H) |
| 102 | 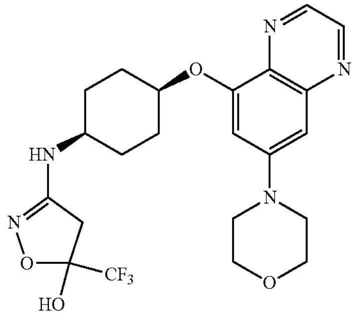 [SMILES: OC1(C(F)(F)F)CC(N[C@H]2CC[C@@H](Oc3cc(N4CCOCC4)cc4nccnc34)CC2)=NO1] | 482.36 | ($CDCl_3$) δ 8.71 (d, J = 1.9 Hz, 1H), 8.59 (d, J = 2.0 Hz, 1H), 6.96 (d, J = 2.5 Hz, 1H), 6.89 (d, J = 2.5 Hz, 1H), 4.73 (d, J = 5.7 Hz, 1H), 4.18 (d, J = 7.7 Hz, 1H), 3.93 (dd, J = 5.9, 3.8 Hz, 4H), 3.69-3.55 (m, 1H), 3.46 (d, J = 16.5 Hz, 1H), 3.41-3.28 (m, 4H), 3.08 (d, J = 16.4 Hz, 1H), 2.17 (d, J = 11.6 Hz, 2H), 2.00-1.75 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 103 | 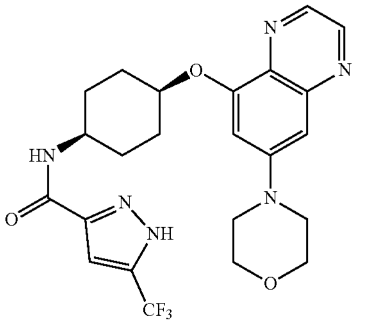 [SMILES: O=C(N[C@H]1CC[C@@H](Oc2cc(N3CCOCC3)cc3nccnc23)CC1)c1cc(C(F)(F)F)[nH]n1] | 463.36 | ($CDCl_3$) δ 8.72 (d, J = 2.0 Hz, 1H), 8.64 (d, J = 2.0 Hz, 1H), 6.99 (d, J = 2.5 Hz, 1H), 6.93 (d, J = 2.5 Hz, 1H), 5.74 (s, 1H), 4.80 (s, 1H), 4.02-3.87 (m, 4H), 3.36 (t, J = 4.9 Hz, 4H), 2.19 (s, 2H), 2.08-1.79 (m, 6H) |
| 104 | 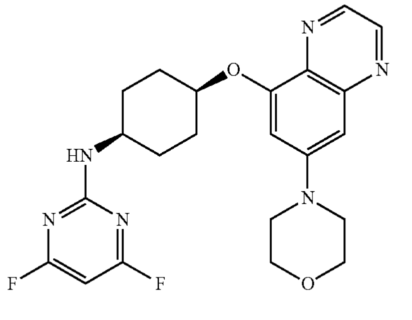 [SMILES: Fc1cc(F)nc(N[C@H]2CC[C@@H](Oc3cc(N4CCOCC4)cc4nccnc34)CC2)n1] | 443.38 | ($CDCl_3$) δ 8.73 (s, 1H), 8.68 (d, J = 2.4 Hz, 1H), 6.99 (d, J = 2.4 Hz, 1H), 6.85 (d, J = 2.4 Hz, 1H), 5.69 (d, J = 2.5 Hz, 1H), 4.76 (s, 1H), 3.84 (dd, J = 5.9, 3.9 Hz, 4H), 3.38 (dd, J = 6.0, 3.9 Hz, 4H), 2.15 (d, J = 11.1 Hz, 2H), 1.96-1.67 (m, 6H) |
| 105 | 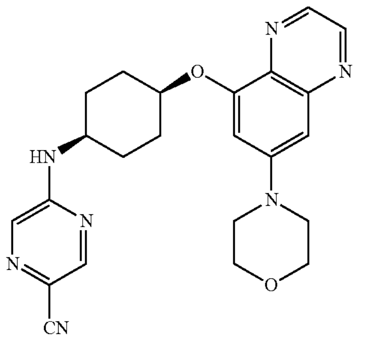 [SMILES: N#Cc1cnc(N[C@H]2CC[C@@H](Oc3cc(N4CCOCC4)cc4nccnc34)CC2)cn1] | 432.4 | ($CDCl_3$) δ 8.70 (d, J = 1.9 Hz, 1H), 8.59 (d, J = 1.9 Hz, 1H), 8.30 (d, J = 1.3 Hz, 1H), 7.89 (d, J = 1.4 Hz, 1H), 6.93 (dd, J = 18.4, 2.5 Hz, 2H), 5.52 (d, J = 7.8 Hz, 1H), 4.83 (tt, J = 4.8, 2.7 Hz, 1H), 4.19-4.01 (m, 1H), 3.96-3.87 (m, 4H), 3.39-3.26 (m, 4H), 2.31-2.14 (m, 2H), 2.09-1.78 (m, 6H) |
| 106 | 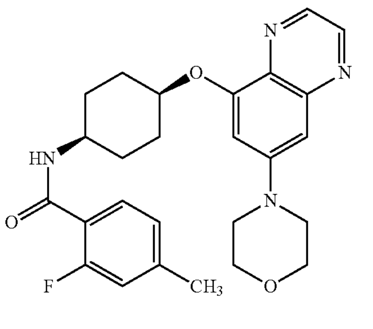 [SMILES: Cc1ccc(C(=O)N[C@H]2CC[C@@H](Oc3cc(N4CCOCC4)cc4nccnc34)CC2)c(F)c1] | 465.14 | (400 MHz, $CDCl_3$) δ 8.71 (d, J = 1.9 Hz, 1H), 8.64 (d, J = 1.9 Hz, 1H), 7.88 (dd, J = 7.4, 2.1 Hz, 1H), 7.02 (dd, J = 11.9, 8.3 Hz, 1H), 6.97 (d, J = 2.4 Hz, 1H), 6.92 (d, J = 2.4 Hz, 1H), 6.83 (dd, J = 12.4, 7.6 Hz, 1H), 4.78 (s, 1H), 4.25 (s, 1H), 4.03-3.85 (m, 4H), 3.44-3.23 (m, 4H), 2.38 (s, 3H), 2.30-2.13 (m, 2H), 2.06-1.88 (m, 6H) |

TABLE 1-continued

| Cmpd. No. | Compound | ESMS (M + H) | $^{1}$H NMR (300 MHz, unless indicated otherwise) NMR peaks given as δ values |
|---|---|---|---|
| 107 | 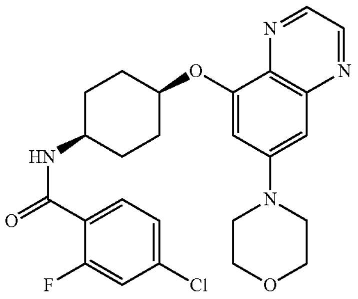 [SMILES: O=C(N[C@H]1CC[C@@H](Oc2cc(N3CCOCC3)cc3nccnc23)CC1)c1ccc(Cl)cc1F] | 485.12 | (400 MHz, $CDCl_3$) δ 8.73-8.66 (m, 1H), 8.65-8.59 (m, 1H), 8.05 (dd, J = 6.6, 2.8 Hz, 1H), 7.46-7.36 (m, 1H), 7.08 (dd, J = 11.1, 8.8 Hz, 1H), 6.95 (d, J = 2.4 Hz, 1H), 6.89 (d, J = 2.4 Hz, 1H), 6.84-6.66 (m, 1H), 4.76 (bs, 1H), 4.22 (bs, 1H), 3.96-3.87 (m, 4H), 3.37-3.28 (m, 4H), 2.28-2.10 (m, 2H), 2.01-1.86 (m, 6H) |
| 108 | 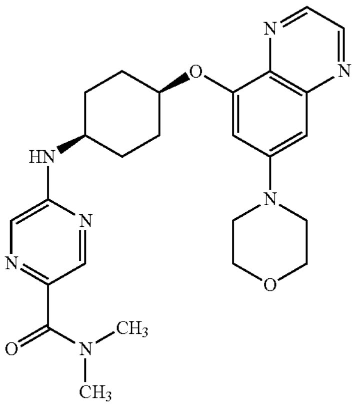 [SMILES: CN(C)C(=O)c1cnc(N[C@H]2CC[C@@H](Oc3cc(N4CCOCC4)cc4nccnc34)CC2)cn1] | 478.26 | ($CDCl_3$) δ 8.69 (d, J = 1.9 Hz, 1H), 8.61 (d, J = 2.0 Hz, 1H), 8.49 (d, J = 1.4 Hz, 1H), 7.77 (d, J = 1.4 Hz, 1H), 6.93 (dd, J = 16.1, 2.5 Hz, 2H), 5.03 (d, J = 7.9 Hz, 1H), 4.81 (td, J = 5.3, 2.6 Hz, 1H), 4.09-3.98 (m, 1H), 3.98-3.87 (m, 4H), 3.39-3.26 (m, 4H), 3.19 (s, 3H), 3.12 (s, 3H), 2.22 (dt, J = 11.2, 4.9 Hz, 2H), 2.02-1.82 (m, 6H) |
| 109 | 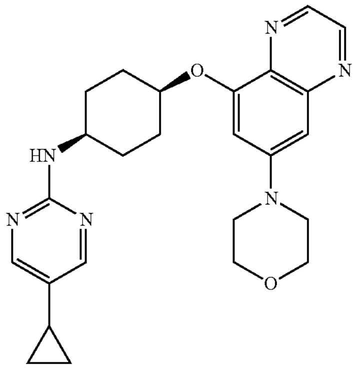 [SMILES: c1cnc2c(O[C@H]3CC[C@@H](Nc4ncc(C5CC5)cn4)CC3)cc(N3CCOCC3)cc2n1] | 447.02 | ($CDCl_3$) δ 8.70 (d, J = 1.9 Hz, 1H), 8.63 (d, J = 1.9 Hz, 1H), 8.10 (d, J = 0.5 Hz, 2H), 6.97 (d, J = 2.5 Hz, 1H), 6.92 (d, J = 2.5 Hz, 1H), 5.13 (d, J = 8.3 Hz, 1H), 4.80 (s, 1H), 4.06-3.86 (m, 5H), 3.35 (dd, J = 5.9, 3.8 Hz, 4H), 2.27-2.14 (m, 2H), 1.92 (d, J = 5.1 Hz, 6H), 1.79-1.44 (m, 6H), 1.28 (t, J = 7.1 Hz, 1H), 1.03-0.83 (m, 2H), 0.68-0.51 (m, 2H) |
| 110 | 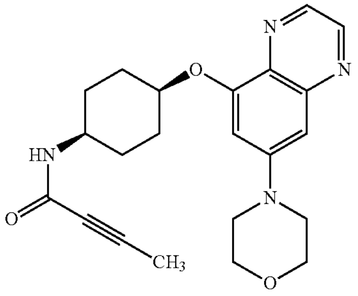 [SMILES: CC#CC(=O)N[C@H]1CC[C@@H](Oc2cc(N3CCOCC3)cc3nccnc23)CC1] | 395.19 | (400 MHz, $CDCl_3$) δ 8.69 (d, J = 1.9 Hz, 1H), 8.64-8.54 (m, 1H), 6.94 (d, J = 2.4 Hz, 1H), 6.86 (d, J = 2.5 Hz, 1H), 6.06-5.78 (m, 1H), 4.79-4.68 (m, 1H), 4.11-3.96 (m, 1H), 3.96-3.86 (m, 4H), 3.40-3.27 (m, 4H), 2.13 (dd, J = 11.0, 5.2 Hz, 2H), 1.94 (s, 3H), 1.90-1.78 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 111 | 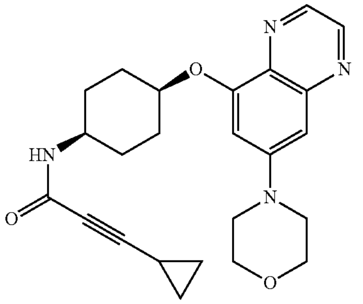 [SMILES: O=C(C#CC1CC1)N[C@H]1CC[C@@H](Oc2cc(N3CCOCC3)cc3nccnc23)CC1] | 421.19 | |
| 112 | 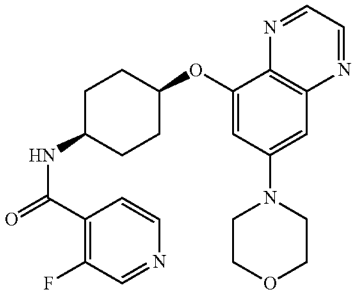 [SMILES: O=C(N[C@H]1CC[C@@H](Oc2cc(N3CCOCC3)cc3nccnc23)CC1)c1ccncc1F] | 452.18 | (400 MHz, $CDCl_3$) δ 8.70 (d, J = 1.9 Hz, 1H), 8.66-8.53 (m, 3H), 7.93 (dd, J = 6.4, 5.0 Hz, 1H), 6.95 (d, J = 2.4 Hz, 1H), 6.90 (d, J = 2.4 Hz, 1H), 6.78 (s, 1H), 4.78 (bs, 1H), 4.23 (bs, 1H), 3.97-3.85 (m, 4H), 3.38-3.27 (m, 4H), 2.30-2.15 (m, 2H), 2.02-1.86 (m, 6H) |
| 113 | 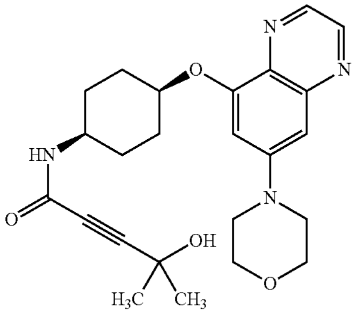 [SMILES: CC(C)(O)C#CC(=O)N[C@H]1CC[C@@H](Oc2cc(N3CCOCC3)cc3nccnc23)CC1] | 439.24 | (400 MHz, $CDCl_3$) δ 8.70 (s, 1H), 8.60 (s, 1H), 6.94 (s, 1H), 6.87 (s, 1H), 5.99 (d, J = 6.8 Hz, 1H), 4.75 (bs, 1H), 4.03 (bs, 1H), 3.99-3.83 (m, 4H), 3.43-3.21 (m, 4H), 2.33 (s, 1H), 2.24-2.04 (m, 2H), 1.94-1.74 (m, 6H), 1.56 (s, 6H) |
| 114 | 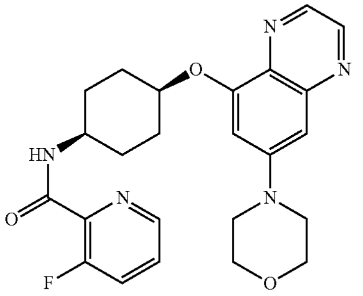 [SMILES: O=C(N[C@H]1CC[C@@H](Oc2cc(N3CCOCC3)cc3nccnc23)CC1)c1ncccc1F] | 452.15 | (400 MHz, $CDCl_3$) δ 8.70 (d, J = 1.9 Hz, 1H), 8.63 (d, J = 1.9 Hz, 1H), 8.40 (dt, J = 4.3, 1.3 Hz, 1H), 8.01 (d, J = 8.5 Hz, 1H), 7.58-7.52 (m, 1H), 7.51-7.46 (m, 1H), 6.95 (d, J = 2.4 Hz, 1H), 6.90 (d, J = 2.4 Hz, 1H), 4.74 (s, 1H), 4.29-4.17 (m, 1H), 3.97-3.88 (m, 4H), 3.39-3.30 (m, 4H), 2.25-2.16 (m, 2H), 2.06-1.88 (m, 6H) |
| 115 | 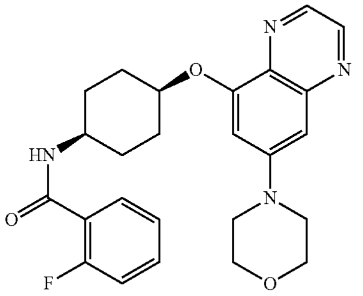 [SMILES: O=C(N[C@H]1CC[C@@H](Oc2cc(N3CCOCC3)cc3nccnc23)CC1)c1ccccc1F] | 451.16 | (400 MHz, $CDCl_3$) δ 8.69 (d, J = 1.8 Hz, 1H), 8.62 (d, J = 1.8 Hz, 1H), 8.09 (dd, J = 7.9, 6.1 Hz, 1H), 7.47 (d, J = 8.1 Hz, 1H), 7.13 (dd, J = 11.8, 7.9 Hz, 1H), 6.95 (d, J = 2.3 Hz, 1H), 6.90 (d, J = 2.3 Hz, 1H), 6.82 (s, 1H), 4.77 (s, 1H), 4.24 (s, 1H), 3.96-3.88 (m, 4H), 3.38-3.30 (m, 4H), 2.27-2.14 (m, 2H), 2.01-1.87 (m, 6H) |

TABLE 1-continued
| Cmpd. No. | Compound | ESMS (M + H) | $^1$H NMR (300 MHz, unless indicated otherwise) NMR peaks given as δ values |
|---|---|---|---|
| 116 | 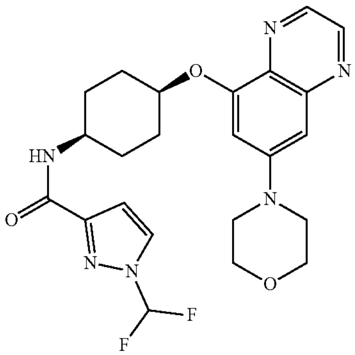 [SMILES: O=C(N[C@H]1CC[C@@H](Oc2cc(N3CCOCC3)cc3nccnc23)CC1)c1ccn(C(F)F)n1] | 473.17 | (400 MHz, $CDCl_3$) δ 8.70 (d, J = 1.9 Hz, 1H), 8.63 (d, J = 1.9 Hz, 1H), 7.83 (d, J = 2.7 Hz, 1H), 7.19-6.93 (m, 4H), 6.89 (d, J = 2.4 Hz, 1H), 4.75 (s, 1H), 4.21 (s, 1H), 3.95-3.89 (m, 4H), 3.38-3.30 (m, 4H), 2.26-2.13 (m, 2H), 2.03-1.86 (m, 6H) |
| 117 | 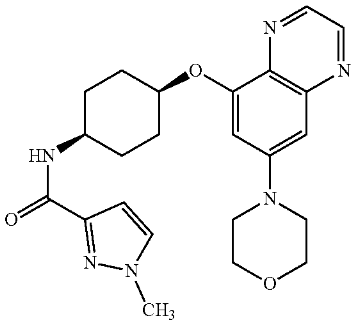 [SMILES: Cn1ccc(C(=O)N[C@H]2CC[C@@H](Oc3cc(N4CCOCC4)cc4nccnc34)CC2)n1] | 437.17 | (400 MHz, $CDCl_3$) δ 8.69 (d, J = 1.9 Hz, 1H), 8.62 (d, J = 1.9 Hz, 1H), 7.35 (d, J = 2.2 Hz, 1H), 6.99 (d, J = 8.2 Hz, 1H), 6.93 (d, J = 2.4 Hz, 1H), 6.88 (d, J = 2.4 Hz, 1H), 6.78 (d, J = 2.3 Hz, 1H), 4.73 (s, 1H), 4.26-4.14 (m, 1H), 3.96-3.87 (m, 7H), 3.36-3.29 (m, 4H), 2.23-2.12 (m, 2H), 2.01-1.82 (m, 6H) |
| 118 | 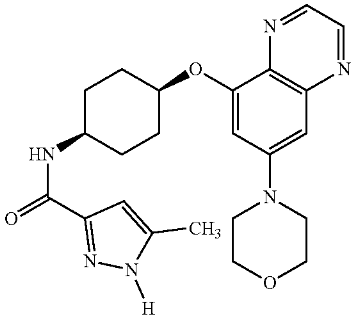 [SMILES: Cc1cc(C(=O)N[C@H]2CC[C@@H](Oc3cc(N4CCOCC4)cc4nccnc34)CC2)n[nH]1] | 437.21 | (400 MHz, $CDCl_3$) δ 10.00 (s, 1H), 8.63 (d, J = 1.9 Hz, 1H), 8.54 (d, J = 1.9 Hz, 1H), 6.93 (s, 1H), 6.87 (d, J = 2.4 Hz, 1H), 6.81 (d, J = 2.4 Hz, 1H), 6.50 (s, 1H), 4.69 (s, 1H), 4.15-4.05 (m, 1H), 3.92-3.77 (m, 4H), 3.35-3.19 (m, 4H), 2.27 (d, J = 0.5 Hz, 3H), 2.18-2.04 (m, 2H), 1.95-1.74 (m, 6H) |
| 119 | 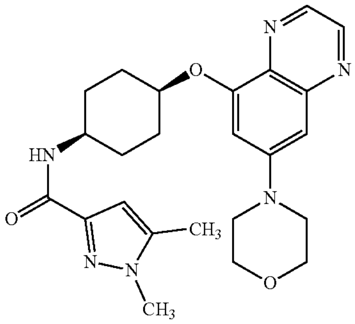 [SMILES: Cc1cc(C(=O)N[C@H]2CC[C@@H](Oc3cc(N4CCOCC4)cc4nccnc34)CC2)nn1C] | 451.25 | (400 MHz, $CDCl_3$) δ 8.70 (s, 1H), 8.63 (s, 1H), 6.99-6.50 (m, 3H), 4.76 (d, J = 20.7 Hz, 1H), 4.19 (s, 1H), 4.13-3.74 (m, 7H), 3.41-3.21 (m, 4H), 2.37-2.08 (m, 5H), 2.03-1.79 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 120 | 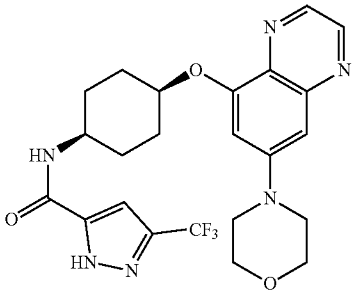 [SMILES: O=C(N[C@H]1CC[C@@H](Oc2cc(N3CCOCC3)cc3nccnc23)CC1)c1cc(C(F)(F)F)n[nH]1] | 491.18 | (400 MHz, $CDCl_3$) δ 8.73 (d, J = 1.9 Hz, 1H), 8.58 (d, J = 1.9 Hz, 1H), 6.97 (d, J = 2.4 Hz, 1H), 6.93 (s, 1H), 6.88 (d, J = 2.3 Hz, 1H), 6.53 (s, 1H), 4.79 (s, 1H), 4.24-4.15 (m, 1H), 3.96-3.86 (m, 4H), 3.40-3.27 (m, 4H), 2.22-2.15 (m, 2H), 1.94-1.82 (m, 6H) |
| 121 | 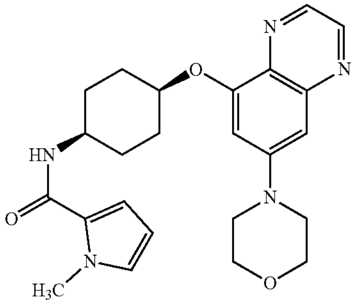 [SMILES: Cn1cccc1C(=O)N[C@H]1CC[C@@H](Oc2cc(N3CCOCC3)cc3nccnc23)CC1] | 436.18 | (400 MHz, $CDCl_3$) δ 8.70 (d, J = 1.9 Hz, 1H), 8.62 (d, J = 1.9 Hz, 1H), 6.95 (d, J = 2.4 Hz, 1H), 6.89 (d, J = 2.4 Hz, 1H), 6.71 (d, J = 2.1 Hz, 1H), 6.54 (dd, J = 3.9, 1.7 Hz, 1H), 6.09 (dd, J = 3.9, 2.6 Hz, 1H), 5.94 (d, J = 8.1 Hz, 1H), 4.76 (s, 1H), 4.11 (s, 1H), 3.98-3.86 (m, 7H), 3.39-3.27 (m, 4H), 2.27-2.14 (m, 2H), 1.95-1.83 (m, 6H) |
| 122 | 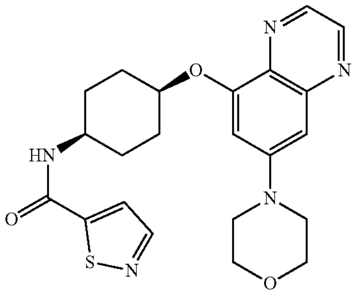 [SMILES: O=C(N[C@H]1CC[C@@H](Oc2cc(N3CCOCC3)cc3nccnc23)CC1)c1ccns1] | 440.18 | (400 MHz, $CDCl_3$) δ 8.70 (s, 1H), 8.61 (s, 1H), 8.51 (s, 1H), 7.50 (s, 1H), 6.95 (s, 1H), 6.89 (s, 1H), 6.16 (d, 1H), 4.80 (s, 1H), 4.18 (s, 1H), 4.01-3.78 (m, 4H), 3.44-3.23 (m, 4H), 2.33-2.16 (m, 2H), 1.91 (d, J = 25.1 Hz, 6H) |
| 123 | 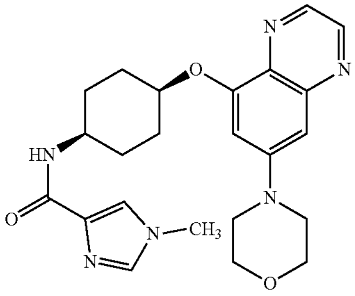 [SMILES: Cn1cnc(C(=O)N[C@H]2CC[C@@H](Oc3cc(N4CCOCC4)cc4nccnc34)CC2)c1] | 437.21 | (400 MHz, $CDCl_3$) δ 8.69 (d, J = 1.8 Hz, 1H), 8.62 (d, J = 1.9 Hz, 1H), 7.50 (d, J = 1.2 Hz, 1H), 7.36 (d, J = 1.0 Hz, 1H), 7.16 (d, J = 7.9 Hz, 1H), 6.94 (d, J = 2.3 Hz, 1H), 6.88 (d, J = 2.3 Hz, 1H), 4.78 (s, 1H), 4.20-4.09 (m, 1H), 3.95-3.87 (m, 4H), 3.73 (s, 3H), 3.38-3.28 (m, 4H), 2.25-2.14 (m, 2H), 2.00-1.82 (m, 6H) |
| 124 | 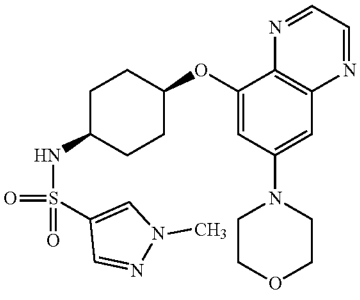 [SMILES: Cn1cc(S(=O)(=O)N[C@H]2CC[C@@H](Oc3cc(N4CCOCC4)cc4nccnc34)CC2)cn1] | 473.2 | ($CDCl_3$) δ 8.68 (d, J = 1.9 Hz, 1H), 8.58 (d, J = 1.9 Hz, 1H), 7.85-7.72 (m, 2H), 6.95 (d, J = 2.5 Hz, 1H), 6.86 (d, J = 2.5 Hz, 1H), 4.89 (d, J = 7.5 Hz, 1H), 4.71 (dq, J = 5.5, 2.7 Hz, 1H), 4.00-3.85 (m, 7H), 3.47-3.27 (m, 5H), 2.19-2.07 (m, 2H), 1.97-1.65 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 125 | 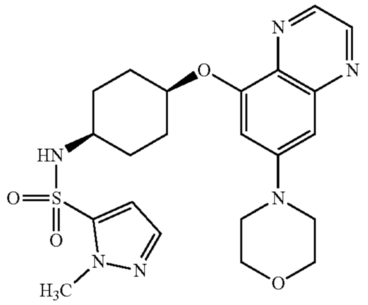 [SMILES: Cn1nccc1S(=O)(=O)N[C@H]1CC[C@@H](Oc2cc(N3CCOCC3)cc3nccnc23)CC1] | 473.25 | ($CDCl_3$) δ 8.70 (d, J = 1.9 Hz, 1H), 8.55 (d, J = 1.9 Hz, 1H), 7.46 (d, J = 2.0 Hz, 1H), 6.97 (d, J = 2.5 Hz, 1H), 6.81 (dd, J = 22.3, 2.3 Hz, 2H), 5.65-5.56 (m, 1H), 4.73 (p, J = 2.5 Hz, 1H), 4.10 (s, 3H), 3.95-3.85 (m, 4H), 3.47 (d, J = 15.3 Hz, 1H), 3.36-3.27 (m, 4H), 2.23-2.08 (m, 2H), 1.98-1.62 (m, 6H) |
| 126 | 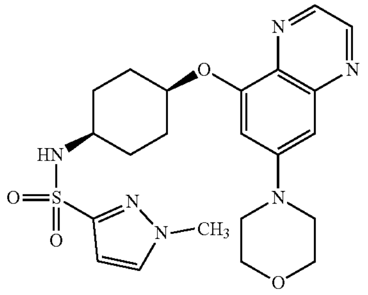 [SMILES: Cn1ccc(S(=O)(=O)N[C@H]2CC[C@@H](Oc3cc(N4CCOCC4)cc4nccnc34)CC2)n1] | 473.25 | ($CDCl_3$) δ 8.68 (d, J = 1.9 Hz, 1H), 8.58 (d, J = 1.9 Hz, 1H), 7.41 (d, J = 2.3 Hz, 1H), 6.95 (d, J = 2.5 Hz, 1H), 6.86 (d, J = 2.5 Hz, 1H), 6.69 (d, J = 2.3 Hz, 1H), 4.95 (d, J = 7.3 Hz, 1H), 4.72 (h, J = 2.6 Hz, 1H), 4.02-3.82 (m, 7H), 3.52 (d, J = 9.0 Hz, 1H), 3.37-3.27 (m, 4H), 2.12 (dt, J = 16.1, 5.7 Hz, 2H), 1.97-1.65 (m, 6H) |
| 127 | 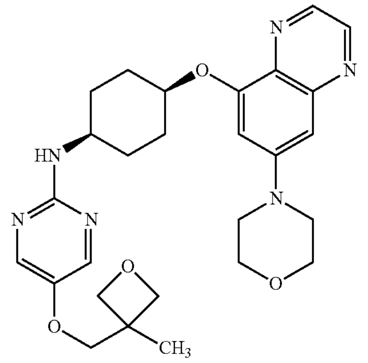 [SMILES: CC1(COc2cnc(N[C@H]3CC[C@@H](Oc4cc(N5CCOCC5)cc5nccnc45)CC3)nc2)COC1] | 507.2 | ($CDCl_3$) δ 8.62 (d, J = 1.9 Hz, 1H), 8.54 (d, J = 1.9 Hz, 1H), 8.01 (s, 2H), 6.88 (s, 1H), 6.83 (d, J = 2.5 Hz, 1H), 4.93 (d, J = 8.1 Hz, 1H), 4.72 (d, J = 5.8 Hz, 1H), 4.53 (d, J = 6.0 Hz, 2H), 4.38 (d, J = 6.0 Hz, 2H), 3.89-3.75 (m, 4H), 3.35-3.13 (m, 4H), 2.10 (s, 3H), 1.95-1.72 (m, 6H), 1.36 (s, 3H) |
| 128 | 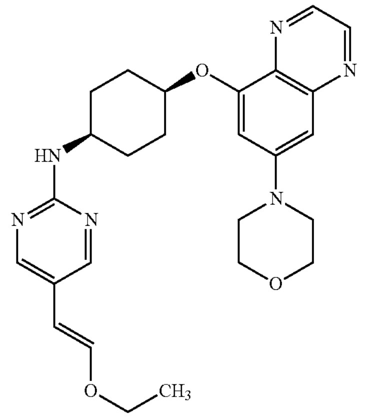 [SMILES: CCO/C=C/c1cnc(N[C@H]2CC[C@@H](Oc3cc(N4CCOCC4)cc4nccnc34)CC2)nc1] | 477.2 | ($CDCl_3$) δ 8.70 (d, J = 1.9 Hz, 1H), 8.63 (d, J = 1.9 Hz, 1H), 8.56 (s, 2H), 7.04-6.87 (m, 2H), 6.19 (d, J = 6.8 Hz, 1H), 5.15 (d, J = 8.2 Hz, 1H), 5.01 (d, J = 6.8 Hz, 1H), 4.81 (s, 1H), 4.11-3.85 (m, 6H), 3.43-3.22 (m, 4H), 2.21 (d, J = 9.5 Hz, 2H), 1.94 (t, J = 3.9 Hz, 6H), 1.36 (t, J = 7.1 Hz, 3H) |

TABLE 1-continued

| Cmpd. No. | Compound | ESMS (M + H) | $^1$H NMR (300 MHz, unless indicated otherwise) NMR peaks given as δ values |
|---|---|---|---|
| 129 | 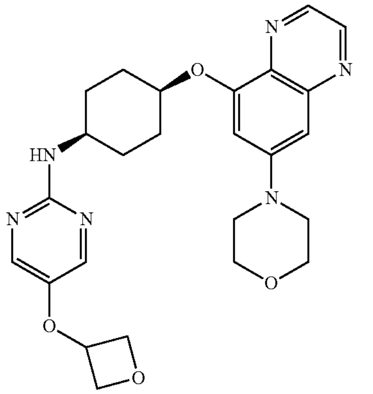 [SMILES: c1cnc2c(O[C@H]3CC[C@@H](Nc4ncc(OC5COC5)cn4)CC3)cc(N3CCOCC3)cc2n1] | 478.93 | ($CDCl_3$) δ 8.60 (d, J = 1.9 Hz, 1H), 8.53 (d, J = 1.9 Hz, 1H), 7.81 (s, 2H), 6.91-6.75 (m, 2H), 5.08-4.89 (m, 2H), 4.89-4.77 (m, 2H), 4.67 (ddd, J = 8.2, 4.7, 1.9 Hz, 3H), 3.94-3.72 (m, 5H), 3.34-3.17 (m, 4H), 2.21-2.00 (m, 2H), 1.91-1.69 (m, 6H) |
| 130 | 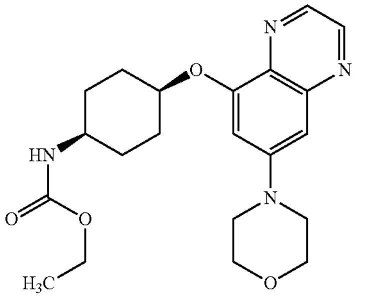 [SMILES: CCOC(=O)N[C@H]1CC[C@@H](Oc2cc(N3CCOCC3)cc3nccnc23)CC1] | 401.24 | (400 MHz, methanol-$d_4$) δ 8.69 (d, J = 2.0 Hz, 1H), 8.55 (d, J = 2.0 Hz, 1H), 7.10 (d, J = 2.3 Hz, 1H), 6.89 (d, J = 2.4 Hz, 1H), 4.85-4.82 (m, 1H), 4.07 (q, J = 6.9 Hz, 2H), 3.95-3.81 (m, 4H), 3.64-3.53 (m, 1H), 3.42-3.35 (m, 4H), 2.20-2.02 (m, 2H), 1.94-1.66 (m, 6H), 1.24 (t, J = 7.1 Hz, 3H) |
| 131 | 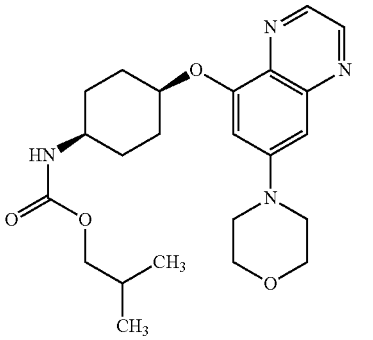 [SMILES: CC(C)COC(=O)N[C@H]1CC[C@@H](Oc2cc(N3CCOCC3)cc3nccnc23)CC1] | 429.21 | (400 MHz, $CDCl_3$) δ 8.73-8.65 (m, 1H), 8.60 (d, J = 1.9 Hz, 1H), 6.94 (d, J = 2.4 Hz, 1H), 6.87 (d, J = 2.3 Hz, 1H), 4.90-4.58 (m, 2H), 3.97-3.88 (m, 4H), 3.83 (d, J = 6.3 Hz, 2H), 3.72 (s, 1H), 3.39-3.27 (m, 4H), 2.20-2.06 (m, 2H), 1.95-1.76 (m, 7H), 0.93 (d, J = 6.7 Hz, 6H) |
| 132 | 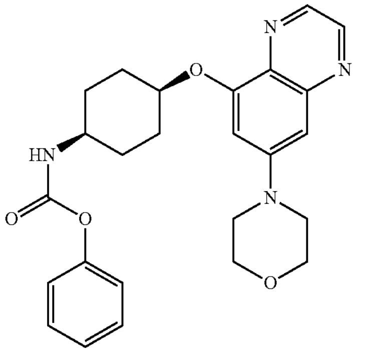 [SMILES: O=C(N[C@H]1CC[C@@H](Oc2cc(N3CCOCC3)cc3nccnc23)CC1)Oc1ccccc1] | 449.16 | (400 MHz, $CDCl_3$) δ 8.70 (d, J = 1.6 Hz, 1H), 8.62 (d, J = 1.7 Hz, 1H), 7.36 (t, J = 7.6 Hz, 2H), 7.19 (t, J = 7.3 Hz, 1H), 7.13 (d, J = 7.7 Hz, 2H), 6.96 (s, 1H), 6.89 (s, 1H), 5.12 (d, J = 7.2 Hz, 1H), 4.77 (s, 1H), 3.98-3.85 (m, 4H), 3.79 (s, 1H), 3.39-3.28 (m, 4H), 2.29-2.11 (m, 2H), 1.98-1.79 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 133 | 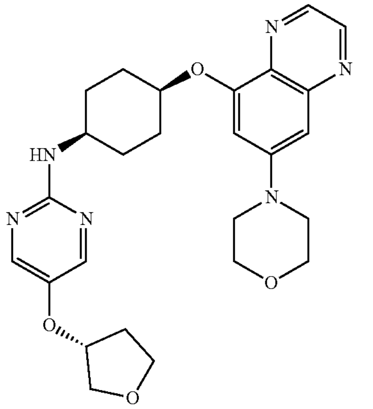 [SMILES: c1cnc2c(O[C@H]3CC[C@@H](Nc4ncc(O[C@@H]5CCOC5)cn4)CC3)cc(N3CCOCC3)cc2n1] | 493.25 | ($CDCl_3$) δ 8.71 (d, J = 1.9 Hz, 1H), 8.63 (d, J = 1.9 Hz, 1H), 8.04 (s, 2H), 6.97 (d, J = 2.5 Hz, 1H), 6.92 (d, J = 2.7 Hz, 1H), 4.79 (s, 2H), 4.07-3.83 (m, 6H), 3.42-3.25 (m, 4H), 2.29-2.02 (m, 2H), 1.92 (d, J = 4.6 Hz, 6H), 1.36-1.12 (m, 3H) |
| 134 | 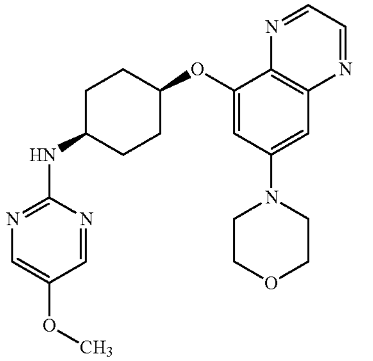 | 437.3 | ($CDCl_3$) δ 8.70 (d, J = 1.9 Hz, 1H), 8.63 (d, J = 1.9 Hz, 1H), 8.07 (s, 2H), 6.97 (d, J = 2.5 Hz, 1H), 6.92 (d, J = 2.6 Hz, 1H), 4.99 (d, J = 8.0 Hz, 1H), 4.81 (d, J = 5.9 Hz, 1H), 3.93 (dd, J = 6.0, 3.7 Hz, 5H), 3.81 (s, 3H), 3.45-3.24 (m, 4H), 2.21 (d, J = 8.6 Hz, 2H), 2.05-1.78 (m, 6H) |
| 135 | 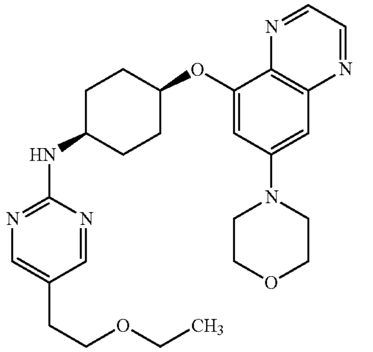 [SMILES: CCOCCc1cnc(N[C@H]2CC[C@@H](Oc3cc(N4CCOCC4)cc4nccnc34)CC2)nc1] | 479.2 | ($CDCl_3$) δ 8.70 (d, J = 1.9 Hz, 1H), 8.63 (d, J = 1.9 Hz, 1H), 8.19 (s, 2H), 6.96 (d, J = 2.5 Hz, 1H), 6.92 (d, J = 2.5 Hz, 1H), 5.12 (d, J = 8.1 Hz, 1H), 4.81 (d, J = 5.6 Hz, 1H), 4.09-3.85 (m, 5H), 3.63-3.41 (m, 4H), 3.43-3.26 (m, 4H), 2.69 (t, J = 6.6 Hz, 2H), 2.33-2.13 (m, 2H), 2.03-1.83 (m, 6H), 1.21 (t, J = 7.0 Hz, 3H) |
| 136 | 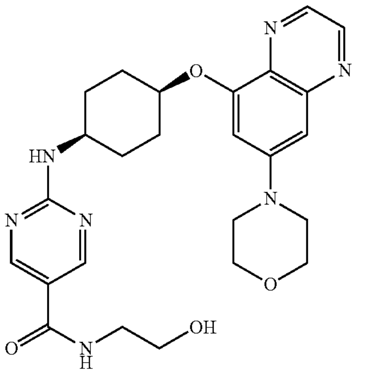 [SMILES: O=C(NCCO)c1cnc(N[C@H]2CC[C@@H](Oc3cc(N4CCOCC4)cc4nccnc34)CC2)nc1] | 494.24 | (methanol-$d_4$) δ 8.77-8.65 (m, 3H), 8.56 (d, J = 2.0 Hz, 1H), 7.11 (d, J = 2.4 Hz, 1H), 6.89 (d, J = 2.4 Hz, 1H), 4.92 (s, 1H), 4.02 (dd, J = 8.4, 4.3 Hz, 1H), 3.93-3.83 (m, 4H), 3.69 (t, J = 5.7 Hz, 2H), 3.47 (t, J = 5.8 Hz, 2H), 3.42-3.33 (m, 5H), 2.26-2.15 (m, 2H), 2.08-1.78 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 137 | 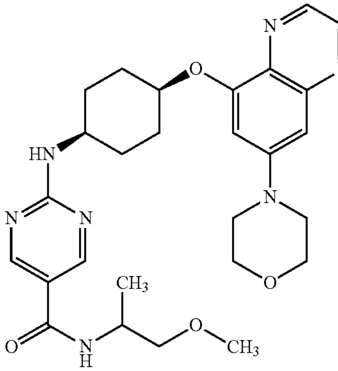 | 522.23 | ($CDCl_3$) δ 8.73-8.58 (m, 4H), 7.01-6.87 (m, 2H), 6.12 (d, J = 7.9 Hz, 1H), 5.57 (d, J = 8.1 Hz, 1H), 4.80 (s, 1H), 4.39-4.28 (m, 1H), 4.10 (d, J = 6.9 Hz, 1H), 3.97-3.87 (m, 4H), 3.54-3.29 (m, 9H), 2.21 (d, J = 9.9 Hz, 2H), 2.08-1.84 (m, 6H), 1.28 (d, J = 6.8 Hz, 3H) |
| 138 | 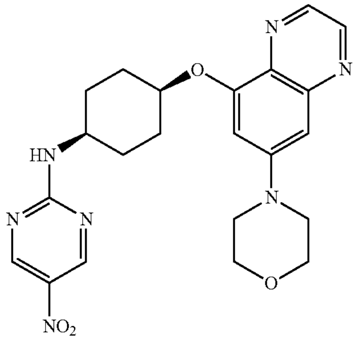 | 452.92 | ($CDCl_3$) δ 9.04 (d, J = 3.2 Hz, 1H), 8.97 (d, J = 3.3 Hz, 1H), 8.64 (d, J = 1.9 Hz, 1H), 8.55 (d, J = 1.9 Hz, 1H), 6.90 (d, J = 2.5 Hz, 1H), 6.84 (d, J = 2.5 Hz, 1H), 6.03 (d, J = 8.2 Hz, 1H), 4.77 (td, J = 5.1, 2.6 Hz, 1H), 4.15-4.07 (m, 1H), 3.92-3.79 (m, 4H), 3.35-3.15 (m, 4H), 2.25-2.11 (m, 2H), 1.95-1.69 (m, 6H) |
| 139 | 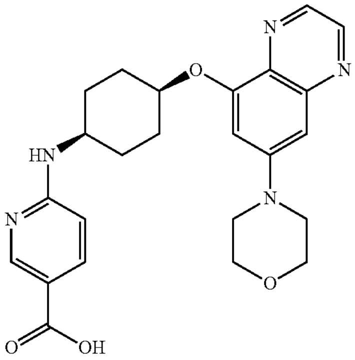 [SMILES: O=C(O)c1ccc(N[C@H]2CC[C@@H](Oc3cc(N4CCOCC4)cc4nccnc34)CC2)nc1] | 450.17 | (400 MHz, $CDCl_3$) δ 8.74 (d, J = 1.9 Hz, 2H), 8.70 (d, J = 1.9 Hz, 1H), 8.03 (dd, J = 8.9, 2.0 Hz, 1H), 6.97 (d, J = 2.4 Hz, 1H), 6.92 (d, J = 2.4 Hz, 1H), 6.37 (d, J = 8.9 Hz, 1H), 6.05 (s, 1H), 4.81 (s, 1H), 3.99-3.88 (m, 4H), 3.84 (s, 1H), 3.39-3.27 (m, 4H), 2.31-2.17 (m, 2H), 2.08-1.98 (m, 2H), 1.98-1.82 (m, 4H) |
| 140 | 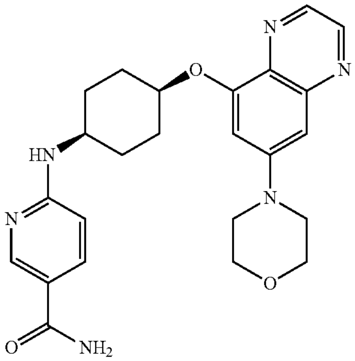 | 449.19 | (400 MHz, $CDCl_3$) δ 8.70 (d, J = 1.9 Hz, 1H), 8.61 (d, J = 1.9 Hz, 1H), 8.53 (d, J = 2.1 Hz, 1H), 7.88 (dd, J = 8.8, 2.4 Hz, 1H), 6.95 (d, J = 2.4 Hz, 1H), 6.90 (d, J = 2.4 Hz, 1H), 6.39 (d, J = 8.7 Hz, 1H), 5.61 (s, 2H), 4.97 (d, J = 7.9 Hz, 1H), 4.80 (s, 1H), 4.02-3.82 (m, 5H), 3.42-3.26 (m, 4H), 2.27-2.14 (m, 2H), 2.00-1.81 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 141 | 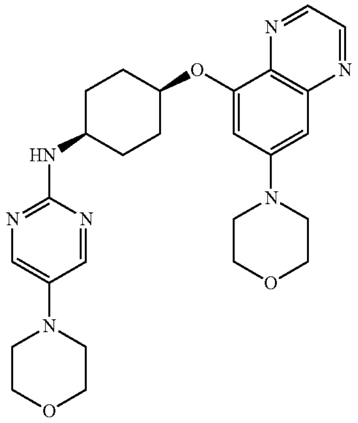 [SMILES: c1cnc2c(O[C@H]3CC[C@@H](Nc4ncc(N5CCOCC5)cn4)CC3)cc(N3CCOCC3)cc2n1] | 492.17 | ($CDCl_3$) δ 8.70 (d, J = 1.9 Hz, 1H), 8.63 (d, J = 1.9 Hz, 1H), 8.09 (s, 2H), 7.01-6.86 (m, 2H), 4.88-4.75 (m, 1H), 4.08-3.80 (m, 9H), 3.43-3.27 (m, 4H), 3.09-2.96 (m, 4H), 2.31-2.15 (m, 2H), 2.05-1.81 (m, 6H) |
| 142 | 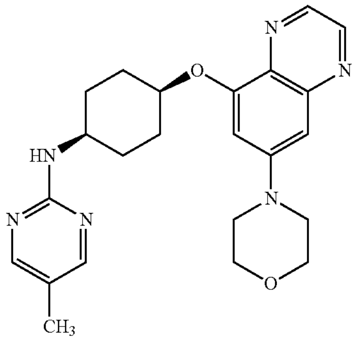 | 421.2 | ($CDCl_3$) δ 8.70 (d, J = 1.9 Hz, 1H), 8.63 (d, J = 1.9 Hz, 1H), 8.14 (d, J = 0.8 Hz, 2H), 7.01-6.90 (m, 2H), 4.81 (td, J = 5.6, 2.7 Hz, 1H), 4.08-3.84 (m, 5H), 3.43-3.26 (m, 4H), 2.25-2.10 (m, 5H), 2.02-1.83 (m, 6H) |
| 143 | 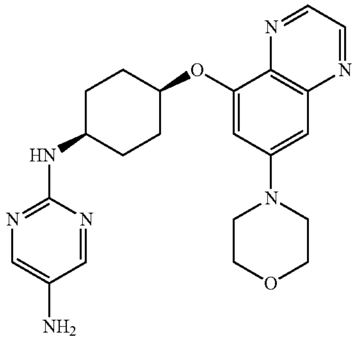 | 422.25 | ($CDCl_3$) δ 8.70 (d, J = 1.9 Hz, 1H), 8.63 (d, J = 1.9 Hz, 1H), 8.02 (s, 2H), 6.95 (dd, J = 11.8, 2.5 Hz, 2H), 4.81 (s, 2H), 4.08-3.85 (m, 5H), 3.41-3.30 (m, 4H), 2.20 (d, J = 10.1 Hz, 2H), 1.95 (d, J = 19.7 Hz, 6H), 1H NMR (300 MHz, Methanol-d4) ? 8.68 (d, J = 2.0 Hz, 1H), 8.56 (d, J = 2.1 Hz, 1H), 7.93 (s, 2H), 7.11 (d, J = 2.5 Hz, 1H), 6.88 (d, J = 2.4 Hz, 1H), 3.96-3.71 (m, 5H), 3.37 (dd, J = 5.8, 3.9 Hz, 4H), 2.27-2.04 (m, 2H), 1.98-1.74 (m, 6H). [2] |
| 144 | 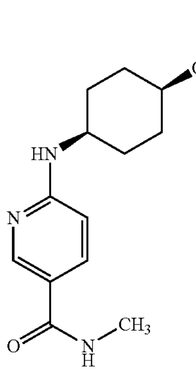 | 463.2 | (400 MHz, $CDCl_3$) δ 8.69 (d, J = 1.9 Hz, 1H), 8.61 (d, J = 1.9 Hz, 1H), 8.47 (d, J = 2.1 Hz, 1H), 7.84 (dd, J = 8.7, 2.4 Hz, 1H), 6.95 (d, J = 2.4 Hz, 1H), 6.90 (d, J = 2.4 Hz, 1H), 6.37 (d, J = 8.7 Hz, 1H), 5.94 (d, J = 3.9 Hz, 1H), 4.92 (d, J = 7.8 Hz, 1H), 4.79 (s, 1H), 3.98-3.84 (m, 5H), 3.39-3.26 (m, 4H), 2.98 (d, J = 4.8 Hz, 3H), 2.27-2.12 (m, 2H), 1.97-1.83 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 145 | 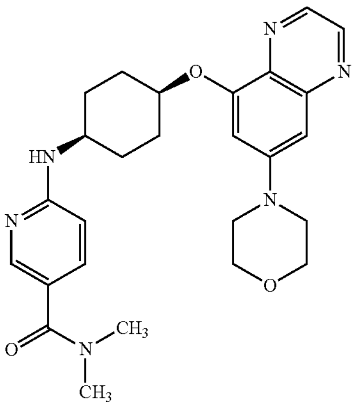 [SMILES: CN(C)C(=O)c1ccc(N[C@H]2CC[C@@H](Oc3cc(N4CCOCC4)cc4nccnc34)CC2)nc1] | 477.2 | (400 MHz, $CDCl_3$) δ 8.69 (d, J = 1.9 Hz, 1H), 8.61 (d, J = 1.9 Hz, 1H), 8.20 (s, 1H), 7.61 (d, J = 8.2 Hz, 1H), 6.95 (d, J = 2.4 Hz, 1H), 6.91 (d, J = 2.4 Hz, 1H), 6.43 (d, J = 7.9 Hz, 1H), 4.81 (s, 1H), 3.98-3.81 (m, 5H), 3.40-3.27 (m, 4H), 3.09 (s, 6H), 2.27-2.15 (m, 2H), 1.99-1.83 (m, 6H) |
| 146 | 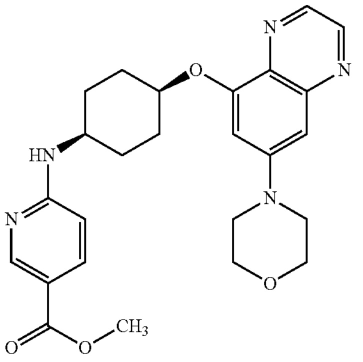 [SMILES: COC(=O)c1ccc(N[C@H]2CC[C@@H](Oc3cc(N4CCOCC4)cc4nccnc34)CC2)nc1] | 464.17 | ($CDCl_3$) δ 8.76 (d, J = 2.0 Hz, 1H), 8.71 (d, J = 1.9 Hz, 1H), 8.63 (d, J = 1.9 Hz, 1H), 7.99 (dd, J = 8.8, 2.2 Hz, 1H), 6.97 (d, J = 2.5 Hz, 1H), 6.92 (d, J = 2.5 Hz, 1H), 6.38 (d, J = 8.9 Hz, 1H), 5.13 (s, 1H), 4.82 (s, 1H), 4.11-3.73 (m, 8H), 3.44-3.27 (m, 4H), 2.30-2.17 (m, 2H), 2.07-1.79 (m, 6H) |
| 147 | 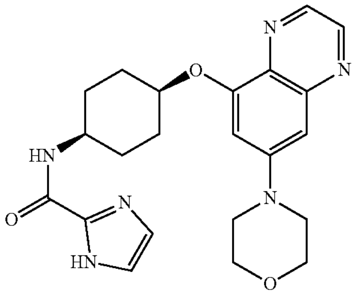 [SMILES: O=C(N[C@H]1CC[C@@H](Oc2cc(N3CCOCC3)cc3nccnc23)CC1)c1ncc[nH]1] | 423.2 | (400 MHz, $CDCl_3$) δ 10.77-10.42 (m, 1H), 8.70 (d, J = 1.9 Hz, 1H), 8.63 (d, J = 1.9 Hz, 1H), 7.30 (d, J = 8.2 Hz, 1H), 7.15 (d, J = 5.7 Hz, 2H), 6.95 (d, J = 2.5 Hz, 1H), 6.90 (d, J = 2.4 Hz, 1H), 4.83 (s, 1H), 4.19-4.05 (m, 1H), 3.99-3.84 (m, 4H), 3.40-3.27 (m, 4H), 2.31-2.15 (m, 2H), 2.06-1.93 (m, 2H), 1.93-1.79 (m, 4H) |
| 148 | 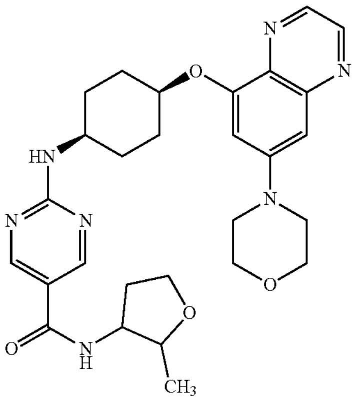 [SMILES: CC1OCCC1NC(=O)c1cnc(N[C@H]2CC[C@@H](Oc3cc(N4CCOCC4)cc4nccnc34)CC2)nc1] | 534.28 | (DMSO-$d_6$) δ 8.73 (d, J = 1.5 Hz, 3H), 8.59 (d, J = 1.9 Hz, 1H), 8.12 (d, J = 8.2 Hz, 1H), 7.84 (d, J = 7.4 Hz, 1H), 7.14 (d, J = 2.4 Hz, 1H), 6.84 (d, J = 2.3 Hz, 1H), 4.93 (s, 1H), 4.51 (ddd, J = 13.3, 8.2, 5.2 Hz, 1H), 4.01-3.74 (m, 6H), 3.55 (q, J = 8.0 Hz, 1H), 3.38-3.27 (m, 4H), 2.33-2.15 (m, 1H), 2.06 (d, J = 11.1 Hz, 2H), 1.96-1.67 (m, 8H), 1.02 (d, J = 6.3 Hz, 3H) |

TABLE 1-continued

| Cmpd. No. | Compound | ESMS (M + H) | $^{1}H$ NMR (300 MHz, unless indicated otherwise) NMR peaks given as δ values |
|---|---|---|---|
| 149 | 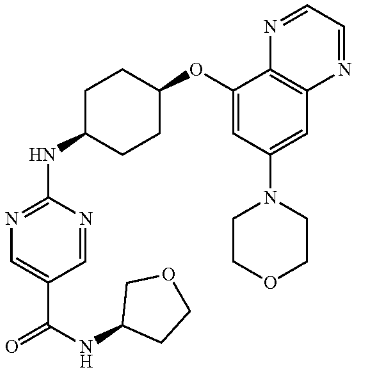 [SMILES: O=C(N[C@@H]1CCOC1)c1cnc(N[C@H]2CC[C@@H](Oc3cc(N4CCOCC4)cc4nccnc34)CC2)nc1] | 520.33 | (DMSO-$d_6$) δ 8.76-8.67 (m, 3H), 8.59 (d, J = 1.9 Hz, 1H), 8.32 (d, J = 6.5 Hz, 1H), 7.84 (d, J = 7.3 Hz, 1H), 7.14 (d, J = 2.5 Hz, 1H), 6.84 (d, J = 2.3 Hz, 1H), 4.93 (s, 1H), 4.49-4.37 (m, 1H), 3.96-3.63 (m, 9H), 3.55 (dd, J = 8.9, 4.2 Hz, 1H), 3.38-3.27 (m, 4H), 2.23-2.00 (m, 4H), 1.95-1.71 (m, 6H) |
| 150 | 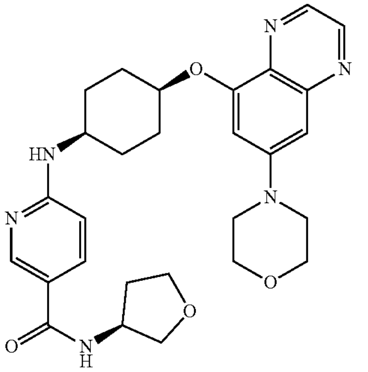 [SMILES: O=C(N[C@H]1CCOC1)c1ccc(N[C@H]2CC[C@@H](Oc3cc(N4CCOCC4)cc4nccnc34)CC2)nc1] | 520.33 | (DMSO-$d_6$) δ 8.76-8.67 (m, 3H), 8.59 (d, J = 1.9 Hz, 1H), 8.32 (d, J = 6.5 Hz, 1H), 7.84 (d, J = 7.3 Hz, 1H), 7.14 (d, J = 2.5 Hz, 1H), 6.84 (d, J = 2.3 Hz, 1H), 4.93 (s, 1H), 4.49-4.37 (m, 1H), 3.96-3.63 (m, 9H), 3.55 (dd, J = 8.9, 4.2 Hz, 1H), 3.38-3.27 (m, 4H), 2.23-2.00 (m, 4H), 1.95-1.71 (m, 6H) |
| 151 | 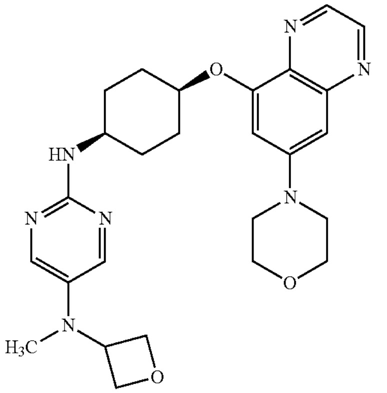 [SMILES: CN(c1cnc(N[C@H]2CC[C@@H](Oc3cc(N4CCOCC4)cc4nccnc34)CC2)nc1)C1COC1] | | ($CDCl_3$) δ 8.70 (d, J = 1.9 Hz, 1H), 8.64 (d, J = 2.0 Hz, 1H), 7.93 (s, 2H), 7.02-6.90 (m, 2H), 4.82 (t, J = 6.7 Hz, 3H), 4.66 (t, J = 6.4 Hz, 2H), 4.14 (q, J = 7.1 Hz, 1H), 4.08-3.89 (m, 5H), 3.42-3.25 (m, 4H), 2.80 (s, 3H), 2.22 (s, 2H), 2.05-1.79 (m, 6H) |
| 152 | 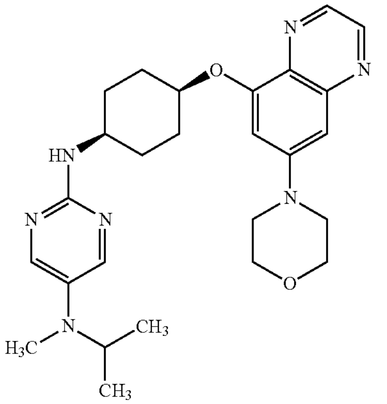 [SMILES: CC(C)N(C)c1cnc(N[C@H]2CC[C@@H](Oc3cc(N4CCOCC4)cc4nccnc34)CC2)nc1] | 464.21 | ($CDCl_3$) δ 8.70 (d, J = 1.9 Hz, 1H), 8.64 (d, J = 1.9 Hz, 1H), 7.94 (s, 2H), 6.99-6.90 (m, 2H), 4.82 (s, 1H), 4.05-3.87 (m, 5H), 3.44 (q, J = 6.3 Hz, 1H), 3.39-3.26 (m, 4H), 2.23 (d, J = 12.4 Hz, 2H), 2.03-1.82 (m, 6H), 1.23 (d, J = 6.3 Hz, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 153 | 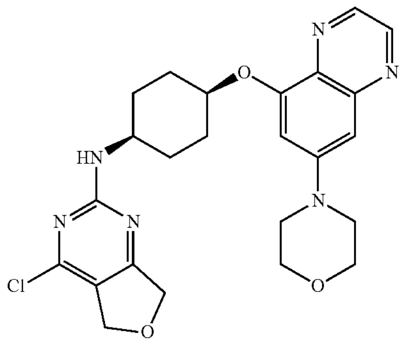 [SMILES: Clc1nc(N[C@H]2CC[C@@H](Oc3cc(N4CCOCC4)cc4nccnc34)CC2)nc2c1COC2] | 483.1 | ($CDCl_3$) δ 8.64-8.49 (m, 2H), 6.93 (d, J = 3.9 Hz, 1H), 6.83 (d, J = 2.4 Hz, 1H), 5.27 (d, J = 8.1 Hz, 1H), 4.94 (t, J = 1.9 Hz, 2H), 4.81 (t, J = 1.9 Hz, 2H), 4.72 (s, 1H), 3.96 (s, 1H), 3.89-3.78 (m, 4H), 3.37-3.25 (m, 4H), 2.11 (s, 2H), 1.82 (d, J = 5.1 Hz, 6H) |
| 154 | 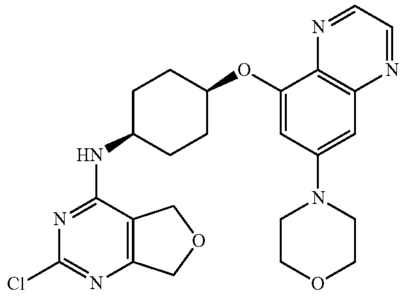 [SMILES: Clc1nc2c(c(N[C@H]3CC[C@@H](Oc4cc(N5CCOCC5)cc5nccnc45)CC3)n1)COC2] | 483.1 | ($CDCl_3$) δ 8.68 (dd, J = 8.7, 2.0 Hz, 1H), 8.56 (d, J = 2.0 Hz, 1H), 6.92 (d, J = 2.3 Hz, 1H), 6.84 (d, J = 2.4 Hz, 1H), 4.92 (t, J = 2.7 Hz, 2H), 4.82 (t, J = 2.7 Hz, 2H), 4.75 (s, 1H), 3.94-3.81 (m, 4H), 3.35-3.15 (m, 4H), 2.14 (d, J = 12.0 Hz, 2H), 1.82 (d, J = 17.3 Hz, 6H) |
| 155 | 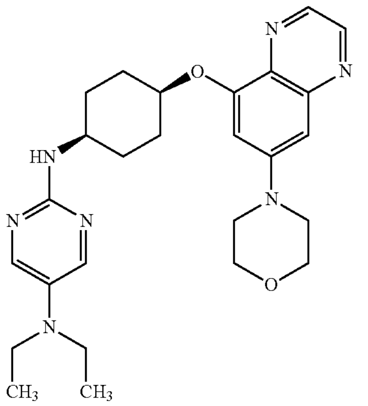 [SMILES: CCN(CC)c1cnc(N[C@H]2CC[C@@H](Oc3cc(N4CCOCC4)cc4nccnc34)CC2)nc1] | 478.3 | ($CDCl_3$) δ 8.71 (d, J = 1.9 Hz, 1H), 8.64 (d, J = 1.9 Hz, 1H), 7.02-6.89 (m, 2H), 4.83 (s, 1H), 4.08-3.87 (m, 5H), 3.44-3.33 (m, 4H), 3.27 (d, J = 26.0 Hz, 4H), 2.23 (d, J = 9.8 Hz, 2H), 2.05-1.80 (m, 6H), 1.14 (s, 6H) |
| 156 | 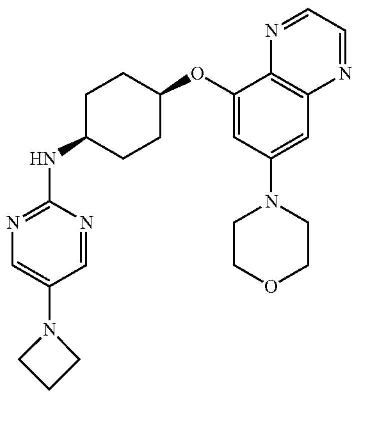 [SMILES: c1cnc2c(O[C@H]3CC[C@@H](Nc4ncc(N5CCC5)cn4)CC3)cc(N3CCOCC3)cc2n1] | 462.23 | ($CDCl_3$) δ 8.70 (d, J = 2.0 Hz, 1H), 8.63 (d, J = 1.9 Hz, 1H), 7.72 (s, 2H), 6.96 (d, J = 2.5 Hz, 1H), 6.92 (d, J = 2.5 Hz, 1H), 5.03 (s, 1H), 4.80 (q, J = 4.4 Hz, 1H), 4.03-3.89 (m, 4H), 3.83 (t, J = 7.1 Hz, 4H), 3.44-3.29 (m, 4H), 2.41 (dq, J = 8.6, 7.1 Hz, 2H), 2.20 (q, J = 5.9 Hz, 2H), 1.99-1.81 (m, 6H) |

TABLE 1-continued
| Cmpd. No. | Compound | ESMS (M + H) | $^1$H NMR (300 MHz, unless indicated otherwise) NMR peaks given as δ values |
|---|---|---|---|
| 157 | 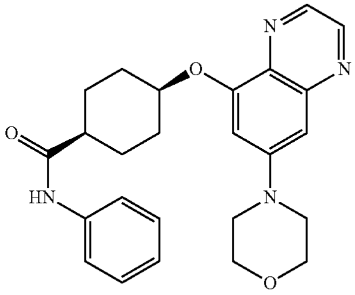 | 433.2 | |
| 158 | 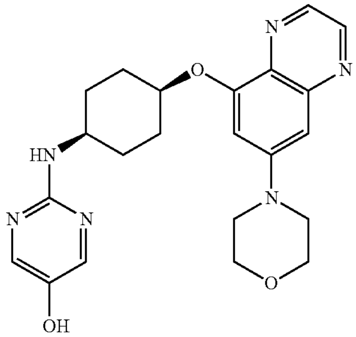 [SMILES: Oc1cnc(N[C@H]2CC[C@@H](Oc3cc(N4CCOCC4)cc4nccnc34)CC2)nc1] | | ($CDCl_3$) δ 8.71 (d, J = 2.0 Hz, 1H), 8.64 (d, J = 1.9 Hz, 1H), 8.41 (s, 2H), 6.97 (d, J = 2.4 Hz, 1H), 6.93 (d, J = 2.5 Hz, 1H), 5.32 (d, J = 8.1 Hz, 1H), 4.82 (s, 1H), 4.07 (s, 1H), 4.00-3.88 (m, 4H), 3.43-3.29 (m, 4H), 2.22 (s, 2H), 2.06-1.81 (m, 6H) |
| 159 | 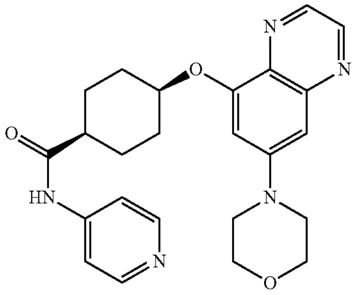 | 434.24 | |
| 160 | 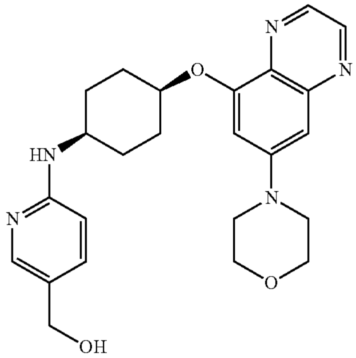 [SMILES: OCc1ccc(N[C@H]2CC[C@@H](Oc3cc(N4CCOCC4)cc4nccnc34)CC2)nc1] | 436.2 | (400 MHz, $CDCl_3$) δ 8.69 (d, J = 1.9 Hz, 1H), 8.61 (d, J = 1.9 Hz, 1H), 8.05 (d, J = 2.2 Hz, 1H), 7.46 (dd, J = 8.5, 2.3 Hz, 1H), 6.94 (d, J = 2.4 Hz, 1H), 6.90 (d, J = 2.4 Hz, 1H), 6.39 (d, J = 8.6 Hz, 1H), 4.77 (s, 1H), 4.53 (s, 2H), 3.95-3.87 (m, 5H), 3.36-3.32 (m, 4H), 2.25-2.12 (m, 2H), 1.90 (d, J = 4.4 Hz, 6H) |

TABLE 1-continued

| Cmpd. No. | Compound | ESMS (M + H) | $^{1}$H NMR (300 MHz, unless indicated otherwise) NMR peaks given as δ values |
|---|---|---|---|
| 161 | 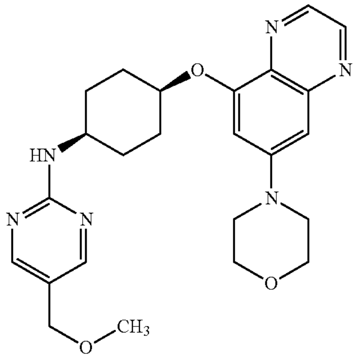 [SMILES: COCc1cnc(N[C@H]2CC[C@@H](Oc3cc(N4CCOCC4)cc4nccnc34)CC2)nc1] | 451.28 | ($CDCl_3$) δ 8.69 (d, J = 1.9 Hz, 1H), 8.61 (d, J = 1.9 Hz, 1H), 8.26 (s, 2H), 6.95 (d, J = 2.5 Hz, 1H), 6.90 (d, J = 2.6 Hz, 1H), 5.23 (d, J = 8.1 Hz, 1H), 4.80 (d, J = 5.8 Hz, 1H), 4.26 (s, 2H), 4.03 (s, 1H), 3.97-3.85 (m, 4H), 3.44-3.21 (m, 7H), 2.32-2.09 (m, 2H), 2.06-1.70 (m, 6H) |
| 162 | 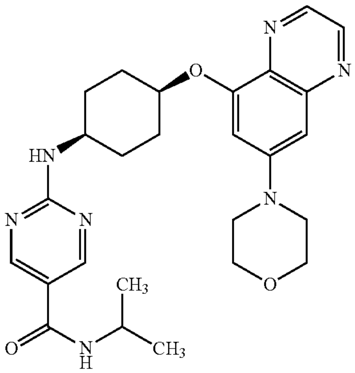 [SMILES: CC(C)NC(=O)c1cnc(N[C@H]2CC[C@@H](Oc3cc(N4CCOCC4)cc4nccnc34)CC2)nc1] | 492.29 | (DMSO-$d_6$) δ 8.81-8.64 (m, 3H), 8.58 (d, J = 1.9 Hz, 1H), 7.99 (d, J = 7.6 Hz, 1H), 7.76 (d, J = 7.4 Hz, 1H), 7.14 (d, J = 2.5 Hz, 1H), 6.84 (d, J = 2.3 Hz, 1H), 4.92 (s, 1H), 3.98-3.84 (m, 1H), 4.05 (dq, J = 13.5, 6.7 Hz, 1H), 3.79 (d, J = 9.6 Hz, 4H), 3.32 (d, J = 8.2 Hz, 4H), 2.06 (d, J = 11.8 Hz, 2H), 1.96-1.66 (m, 6H), 1.14 (d, J = 6.6 Hz, 6H) |
| 163 | 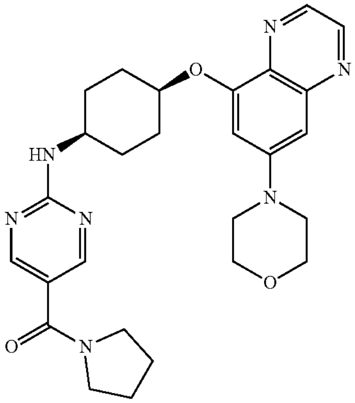 [SMILES: O=C(c1cnc(N[C@H]2CC[C@@H](Oc3cc(N4CCOCC4)cc4nccnc34)CC2)nc1)N1CCCC1] | 504.26 | ($CDCl_3$) δ 8.69 (d, J = 1.9 Hz, 1H), 8.65-8.53 (m, 3H), 6.93 (dd, J = 14.6, 2.5 Hz, 2H), 5.48 (d, J = 8.0 Hz, 1H), 4.81 (d, J = 6.1 Hz, 1H), 4.19-4.03 (m, 1H), 3.92 (dd, J = 6.0, 3.7 Hz, 4H), 3.65-3.54 (m, 4H), 3.34 (dd, J = 5.9, 3.7 Hz, 4H), 2.27-2.15 (m, 2H), 2.08-1.81 (m, 10H) |
| 164 | 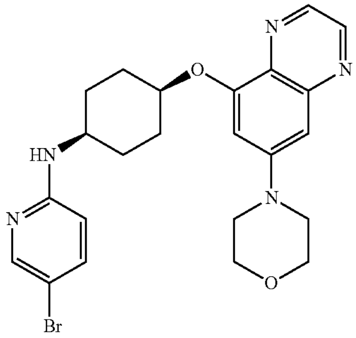 [SMILES: Brc1ccc(N[C@H]2CC[C@@H](Oc3cc(N4CCOCC4)cc4nccnc34)CC2)nc1] | 484.12 | (400 MHz, $CDCl_3$) δ 8.60 (d, J = 1.9 Hz, 1H), 8.52 (d, J = 1.9 Hz, 1H), 8.01 (d, J = 2.1 Hz, 1H), 7.35 (dd, J = 8.8, 2.5 Hz, 1H), 6.86 (d, J = 2.5 Hz, 1H), 6.80 (d, J = 2.5 Hz, 1H), 6.20 (d, J = 8.4 Hz, 1H), 4.68 (s, 1H), 4.47 (d, J = 8.0 Hz, 1H), 3.92-3.80 (m, 4H), 3.74 (s, 1H), 3.34-3.14 (m, 4H), 2.18-2.02 (m, 2H), 1.94-1.67 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 165 | 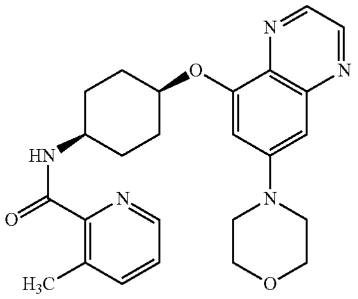 [SMILES: Cc1cccnc1C(=O)N[C@H]1CC[C@@H](Oc2cc(N3CCOCC3)cc3nccnc23)CC1] | 448.15 | (400 MHz, $CDCl_3$) δ 8.69 (d, J = 1.9 Hz, 1H), 8.63 (d, J = 1.9 Hz, 1H), 8.44-8.37 (m, 1H), 8.33 (d, J = 8.1 Hz, 1H), 7.58 (dd, J = 7.8, 0.9 Hz, 1H), 7.31 (dd, J = 7.7, 4.6 Hz, 1H), 6.95 (d, J = 2.4 Hz, 1H), 6.90 (d, J = 2.4 Hz, 1H), 4.75 (s, 1H), 4.25-4.10 (m, 1H), 3.97-3.85 (m, 4H), 3.41-3.26 (m, 4H), 2.75 (s, 3H), 2.29-2.13 (m, 2H), 2.06-1.85 (m, 6H) |
| 166 | 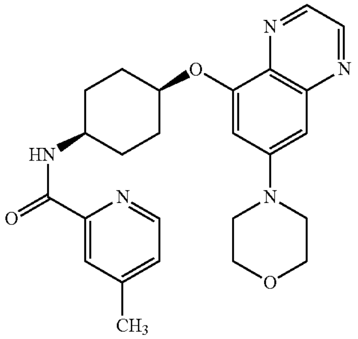 [SMILES: Cc1ccnc(C(=O)N[C@H]2CC[C@@H](Oc3cc(N4CCOCC4)cc4nccnc34)CC2)c1] | 448.19 | (400 MHz, $CDCl_3$) δ 8.69 (d, J = 1.9 Hz, 1H), 8.63 (d, J = 1.9 Hz, 1H), 8.41 (d, J = 4.5 Hz, 1H), 8.21 (d, J = 8.0 Hz, 1H), 8.08-7.98 (m, 1H), 7.25-7.22 (m, 1H), 6.95 (d, J = 2.5 Hz, 1H), 6.90 (d, J = 2.4 Hz, 1H), 4.76 (s, 1H), 4.27-4.15 (m, 1H), 3.98-3.86 (m, 4H), 3.40-3.29 (m, 4H), 2.43 (s, 3H), 2.29-2.16 (m, 2H), 2.07-1.86 (m, 6H) |
| 167 | 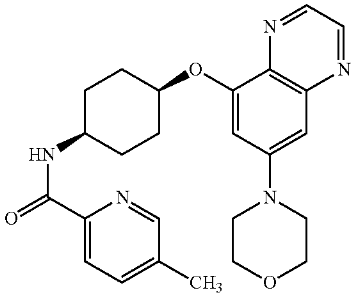 [SMILES: Cc1ccc(C(=O)N[C@H]2CC[C@@H](Oc3cc(N4CCOCC4)cc4nccnc34)CC2)nc1] | 448.19 | (400 MHz, $CDCl_3$) δ 8.70 (d, J = 1.9 Hz, 1H), 8.63 (d, J = 1.9 Hz, 1H), 8.37 (dd, J = 1.4, 0.7 Hz, 1H), 8.16 (d, J = 8.4 Hz, 1H), 8.09 (d, J = 8.0 Hz, 1H), 7.66-7.61 (m, 1H), 6.95 (d, J = 2.4 Hz, 1H), 6.90 (d, J = 2.4 Hz, 1H), 4.75 (s, 1H), 4.29-4.16 (m, 1H), 3.97-3.86 (m, 4H), 3.39-3.29 (m, 4H), 2.41 (s, 3H), 2.28-2.15 (m, 2H), 2.04-1.84 (m, 6H) |
| 168 | 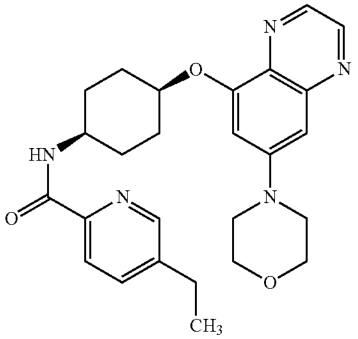 [SMILES: CCc1ccc(C(=O)N[C@H]2CC[C@@H](Oc3cc(N4CCOCC4)cc4nccnc34)CC2)nc1] | 462.16 | (400 MHz, $CDCl_3$) δ 8.69 (d, J = 1.8 Hz, 1H), 8.63 (d, J = 1.9 Hz, 1H), 8.39 (d, J = 1.6 Hz, 1H), 8.17 (d, J = 8.6 Hz, 1H), 8.11 (d, J = 8.0 Hz, 1H), 7.66 (dd, J = 7.9, 2.0 Hz, 1H), 6.95 (d, J = 2.3 Hz, 1H), 6.90 (d, J = 2.4 Hz, 1H), 4.76 (s, 1H), 4.31-4.14 (m, 1H), 4.00-3.85 (m, 4H), 3.42-3.25 (m, 4H), 2.73 (q, J = 7.6 Hz, 2H), 2.30-2.14 (m, 2H), 1.99 (ddd, J = 34.6, 19.6, 10.3 Hz, 7H), 1.29 (t, J = 7.6 Hz, 3H) |

TABLE 1-continued

| Cmpd. No. | Compound | ESMS (M + H) | $^{1}$H NMR (300 MHz, unless indicated otherwise) NMR peaks given as δ values |
|---|---|---|---|
| 169 | 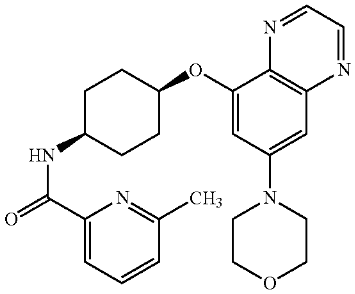 [SMILES: Cc1cccc(C(=O)N[C@H]2CC[C@@H](Oc3cc(N4CCOCC4)cc4nccnc34)CC2)n1] | 448.19 | (400 MHz, $CDCl_3$) δ 8.70 (d, J = 1.9 Hz, 1H), 8.64 (d, J = 1.9 Hz, 1H), 8.24 (d, J = 7.8 Hz, 1H), 8.01 (d, J = 7.5 Hz, 1H), 7.72 (t, J = 7.7 Hz, 1H), 7.27 (d, J = 6.6 Hz, 1H), 6.95 (d, J = 2.4 Hz, 1H), 6.90 (d, J = 2.4 Hz, 1H), 4.82-4.68 (m, 1H), 4.27-4.13 (m, 1H), 3.98-3.86 (m, 4H), 3.41-3.28 (m, 4H), 2.60 (s, 3H), 2.30-2.18 (m, 2H), 2.09-1.88 (m, 6H) |
| 170 | 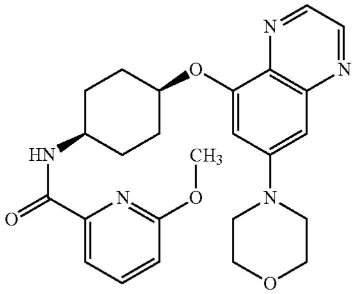 [SMILES: COc1cccc(C(=O)N[C@H]2CC[C@@H](Oc3cc(N4CCOCC4)cc4nccnc34)CC2)n1] | 464.17 | (400 MHz, $CDCl_3$) δ 8.69 (d, J = 1.8 Hz, 1H), 8.61 (d, J = 1.9 Hz, 1H), 7.90 (d, J = 7.2 Hz, 1H), 7.83-7.78 (m, 1H), 7.76-7.69 (m, 1H), 6.96 (d, J = 2.3 Hz, 1H), 6.94-6.86 (m, 2H), 4.77 (s, 1H), 4.17 (s, 1H), 4.00 (s, 3H), 3.95-3.86 (m, 4H), 3.40-3.29 (m, 4H), 2.30-2.17 (m, 2H), 2.06-1.88 (m, 6H) |
| 171 | 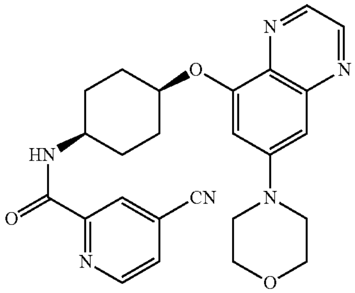 [SMILES: N#Cc1ccnc(C(=O)N[C@H]2CC[C@@H](Oc3cc(N4CCOCC4)cc4nccnc34)CC2)c1] | 459.17 | (400 MHz, $CDCl_3$) δ 8.76 (dd, J = 4.9, 0.8 Hz, 1H), 8.70 (d, J = 1.9 Hz, 1H), 8.62 (d, J = 1.9 Hz, 1H), 8.48-8.38 (m, 1H), 8.09 (d, J = 8.0 Hz, 1H), 7.67 (dd, J = 4.9, 1.6 Hz, 1H), 6.96 (d, J = 2.4 Hz, 1H), 6.90 (d, J = 2.4 Hz, 1H), 4.76 (s, 1H), 4.31-4.14 (m, 1H), 4.01-3.83 (m, 4H), 3.43-3.26 (m, 4H), 2.31-2.15 (m, 2H), 2.08-1.87 (m, 6H) |
| 172 | 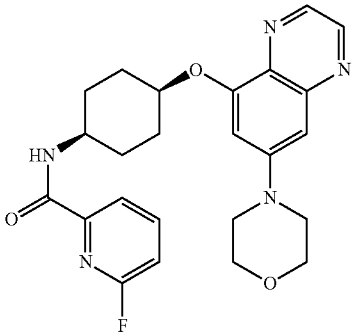 [SMILES: O=C(N[C@H]1CC[C@@H](Oc2cc(N3CCOCC3)cc3nccnc23)CC1)c1cccc(F)n1] | 452.22 | (400 MHz, $CDCl_3$) δ 8.70 (d, J = 1.9 Hz, 1H), 8.64 (d, J = 1.9 Hz, 1H), 8.11 (dd, J = 7.4, 1.4 Hz, 1H), 7.96 (dd, J = 15.6, 7.7 Hz, 1H), 7.82 (d, J = 7.7 Hz, 1H), 7.09 (dd, J = 8.1, 1.8 Hz, 1H), 6.96 (d, J = 2.4 Hz, 1H), 6.91 (d, J = 2.4 Hz, 1H), 4.80 (s, 1H), 4.26-4.09 (m, 1H), 3.99-3.86 (m, 4H), 3.41-3.25 (m, 4H), 2.31-2.17 (m, 2H), 2.05-1.86 (m, 6H) |
| 173 | 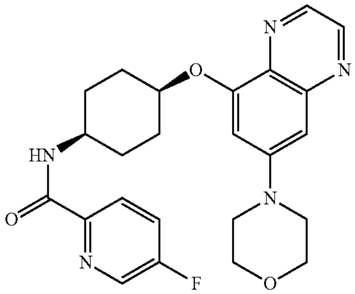 [SMILES: O=C(N[C@H]1CC[C@@H](Oc2cc(N3CCOCC3)cc3nccnc23)CC1)c1ccc(F)cn1] | 452.22 | |

TABLE 1-continued
| Cmpd. No. | Compound | ESMS (M + H) | $^1$H NMR (300 MHz, unless indicated otherwise) NMR peaks given as δ values |
|---|---|---|---|
| 174 | 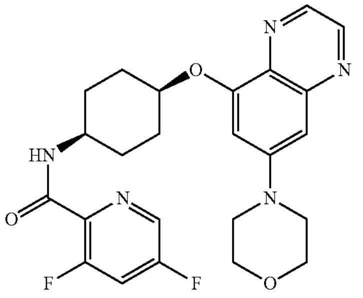 [SMILES: O=C(N[C@H]1CC[C@@H](Oc2cc(N3CCOCC3)cc3nccnc23)CC1)c1ncc(F)cc1F] | 470.22 | (400 MHz, $CDCl_3$) δ 8.69 (d, J = 1.9 Hz, 1H), 8.62 (d, J = 1.9 Hz, 1H), 8.30 (d, J = 2.1 Hz, 1H), 7.80 (d, J = 7.9 Hz, 1H), 7.32 (ddd, J = 10.3, 8.1, 2.3 Hz, 1H), 6.95 (d, J = 2.4 Hz, 1H), 6.89 (d, J = 2.4 Hz, 1H), 4.74 (s, 1H), 4.27-4.15 (m, 1H), 4.00-3.86 (m, 4H), 3.41-3.27 (m, 4H), 2.27-2.13 (m, 2H), 2.08-1.86 (m, 6H) |
| 175 | 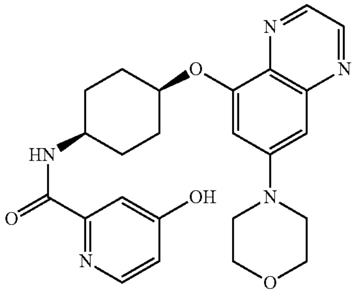 [SMILES: O=C(N[C@H]1CC[C@@H](Oc2cc(N3CCOCC3)cc3nccnc23)CC1)c1cc(O)ccn1] | 450.13 | |
| 176 | 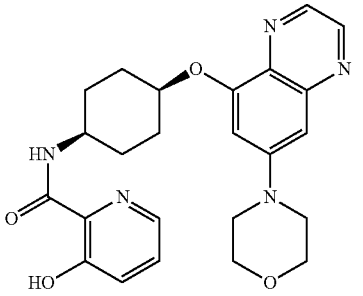 [SMILES: O=C(N[C@H]1CC[C@@H](Oc2cc(N3CCOCC3)cc3nccnc23)CC1)c1ncccc1O] | 450.2 | (400 MHz, $CDCl_3$) δ 12.21 (s, 1H), 8.70 (d, J = 1.9 Hz, 1H), 8.63 (d, J = 1.9 Hz, 1H), 8.17 (d, J = 7.4 Hz, 1H), 8.07 (dd, J = 4.2, 1.5 Hz, 1H), 7.33 (ddd, J = 10.0, 8.5, 2.9 Hz, 2H), 6.97 (d, J = 2.4 Hz, 1H), 6.90 (d, J = 2.5 Hz, 1H), 4.83-4.74 (m, 1H), 4.24-4.11 (m, 1H), 3.99-3.86 (m, 4H), 3.41-3.26 (m, 4H), 2.30-2.18 (m, 2H), 2.08-1.87 (m, 6H) |
| 177 | 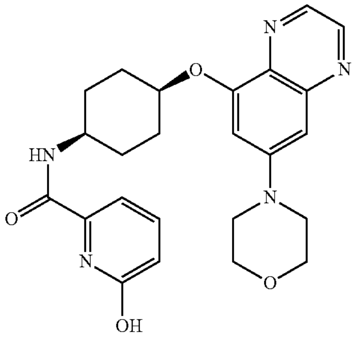 [SMILES: O=C(N[C@H]1CC[C@@H](Oc2cc(N3CCOCC3)cc3nccnc23)CC1)c1cccc(O)n1] | 450.17 | (400 MHz, $CDCl_3$) δ 11.13 (s, 1H), 8.71 (d, J = 1.9 Hz, 1H), 8.59 (d, J = 1.9 Hz, 1H), 7.64-7.39 (m, 2H), 7.07 (d, J = 6.8 Hz, 1H), 7.02-6.79 (m, 3H), 4.76 (s, 1H), 4.32-4.15 (m, 1H), 3.96-3.85 (m, 4H), 3.42-3.24 (m, 4H), 2.39-2.14 (m, 2H), 2.10-1.84 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 178 | 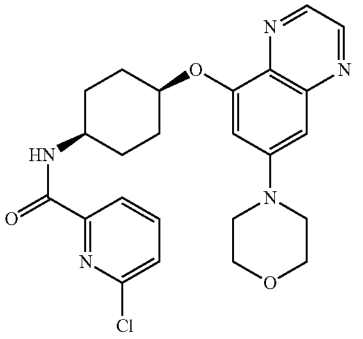 [SMILES: O=C(N[C@H]1CC[C@@H](Oc2cc(N3CCOCC3)cc3nccnc23)CC1)c1cccc(Cl)n1] | 468.17 | (400 MHz, $CDCl_3$) δ 8.70 (d, J = 1.9 Hz, 1H), 8.64 (d, J = 1.9 Hz, 1H), 8.14 (dd, J = 7.6, 0.7 Hz, 1H), 7.91 (d, J = 8.1 Hz, 1H), 7.81 (t, J = 7.8 Hz, 1H), 7.46 (dd, J = 7.9, 0.7 Hz, 1H), 6.96 (d, J = 2.4 Hz, 1H), 6.91 (d, J = 2.4 Hz, 1H), 4.80 (s, 1H), 4.24-4.08 (m, 1H), 3.99-3.83 (m, 4H), 3.41-3.26 (m, 4H), 2.33-2.18 (m, 2H), 2.11-1.98 (m, 2H), 1.98-1.87 (m, 4H) |
| 179 | 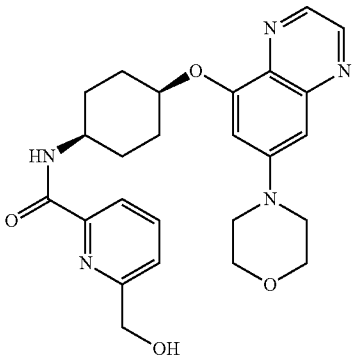 [SMILES: O=C(N[C@H]1CC[C@@H](Oc2cc(N3CCOCC3)cc3nccnc23)CC1)c1cccc(CO)n1] | 464.28 | (400 MHz, $CDCl_3$) δ 8.70 (d, J = 1.9 Hz, 1H), 8.63 (d, J = 1.9 Hz, 1H), 8.13 (d, J = 7.7 Hz, 1H), 8.02 (d, J = 7.8 Hz, 1H), 7.86 (t, J = 7.7 Hz, 1H), 7.48 (d, J = 7.8 Hz, 1H), 6.96 (d, J = 2.4 Hz, 1H), 6.91 (d, J = 2.4 Hz, 1H), 4.85 (s, 2H), 4.79 (s, 1H), 4.28-4.15 (m, 1H), 4.00-3.87 (m, 4H), 3.41-3.27 (m, 4H), 2.88 (s, 1H), 2.33-2.16 (m, 2H), 2.07-1.88 (m, 6H) |
| 180 | 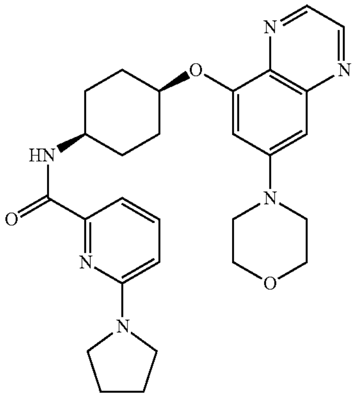 [SMILES: O=C(N[C@H]1CC[C@@H](Oc2cc(N3CCOCC3)cc3nccnc23)CC1)c1cccc(N2CCCC2)n1] | 503.27 | (400 MHz, $CDCl_3$) δ 8.68 (d, J = 1.9 Hz, 1H), 8.62 (d, J = 1.9 Hz, 1H), 8.16 (d, J = 7.8 Hz, 1H), 7.56 (dd, J = 8.4, 7.3 Hz, 1H), 7.43 (d, J = 6.7 Hz, 1H), 6.96 (d, J = 2.4 Hz, 1H), 6.91 (d, J = 2.4 Hz, 1H), 6.50 (d, J = 7.8 Hz, 1H), 4.74 (s, 1H), 4.21-4.07 (m, 1H), 3.97-3.86 (m, 4H), 3.54-3.48 (m, 4H), 3.40-3.29 (m, 4H), 2.26-2.14 (m, 2H), 2.07-1.88 (m, 10H) |
| 181 | 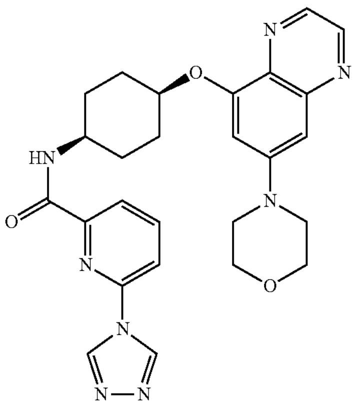 [SMILES: O=C(N[C@H]1CC[C@@H](Oc2cc(N3CCOCC3)cc3nccnc23)CC1)c1cccc(-n2cnnc2)n1] | 501.25 | (400 MHz, $CDCl_3$) δ 8.91 (s, 2H), 8.71 (d, J = 1.9 Hz, 1H), 8.64 (d, J = 1.9 Hz, 1H), 8.30 (dd, J = 7.7, 0.7 Hz, 1H), 8.11 (t, J = 7.9 Hz, 1H), 7.74 (d, J = 8.2 Hz, 1H), 7.57 (dd, J = 8.0, 0.7 Hz, 1H), 6.97 (d, J = 2.4 Hz, 1H), 6.92 (d, J = 2.4 Hz, 1H), 4.82 (s, 1H), 4.27-4.11 (m, 1H), 3.99-3.85 (m, 4H), 3.42-3.27 (m, 4H), 2.34-2.20 (m, 2H), 2.12-2.00 (m, 2H), 2.00-1.84 (m, 4H) |

TABLE 1-continued

| Cmpd. No. | Compound | ESMS (M + H) | $^1$H NMR (300 MHz, unless indicated otherwise) NMR peaks given as δ values |
|---|---|---|---|
| 182 | 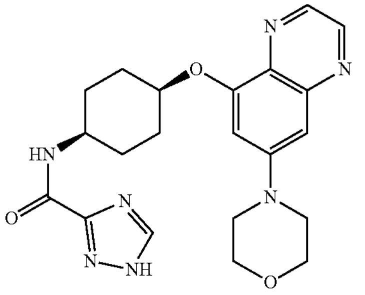 [SMILES: O=C(N[C@H]1CC[C@@H](Oc2cc(N3CCOCC3)cc3nccnc23)CC1)c1nc[nH]n1] | 424.21 | (400 MHz, $CDCl_3$) δ 8.71 (d, J = 1.9 Hz, 1H), 8.63 (d, J = 1.9 Hz, 1H), 8.15 (s, 1H), 7.43 (d, J = 8.1 Hz, 1H), 6.97 (d, J = 2.3 Hz, 1H), 6.90 (d, J = 2.4 Hz, 1H), 4.82 (s, 1H), 4.24-4.13 (m, 1H), 3.98-3.86 (m, 4H), 3.40-3.27 (m, 4H), 2.30-2.16 (m, 2H), 2.05-1.78 (m, 6H) |
| 183 | 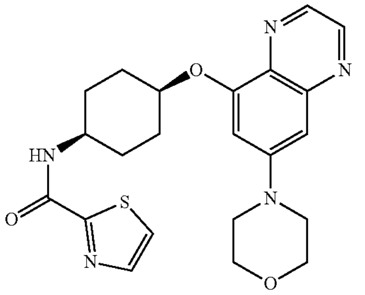 [SMILES: O=C(N[C@H]1CC[C@@H](Oc2cc(N3CCOCC3)cc3nccnc23)CC1)c1nccs1] | 440.12 | (400 MHz, $CDCl_3$) δ 8.69 (d, J = 1.9 Hz, 1H), 8.63 (d, J = 1.9 Hz, 1H), 7.86 (d, J = 3.1 Hz, 1H), 7.57 (d, J = 3.1 Hz, 1H), 7.38 (d, J = 8.0 Hz, 1H), 6.95 (d, J = 2.4 Hz, 1H), 6.90 (d, J = 2.4 Hz, 1H), 4.79 (s, 1H), 4.25-4.09 (m, 1H), 3.97-3.88 (m, 4H), 3.39-3.29 (m, 4H), 2.28-2.17 (m, 2H), 2.07-1.96 (m, 2H), 1.96-1.85 (m, 4H) |
| 184 | 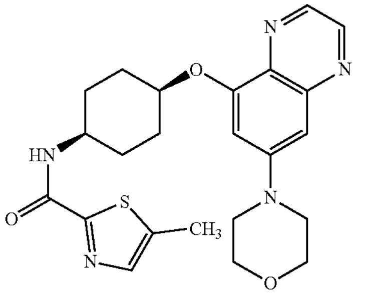 [SMILES: Cc1cnc(C(=O)N[C@H]2CC[C@@H](Oc3cc(N4CCOCC4)cc4nccnc34)CC2)s1] | 454.09 | (400 MHz, $CDCl_3$) δ 8.69 (d, J = 1.9 Hz, 1H), 8.62 (d, J = 1.9 Hz, 1H), 7.50 (d, J = 1.1 Hz, 1H), 7.28 (d, J = 8.3 Hz, 1H), 6.95 (d, J = 2.4 Hz, 1H), 6.89 (d, J = 2.4 Hz, 1H), 4.78 (s, 1H), 4.23-4.07 (m, 1H), 3.99-3.87 (m, 4H), 3.40-3.27 (m, 4H), 2.53 (d, J = 1.0 Hz, 3H), 2.28-2.14 (m, 2H), 2.04-1.95 (m, 2H), 1.95-1.84 (m, 4H) |
| 185 | 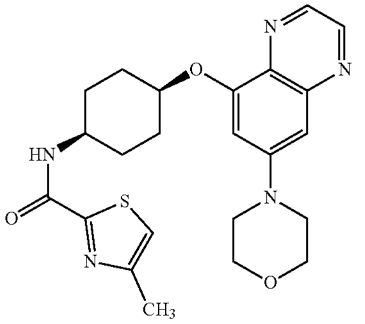 [SMILES: Cc1csc(C(=O)N[C@H]2CC[C@@H](Oc3cc(N4CCOCC4)cc4nccnc34)CC2)n1] | 454.13 | (400 MHz, $CDCl_3$) δ 8.70 (t, J = 5.6 Hz, 1H), 8.61 (dd, J = 12.5, 1.9 Hz, 1H), 7.35 (d, J = 8.0 Hz, 1H), 7.11 (d, J = 0.9 Hz, 1H), 7.01-6.92 (m, 1H), 6.89 (d, J = 2.4 Hz, 1H), 4.85-4.70 (m, 1H), 4.26-4.11 (m, 1H), 3.90 (dd, J = 15.3, 10.4 Hz, 4H), 3.42-3.25 (m, 4H), 2.49 (d, J = 0.9 Hz, 3H), 2.30-2.16 (m, 2H), 2.12-1.84 (m, 6H) |
| 186 | 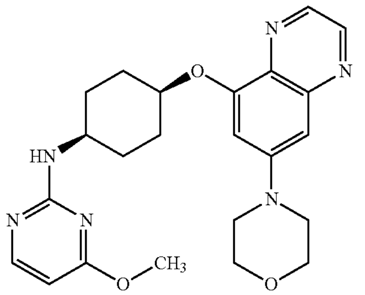 [SMILES: COc1ccnc(N[C@H]2CC[C@@H](Oc3cc(N4CCOCC4)cc4nccnc34)CC2)n1] | 437.2 | ($CDCl_3$) δ 8.71 (d, J = 1.9 Hz, 1H), 8.63 (d, J = 1.9 Hz, 1H), 8.01 (d, J = 5.8 Hz, 1H), 7.00-6.86 (m, 2H), 6.03 (d, J = 5.8 Hz, 1H), 4.80 (d, J = 5.8 Hz, 1H), 4.07 (s, 1H), 3.97-3.83 (m, 7H), 3.41-3.28 (m, 4H), 2.20 (dd, J = 12.3, 5.6 Hz, 2H), 1.95 (dh, J = 11.8, 5.6, 4.7 Hz, 6H) |

TABLE 1-continued

| Cmpd. No. | Compound | ESMS (M + H) | $^{1}$H NMR (300 MHz, unless indicated otherwise) NMR peaks given as δ values |
|---|---|---|---|
| 187 | 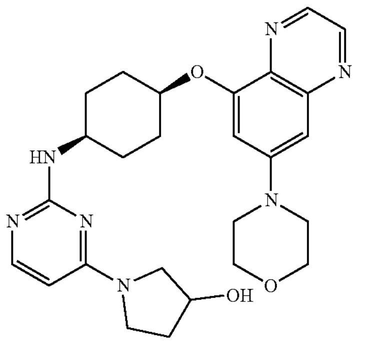 [SMILES: OC1CCN(c2ccnc(N[C@H]3CC[C@@H](Oc4cc(N5CCOCC5)cc5nccnc45)CC3)n2)C1] | 492.26 | ($CDCl_3$) δ 8.70 (d, J = 1.9 Hz, 1H), 8.63 (d, J = 1.9 Hz, 1H), 7.70 (s, 1H), 6.96 (q, J = 2.6 Hz, 2H), 5.75 (d, J = 6.5 Hz, 1H), 4.82 (s, 1H), 4.65 (s, 1H), 3.93 (dd, J = 5.9, 3.8 Hz, 4H), 3.63 (s, 3H), 3.36 (dd, J = 6.1, 3.7 Hz, 4H), 2.14 (s, 2H), 1.95 (d, J = 31.2 Hz, 6H) |
| 188 | 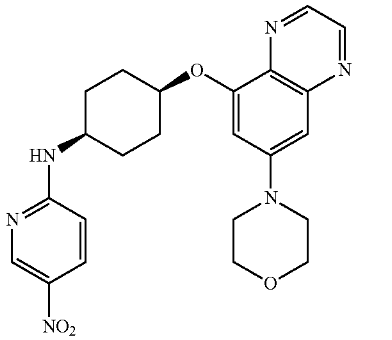 | 451.14 | (400 MHz, $CDCl_3$) δ 9.02 d, J = 2.6 Hz, 1H), 8.70 (d, J = 1.9 Hz, 1H), 8.61 (d, J = 1.9 Hz, 1H), 8.17 (dd, J = 9.3, 2.6 Hz, 1H), 6.97 (d, J = 2.4 Hz, 1H), 6.91 (d, J = 2.4 Hz, 1H), 6.36 (d, J = 9.3 Hz, 1H), 5.37 (s, 1H), 4.82 (s, 1H), 4.04 (s, 1H), 3.96-3.87 (m, 4H), 3.40-3.27 (m, 4H), 2.31-2.18 (m, 2H), 2.03-1.84 (m, 6H) |
| 189 | 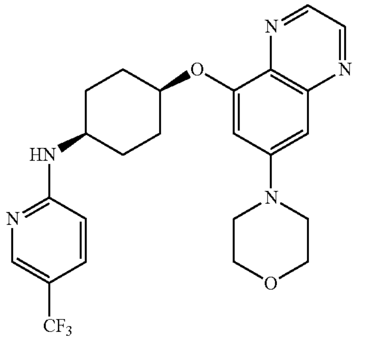 [SMILES: O=[N+]([O-])c1ccc(N[C@H]2CC[C@@H](Oc3cc(N4CCOCC4)cc4nccnc34)CC2)nc1] | 474.147 | (400 MHz, $CDCl_3$) δ 8.69 (d, J = 1.6 Hz, 1H), 8.61 (d, J = 1.7 Hz, 1H), 8.32 (s, 1H), 7.56 (d, J = 6.7 Hz, 1H), 6.96 (d, J = 2.2 Hz, 1H), 6.90 (d, J = 2.3 Hz, 1H), 6.40 (d, J = 8.7 Hz, 1H), 4.96 (s, 1H), 4.80 (s, 1H), 4.01-3.84 (m, 5H), 3.42-3.24 (m, 4H), 2.21 (d, J = 8.4 Hz, 2H), 1.92 (d, J = 6.4 Hz, 6H) |
| 190 | 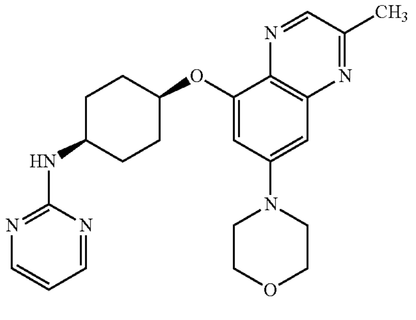 [SMILES: Cc1cnc2c(O[C@H]3CC[C@@H](Nc4ncccn4)CC3)cc(N3CCOCC3)cc2n1] | | ($CDCl_3$) δ 8.52 (s, 1H), 8.29 (d, J = 4.8 Hz, 2H), 6.90 (d, J = 2.5 Hz, 1H), 6.85 (d, J = 2.5 Hz, 1H), 6.52 (t, J = 4.8 Hz, 1H), 5.36 (s, 1H), 4.79 (dq, J = 5.6, 2.9 Hz, 1H), 4.04 (dp, J = 8.0, 3.8 Hz, 1H), 3.97-3.85 (m, 4H), 3.38-3.26 (m, 4H), 2.70 (s, 3H), 2.29-2.11 (m, 2H), 2.00-1.78 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 191 | 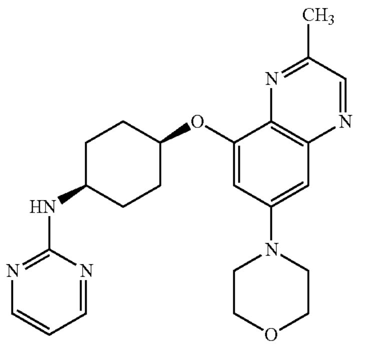 [SMILES: Cc1cnc2cc(N3CCOCC3)cc(O[C@H]3CC[C@@H](Nc4ncccn4)CC3)c2n1] | 421.24 | ($CDCl_3$) δ 8.52 (s, 1H), 8.29 (d, J = 4.8 Hz, 2H), 6.90 (d, J = 2.5 Hz, 1H), 6.85 (d, J = 2.5 Hz, 1H), 6.53 (t, J = 4.8 Hz, 1H), 5.42 (d, J = 7.9 Hz, 1H), 4.80 (dq, J = 5.9, 2.9 Hz, 1H), 4.11-3.98 (m, 1H), 3.91 (dd, J = 5.9, 3.8 Hz, 4H), 3.42-3.21 (m, 4H), 2.71 (s, 3H), 2.31-2.07 (m, 2H), 2.04-1.77 (m, 6H) |
| 192 | 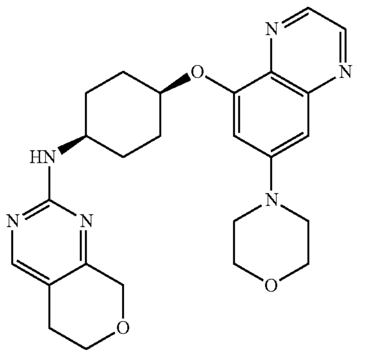 [SMILES: c1cnc2c(O[C@H]3CC[C@@H](Nc4ncc5c(n4)COCC5)CC3)cc(N3CCOCC3)cc2n1] | 463.2 | ($CDCl_3$) δ 8.70 (d, J = 1.9 Hz, 1H), 8.63 (d, J = 1.9 Hz, 1H), 7.97 (s, 1H), 6.97 (d, J = 2.5 Hz, 1H), 6.93 (d, J = 2.5 Hz, 1H), 5.36 (s, 1H), 4.80 (d, J = 6.2 Hz, 1H), 4.65 (d, J = 0.9 Hz, 2H), 4.02 (t, J = 5.8 Hz, 3H), 3.98-3.82 (m, 4H), 3.42-3.30 (m, 4H), 2.80 (t, J = 5.8 Hz, 2H), 2.29-2.11 (m, 2H), 2.03-1.77 (m, 7H) |
| 193 | 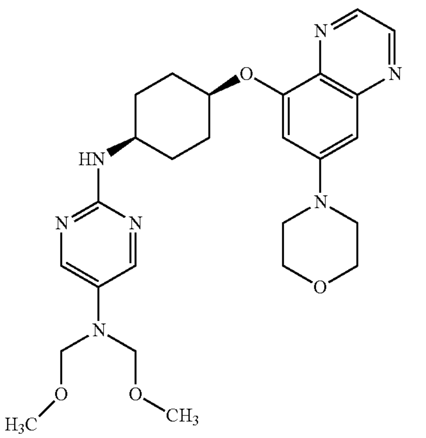 [SMILES: COCN(COC)c1cnc(N[C@H]2CC[C@@H](Oc3cc(N4CCOCC4)cc4nccnc34)CC2)nc1] | 524.21 | ($CDCl_3$) δ 8.70 (d, J = 1.9 Hz, 1H), 8.63 (d, J = 1.9 Hz, 1H), 7.95 (s, 2H), 7.05-6.88 (m, 2H), 4.92 (s, 1H), 4.79 (s, 1H), 3.93 (t, J = 4.8 Hz, 5H), 3.60-3.44 (m, 4H), 3.37 (d, J = 10.5 Hz, 9H), 2.20 (d, J = 6.9 Hz, 2H), 1.91 (d, J = 4.6 Hz, 6H) |
| 194 | 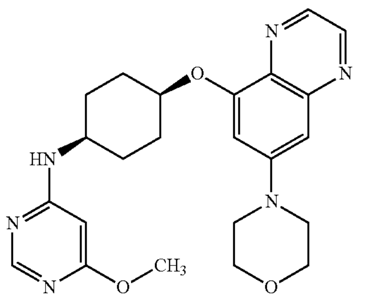 [SMILES: COc1cc(N[C@H]2CC[C@@H](Oc3cc(N4CCOCC4)cc4nccnc34)CC2)ncn1] | 437.23 | ($CDCl_3$) δ 8.70 (d, J = 1.9 Hz, 1H), 8.62 (d, J = 1.9 Hz, 1H), 8.28 (d, J = 0.9 Hz, 1H), 6.97 (d, J = 2.5 Hz, 1H), 6.91 (d, J = 2.5 Hz, 1H), 5.74-5.58 (m, 1H), 5.16 (d, J = 8.0 Hz, 1H), 4.82 (dq, J = 5.4, 2.7 Hz, 1H), 4.06-3.85 (m, 7H), 3.70 (d, J = 14.0 Hz, 1H), 3.42-3.28 (m, 4H), 2.30-2.16 (m, 2H), 1.99-1.75 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 195 | 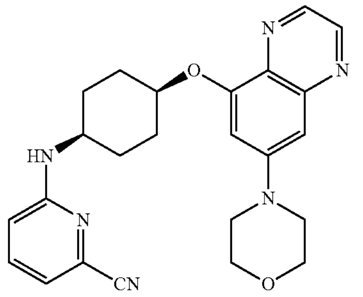 [SMILES: N#Cc1cccc(N[C@H]2CC[C@@H](Oc3cc(N4CCOCC4)cc4nccnc34)CC2)n1] | 431.22 | ($CDCl_3$) δ 8.70 (d, J = 1.9 Hz, 1H), 8.62 (d, J = 2.0 Hz, 1H), 7.43 (dd, J = 8.6, 7.2 Hz, 1H), 7.02-6.86 (m, 3H), 6.55 (dd, J = 8.6, 0.8 Hz, 1H), 4.80 (d, J = 6.6 Hz, 2H), 4.10-3.81 (m, 5H), 3.47-3.25 (m, 4H), 2.30-2.11 (m, 2H), 1.99-1.81 (m, 6H) |
| 196 | 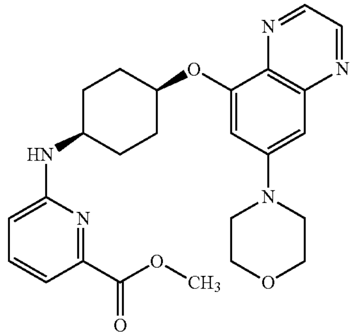 [SMILES: COC(=O)c1cccc(N[C@H]2CC[C@@H](Oc3cc(N4CCOCC4)cc4nccnc34)CC2)n1] | 463.27 | ($CDCl_3$) δ 8.71 (d, J = 1.9 Hz, 1H), 8.63 (d, J = 1.9 Hz, 1H), 7.61 (d, J = 9.4 Hz, 1H), 7.41 (d, J = 7.2 Hz, 1H), 7.05-6.87 (m, 2H), 6.65 (s, 1H), 4.86 (s, 1H), 4.04-3.87 (m, 7H), 3.74 (s, 1H), 3.43-3.27 (m, 4H), 2.21 (d, J = 10.8 Hz, 2H), 1.98 (d, J = 23.5 Hz, 6H) |
| 197 | 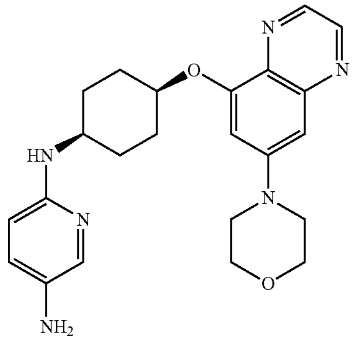 [SMILES: Nc1ccc(N[C@H]2CC[C@@H](Oc3cc(N4CCOCC4)cc4nccnc34)CC2)nc1] | 421.69 | (400 MHz, $CDCl_3$) δ 8.68 (d, J = 1.9 Hz, 1H), 8.61 (d, J = 1.9 Hz, 1H), 8.13-8.04 (m, 1H), 7.67 (d, J = 2.4 Hz, 1H), 6.99-6.93 (m, 2H), 6.90 (d, J = 2.4 Hz, 1H), 6.33 (d, J = 8.7 Hz, 1H), 4.77 (s, 1H), 3.99-3.65 (m, 7H), 3.39-3.27 (m, 4H), 2.25-2.10 (m, 2H), 1.96-1.82 (m, 6H) |
| 198 | 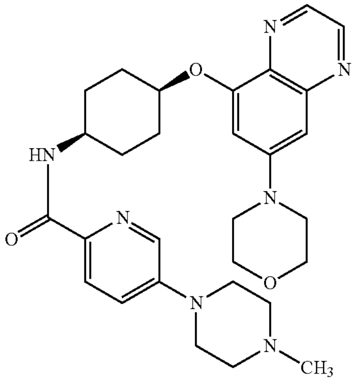 [SMILES: CN1CCN(c2ccc(C(=O)N[C@H]3CC[C@@H](Oc4cc(N5CCOCC5)cc5nccnc45)CC3)nc2)CC1] | 532.11 | (400 MHz, $CDCl_3$) δ 8.69 (d, J = 1.6 Hz, 1H), 8.61 (d, J = 1.7 Hz, 1H), 8.57 (d, J = 2.1 Hz, 1H), 7.89 (dd, J = 8.9, 2.3 Hz, 1H), 6.95 (s, 1H), 6.90 (s, 1H), 6.62 (d, J = 9.0 Hz, 1H), 5.99 (d, J = 7.7 Hz, 1H), 4.78 (s, 1H), 4.18 (s, 1H), 4.03-3.81 (m, 4H), 3.76-3.60 (m, 4H), 3.42-3.25 (m, 4H), 2.62-2.44 (m, 4H), 2.36 (s, 3H), 2.29-2.14 (m, 2H), 1.99-1.84 (m, 6H) |

TABLE 1-continued

| Cmpd. No. | Compound | ESMS (M + H) | $^1H$ NMR (300 MHz, unless indicated otherwise) NMR peaks given as δ values |
|---|---|---|---|
| 199 | 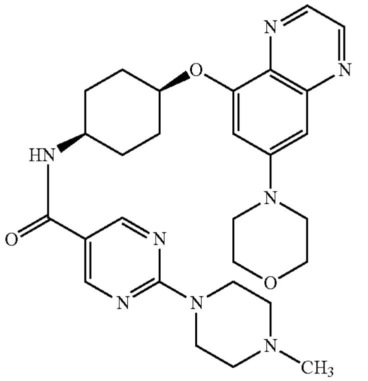 [SMILES: CN1CCN(c2ncc(C(=O)N[C@H]3CC[C@@H](Oc4cc(N5CCOCC5)cc5nccnc45)CC3)cn2)CC1] | 533.01 | (400 MHz, $CDCl_3$) δ 8.73-8.65 (m, 3H), 8.60 (d, J = 1.9 Hz, 1H), 6.95 (d, J = 2.4 Hz, 1H), 6.89 (d, J = 2.4 Hz, 1H), 5.93 (d, J = 8.0 Hz, 1H), 4.79 (s, 1H), 4.23-4.09 (m, 1H), 3.97-3.88 (m, 8H), 3.40-3.25 (m, 4H), 2.53-2.42 (m, 4H), 2.34 (s, 3H), 2.26-2.18 (m, 2H), 1.97-1.83 (m, 6H) |
| 200 | 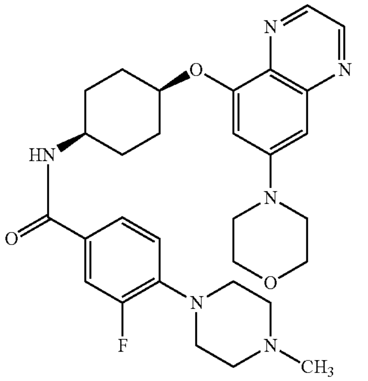 [SMILES: CN1CCN(c2ccc(C(=O)N[C@H]3CC[C@@H](Oc4cc(N5CCOCC5)cc5nccnc45)CC3)cc2F)CC1] | 549.17 | (400 MHz, $CDCl_3$) δ 8.69 (d, J = 1.9 Hz, 1H), 8.61 (d, J = 1.9 Hz, 1H), 7.51-7.42 (m, 2H), 6.98-6.85 (m, 3H), 6.07 (d, J = 8.0 Hz, 1H), 4.77 (s, 1H), 4.25-4.11 (m, 1H), 3.99-3.85 (m, 4H), 3.40-3.27 (m, 4H), 3.26-3.14 (m, 4H), 2.67-2.52 (m, 4H), 2.36 (s, 3H), 2.28-2.13 (m, 2H), 1.98-1.84 (m, 6H) |
| 201 | 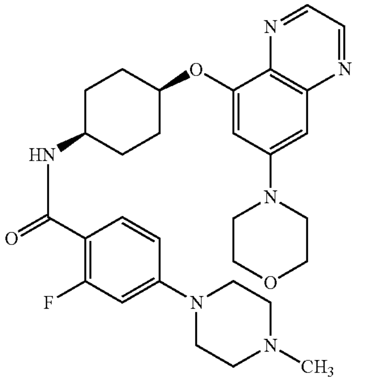 [SMILES: CN1CCN(c2ccc(C(=O)N[C@H]3CC[C@@H](Oc4cc(N5CCOCC5)cc5nccnc45)CC3)c(F)c2)CC1] | 549.1 | (400 MHz, $CDCl_3$) δ 9.47 (s, 1H), 8.68 (d, J = 1.7 Hz, 1H), 8.56 (d, J = 1.7 Hz, 1H), 8.21-8.11 (m, 1H), 6.97-6.85 (m, 4H), 4.82 (s, 1H), 4.23-4.07 (m, 1H), 3.96-3.87 (m, 4H), 3.38-3.29 (m, 4H), 3.03 (s, 4H), 2.65 (s, 4H), 2.37-2.25 (m, 5H), 2.02-1.84 (m, 6H) |
| 202 | 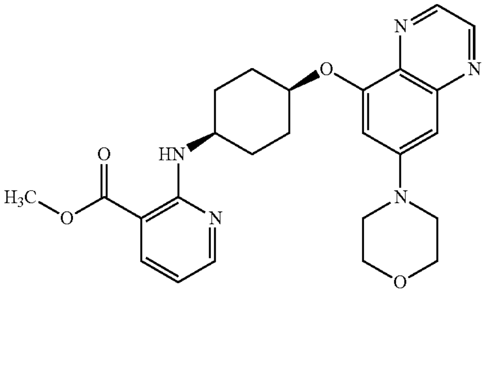 [SMILES: COC(=O)c1cccnc1N[C@H]1CC[C@@H](Oc2cc(N3CCOCC3)cc3nccnc23)CC1] | 464.13 | (400 MHz, $CDCl_3$) δ 8.69 (d, J = 1.8 Hz, 1H), 8.63 (d, J = 1.9 Hz, 1H), 8.27 (dd, J = 4.7, 1.9 Hz, 1H), 8.19 (s, 1H), 8.11 (d, J = 6.8 Hz, 1H), 6.95 (d, J = 2.4 Hz, 1H), 6.92 (d, J = 2.3 Hz, 1H), 6.51 (dd, J = 7.4, 4.9 Hz, 1H), 4.76 (s, 1H), 4.30 (s, 1H), 4.02-3.90 (m, 4H), 3.88 (s, 3H), 3.41-3.26 (m, 4H), 2.29-2.11 (m, 2H), 2.11-1.85 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 203 | 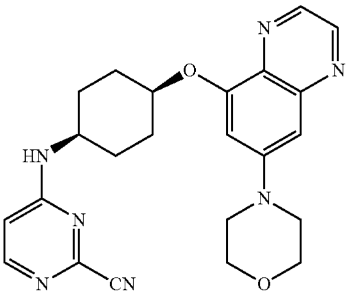 | 432.58 | ($CDCl_3$) δ 8.70 (d, J = 1.9 Hz, 1H), 8.60 (d, J = 1.9 Hz, 1H), 8.15 (s, 1H), 6.93 (dd, J = 17.9, 2.5 Hz, 2H), 6.43 (d, J = 6.1 Hz, 1H), 5.20 (s, 1H), 4.82 (s, 1H), 4.00-3.82 (m, 4H), 3.44-3.25 (m, 4H), 2.23 (d, J = 11.2 Hz, 2H), 1.91 (s, 6H) |
| 204 | 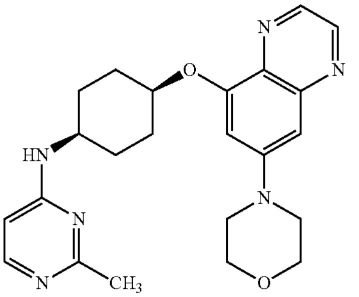 [SMILES: Cc1nccc(N[C@H]2CC[C@@H](Oc3cc(N4CCOCC4)cc4nccnc34)CC2)n1] | 421.65 | ($CDCl_3$) δ 8.70 (d, J = 1.9 Hz, 1H), 8.61 (d, J = 1.9 Hz, 1H), 8.09 (d, J = 6.0 Hz, 1H), 6.93 (dd, J = 16.1, 2.5 Hz, 2H), 6.15 (d, J = 6.0 Hz, 1H), 5.10 (d, J = 8.0 Hz, 1H), 4.81 (td, J = 5.5, 2.7 Hz, 1H), 3.97-3.87 (m, 4H), 3.49 (s, 1H), 3.39-3.27 (m, 4H), 2.49 (s, 3H), 2.27-2.14 (m, 2H), 2.03-1.80 (m, 6H) |
| 205 | 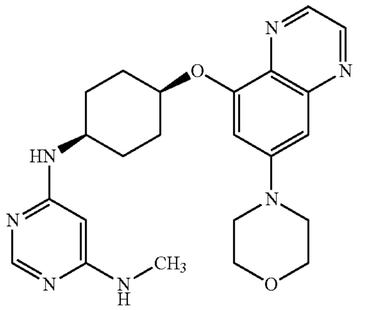 [SMILES: CNc1cc(N[C@H]2CC[C@@H](Oc3cc(N4CCOCC4)cc4nccnc34)CC2)ncn1] | 436.63 | ($CDCl_3$) δ 8.70 (d, J = 1.9 Hz, 1H), 8.61 (dd, J = 5.3, 1.9 Hz, 1H), 8.19-8.06 (m, 1H), 6.99-6.84 (m, 2H), 5.34-5.21 (m, 1H), 4.76 (d, J = 9.7 Hz, 3H), 3.92 (t, J = 4.9 Hz, 4H), 3.81 (s, 1H), 3.33 (dd, J = 5.7, 4.1 Hz, 4H), 2.87 (d, J = 5.2 Hz, 3H), 2.19 (d, J = 8.5 Hz, 2H), 1.88 (dd, J = 13.3, 5.1 Hz, 6H) |
| 206 | 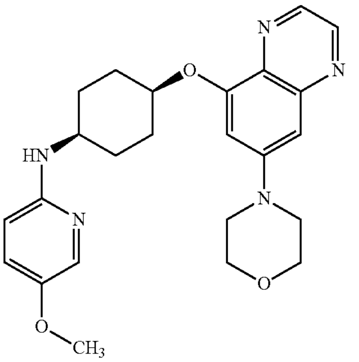 [SMILES: COc1ccc(N[C@H]2CC[C@@H](Oc3cc(N4CCOCC4)cc4nccnc34)CC2)nc1] | 436.18 | (400 MHz, $CDCl_3$) δ 8.68 (d, J = 1.9 Hz, 1H), 8.61 (d, J = 1.9 Hz, 1H), 7.82 (d, J = 2.8 Hz, 1H), 7.09 (dd, J = 8.9, 3.0 Hz, 1H), 6.94 (d, J = 2.5 Hz, 1H), 6.90 (d, J = 2.5 Hz, 1H), 6.37 (d, J = 8.8 Hz, 1H), 4.77 (s, 1H), 4.29 (bs, 1H), 3.98-3.87 (m, 4H), 3.85-3.79 (m, 1H), 3.77 (s, 3H), 3.41-3.24 (m, 4H), 2.27-2.12 (m, 2H), 1.97-1.79 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 207 | 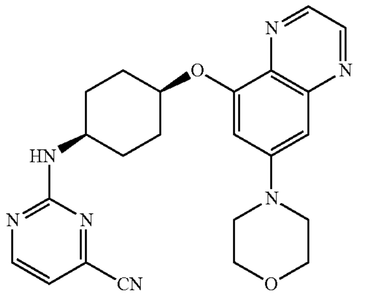 | | ($CDCl_3$) δ 8.71 (d, J = 2.0 Hz, 1H), 8.64 (d, J = 1.9 Hz, 1H), 8.44 (s, 1H), 6.98 (d, J = 2.5 Hz, 1H), 6.92 (d, J = 2.5 Hz, 1H), 6.82 (d, J = 4.7 Hz, 1H), 5.56 (d, J = 30.8 Hz, 1H), 4.83 (d, J = 5.2 Hz, 1H), 4.04 (s, 2H), 3.97-3.84 (m, 4H), 3.44-3.29 (m, 4H), 2.23 (d, J = 8.2 Hz, 2H), 2.02-1.77 (m, 6H) |
| 208 | 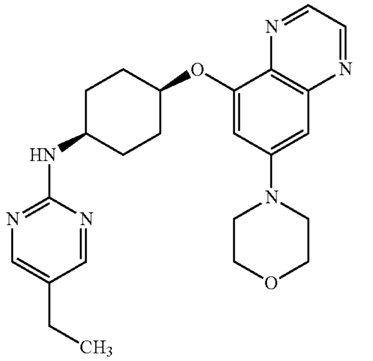 | 435.6 | ($CDCl_3$) δ 8.70 (d, J = 1.9 Hz, 1H), 8.64 (d, J = 1.9 Hz, 1H), 8.16 (s, 2H), 7.00-6.84 (m, 2H), 5.32 (s, 1H), 4.81 (s, 1H), 4.03 (s, 1H), 3.96-3.85 (m, 4H), 3.43-3.32 (m, 4H), 2.49 (q, J = 7.6 Hz, 2H), 2.21 (d, J = 8.8 Hz, 2H), 2.06-1.75 (m, 6H), 1.21 (t, J = 7.6 Hz, 3H) |
| 209 | 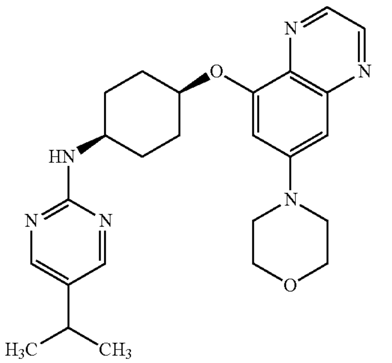 [SMILES: CC(C)c1cnc(N[C@H]2CC[C@@H](Oc3cc(N4CCOCC4)cc4nccnc34)CC2)nc1] | | ($CDCl_3$) δ 8.70 (d, J = 1.9 Hz, 1H), 8.63 (d, J = 1.9 Hz, 1H), 8.18 (s, 2H), 7.01-6.88 (m, 2H), 5.30 (d, J = 9.0 Hz, 1H), 4.81 (d, J = 5.9 Hz, 1H), 4.02 (s, 1H), 3.96-3.85 (m, 4H), 3.42-3.29 (m, 4H), 2.78 (p, J = 6.9 Hz, 1H), 2.31-2.14 (m, 2H), 2.01-1.83 (m, 6H), 1.25 (d, J = 6.9 Hz, 6H) |
| 210 | 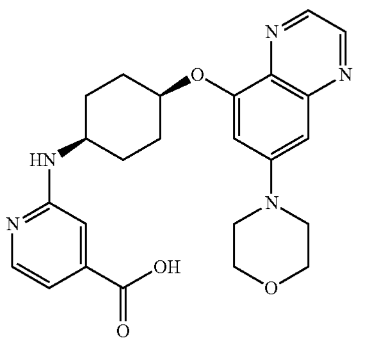 [SMILES: O=C(O)c1ccnc(N[C@H]2CC[C@@H](Oc3cc(N4CCOCC4)cc4nccnc34)CC2)c1] | 450.17 | (400 MHz, methanol-$d_4$) δ 8.69 (d, J = 2.0 Hz, 1H), 8.57 (d, J = 2.0 Hz, 1H), 7.92 (d, J = 6.2 Hz, 1H), 7.17-7.10 (m, 2H), 7.02 (d, J = 7.1 Hz, 1H), 6.90 (d, J = 2.5 Hz, 1H), 4.93 (s, 1H), 3.93-3.87 (m, 4H), 3.84-3.79 (m, 1H), 3.44-3.37 (m, 4H), 2.24-2.15 (m, 2H), 1.97-1.82 (m, 6H) |

TABLE 1-continued
| Cmpd. No. | Compound | ESMS (M + H) | $^1$H NMR (300 MHz, unless indicated otherwise) NMR peaks given as δ values |
|---|---|---|---|
| 211 | 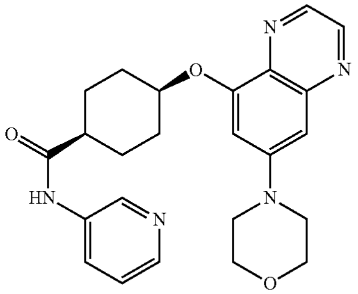 [SMILES: O=C(Nc1cccnc1)[C@H]1CC[C@@H](Oc2cc(N3CCOCC3)cc3nccnc23)CC1] | 434.19 | |
| 212 | 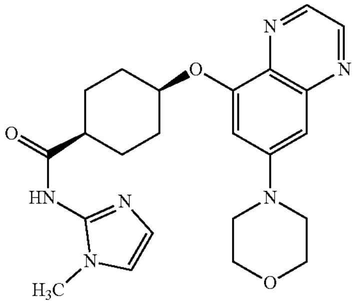 [SMILES: Cn1ccnc1NC(=O)[C@H]1CC[C@@H](Oc2cc(N3CCOCC3)cc3nccnc23)CC1] | 437.12 | |
| 213 | 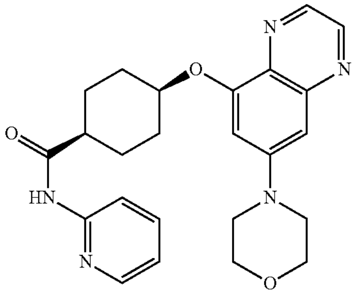 [SMILES: O=C(Nc1ccccn1)[C@H]1CC[C@@H](Oc2cc(N3CCOCC3)cc3nccnc23)CC1] | 434.15 | |
| 214 | 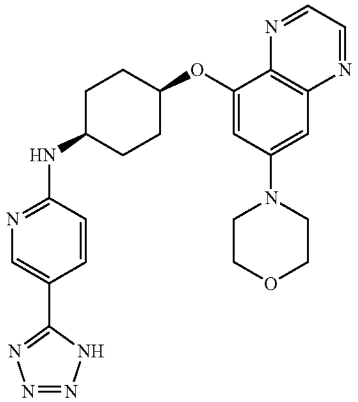 [SMILES: c1cnc2c(O[C@H]3CC[C@@H](Nc4ccc(-c5nnn[nH]5)cn4)CC3)cc(N3CCOCC3)cc2n1] | 474.12 | (400 MHz, $CDCl_3$) δ 8.98-8.83 (m, 1H), 8.79-8.67 (m, 1H), 8.64-8.50 (m, 1H), 8.35 (d, J = 9.2 Hz, 1H), 7.04-6.86 (m, 2H), 6.75 (d, J = 9.0 Hz, 2H), 4.78 (s, 1H), 4.00-3.79 (m, 5H), 3.42-3.21 (m, 4H), 2.17-2.11 (m, 2H), 2.02-1.81 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 215 | 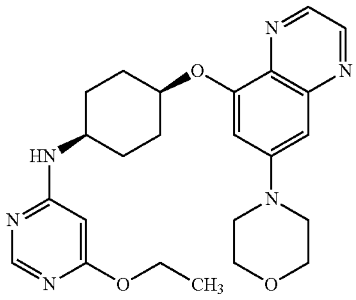 [SMILES: CCOc1cc(N[C@H]2CC[C@@H](Oc3cc(N4CCOCC4)cc4nccnc34)CC2)ncn1] | 451.21 | ($CDCl_3$) δ 8.70 (d, J = 1.9 Hz, 1H), 8.61 (d, J = 1.9 Hz, 1H), 8.25 (d, J = 0.9 Hz, 1H), 6.93 (dd, J = 17.1, 2.5 Hz, 2H), 5.64 (d, J = 0.9 Hz, 1H), 5.00 (d, J = 8.1 Hz, 1H), 4.80 (dq, J = 5.5, 2.7 Hz, 1H), 4.33 (q, J = 7.1 Hz, 2H), 3.97-3.87 (m, 4H), 3.71 (s, 1H), 3.38-3.29 (m, 4H), 2.27-2.14 (m, 2H), 2.03-1.80 (m, 6H), 1.37 (t, J = 7.1 Hz, 3H) |
| 216 | 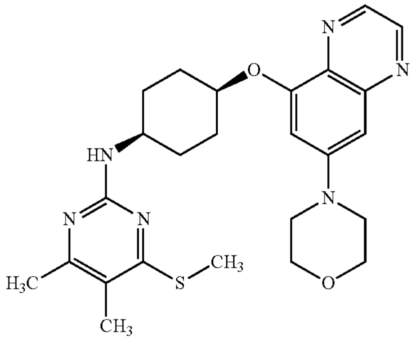 [SMILES: CSc1nc(N[C@H]2CC[C@@H](Oc3cc(N4CCOCC4)cc4nccnc34)CC2)nc(C)c1C] | 481.26 | ($CDCl_3$) δ 8.69 (d, J = 1.9 Hz, 1H), 8.62 (d, J = 1.9 Hz, 1H), 6.95 (d, J = 2.5 Hz, 1H), 6.90 (d, J = 2.5 Hz, 1H), 0.23-0.16 (m, 0H), 4.93 (s, 1H), 4.76 (s, 1H), 4.19-4.01 (m, 1H), 3.97-3.87 (m, 4H), 3.38-3.29 (m, 4H), 2.49 (s, 3H), 2.26 (s, 3H), 2.21-2.10 (m, 2H), 2.05 (d, J = 1.8 Hz, 3H), 2.00-1.85 (m, 6H) |
| 217 | 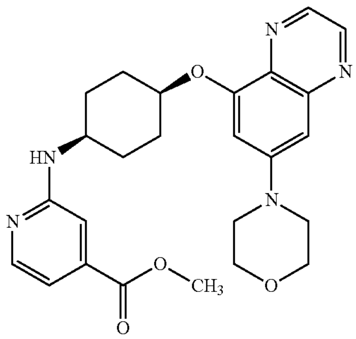 [SMILES: COC(=O)c1ccnc(N[C@H]2CC[C@@H](Oc3cc(N4CCOCC4)cc4nccnc34)CC2)c1] | 464.17 | (400 MHz, $CDCl_3$) δ 8.69 (d, J = 1.9 Hz, 1H), 8.61 (d, J = 1.9 Hz, 1H), 8.15 (d, J = 5.3 Hz, 1H), 7.06 (dd, J = 5.4, 1.3 Hz, 1H), 7.00 (s, 1H), 6.95 (d, J = 2.4 Hz, 1H), 6.91 (d, J = 2.4 Hz, 1H), 5.15 (s, 1H), 4.81 (d, J = 2.5 Hz, 1H), 3.95-3.83 (m, 8H), 3.38-3.30 (m, 4H), 2.27-2.16 (m, 2H), 1.97-1.85 (m, 6H) |
| 218 | 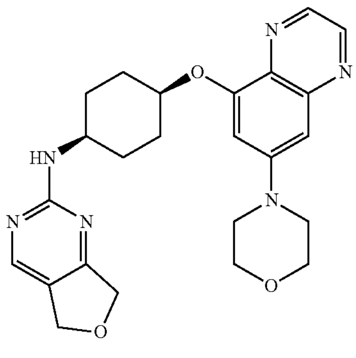 [SMILES: c1cnc2c(O[C@H]3CC[C@@H](Nc4ncc5c(n4)COC5)CC3)cc(N3CCOCC3)cc2n1] | | ($CDCl_3$) δ 8.70 (d, J = 2.0 Hz, 1H), 8.63 (d, J = 1.9 Hz, 1H), 8.17 (d, J = 0.9 Hz, 1H), 7.02-6.85 (m, 2H), 5.40 (s, 1H), 5.05 (td, J = 1.8, 0.8 Hz, 2H), 4.91-4.73 (m, 3H), 4.05 (s, 0H), 3.99-3.85 (m, 4H), 3.43-3.27 (m, 4H), 2.30-2.12 (m, 2H), 2.02-1.82 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 219 | 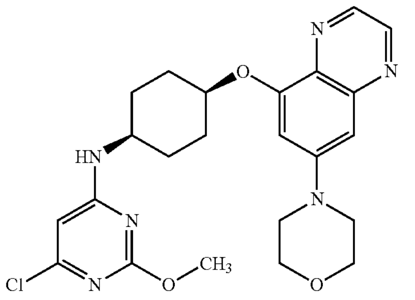 [SMILES: COc1nc(Cl)cc(N[C@H]2CC[C@@H](Oc3cc(N4CCOCC4)cc4nccnc34)CC2)n1] | 471.06 | ($CDCl_3$) δ 8.70 (d, J = 1.9 Hz, 1H), 8.61 (d, J = 1.9 Hz, 1H), 6.96 (d, J = 2.5 Hz, 1H), 6.89 (d, J = 2.5 Hz, 1H), 6.03 (s, 1H), 5.00 (s, 1H), 4.79 (s, 1H), 3.92 (d, J = 9.3 Hz, 7H), 3.41-3.25 (m, 4H), 2.28-2.13 (m, 2H), 1.92 (d, J = 18.6 Hz, 6H) |
| 220 | 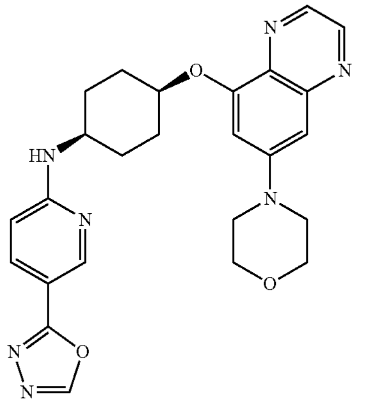 [SMILES: c1cnc2c(O[C@H]3CC[C@@H](Nc4ccc(-c5nnco5)cn4)CC3)cc(N3CCOCC3)cc2n1] | 474.07 | (400 MHz, $CDCl_3$) δ 8.69 (s, 1H), 8.62 (s, 1H), 8.54 (s, 1H), 8.21 (d, J = 4.9 Hz, 1H), 7.22-7.08 (m, 2H), 6.96 (s, 1H), 6.93 (s, 1H), 4.84 (s, 1H), 3.98-3.86 (m, 5H), 3.38-3.26 (m, 4H), 2.31-2.19 (m, 2H), 2.03-1.86 (m, 6H) |
| 221 | 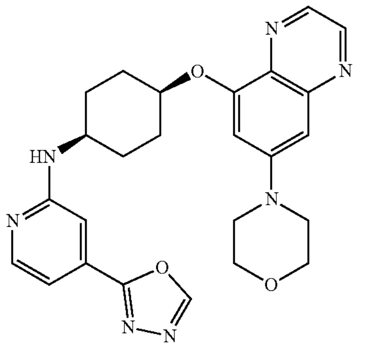 [SMILES: c1cc(-c2nnco2)cc(N[C@H]2CC[C@@H](Oc3cc(N4CCOCC4)cc4nccnc34)CC2)n1] | 474.12 | (400 MHz, $CDCl_3$) δ 8.75 (d, J = 1.9 Hz, 1H), 8.69 (d, J = 1.9 Hz, 1H), 8.61 (d, J = 1.9 Hz, 1H), 8.39 (s, 1H), 8.05 (dd, J = 8.8, 2.3 Hz, 1H), 6.95 (d, J = 2.4 Hz, 1H), 6.91 (d, J = 2.4 Hz, 1H), 6.49 (d, J = 8.8 Hz, 1H), 5.23 (s, 1H), 4.88-4.71 (m, 1H), 4.05-3.95 (m, 1H), 3.95-3.85 (m, 4H), 3.39-3.26 (m, 4H), 2.28-2.16 (m, 2H), 2.00-1.83 (m, 6H) |
| 222 | 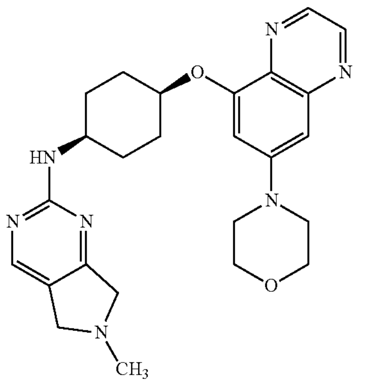 [SMILES: CN1Cc2cnc(N[C@H]3CC[C@@H](Oc4cc(N5CCOCC5)cc5nccnc45)CC3)nc2C1] | 485.14 | ($CDCl_3$) δ 8.63 (d, J = 1.9 Hz, 1H), 8.53 (dd, J = 1.9, 0.6 Hz, 1H), 7.71 (d, J = 9.4 Hz, 1H), 6.89 (d, J = 2.4 Hz, 1H), 6.83 (d, J = 2.5 Hz, 1H), 6.68 (d, J = 9.4 Hz, 1H), 5.33 (s, 1H), 4.76 (dq, J = 5.0, 2.5 Hz, 1H), 4.14 (s, 1H), 3.93-3.77 (m, 4H), 3.28 (d, J = 5.1 Hz, 7H), 2.18 (dt, J = 13.4, 4.6 Hz, 2H), 2.02-1.75 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 223 | 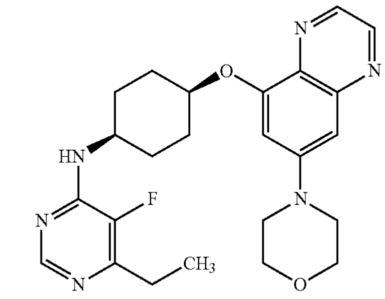 [SMILES: CCc1ncnc(N[C@H]2CC[C@@H](Oc3cc(N4CCOCC4)cc4nccnc34)CC2)c1F] | 435.18 | ($CDCl_3$) δ 8.71 (d, J = 1.9 Hz, 1H), 8.61 (d, J = 1.9 Hz, 1H), 6.94 (dd, J = 15.2, 2.5 Hz, 2H), 6.07 (s, 1H), 4.82 (dt, J = 5.8, 3.0 Hz, 1H), 4.02-3.83 (m, 4H), 3.77-3.57 (m, 1H), 3.43-3.28 (m, 4H), 2.52 (s, 3H), 2.37 (s, 3H), 2.30-2.16 (m, 2H), 2.05-1.78 (m, 6H) |
| 224 | 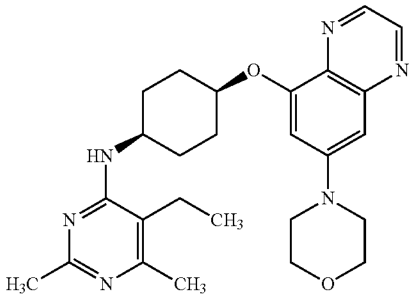 [SMILES: CCc1c(C)nc(C)nc1N[C@H]1CC[C@@H](Oc2cc(N3CCOCC3)cc3nccnc23)CC1] | 475.02 | ($CDCl_3$) δ 8.72 (d, J = 1.9 Hz, 1H), 8.63 (d, J = 1.9 Hz, 1H), 8.27 (s, 1H), 6.98 (d, J = 2.4 Hz, 1H), 6.98 (d, J = 2.6 Hz, 1H), 6.44 (d, J = 6.0 Hz, 1H), 4.84 (s, 1H), 3.93 (dd, J = 6.0, 3.7 Hz, 4H), 3.43-3.25 (m, 4H), 2.23 (s, 2H), 2.08-1.83 (m, 6H) |
| 225 | 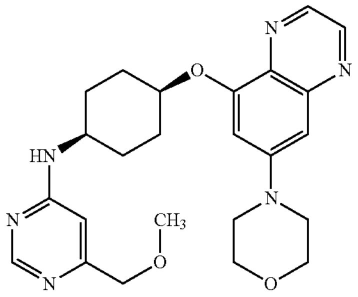 [SMILES: COCc1cc(N[C@H]2CC[C@@H](Oc3cc(N4CCOCC4)cc4nccnc34)CC2)ncn1] | 451.16 | ($CDCl_3$) δ 8.70 (d, J = 1.9 Hz, 1H), 8.62 (d, J = 1.9 Hz, 1H), 8.49 (d, J = 1.1 Hz, 1H), 6.93 (dd, J = 16.7, 2.5 Hz, 2H), 6.45 (d, J = 1.2 Hz, 1H), 5.01 (s, 1H), 4.81 (s, 1H), 4.39 (d, J = 0.9 Hz, 2H), 3.97-3.87 (m, 4H), 3.49 (s, 3H), 3.39-3.29 (m, 4H), 2.22 (d, J = 9.4 Hz, 2H), 1.99-1.87 (m, 6H) |
| 226 | 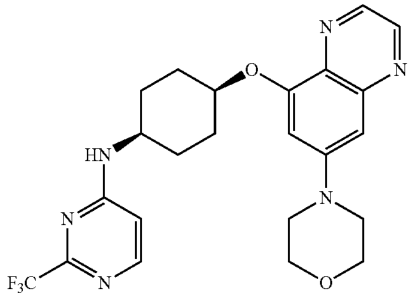 [SMILES: FC(F)(F)c1nccc(N[C@H]2CC[C@@H](Oc3cc(N4CCOCC4)cc4nccnc34)CC2)n1] | 463.18 | ($CDCl_3$) δ 8.70 (d, J = 2.0 Hz, 1H), 8.63 (d, J = 1.9 Hz, 1H), 6.95 (d, J = 2.5 Hz, 1H), 6.91 (d, J = 2.5 Hz, 1H), 4.75 (d, J = 5.6 Hz, 1H), 4.66 (s, 1H), 4.32 (s, 1H), 4.00-3.83 (m, 4H), 3.43-3.22 (m, 4H), 2.46 (d, J = 15.1 Hz, 5H), 2.36 (s, 3H), 2.19 (q, J = 6.3, 3.9 Hz, 2H), 1.12 (t, J = 7.6 Hz, 3H) |
| 227 | 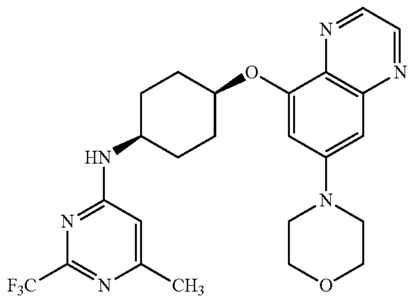 [SMILES: Cc1cc(N[C@H]2CC[C@@H](Oc3cc(N4CCOCC4)cc4nccnc34)CC2)nc(C(F)(F)F)n1] | 453.2 | ($CDCl_3$) δ 8.72 (d, J = 1.9 Hz, 1H), 8.64 (d, J = 1.9 Hz, 1H), 8.33 (d, J = 1.8 Hz, 1H), 7.04-6.87 (m, 2H), 5.15 (s, 1H), 4.82 (dq, J = 5.2, 2.6 Hz, 1H), 4.24 (dt, J = 8.3, 4.7 Hz, 1H), 4.03-3.86 (m, 4H), 3.44-3.28 (m, 4H), 2.74 (qd, J = 7.6, 2.3 Hz, 2H), 2.24 (dq, J = 9.6, 4.6 Hz, 2H), 2.09-1.85 (m, 6H), 1.29 (t, J = 7.6 Hz, 3H) |

TABLE 1-continued
| Cmpd. No. | Compound | ESMS (M + H) | $^1$H NMR (300 MHz, unless indicated otherwise) NMR peaks given as δ values |
|---|---|---|---|
| 228 | 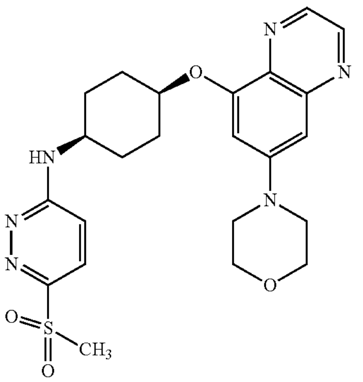 [SMILES: CS(=O)(=O)c1ccc(N[C@H]2CC[C@@H](Oc3cc(N4CCOCC4)cc4nccnc34)CC2)nn1] | 462.14 | ($CDCl_3$) δ 8.60 (dd, J = 8.1, 1.9 Hz, 1H), 8.54 (d, J = 1.9 Hz, 1H), 8.00 (s, 1H), 6.92-6.75 (m, 2H), 5.06 (d, J = 8.0 Hz, 1H), 4.70 (s, 1H), 3.94 (s, 1H), 3.89-3.76 (m, 4H), 3.75-3.62 (m, 4H), 3.34-3.17 (m, 4H), 2.50 (s, 3H), 2.11 (s, 2H), 1.82 (d, J = 5.0 Hz, 5H) |
| 229 | 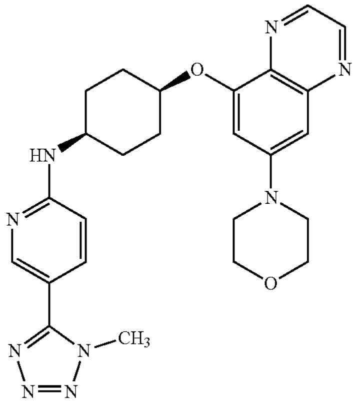 [SMILES: Cn1nnnc1-c1ccc(N[C@H]2CC[C@@H](Oc3cc(N4CCOCC4)cc4nccnc34)CC2)nc1] | 488.57 | (400 MHz, $CDCl_3$) δ 8.70 (d, J = 1.9 Hz, 1H), 8.62 (d, J = 1.9 Hz, 1H), 8.44 (d, J = 2.0 Hz, 1H), 7.91 (d, J = 8.8 Hz, 1H), 6.97 (d, J = 2.4 Hz, 1H), 6.92 (d, J = 2.4 Hz, 1H), 6.60 (d, J = 8.6 Hz, 1H), 5.52 (s, 1H), 4.83 (s, 1H), 4.18 (s, 3H), 4.00-3.87 (m, 5H), 3.39-3.24 (m, 4H), 2.31-2.18 (m, 2H), 2.04-1.87 (m, 6H) |
| 230 | 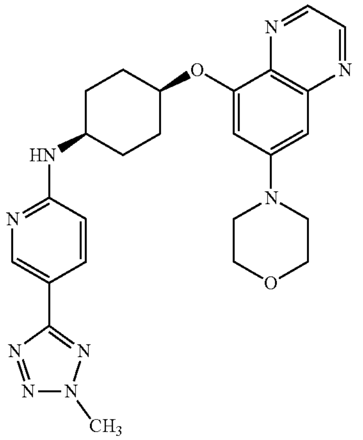 [SMILES: Cn1nnc(-c2ccc(N[C@H]3CC[C@@H](Oc4cc(N5CCOCC5)cc5nccnc45)CC3)nc2)n1] | 488.57 | (400 MHz, $CDCl_3$) δ 8.81 (d, J = 1.8 Hz, 1H), 8.69 (d, J = 1.9 Hz, 1H), 8.61 (d, J = 1.9 Hz, 1H), 8.13 (dd, J = 8.8, 2.2 Hz, 1H), 6.95 (d, J = 2.4 Hz, 1H), 6.92 (d, J = 2.4 Hz, 1H), 6.52 (d, J = 8.8 Hz, 1H), 4.82 (s, 1H), 4.36 (s, 3H), 3.96-3.85 (m, 5H), 3.41-3.28 (m, 4H), 2.28-2.17 (m, 2H), 2.06-1.83 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 231 | 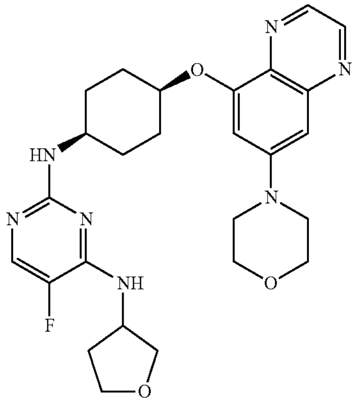 [SMILES: Fc1cnc(N[C@H]2CC[C@@H](Oc3cc(N4CCOCC4)cc4nccnc34)CC2)nc1NC1CCOC1] | 510.2 | ($CDCl_3$) δ 8.70 (d, J = 1.9 Hz, 1H), 8.62 (d, J = 2.0 Hz, 1H), 7.70 (d, J = 3.4 Hz, 1H), 6.93 (dd, J = 14.6, 2.5 Hz, 2H), 4.96 (dd, J = 17.8, 7.1 Hz, 2H), 4.76 (d, J = 6.2 Hz, 1H), 4.62 (ddt, J = 12.6, 7.1, 3.5 Hz, 1H), 4.05-3.82 (m, 8H), 3.75 (dd, J = 9.4, 3.2 Hz, 1H), 3.40-3.27 (m, 4H), 2.35 (ddt, J = 13.0, 8.2, 7.1 Hz, 1H), 2.25-2.08 (m, 2H), 2.00-1.77 (m, 6H) |
| 232 | 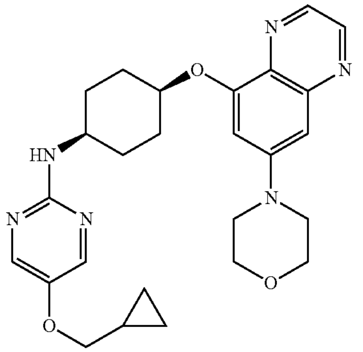 [SMILES: c1cnc2c(O[C@H]3CC[C@@H](Nc4ncc(OCC5CC5)cn4)CC3)cc(N3CCOCC3)cc2n1] | 477.18 | ($CDCl_3$) δ 8.61 (d, J = 9.1 Hz, 1H), 8.54 (d, J = 1.9 Hz, 1H), 7.98 (s, 2H), 6.94-6.75 (m, 2H), 5.01 (s, 1H), 4.71 (d, J = 5.9 Hz, 1H), 3.96-3.78 (m, 5H), 3.68 (d, J = 7.0 Hz, 2H), 3.37-3.17 (m, 4H), 2.21-1.96 (m, 2H), 1.92-1.75 (m, 6H), 1.25-1.06 (m, 1H), 0.66-0.44 (m, 2H), 0.34-0.18 (m, 2H) |
| 233 | 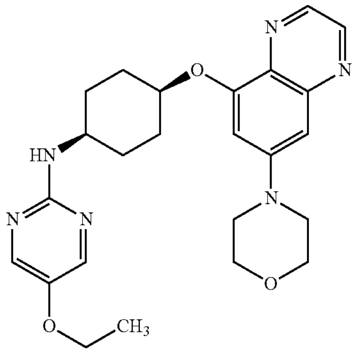 [SMILES: CCOc1cnc(N[C@H]2CC[C@@H](Oc3cc(N4CCOCC4)cc4nccnc34)CC2)nc1] | 451.2 | ($CDCl_3$) δ 8.70 (d, J = 1.9 Hz, 1H), 8.63 (d, J = 1.9 Hz, 1H), 8.06 (s, 2H), 7.01-6.86 (m, 2H), 5.00 (d, J = 8.1 Hz, 1H), 4.80 (d, J = 5.6 Hz, 1H), 4.10-3.82 (m, 7H), 3.42-3.26 (m, 5H), 2.20 (d, J = 8.2 Hz, 2H), 2.01-1.80 (m, 6H), 1.39 (t, J = 7.0 Hz, 3H) |
| 234 | 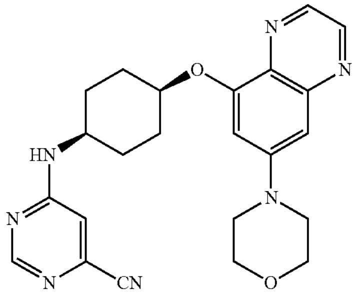 | 432.17 | ($CDCl_3$) δ 8.72 (d, J = 1.9 Hz, 1H), 8.60 (t, J = 1.9 Hz, 2H), 6.97 (d, J = 2.5 Hz, 1H), 6.91 (d, J = 2.5 Hz, 1H), 6.70 (d, J = 1.2 Hz, 1H), 4.85 (d, J = 4.9 Hz, 1H), 3.98-3.84 (m, 4H), 3.42-3.26 (m, 4H), 2.33-2.17 (m, 2H), 2.01-1.77 (m, 5H) |

TABLE 1-continued
| Cmpd. No. | Compound | ESMS (M + H) | $^1$H NMR (300 MHz, unless indicated otherwise) NMR peaks given as δ values |
|---|---|---|---|
| 235 | 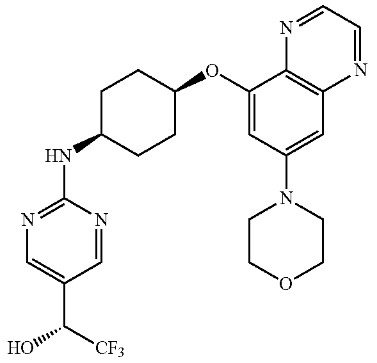 | 505.04 | ($CDCl_3$) δ 8.68 (d, J = 2.0 Hz, 1H), 8.59 (d, J = 1.9 Hz, 1H), 8.36 (s, 2H), 6.97-6.86 (m, 2H), 5.53 (d, J = 8.1 Hz, 1H), 4.96-4.72 (m, 3H), 4.09-3.86 (m, 5H), 3.33 (dd, J = 5.8, 4.0 Hz, 4H), 2.28-2.10 (m, 2H), 1.98-1.78 (m, 6H) |
| 236 | 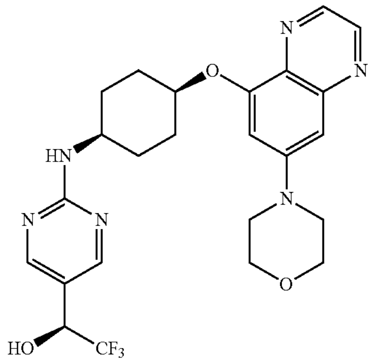 [SMILES: O[C@@H](c1cnc(N[C@H]2CC[C@@H](Oc3cc(N4CCOCC4)cc4nccnc34)CC2)nc1)C(F)(F)F] | 505.17 | ($CDCl_3$) δ 8.68 (d, J = 2.0 Hz, 1H), 8.59 (d, J = 1.9 Hz, 1H), 8.36 (s, 2H), 6.97-6.86 (m, 2H), 5.53 (d, J = 8.1 Hz, 1H), 4.96-4.72 (m, 3H), 4.09-3.86 (m, 5H), 3.33 (dd, J = 5.8, 4.0 Hz, 4H), 2.28-2.10 (m, 2H), 1.98-1.78 (m, 6H) |
| 237 | 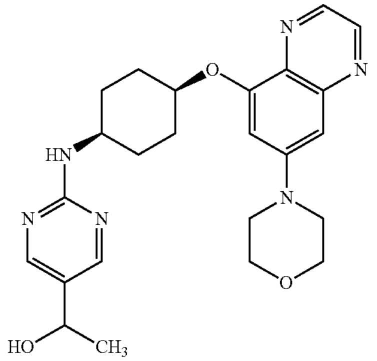 [SMILES: CC(O)c1cnc(N[C@H]2CC[C@@H](Oc3cc(N4CCOCC4)cc4nccnc34)CC2)nc1] | 451.16 | ($CDCl_3$) δ 8.69 (d, J = 1.9 Hz, 1H), 8.61 (d, J = 1.9 Hz, 1H), 8.31 (s, 2H), 6.99-6.87 (m, 2H), 5.34 (d, J = 8.1 Hz, 1H), 4.87-4.73 (m, 2H), 4.06-3.87 (m, 6H), 3.38-3.29 (m, 4H), 2.20 (q, J = 5.8 Hz, 2H), 2.04-1.84 (m, 6H), 1.51 (d, J = 6.5 Hz, 3H) |
| 238 | 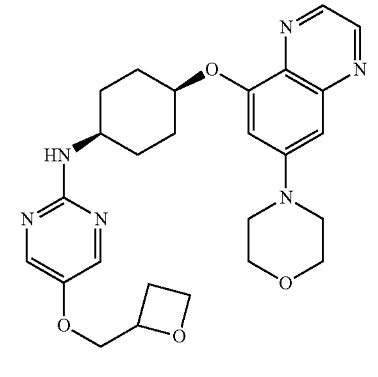 [SMILES: c1cnc2c(O[C@H]3CC[C@@H](Nc4ncc(OCC5CCO5)cn4)CC3)cc(N3CCOCC3)cc2n1] | 492.98 | ($CDCl_3$) δ 8.71 (d, J = 1.9 Hz, 1H), 8.64 (d, J = 1.9 Hz, 1H), 8.15 (s, 2H), 6.99-6.86 (m, 2H), 5.11 (td, J = 7.9, 7.4, 3.8 Hz, 1H), 4.82-4.55 (m, 3H), 4.10 (dd, J = 4.1, 2.7 Hz, 2H), 3.93 (dd, J = 6.0, 3.7 Hz, 5H), 3.60-3.43 (m, 1H), 3.36 (dd, J = 6.0, 3.7 Hz, 4H), 2.85-2.61 (m, 1H), 2.30-2.10 (m, 2H), 1.92 (s, 6H), 1.24 (q, J = 6.9 Hz, 1H) |

TABLE 1-continued

| Cmpd. No. | Compound | ESMS (M + H) | $^1$H NMR (300 MHz, unless indicated otherwise) NMR peaks given as δ values |
|---|---|---|---|
| 239 | 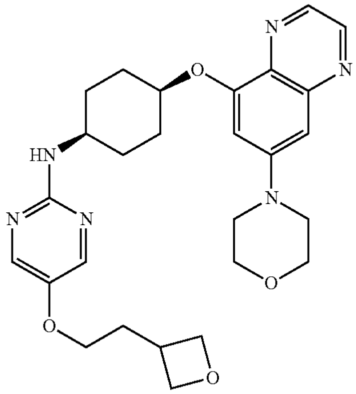 [SMILES: c1cnc2c(O[C@H]3CC[C@@H](Nc4ncc(OCCC5COC5)cn4)CC3)cc(N3CCOCC3)cc2n1] | 507 | ($CDCl_3$) δ 8.61 (d, J = 1.9 Hz, 1H), 8.54 (d, J = 1.9 Hz, 1H), 7.95 (d, J = 13.9 Hz, 2H), 6.92-6.72 (m, 2H), 4.85-4.64 (m, 3H), 4.41 (t, J = 6.2 Hz, 2H), 3.83 (q, J = 6.7, 5.7 Hz, 6H), 3.33-3.18 (m, 5H), 2.20-1.97 (m, 1H), 1.82 (s, 7H) |
| 240 | 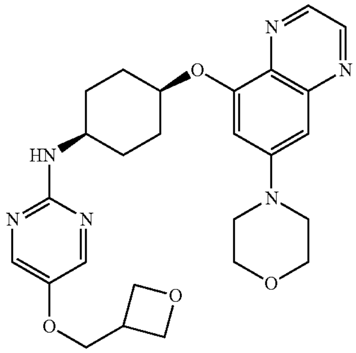 [SMILES: c1cnc2c(O[C@H]3CC[C@@H](Nc4ncc(OCC5COC5)cn4)CC3)cc(N3CCOCC3)cc2n1] | 493.16 | ($CDCl_3$) δ 8.70 (d, J = 1.9 Hz, 1H), 8.63 (d, J = 1.9 Hz, 1H), 8.08 (s, 2H), 7.01-6.87 (m, 2H), 5.11 (d, J = 8.1 Hz, 1H), 4.95-4.74 (m, 3H), 4.56 (t, J = 6.0 Hz, 2H), 4.17 (d, J = 6.7 Hz, 2H), 4.05-3.81 (m, 4H), 3.51-3.29 (m, 5H), 2.21 (q, J = 6.4, 5.7 Hz, 2H), 2.03-1.80 (m, 8H) |
| 241 | 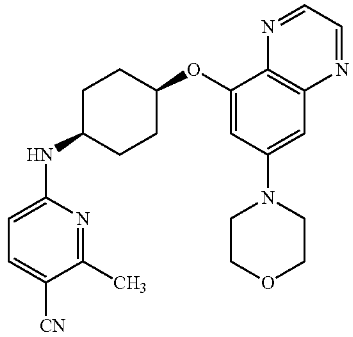 [SMILES: Cc1nc(N[C@H]2CC[C@@H](Oc3cc(N4CCOCC4)cc4nccnc34)CC2)ccc1C#N] | 445.54 | (400 MHz, $CDCl_3$) δ 8.69 (d, J = 1.9 Hz, 1H), 8.61 (d, J = 1.9 Hz, 1H), 7.52 (d, J = 8.7 Hz, 1H), 6.96 (d, J = 2.5 Hz, 1H), 6.90 (d, J = 2.5 Hz, 1H), 6.23 (d, J = 8.7 Hz, 1H), 5.09 (s, 1H), 4.80 (s, 1H), 4.00-3.78 (m, 5H), 3.40-3.24 (m, 4H), 2.56 (s, 3H), 2.29-2.14 (m, 2H), 2.01-1.80 (m, 6H) |
| 242 | 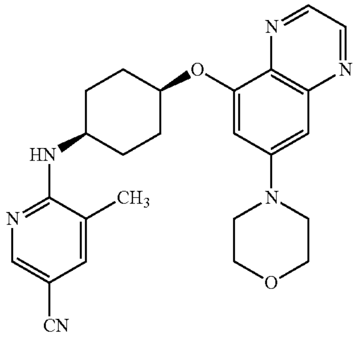 [SMILES: Cc1cc(C#N)cnc1N[C@H]1CC[C@@H](Oc2cc(N3CCOCC3)cc3nccnc23)CC1] | 445.54 | (400 MHz, $CDCl_3$) δ 8.70 (d, J = 1.8 Hz, 1H), 8.62 (d, J = 1.9 Hz, 1H), 8.30 (d, J = 1.8 Hz, 1H), 7.37 (s, 1H), 6.96 (d, J = 2.3 Hz, 1H), 6.91 (d, J = 2.3 Hz, 1H), 4.79 (s, 1H), 4.74 (s, 1H), 4.28 (s, 1H), 4.01-3.83 (m, 4H), 3.40-3.25 (m, 4H), 2.30-2.17 (m, 2H), 2.11 (s, 3H), 1.99-1.87 (m, 6H) |

TABLE 1-continued
| Cmpd. No. | Compound | ESMS (M + H) | $^1$H NMR (300 MHz, unless indicated otherwise) NMR peaks given as δ values |
|---|---|---|---|
| 243 | 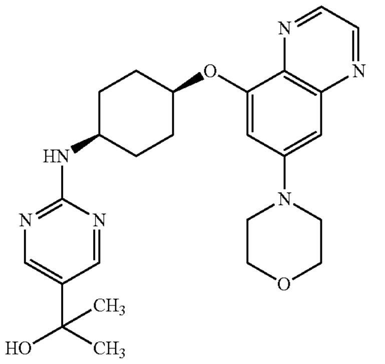 [SMILES: CC(C)(O)c1cnc(N[C@H]2CC[C@@H](Oc3cc(N4CCOCC4)cc4nccnc34)CC2)nc1] | 465.2 | ($CDCl_3$) δ 8.69 (d, J = 2.0 Hz, 1H), 8.62 (d, J = 1.9 Hz, 1H), 5.36 (s, 1H), 4.03 (s, 1H), 1.57 (s, 6H), 2.02-1.80 (m, 6H), 8.42 (s, 2H), 6.99-6.87 (m, 2H), 4.80 (s, 1H), 3.92 (dd, J = 6.0, 3.7 Hz, 4H), 3.39-3.29 (m, 4H), 2.20 (d, J = 9.0 Hz, 2H) |
| 244 | 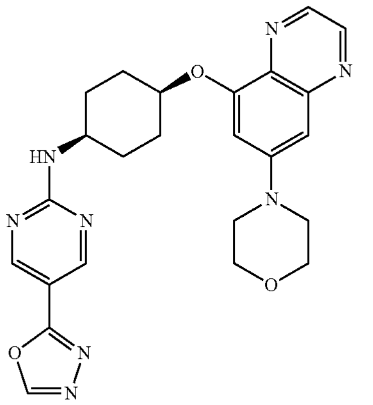 [SMILES: c1cnc2c(O[C@H]3CC[C@@H](Nc4ncc(-c5nnco5)cn4)CC3)cc(N3CCOCC3)cc2n1] | 475.15 | ($CDCl_3$) δ 8.98-8.86 (m, 2H), 8.66 (dd, J = 23.8, 1.9 Hz, 2H), 8.44 (s, 1H), 7.00-6.88 (m, 2H), 5.89 (d, J = 8.1 Hz, 1H), 4.83 (dq, J = 5.4, 2.6 Hz, 1H), 4.22-4.04 (m, 1H), 3.97-3.87 (m, 4H), 3.43-3.29 (m, 4H), 2.24 (td, J = 8.3, 7.4, 4.0 Hz, 2H), 2.15-1.81 (m, 6H) |
| 245 | 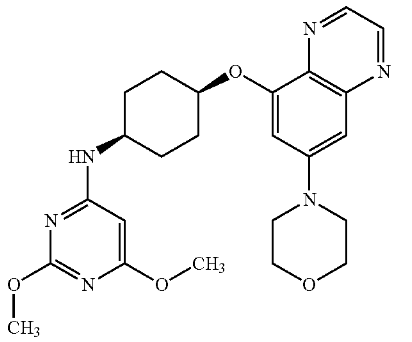 [SMILES: COc1cc(N[C@H]2CC[C@@H](Oc3cc(N4CCOCC4)cc4nccnc34)CC2)nc(OC)n1] | 467.14 | ($CDCl_3$) δ 8.61 (d, J = 1.9 Hz, 1H), 8.53 (d, J = 1.9 Hz, 1H), 6.84 (dd, J = 18.2, 2.5 Hz, 2H), 5.26 (s, 1H), 4.78 (d, J = 8.0 Hz, 1H), 4.68 (d, J = 5.6 Hz, 1H), 3.82 (t, J = 4.0 Hz, 10H), 3.30-3.15 (m, 4H), 2.10 (q, J = 6.2, 5.7 Hz, 2H), 1.94-1.69 (m, 6H) |
| 246 | 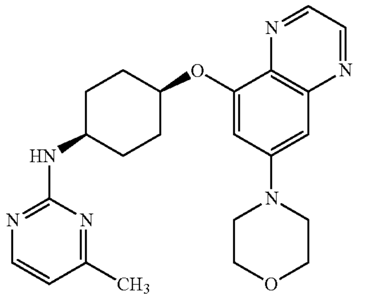 | 421.33 | ($CDCl_3$) δ 8.61 (d, J = 1.9 Hz, 1H), 8.54 (d, J = 1.9 Hz, 1H), 8.06 (d, J = 5.0 Hz, 1H), 6.94-6.78 (m, 2H), 6.32 (d, J = 5.0 Hz, 1H), 5.09 (s, 1H), 4.70 (d, J = 6.0 Hz, 1H), 3.95 (s, 1H), 3.91-3.77 (m, 5H), 3.37-3.13 (m, 4H), 2.20-2.00 (m, 2H), 1.94-1.71 (m, 6H) |

TABLE 1-continued
| Cmpd. No. | Compound | ESMS (M + H) | $^1$H NMR (300 MHz, unless indicated otherwise) NMR peaks given as δ values |
|---|---|---|---|
| 247 | 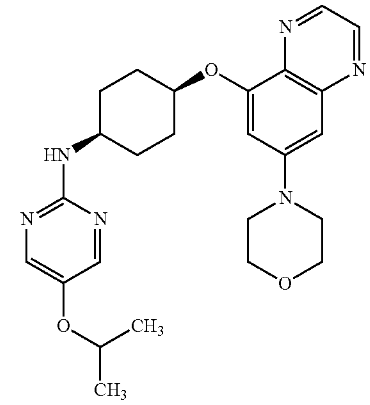 [SMILES: CC(C)Oc1cnc(N[C@H]2CC[C@@H](Oc3cc(N4CCOCC4)cc4nccnc34)CC2)nc1] | 465.1 | ($CDCl_3$) δ 8.71 (d, J = 1.9 Hz, 1H), 8.64 (t, J = 2.4 Hz, 1H), 8.05 (s, 2H), 7.04-6.87 (m, 2H), 5.20 (s, 1H), 4.80 (s, 1H), 4.30 (p, J = 6.1 Hz, 1H), 4.05-3.81 (m, 4H), 3.44-3.27 (m, 4H), 2.22 (t, J = 7.3 Hz, 2H), 1.93 (d, J = 4.6 Hz, 6H), 1.33 (d, J = 6.1 Hz, 6H) |
| 248 | 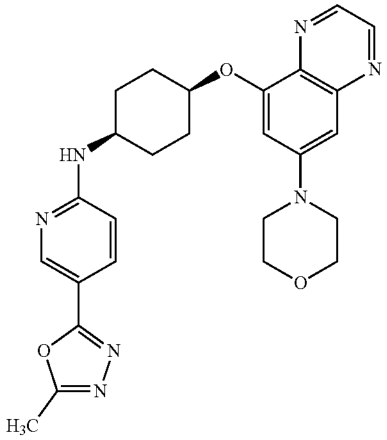 [SMILES: Cc1nnc(-c2ccc(N[C@H]3CC[C@@H](Oc4cc(N5CCOCC5)cc5nccnc45)CC3)nc2)o1] | 488.48 | (400 MHz, $CDCl_3$) δ 8.69 (d, J = 1.9 Hz, 1H), 8.66 (d, J = 1.9 Hz, 1H), 8.62 (d, J = 1.9 Hz, 1H), 8.05 (d, J = 8.5 Hz, 1H), 6.96 (d, J = 2.4 Hz, 1H), 6.92 (d, J = 2.5 Hz, 1H), 6.51 (d, J = 8.7 Hz, 1H), 4.82 (s, 1H), 3.99-3.85 (m, 5H), 3.38-3.27 (m, 4H), 2.59 (s, 3H), 2.29-2.18 (m, 2H), 2.01-1.84 (m, 6H) |
| 249 | 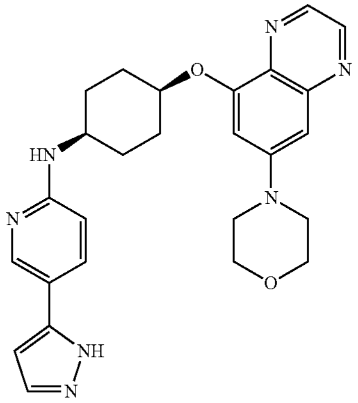 [SMILES: c1cc(-c2ccc(N[C@H]3CC[C@@H](Oc4cc(N5CCOCC5)cc5nccnc45)CC3)nc2)[nH]n1] | 472.54 | (400 MHz, $CDCl_3$) δ 8.69 (d, J = 1.9 Hz, 1H), 8.61 (d, J = 1.9 Hz, 1H), 8.45 (d, J = 1.9 Hz, 1H), 7.86 (d, J = 7.7 Hz, 1H), 7.60 (d, J = 2.3 Hz, 1H), 6.96 (d, J = 2.4 Hz, 1H), 6.92 (d, J = 2.4 Hz, 1H), 6.50 (d, J = 2.3 Hz, 1H), 6.48 (d, J = 8.9 Hz, 1H), 4.81 (s, 1H), 3.95-3.85 (m, 5H), 3.39-3.30 (m, 4H), 2.26-2.17 (m, 2H), 1.99-1.84 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 250 | 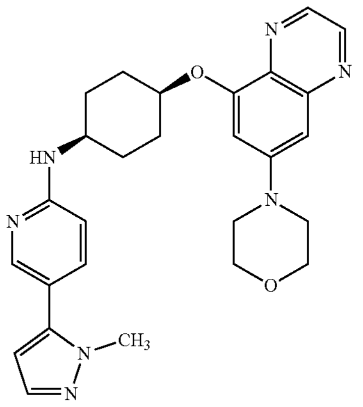 [SMILES: Cn1nccc1-c1ccc(N[C@H]2CC[C@@H](Oc3cc(N4CCOCC4)cc4nccnc34)CC2)nc1] | 486.5 | (400 MHz, $CDCl_3$) δ 8.69 (d, J = 1.9 Hz, 1H), 8.61 (d, J = 1.9 Hz, 1H), 8.09 (d, J = 1.7 Hz, 1H), 7.56-7.45 (m, 2H), 6.96 (d, J = 2.4 Hz, 1H), 6.93 (d, J = 2.4 Hz, 1H), 6.55 (d, J = 8.5 Hz, 1H), 6.25 (d, J = 1.9 Hz, 1H), 4.84 (s, 1H), 3.96-3.83 (m, 8H), 3.39-3.30 (m, 4H), 2.28-2.19 (m, 2H), 2.03-1.83 (m, 6H) |
| 251 | 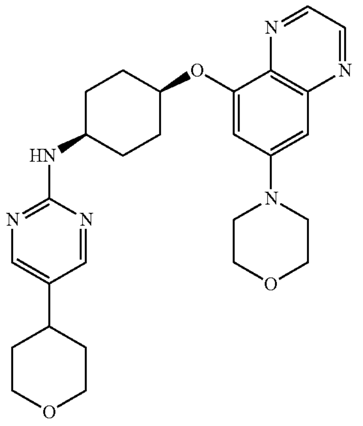 | 491.1 | ($CDCl_3$) δ 8.71 (d, J = 1.9 Hz, 1H), 8.63 (d, J = 1.9 Hz, 1H), 8.18 (s, 2H), 7.04-6.87 (m, 2H), 5.21 (d, J = 8.2 Hz, 1H), 4.80 (s, 1H), 4.2-4.0 (m, 3H), 3.98-3.85 (m, 4H), 3.61-3.44 (m, 2H), 3.41-3.21 (m, 4H), 2.75-2.47 (m, 1H), 2.21 (d, J = 9.6 Hz, 2H), 1.92 (t, J = 6.4 Hz, 6H), 1.83-1.66 (m, 4H) |
| 252 | 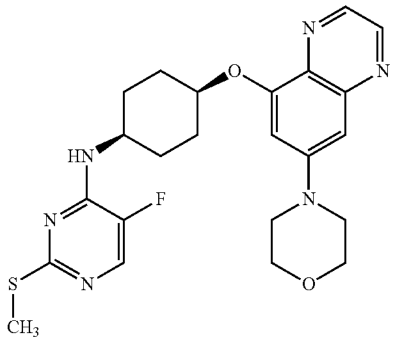 [SMILES: CSc1ncc(F)c(N[C@H]2CC[C@@H](Oc3cc(N4CCOCC4)cc4nccnc34)CC2)n1] | 471.1 | ($CDCl_3$) δ 3.97-3.87 (m, 4H), 3.39-3.29 (m, 4H), 2.50 (s, 3H), 2.28-2.16 (m, 2H), 2.02-1.89 (m, 6H), 4.26-4.17 (m, 1H), 8.70 (d, J = 1.9 Hz, 1H), 8.63 (d, J = 1.9 Hz, 1H), 7.88 (d, J = 3.3 Hz, 1H), 6.93 (dd, J = 18.7, 2.5 Hz, 2H), 5.10 (d, J = 7.9 Hz, 1H), 4.79 (d, J = 3.7 Hz, 1H) |
| 253 | 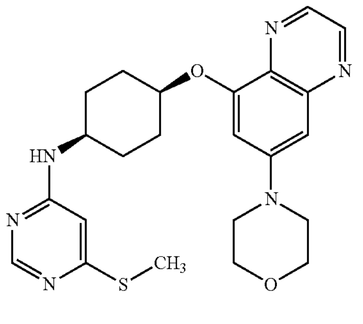 | 453.19 | ($CDCl_3$) δ 8.70 (d, J = 1.9 Hz, 1H), 8.61 (d, J = 2.0 Hz, 1H), 8.38 (d, J = 1.1 Hz, 1H), 6.93 (dd, J = 17.3, 2.5 Hz, 2H), 6.18 (d, J = 1.2 Hz, 1H), 5.03 (s, 1H), 4.81 (d, J = 6.1 Hz, 1H), 3.97-3.87 (m, 4H), 3.83 (s, 1H), 3.39-3.29 (m, 4H), 2.51 (s, 3H), 2.21 (d, J = 8.8 Hz, 2H), 2.05 (s, 0H), 1.91 (d, J = 10.6 Hz, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 254 | 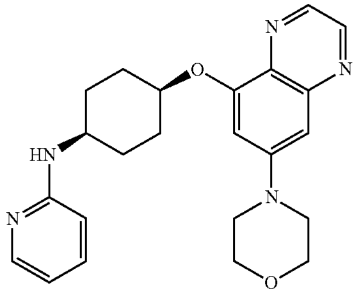 | 406.57 | (400 MHz, $CDCl_3$) δ 8.71 (d, J = 1.9 Hz, 1H), 8.63 (d, J = 1.9 Hz, 1H), 8.15-8.04 (m, 1H), 7.46-7.39 (m, 1H), 6.97 (d, J = 2.5 Hz, 1H), 6.93 (d, J = 2.5 Hz, 1H), 6.60-6.52 (m, 1H), 6.41 (d, J = 8.4 Hz, 1H), 4.80 (s, 1H), 4.68 (s, 1H), 3.98-3.85 (m, 5H), 3.41-3.30 (m, 4H), 2.27-2.15 (m, 2H), 1.97-1.86 (m, 6H) |
| 255 | 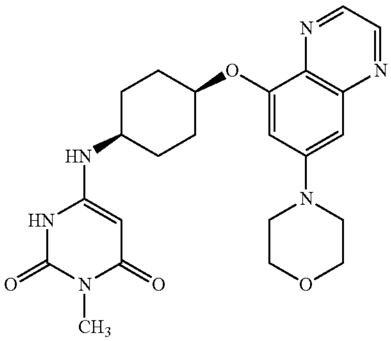 [SMILES: Cn1c(=O)cc(N[C@H]2CC[C@@H](Oc3cc(N4CCOCC4)cc4nccnc34)CC2)[nH]c1=O] | 450.96 | (methanol-$d_4$) δ 8.71 (dd, J = 7.5, 2.1 Hz, 1H), 8.57 (dd, J = 8.8, 2.1 Hz, 1H), 7.12 (d, J = 2.5 Hz, 1H), 6.88 (d, J = 2.4 Hz, 1H), 3.88 (t, J = 4.8 Hz, 4H), 3.45-3.35 (m, 4H), 3.19 (s, 3H), 2.25-2.01 (m, 2H), 2.00-1.80 (m, 6H) |
| 256 | 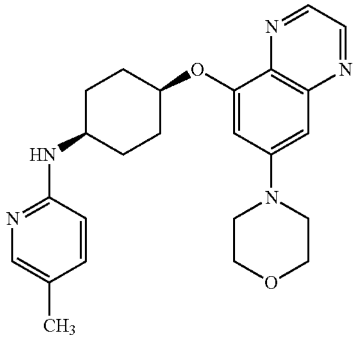 | 420.1 | ($CDCl_3$) δ 8.71 (d, J = 1.9 Hz, 1H), 8.64 (d, J = 1.9 Hz, 1H), 7.80 (d, J = 1.5 Hz, 1H), 7.47 (d, J = 1.5 Hz, 1H), 7.02-6.86 (m, 2H), 4.80 (s, 1H), 4.27 (d, J = 8.3 Hz, 1H), 4.00-3.72 (m, 7H), 3.35 (dd, J = 6.0, 3.8 Hz, 4H), 2.23 (s, 2H), 2.02-1.80 (m, 6H) |
| 257 | 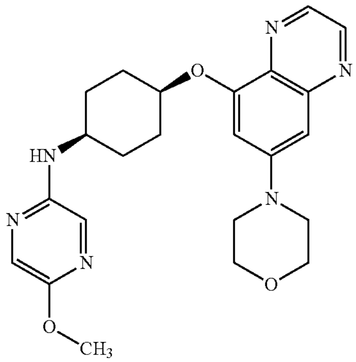 [SMILES: COc1cnc(N[C@H]2CC[C@@H](Oc3cc(N4CCOCC4)cc4nccnc34)CC2)cn1] | 437.1 | ($CDCl_3$) δ 8.71 (d, J = 1.9 Hz, 1H), 8.63 (dd, J = 1.9, 0.7 Hz, 1H), 7.99-7.88 (m, 1H), 7.02-6.87 (m, 2H), 6.34 (d, J = 8.4 Hz, 1H), 4.78 (s, 1H), 4.40 (d, J = 8.2 Hz, 1H), 4.03-3.75 (m, 5H), 3.35 (dd, J = 6.0, 3.7 Hz, 4H), 2.18 (s, 5H), 2.03-1.81 (m, 6H) |

TABLE 1-continued
| Cmpd. No. | Compound | ESMS (M + H) | $^1$H NMR (300 MHz, unless indicated otherwise) NMR peaks given as δ values |
|---|---|---|---|
| 258 | 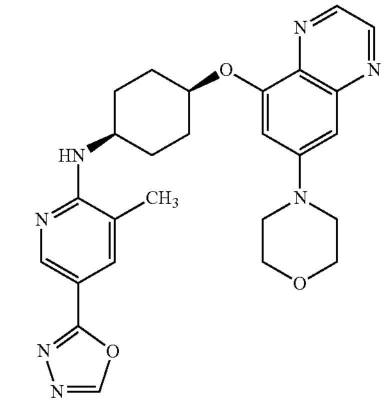 [SMILES: Cc1cc(-c2nnco2)cnc1N[C@H]1CC[C@@H](Oc2cc(N3CCOCC3)cc3nccnc23)CC1] | 488.52 | ($CDCl_3$) δ 8.78-8.59 (m, 3H), 8.38 (s, 1H), 7.85 (s, 1H), 6.95 (d, J = 2.4 Hz, 1H), 6.91 (d, J = 2.3 Hz, 1H), 4.79 (s, 1H), 4.67 (d, J = 7.6 Hz, 1H), 4.32 (s, 1H), 3.99-3.82 (m, 4H), 3.40-3.27 (m, 4H), 2.33-2.06 (m, 5H), 2.03-1.87 (m, 6H) |
| 259 | 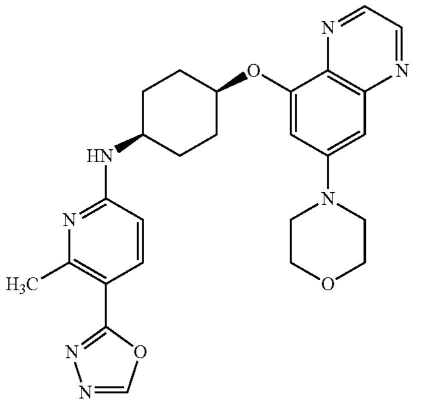 [SMILES: Cc1nc(N[C@H]2CC[C@@H](Oc3cc(N4CCOCC4)cc4nccnc34)CC2)ccc1-c1nnco1] | 488.48 | ($CDCl_3$) δ 8.70 (d, J = 1.9 Hz, 1H), 8.62 (d, 1H), 8.41 (s, 1H), 8.04-7.93 (m, 1H), 6.96 (d, J = 2.5 Hz, 1H), 6.91 (d, J = 2.1 Hz, 1H), 6.35 (d, J = 9.1 Hz, 1H), 5.07 (s, 1H), 4.82 (s, 1H), 4.02-3.79 (m, 5H), 3.41-3.27 (m, 4H), 2.83-2.72 (m, 3H), 2.30-2.17 (m, 2H), 2.02-1.80 (m, 6H) |
| 260 | 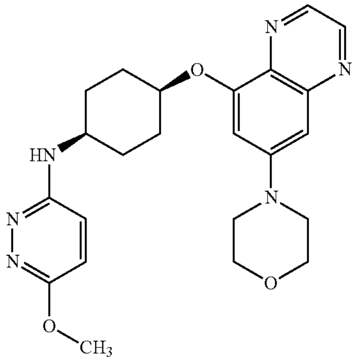 | 437.24 | ($CDCl_3$) δ 8.70 (d, J = 1.9 Hz, 1H), 8.62 (d, J = 1.9 Hz, 1H), 6.93 (dd, J = 14.5, 2.5 Hz, 2H), 6.79 (d, J = 9.4 Hz, 1H), 6.64 (d, J = 9.4 Hz, 1H), 4.80 (d, J = 5.5 Hz, 1H), 4.27 (d, J = 7.5 Hz, 1H), 4.14 (s, 1H), 4.02 (s, 3H), 3.98-3.88 (m, 4H), 3.42-3.29 (m, 4H), 2.31-2.12 (m, 2H), 1.95 (ddd, J = 17.2, 9.2 6.0 Hz, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 261 | 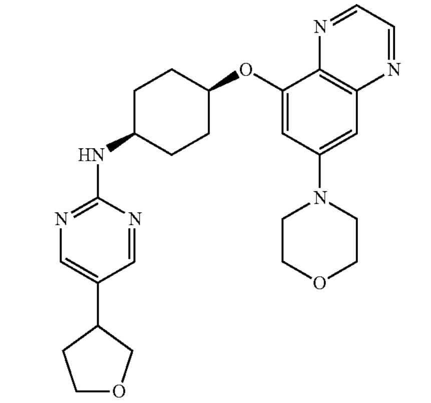 [SMILES: c1cnc2c(O[C@H]3CC[C@@H](Nc4ncc(C5CCOC5)cn4)CC3)cc(N3CCOCC3)cc2n1] | 477.3 | ($CDCl_3$) δ 8.71 (d, J = 1.9 Hz, 1H), 8.64 (d, J = 1.9 Hz, 1H), 8.20 (s, 2H), 7.04-6.84 (m, 2H), 5.16 (d, J = 8.0 Hz, 1H), 4.80 (s, 1H), 4.19-3.85 (m, 7H), 3.66 (dd, J = 8.5, 7.1 Hz, 1H), 3.35 (dd, J = 5.9, 3.8 Hz, 4H), 3.24 (t, J = 7.5 Hz, 1H), 2.48-2.11 (m, 4H), 2.05-1.82 (m, 6H) |
| 262 | 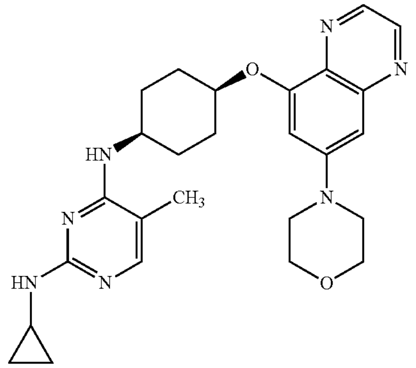 [SMILES: Cc1cnc(NC2CC2)nc1N[C@H]1CC[C@@H](Oc2cc(N3CCOCC3)cc3nccnc23)CC1] | 476.26 | ($CDCl_3$) δ 8.69 (d, J = 1.9 Hz, 1H), 8.62 (d, J = 1.9 Hz, 1H), 7.61 (d, J = 1.0 Hz, 1H), 6.98-6.86 (m, 2H), 4.96 (s, 1H), 4.82-4.71 (m, 1H), 4.63-4.56 (m, 1H), 4.08-3.87 (m, 5H), 3.38-3.29 (m, 4H), 2.80 (tdd, J = 6.8, 5.0, 3.1 Hz, 1H), 2.23-2.11 (m, 2H), 2.08-1.82 (m, 9H), 0.90-0.72 (m, 2H), 0.59-0.47 (m, 2H) |
| 263 | 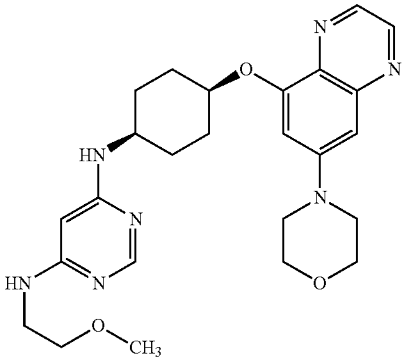 [SMILES: COCCNc1cc(N[C@H]2CC[C@@H](Oc3cc(N4CCOCC4)cc4nccnc34)CC2)ncn1] | 480.22 | ($CDCl_3$) δ 8.70 (d, J = 1.9 Hz, 1H), 8.61 (d, J = 1.9 Hz, 1H), 8.11 (d, J = 0.9 Hz, 1H), 6.93 (dd, J = 15.5, 2.5 Hz, 2H), 5.30 (d, J = 1.0 Hz, 1H), 5.16 (s, 1H), 4.95 (s, 1H), −0.17-−0.23 (m, 0H), 4.80 (s, 1H), 3.92 (dd, J = 5.9, 3.7 Hz, 4H), 3.74 (s, 1H), 3.57 (dd, J = 5.6, 4.6 Hz, 2H), 3.50-3.29 (m, 9H), 2.20 (d, J = 9.1 Hz, 2H), 1.93 (d, J = 13.1 Hz, 6H) |
| 264 | 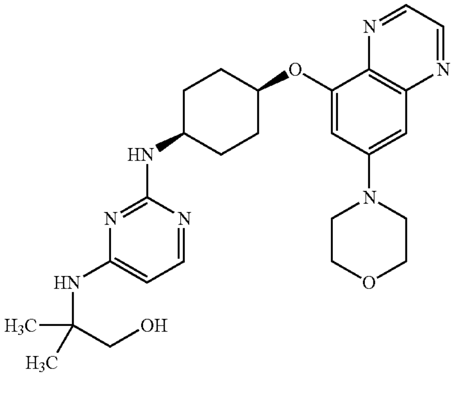 [SMILES: CC(C)(CO)Nc1ccnc(N[C@H]2CC[C@@H](Oc3cc(N4CCOCC4)cc4nccnc34)CC2)n1] | 494.1 | ($CDCl_3$) δ 8.69 (d, J = 1.9 Hz, 1H), 8.62 (d, J = 2.0 Hz, 1H), 7.76 (d, J = 5.8 Hz, 1H), 7.02-6.86 (m, 2H), 5.66 (d, J = 5.9 Hz, 1H), 4.80 (d, J = 5.5 Hz, 1H), 4.63 (s, 1H), 3.97-3.84 (m, 5H), 1.30-1.20 (m, 1H), 3.64 (s, 2H), 3.38-3.28 (m, 4H), 1.37 (s, 6H), 5.16-4.86 (m, 1H), 2.24-2.13 (m, 2H), 1.96-1.82 (m, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 265 | 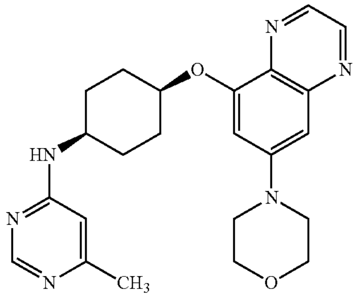 | 421.18 | ($CDCl_3$) δ 8.70 (d, J = 1.9 Hz, 1H), 8.61 (d, J = 1.9 Hz, 1H), 8.47 (d, J = 1.1 Hz, 1H), 6.93 (dd, J = 16.7, 2.5 Hz, 2H), 6.17 (t, J = 0.9 Hz, 1H), 4.95 (s, 1H), 4.81 (td, J = 5.3, 2.5 Hz, 1H), 4.07-3.83 (m, 5H), 3.39-3.29 (m, 4H), 2.34 (s, 3H), 2.21 (dt, J = 11.1, 5.1 Hz, 2H), 2.04-1.76 (m, 6H) |
| 266 | 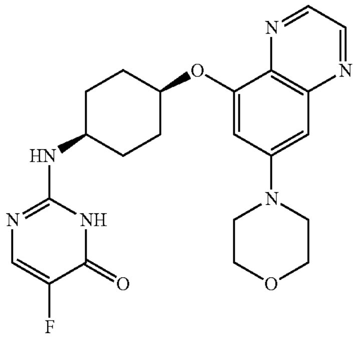 [SMILES: O=c1[nH]c(N[C@H]2CC[C@@H](Oc3cc(N4CCOCC4)cc4nccnc34)CC2)ncc1F] | 441.2 | ($CDCl_3$) δ 11.49 (s, 1H), 8.69 (d, J = 1.9 Hz, 1H), 8.59 (d, J = 1.9 Hz, 1H), 7.73 (d, J = 3.0 Hz, 1H), 7.03-6.89 (m, 2H), 6.56 (d, J = 7.2 Hz, 1H), 4.82 (s, 1H), 3.91 (dd, J = 6.0, 3.8 Hz, 5H), 3.39-3.29 (m, 4H), 2.27-2.14 (m, 2H), 2.07-1.81 (m, 6H) |
| 267 | 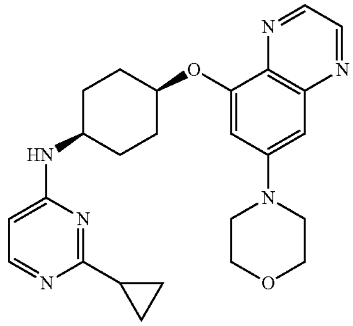 [SMILES: c1cc(N[C@H]2CC[C@@H](Oc3cc(N4CCOCC4)cc4nccnc34)CC2)nc(C2CC2)n1] | 447.11 | ($CDCl_3$) δ 8.70 (d, J = 1.9 Hz, 1H), 8.60 (d, J = 1.9 Hz, 1H), 8.03 (d, J = 6.1 Hz, 1H), 6.93 (dd, J = 18.6, 2.5 Hz, 2H), 6.13 (d, J = 6.1 Hz, 1H), 5.09 (s, 1H), 4.79 (s, 1H), 4.03-3.78 (m, 5H), 3.34 (dd, J = 6.0, 3.8 Hz, 4H), 2.20 (d, J = 8.1 Hz, 2H), 1.96 (s, 7H), 1.10 (d, J = 2.8 Hz, 2H), 1.00 (d, J = 8.0 Hz, 2H) |
| 268 | 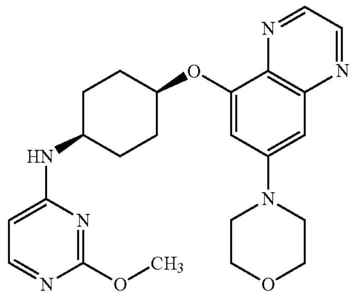 [SMILES: COc1nccc(N[C@H]2CC[C@@H](Oc3cc(N4CCOCC4)cc4nccnc34)CC2)n1] | 437.19 | ($CDCl_3$) δ 8.69 (d, J = 1.9 Hz, 1H), 8.60 (d, J = 1.9 Hz, 1H), 7.95 (d, J = 5.8 Hz, 1H), 6.92 (dd, J = 17.9, 2.5 Hz, 2H), 5.99 (d, J = 5.9 Hz, 1H), 5.01 (s, 1H), 4.79 (dt, J = 6.9, 3.4 Hz, 1H), 3.91 (d, J = 8.7 Hz, 8H), 3.43-3.25 (m, 4H), 2.32-2.09 (m, 2H), 2.05-1.74 (m, 6H) |

TABLE 1-continued
| Cmpd. No. | Compound | ESMS (M + H) | $^1$H NMR (300 MHz, unless indicated otherwise) NMR peaks given as δ values |
|---|---|---|---|
| 269 | 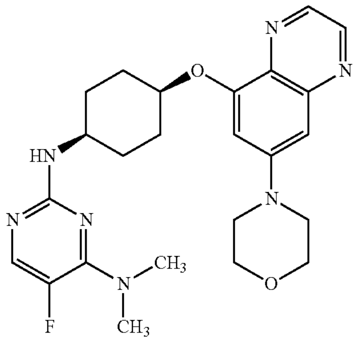 [SMILES: CN(C)c1nc(N[C@H]2CC[C@@H](Oc3cc(N4CCOCC4)cc4nccnc34)CC2)ncc1F] | 468.13 | ($CDCl_3$) δ 8.69 (d, J = 1.9 Hz, 1H), 8.62 (d, J = 1.9 Hz, 1H), 7.70 (d, J = 6.8 Hz, 1H), 6.92 (dd, J = 14.4, 2.5 Hz, 2H), 4.86 (d, J = 8.1 Hz, 1H), 4.75 (dt, J = 8.6, 4.0 Hz, 1H), 3.97-3.87 (m, 5H), 3.38-3.28 (m, 4H), 3.14 (d, J = 2.2 Hz, 6H), 2.24-2.07 (m, 2H), 2.02-1.79 (m, 6H) |
| 270 | 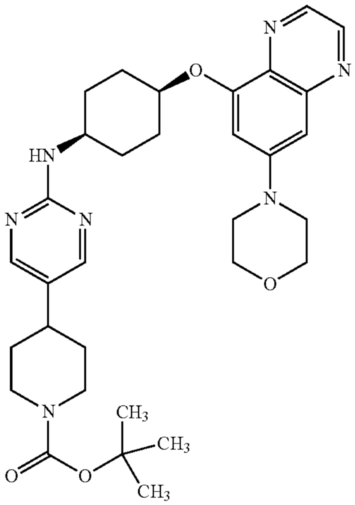 [SMILES: CC(C)(C)OC(=O)N1CCC(c2cnc(N[C@H]3CC[C@@H](Oc4cc(N5CCOCC5)cc5nccnc45)CC3)nc2)CC1] | | ($CDCl_3$) δ 8.71 (d, J = 1.9 Hz, 1H), 8.64 (d, J = 2.0 Hz, 1H), 8.15 (s, 2H), 7.01-6.87 (m, 2H), 5.13 (d, J = 8.1 Hz, 1H), 4.80 (s, 1H), 4.24 (s, 1H), 4.01 (s, 2H), 3.93 (dd, J = 6.0, 3.7 Hz, 4H), 3.35 (dd, J = 5.9, 3.9 Hz, 4H), 2.80 (t, J = 12.7 Hz, 2H), 2.51 (t, J = 12.1 Hz, 1H), 2.21 (d, J = 8.3 Hz, 2H), 2.05-1.72 (m, 8H), 1.49 (s, 9H) |
| 271 | 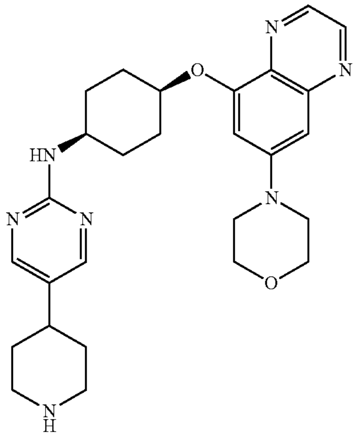 [SMILES: c1cnc2c(O[C@H]3CC[C@@H](Nc4ncc(C5CCNCC5)cn4)CC3)cc(N3CCOCC3)cc2n1] | 490.2 | ($CDCl_3$) δ 8.62 (d, J = 1.9 Hz, 1H), 8.55 (d, J = 1.9 Hz, 1H), 8.09 (s, 2H), 6.93-6.78 (m, 2H), 5.03 (d, J = 8.1 Hz, 1H), 4.72 (d, J = 5.8 Hz, 1H), 4.02-3.75 (m, 5H), 3.34-3.21 (m, 4H), 3.20-3.06 (m, 2H), 2.66 (td, J = 12.1, 2.5 Hz, 2H), 2.38 (ddt, J = 12.2, 7.6, 3.8 Hz, 1H), 2.12 (d, J = 8.9 Hz, 2H), 1.96-1.65 (m, 10H), 1.53 (qd, J = 12.3, 3.9 Hz, 2H) |

TABLE 1-continued

| Cmpd. No. | Compound | ESMS (M + H) | $^1$H NMR (300 MHz, unless indicated otherwise) NMR peaks given as δ values |
|---|---|---|---|
| 272 | 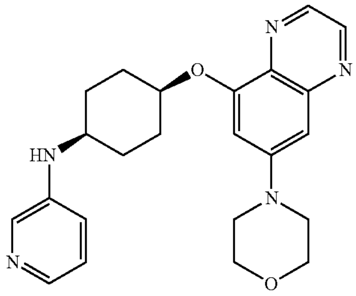 [SMILES: c1cncc(N[C@H]2CC[C@@H](Oc3cc(N4CCOCC4)cc4nccnc34)CC2)c1] | 406.53 | ($CDCl_3$) δ 8.69 (d, J = 1.9 Hz, 1H), 8.61 (d, J = 1.9 Hz, 1H), 8.04 (d, J = 2.8 Hz, 1H), 7.94 (dd, J = 4.7, 1.3 Hz, 1H), 7.11 (dd, J = 8.3, 4.7 Hz, 1H), 7.00-6.84 (m, 3H), 4.78 (s, 1H), 3.98-3.88 (m, 4H), 3.85 (d, J = 8.1 Hz, 1H), 3.38-3.28 (m, 4H), 2.27-2.15 (m, 2H), 1.97-1.84 (m, 6H) |
| 273 | 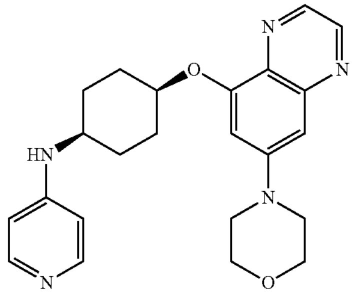 [SMILES: c1cc(N[C@H]2CC[C@@H](Oc3cc(N4CCOCC4)cc4nccnc34)CC2)ccn1] | 406.57 | ($CDCl_3$) δ 8.70 (d, J = 1.9 Hz, 1H), 8.61 (d, J = 1.9 Hz, 1H), 8.18 (d, J = 6.3 Hz, 2H), 6.96 (d, J = 2.4 Hz, 1H), 6.90 (d, J = 2.4 Hz, 1H), 6.51-6.42 (m, 2H), 4.79 (s, 1H), 4.47 (d, J = 7.7 Hz, 1H), 3.98-3.86 (m, 4H), 3.56 (s, 1H), 3.39-3.26 (m, 4H), 2.27-2.15 (m, 2H), 2.01-1.79 (m, 6H) |
| 274 | 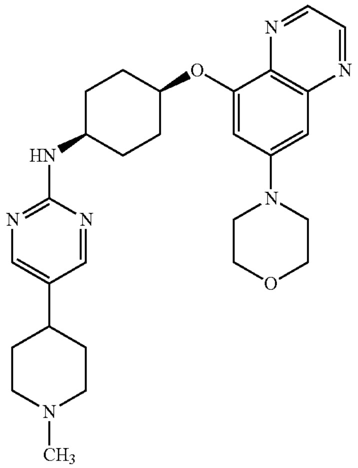 [SMILES: CN1CCC(c2cnc(N[C@H]3CC[C@@H](Oc4cc(N5CCOCC5)cc5nccnc45)CC3)nc2)CC1] | 504.1 | ($CDCl_3$) δ 8.71 (d, J = 1.9 Hz, 1H), 8.63 (d, J = 1.9 Hz, 1H), 8.18 (s, 2H), 7.03-6.86 (m, 2H), 5.11 (d, J = 8.1 Hz, 1H), 4.81 (d, J = 5.9 Hz, 1H), 4.12-3.84 (m, 5H), 3.42-3.29 (m, 4H), 3.05-2.89 (m, 2H), 2.33 (s, 4H), 2.21 (d, J = 8.8 Hz, 2H), 2.11-1.61 (m, 10H) |
| 275 | 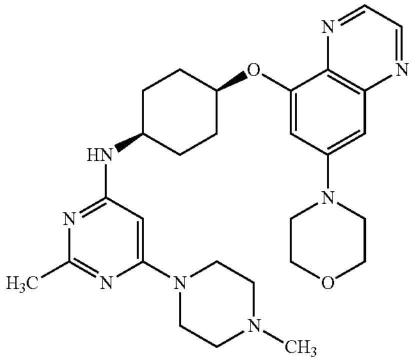 [SMILES: Cc1nc(N[C@H]2CC[C@@H](Oc3cc(N4CCOCC4)cc4nccnc34)CC2)cc(N2CCN(C)CC2)n1] | 519.2 | ($CDCl_3$) δ 8.62 (d, J = 1.9 Hz, 1H), 8.54 (d, J = 1.9 Hz, 1H), 6.93-6.77 (m, 2H), 5.20 (s, 1H), 4.78-4.60 (m, 2H), 3.92-3.79 (m, 5H), 3.64 (s, 0H), 3.51 (t, J = 5.1 Hz, 4H), 3.36-3.16 (m, 4H), 2.40 (t, J = 5.1 Hz, 4H), 2.27 (d, J = 4.8 Hz, 6H), 2.16-2.02 (m, 2H), 1.81 (q, J = 8.1, 5.7 Hz, 6H) |

TABLE 1-continued

| Cmpd. No. | Compound | ESMS (M + H) | $^1$H NMR (300 MHz, unless indicated otherwise) NMR peaks given as δ values |
|---|---|---|---|
| 276 | 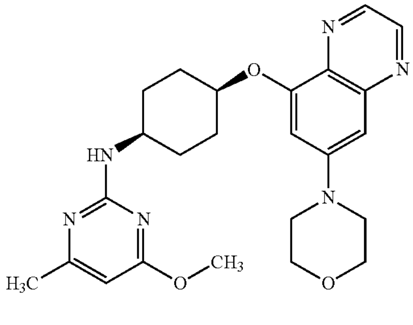 [SMILES: COc1cc(C)nc(N[C@H]2CC[C@@H](Oc3cc(N4CCOCC4)cc4nccnc34)CC2)n1] | 451.53 | ($CDCl_3$) δ 8.69 (d, J = 1.8 Hz, 1H), 8.61 (d, J = 1.9 Hz, 1H), 6.94 (d, J = 2.3 Hz, 1H), 6.90 (d, J = 2.3 Hz, 1H), 5.87 (s, 1H), 5.13 (s, 1H), 4.76 (s, 1H), 4.04 (s, 1H), 3.98-3.89 (m, 4H), 3.87 (s, 3H), 3.41-3.23 (m, 4H), 2.25 (s, 3H), 2.23-2.09 (m, 2H), 1.99-1.80 (m, 6H) |
| 277 | 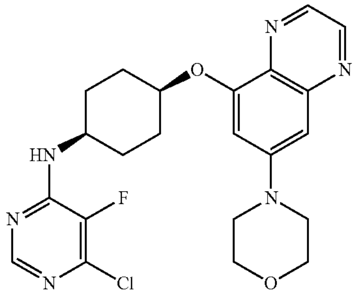 [SMILES: Fc1c(Cl)ncnc1N[C@H]1CC[C@@H](Oc2cc(N3CCOCC3)cc3nccnc23)CC1] | 459.08 | ($CDCl_3$) δ 8.71 (d, J = 1.9 Hz, 1H), 8.62 (d, J = 1.9 Hz, 1H), 8.17 (d, J = 0.9 Hz, 1H), 6.94 (dd, J = 15.8, 2.5 Hz, 2H), 5.31 (s, 1H), 5.83 (dp, J = 4.6, 2.5 Hz, 1H), 4.22 (qt, J = 8.5, 4.9 Hz, 1H), 4.03-3.87 (m, 4H), 3.39-3.29 (m, 4H), 2.25 (td, J = 7.9, 6.6, 3.9 Hz, 2H), 2.09-1.80 (m, 6H) |
| 278 | 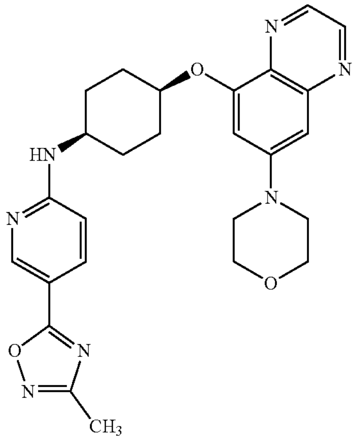 [SMILES: Cc1noc(-c2ccc(N[C@H]3CC[C@@H](Oc4cc(N5CCOCC5)cc5nccnc45)CC3)nc2)n1] | 488.8 | (400 MHz, $CDCl_3$) δ 8.83 (d, J = 2.2 Hz, 1H), 8.69 (d, J = 1.9 Hz, 1H), 8.61 (d, J = 1.9 Hz, 1H), 8.02 (dd, J = 8.8, 2.3 Hz, 1H), 6.96 (d, J = 2.4 Hz, 1H), 6.91 (d, J = 2.5 Hz, 1H), 6.45 (d, J = 8.9 Hz, 1H), 5.12 (s, 1H), 4.81 (d, J = 2.6 Hz, 1H), 3.98 (s, 1H), 3.95-3.87 (m, 4H), 3.40-3.26 (m, 5H), 2.42 (s, 3H), 2.29-2.16 (m, 2H), 1.99-1.87 (m, 6H) |
| 279 | 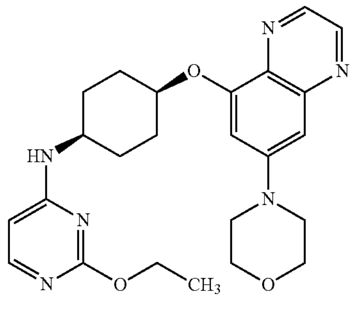 [SMILES: CCOc1nccc(N[C@H]2CC[C@@H](Oc3cc(N4CCOCC4)cc4nccnc34)CC2)n1] | 451.12 | ($CDCl_3$) δ 8.69 (d, J = 1.9 Hz, 1H), 8.60 (d, J = 2.0 Hz, 1H), 7.21-7.11 (m, 1H), 7.00-6.85 (m, 2H), 5.51 (s, 1H), 4.95-4.70 (m, 2H), 4.53-4.34 (m, 1H), 4.01-3.74 (m, 5H), 3.45-3.25 (m, 4H), 2.25-2.09 (m, 2H), 2.03-1.73 (m, 6H), 1.39-1.25 (m, 3H) |

TABLE 1-continued

| Cmpd. No. | Compound | ESMS (M + H) | $^1$H NMR (300 MHz, unless indicated otherwise) NMR peaks given as δ values |
|---|---|---|---|
| 280 | 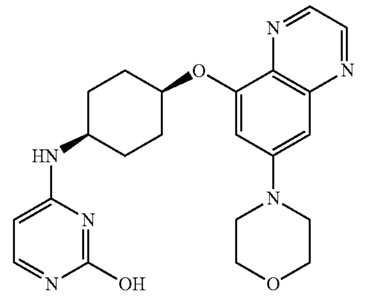 [SMILES: Oc1nccc(N[C@H]2CC[C@@H](Oc3cc(N4CCOCC4)cc4nccnc34)CC2)n1] | 423.08 | (methanol-$d_4$) δ 8.68 (d, J = 2.0 Hz, 1H), 8.54 (d, J = 2.0 Hz, 1H), 7.30 (d, J = 7.2 Hz, 1H), 7.10 (d, J = 2.4 Hz, 1H), 6.87 (d, J = 2.4 Hz, 1H), 5.79 (d, J = 7.2 Hz, 1H), 4.13 (qd, J = 8.5, 6.7, 2.4 Hz, 1H), 3.87 (dd, J = 5.9, 3.8 Hz, 4H), 3.42-3.32 (m, 5H), 2.21-2.07 (m, 2H), 2.01-1.78 (m, 6H) |
| 281 | 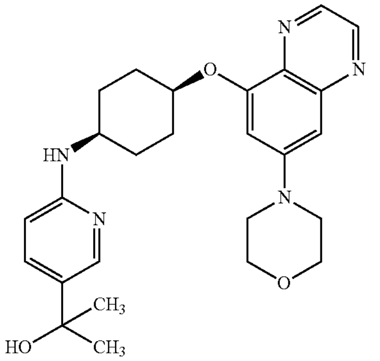 [SMILES: CC(C)(O)c1ccc(N[C@H]2CC[C@@H](Oc3cc(N4CCOCC4)cc4nccnc34)CC2)nc1] | 464.53 | (400 MHz, $CDCl_3$) δ 8.68 (d, J = 1.9 Hz, 1H), 8.61 (d, J = 1.9 Hz, 1H), 8.18 (d, J = 2.2 Hz, 1H), 7.58 (dd, J = 8.7, 2.5 Hz, 1H), 6.95 (d, J = 2.5 Hz, 1H), 6.91 (d, J = 2.4 Hz, 1H), 6.39 (d, J = 8.8 Hz, 1H), 4.78 (s, 1H), 4.69 (s, 1H), 3.96-3.83 (m, 5H), 3.49 (s, 1H), 3.38-3.28 (m, 4H), 2.26-2.13 (m, 2H), 1.95-1.84 (m, 6H), 1.56 (s, 6H) |
| 282 | 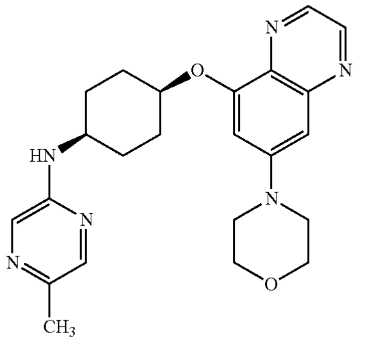 | 421.2 | ($CDCl_3$) δ 8.71 (d, J = 1.9 Hz, 1H), 8.63 (d, J = 1.9 Hz, 1H), 7.93-7.74 (m, 2H), 7.04-6.82 (m, 2H), 4.80 (s, 1H), 4.50 (d, J = 8.1 Hz, 1H), 3.93 (dd, J = 6.4, 3.4 Hz, 5H), 3.41-3.25 (m, 4H), 2.51-2.33 (m, 3H), 2.23 (s, 2H), 2.04-1.82 (m, 6H) |
| 283 | 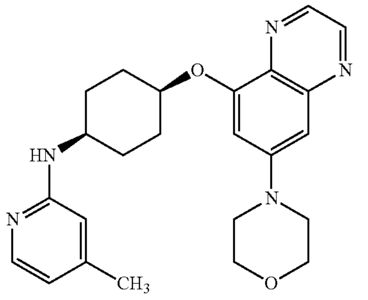 [SMILES: Cc1ccnc(N[C@H]2CC[C@@H](Oc3cc(N4CCOCC4)cc4nccnc34)CC2)c1] | 420.2 | ($CDCl_3$) δ 8.62 (d, J = 1.9 Hz, 1H), 8.55 (d, J = 1.9 Hz, 1H), 7.88 (dd, J = 5.3, 0.7 Hz, 1H), 6.95-6.79 (m, 2H), 6.32 (ddd, J = 5.2, 1.5, 0.7 Hz, 1H), 6.12 (dt, J = 1.6, 0.8 Hz, 1H), 4.71 (d, J = 5.9 Hz, 1H), 4.40 (d, J = 8.2 Hz, 1H), 3.98-3.67 (m, 4H), 3.35-3.17 (m, 4H), 2.15 (s, 4H), 1.83 (d, J = 5.2 Hz, 5H) |

TABLE 1-continued

| Cmpd. No. | Compound | ESMS (M + H) | $^1$H NMR (300 MHz, unless indicated otherwise) NMR peaks given as δ values |
|---|---|---|---|
| 284 | 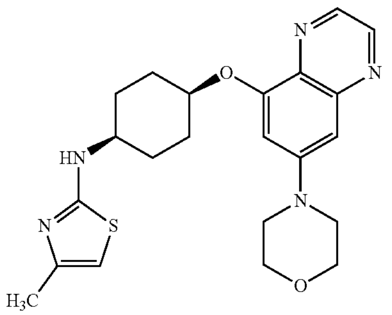 [SMILES: Cc1csc(N[C@H]2CC[C@@H](Oc3cc(N4CCOCC4)cc4nccnc34)CC2)n1] | 426.1 | ($CDCl_3$) δ 8.62 (d, J = 1.9 Hz, 1H), 8.54 (d, J = 1.9 Hz, 1H), 6.86 (dd, J = 16.6, 2.5 Hz, 2H), 5.97 (d, J = 1.2 Hz, 1H), 5.02 (s, 1H), 4.71 (dt, J = 5.7, 3.0 Hz, 1H), 3.91-3.75 (m, 4H), 3.63-3.42 (m, 1H), 3.33-3.17 (m, 4H), 2.21-2.03 (m, 5H), 1.94-1.71 (m, 6H) |
| 285 | 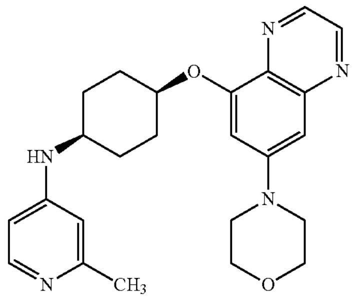 | 420.57 | (400 MHz, $CDCl_3$) δ 8.69 (d, J = 1.9 Hz, 1H), 8.61 (d, J = 1.9 Hz, 1H), 8.08 (d, J = 5.7 Hz, 1H), 6.96 (d, J = 2.4 Hz, 1H), 6.90 (d, J = 2.4 Hz, 1H), 6.30 (s, 1H), 6.28 (dd, J = 5.7, 2.2 Hz, 1H), 4.78 (s, 1H), 4.19 (d, J = 7.7 Hz, 1H), 3.97-3.82 (m, 4H), 3.53 (s, 1H), 3.40-3.24 (m, 4H), 2.41 (s, 3H), 2.27-2.11 (m, 2H), 1.92-1.84 (m, 6H) |
| 286 | 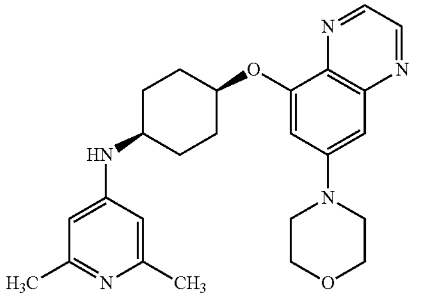 [SMILES: Cc1cc(N[C@H]2CC[C@@H](Oc3cc(N4CCOCC4)cc4nccnc34)CC2)cc(C)n1] | 434.56 | (400 MHz, $CDCl_3$) δ 8.69 (d, J = 1.9 Hz, 1H), 8.60 (d, J = 1.9 Hz, 1H), 6.95 (d, J = 2.4 Hz, 1H), 6.89 (d, J = 2.4 Hz, 1H), 6.15 (s, 2H), 4.77 (s, 1H), 4.12 (d, J = 7.8 Hz, 1H), 3.99-3.81 (m, 4H), 3.53 (s, 1H), 3.40-3.23 (m, 4H), 2.36 (d, J = 14.5 Hz, 6H), 2.25-2.14 (m, 2H), 1.89 (t, J = 7.8 Hz, 6H) |

Biological Assay of Compounds of the Invention

Example 7 DNA-PK Inhibition Assay

Compounds were screened for their ability to inhibit DNA-PK kinase using a standard radiometric assay. Briefly, in this kinase assay the transfer of the terminal $^{33}$P-phosphate in $^{33}$P-ATP to a peptide substrate is interrogated. The assay was carried out in 384-well plates to a final volume of 50 L per well containing approximately 6 nM DNA-PK, 50 mM HEPES (pH 7.5), 10 mM $MgCl_2$, 25 mM NaCl, 0.01% BSA, 1 mM DTT, 10 μg/mL sheared double-stranded DNA (obtained from Sigma), 0.8 mg/mL DNA-PK peptide (Glu-Pro-Pro-Leu-Ser-Gln-Glu-Ala-Phe-Ala-Asp-Leu-Trp-Lys-Lys-Lys, obtained from American Peptide), and 100 μM ATP. Accordingly, compounds of the invention were dissolved in DMSO to make 10 mM initial stock solutions. Serial dilutions in DMSO were then made to obtain the final solutions for the assay. A 0.75 μL aliquot of DMSO or inhibitor in DMSO was added to each well, followed by the addition of ATP substrate solution containing $^{33}$P-ATP (obtained from Perkin Elmer). The reaction was started by the addition of DNA-PK, peptide and ds-DNA. After 45 min, the reaction was quenched with 25 μL of 5% phosphoric acid. The reaction mixture was transferred to MultiScreen HTS 384-well PH plates (obtained from Millipore), allowed to bind for one hour, and washed three times with 1% phosphoric acid. Following the addition of 50 μL of Ultima Gold™ high efficiency scintillant (obtained from Perkin Elmer), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition.

Each of compounds 1 to 249 had a $K_i$ of less than 1.0 micromolar for the inhibition of DNA-PK. Each of compounds 3, 6-14, 16-18, 23-34, 36-37, 39-41, 43-46, 49-72, 74-76, 78, 84-101, 103-123, 127-200, and 202-277 had a $K_i$ of less than 0.10 micromolar for the inhibition of DNA-PK.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of potentiating radiotherapy or a chemotherapeutic agent for the treatment of cancer in a patient comprising the step of administering to said patient an effective amount of a compound of formula:

(I)

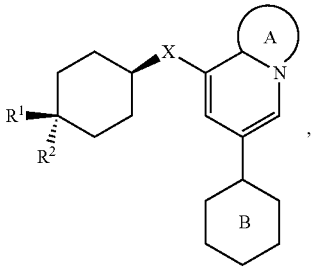

or a pharmaceutically acceptable salt thereof, wherein:

Ring A is

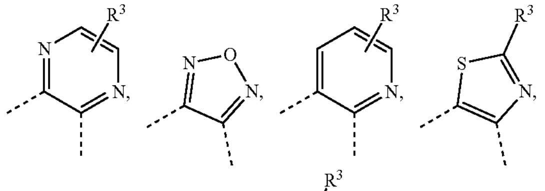

or

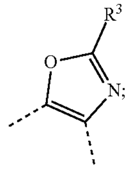

Ring B is

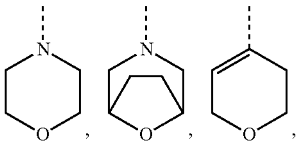

or

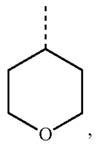

wherein Ring B is optionally substituted with up to four fluorine atoms or up to two $C_{1-4}$ alkyl optionally substituted with up to three fluorine atoms, up to two OH, or up to two $OC_{1-2}$ alkyl groups;

X is NH or O;

each of $R^1$ and $R^2$ is, independently, hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, or —OR$^4$, wherein $R^1$ and $R^2$ cannot simultaneously be hydrogen, and wherein $R^1$ and $R^2$ and the intervening carbon atom can form a dioxane or dioxolane ring;

$R^3$ is hydrogen, $C_{1-4}$ alkyl, fluoro, chloro, $OC_{1-2}$ alkyl, C(O)OH, C(O)OC$_{1-2}$ alkyl, CN, C(O)NHC$_{1-2}$ alkyl, or C(O)NH$_2$, wherein each of said $R^3$ alkyl is optionally substituted with up to 3 fluorine atoms, up to two OH, or up to two $OC_{1-2}$ alkyl groups;

$R^4$ is hydrogen, $C_{1-4}$ alkyl, $C_{2-4}$ alkenyl, $C_{2-4}$ alkynyl, $C_{3-5}$ cycloalkyl, phenyl, pyrrole, imidazole, pyrazole, triazole, thiazole, isothiazole, oxazole, pyridine, pyrimidine, pyrimidinone, pyrazine, pyridazine, quinoline, oxetane, tetrahydrofuran, tetrahydropyran, dihydroisoxazole, pyrimidine-2,4(1H,3H)-dione, dihydrofuropyrimidine, dihydropyranopyrimidine, dihydropyrrolopyrimidine, tetrahydropteridine, or tetrahydropyridopyrimidine, wherein each of said $R^4$ groups is optionally substituted with Br, Cl, up to three fluorine atoms, up to three $C_{1-4}$ alkyl, $C_{2-4}$alkenyl, $C_{2-4}$ alkynyl, $C_{3-6}$ cycloalkyl, an oxetane ring, a tetrahydrofuran ring, a dihydropyran ring, a tetrahydropyran ring, a pyrrolidine ring, a pyrazole ring, a triazole ring, a tetrazole ring, an oxadiazole ring, CN, CH$_2$OR$^5$, C(O)R$^5$, C(O)N(R$^5$)$_2$, C(O)OR$^5$, NO$_2$, NHC(O)R$^5$, N(R$^5$)$_2$, or up to two OR$^5$, wherein each of said optional $R^4$ substituents is optionally substituted with up to three fluorine atoms, up to two $C_{1-4}$ alkyl groups, up to two OH groups, up to two $OC_{1-4}$ alkyl groups, or up to two $SC_{1-4}$ alkyl groups; and each $R^5$ is, independently, hydrogen, $C_{1-4}$ alkyl, imidazole, triazole, thiazole, pyridine, pyrimidine, oxetane, tetrahydrofuran, or tetrahydropyran, and each $R^5$ group is optionally substituted with chloro, up to three fluorine atoms, up to two $C_{1-2}$ alkyl, CH$_2$OH, CN, up to two OH, up to two $OC_{1-2}$ alkyl, a spirooxetane, pyrrolidine, or triazole, or two $R^5$ groups together with the intervening nitrogen atom form a morpholine ring, azetidine ring, pyrrolidine ring, piperidine ring, or piperazine ring, wherein each of said rings is optionally substituted with up to three fluorine atoms, up to two OH, or up to two $OC_{1-2}$ alkyl groups;

or a pharmaceutical composition comprising said compound, or a pharmaceutically acceptable salt thereof.

2. The method of claim 1, wherein X is NH.

3. The method of claim 1, wherein the compound is of formula:

(I-A)

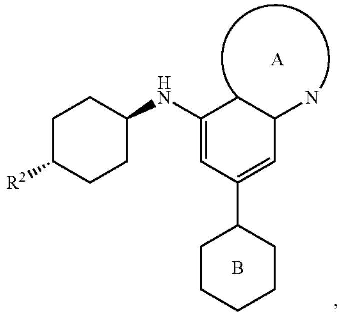

or a pharmaceutically acceptable salt thereof.

4. The method of claim 3, wherein the compound is of formula:

(I-A-1)

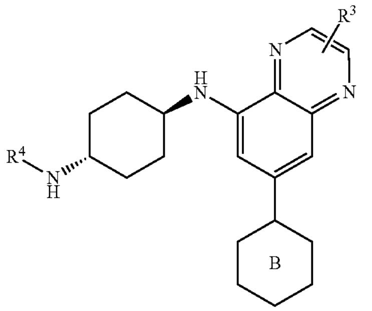

or

-continued (I-A-2)

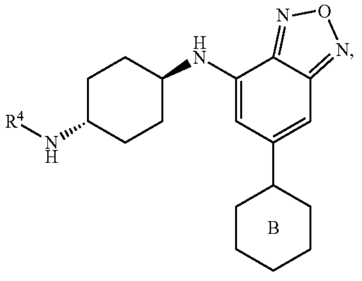

or a pharmaceutically acceptable salt thereof.

5. The method of claim 2, wherein the compound is of formula:

(I-B)

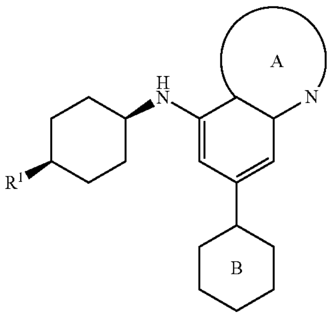

, or a pharmaceutically acceptable salt thereof.

6. The method of claim 5, wherein the compound is of formula:

(I-B-1)

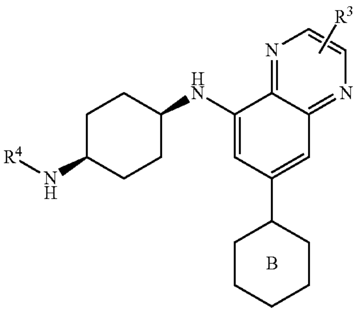

or (I-B-2)

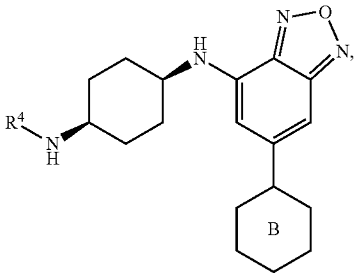

or a pharmaceutically acceptable salt thereof.

7. The method of claim 6, wherein $R^3$ is hydrogen, $C_{1-4}$ alkyl, fluoro, chloro, $OC_{1-2}$ alkyl, C(O)OH, $C(O)OC_{1-2}$ alkyl, CN, $C(O)NHC_{1-2}$ alkyl, or $C(O)NH_2$, wherein each of said $R^3$ alkyl is optionally substituted with up to three fluorine atoms, up to two OH, or up to two $OC_{1-2}$ alkyl groups;

$R^4$ is hydrogen, $C_{1-4}$ alkyl, $C_{2-4}$ alkenyl, $C_{2-4}$ alkynyl, $C_{3-5}$ cycloalkyl, phenyl, pyrrole, imidazole, pyrazole, triazole, thiazole, isothiazole, oxazole, pyridine, pyrimidine, pyrimidinone, pyrazine, pyridazine, quinoline, oxetane, tetrahydrofuran, tetrahydropyran, dihydroisoxazole, pyrimidine-2,4(1H,3H)-dione, dihydrofuropyrimidine, dihydropyranopyrimidine, dihydropyrrolopyrimidine, tetrahydropteridine, or tetrahydropyridopyrimidine;

each of said $R^4$ groups is optionally substituted with Br, Cl, up to three fluorine atoms, up to three $C_{1-4}$ alkyl, $C_{2-4}$ alkenyl, $C_{2-4}$ alkynyl, $C_{3-6}$ cycloalkyl, an oxetane ring, a tetrahydrofuran ring, a dihydropyran ring, a tetrahydropyran ring, a pyrrolidine ring, a pyrazole ring, a triazole ring, a tetrazole ring, an oxadiazole ring, CN, $CH_2OR^5$, $C(O)R^5$, $C(O)N(R^5)_2$, $C(O)OR^5$, $NO_2$, $NHC(O)R^5$, $N(R^5)_2$, or up to two $OR^5$, wherein each of said optional $R^4$ substituents is optionally substituted with up to three fluorine atoms, up to two $C_{1-4}$ alkyl groups, up to two OH groups, up to two $OC_{1-4}$alkyl groups, or up to two $SC_{1-4}$ alkyl groups; and each $R^5$ is, independently, hydrogen, $C_{1-4}$ alkyl, imidazole, triazole, thiazole, pyridine, pyrimidine, oxetane, tetrahydrofuran, or tetrahydropyran, and each $R^5$ group is optionally substituted with chloro, up to three fluorine atoms, up to two $C_{1-2}$ alkyl, $CH_2OH$, CN, up to two OH, up to two $OC_{1-2}$ alkyl, pyrrolidine, or triazole, or two $R^5$ groups together with the intervening nitrogen atom form a morpholine ring, azetidine ring, pyrrolidine ring, piperidine ring, or piperazine ring, wherein each of said rings is optionally substituted with up to three fluorine atoms, up to two OH, or up to two $OC_{1-2}$ alkyl groups.

8. The method of claim 6, wherein the compound is of formula:

(II)

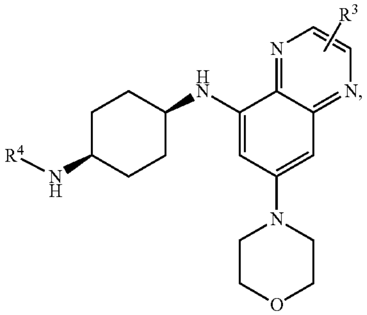

or a pharmaceutically acceptable salt thereof.

9. The method of claim 1, wherein X is O.

10. The method of claim 9, wherein the compound is of formula:

(I-C)

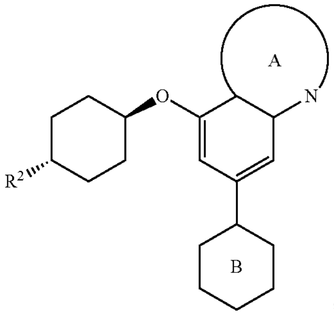

, or a pharmaceutically acceptable salt thereof.

11. The method of claim 10, wherein the compound is of formula:

(I-C-1)

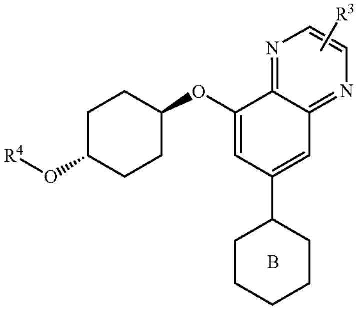

or (I-C-2)

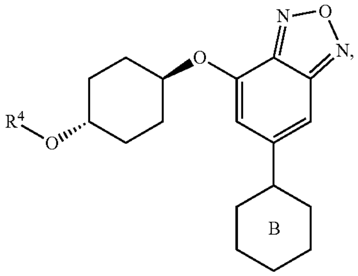

or a pharmaceutically acceptable salt thereof.

12. The method of claim 10, wherein the compound is of formula:

(I-C-3)

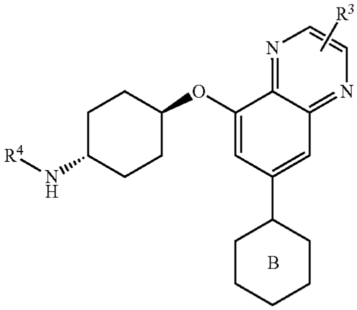

or

-continued (I-C-4)

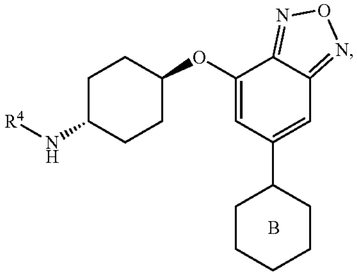

or a pharmaceutically acceptable salt thereof.

13. The method of claim 9, wherein the compound is of formula:

(I-D)

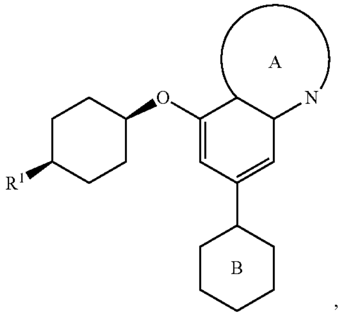

, or a pharmaceutically acceptable salt thereof.

14. The method of claim 13, wherein the compound is of formula:

(I-D-1)

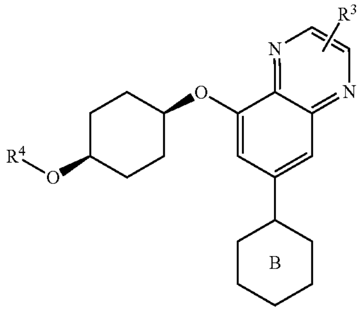

or (I-D-2)

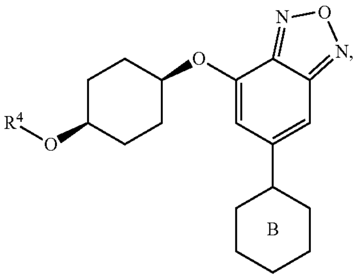

or a pharmaceutically acceptable salt thereof.

15. The method of claim 13, wherein the compound is of formula:

(I-D-3)

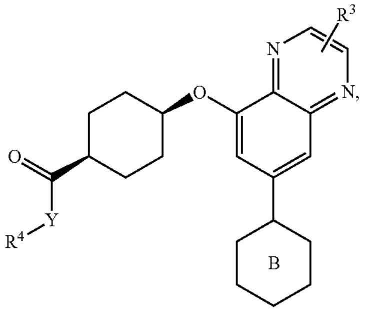

or a pharmaceutically acceptable salt thereof, wherein Y is O or NH.

16. The method of claim 13, wherein the compound is of formula:

(I-D-4)

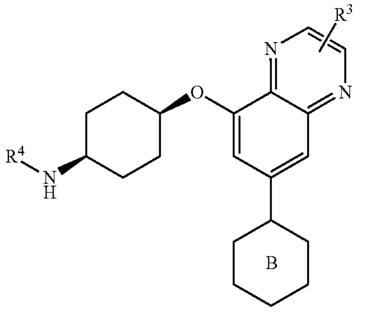

or (I-D-5)

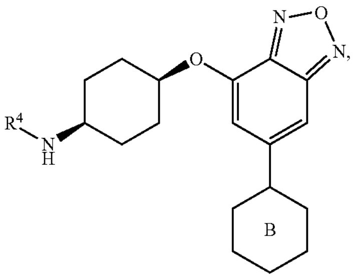

or a pharmaceutically acceptable salt thereof.

17. The method of claim 16, wherein $R^3$ is hydrogen, $C_{1-4}$ alkyl, fluoro, chloro, $OC_{1-2}$ alkyl, C(O)OH, C(O)$OC_{1-2}$ alkyl, CN, C(O)$NHC_{1-2}$ alkyl, or C(O)$NH_2$, wherein each of said $R^3$ alkyl is optionally substituted with up to 3 fluorine atoms, up to two OH, or up to two $OC_{1-2}$ alkyl groups;

$R^4$ is hydrogen, $C_{1-4}$ alkyl, $C_{2-4}$ alkenyl, $C_{2-4}$ alkynyl, $C_{3-5}$ cycloalkyl, phenyl, pyrrole, imidazole, pyrazole, triazole, thiazole, isothiazole, oxazole, pyridine, pyrimidine, pyrimidinone, pyrazine, pyridazine, quinoline, oxetane, tetrahydrofuran, tetrahydropyran, dihydroisoxazole, pyrimidine-2,4(1H,3H)-dione, dihydrofuropyrimidine, dihydropyranopyrimidine, dihydropyrrolopyrimidine, tetrahydropteridine, or tetrahydropyridopyrimidine;

each of said $R^4$ groups except hydrogen is optionally substituted with Br, Cl, up to three fluorine atoms, up to three $C_{1-4}$ alkyl, up to two $C_{0-4}$ alkyl-$R^5$, up to two $C_{0-4}$ alkyl-O—$C_{0-4}$ alkyl-$R^5$, $C^{2-4}$ alkenyl, $C_{2-4}$ alkenyl, $C_{2-4}$ alkynyl, $C_{3-6}$ cycloalkyl, CN, $NO_2$, C(O)$R^5$, C(O)$N(R^5)_2$, C(O)$OC_{0-4}$ alkyl-$R^5$, NHC(O)$R^5$, $N(R^5)_2$, oxetane, azetidine tetrahydrofuran, dihydropyran, tetrahydropyran, pyrrolidine, pyrazole, triazole, tetrazole, or oxadiazole, wherein each of said optional $R^4$ substituents is optionally substituted with up to 3 fluorine atoms, up to two $C_{1-4}$ alkyl groups, up to two OH groups, up to two $OC_{1-4}$ alkyl groups, or up to two $SC_{1-4}$alkyl groups; and each $R^5$ is, independently, hydrogen, $C_{1-4}$ alkyl, $C_{3-5}$ cycloalkyl, imidazole, triazole, thiazole, pyridine, pyrimidine, oxetane, tetrahydrofuran, or tetrahydropyran, and each $R^5$ group is optionally substituted with chloro, up to three fluorine atoms, up to two $C_{1-2}$ alkyl, $CH_2OH$, CN, up to two OH, up to two $OC_{1-2}$ alkyl, pyrrolidine, or triazole, or two $R^5$ groups together with an intervening nitrogen atom form a morpholine ring, azetidine ring, pyrrolidine ring, piperidine ring, or piperazine ring, wherein each of said rings is optionally substituted with up to 3 fluorine atoms, up to two OH, or up to two $OC_{1-2}$ alkyl groups.

18. The method of claim 1, wherein

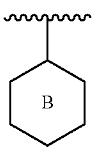

is

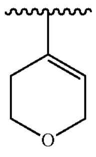

or

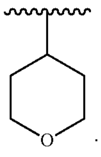

.

19. The method of claim 1, wherein the compound is of formula:

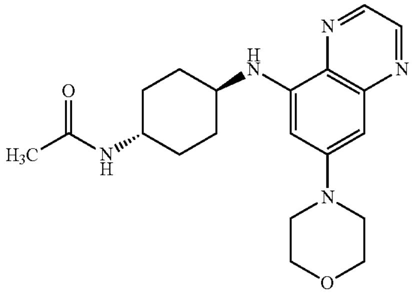

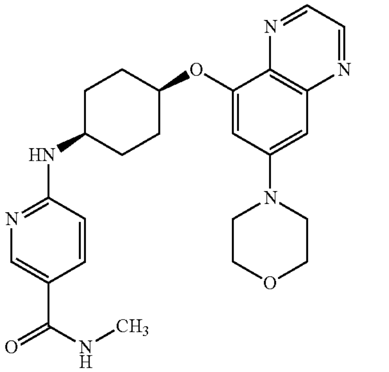

-continued
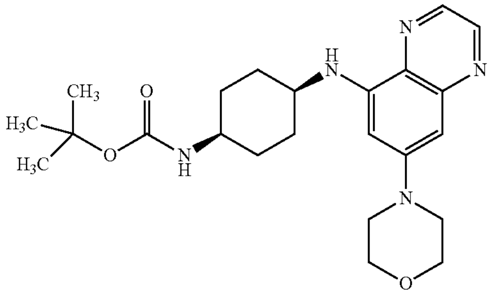
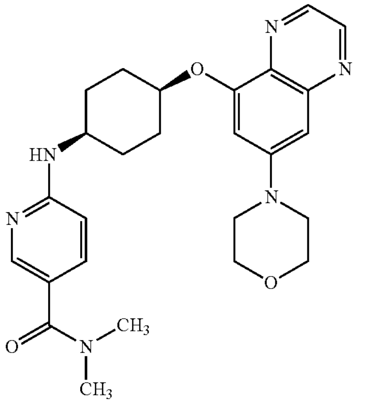
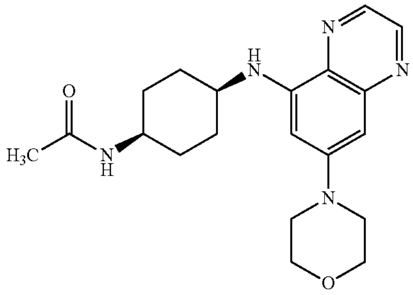
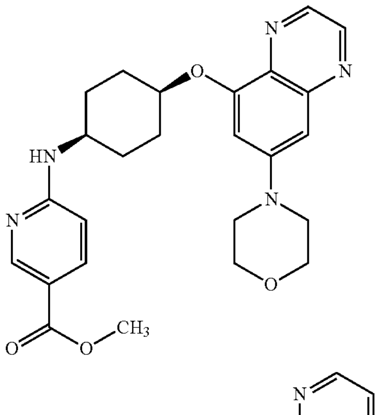
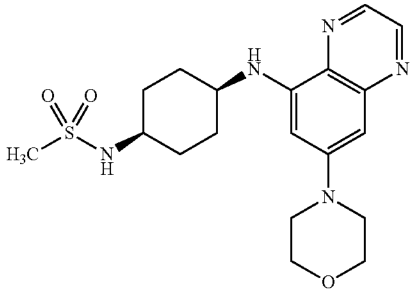
-continued
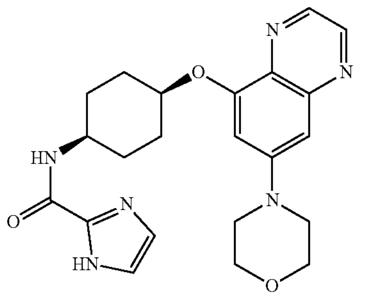
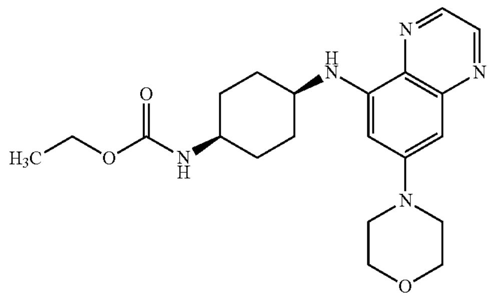
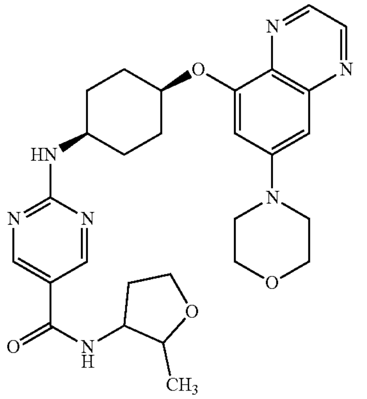
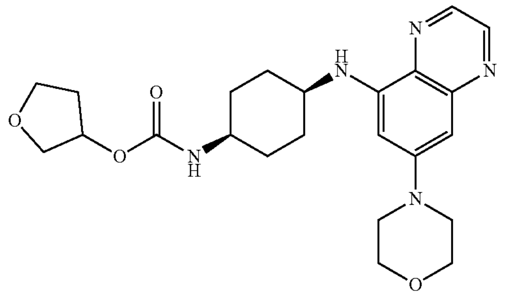
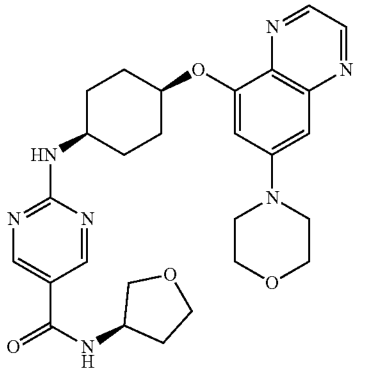

-continued
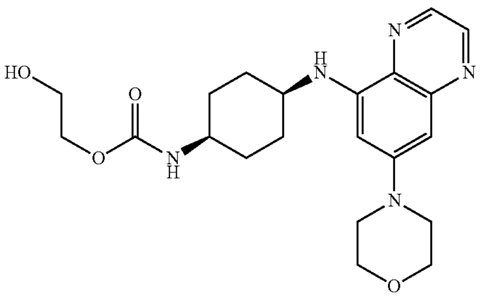
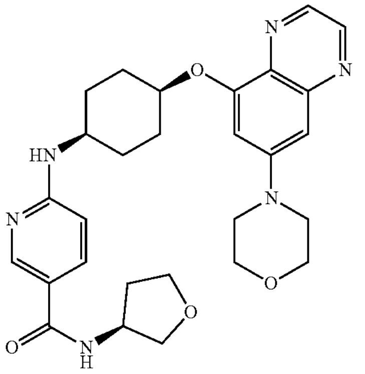
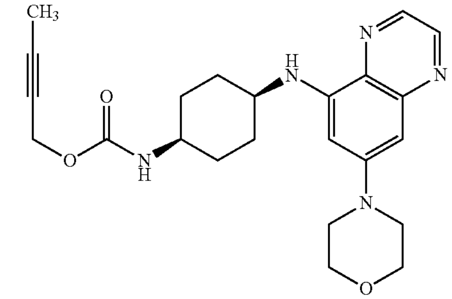
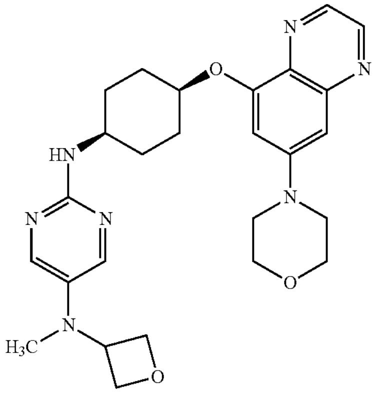
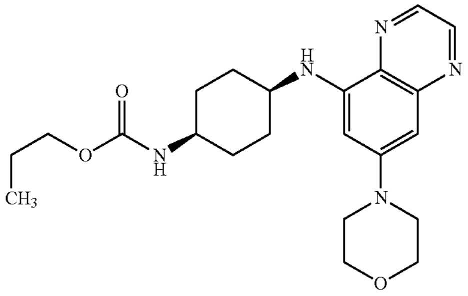
-continued
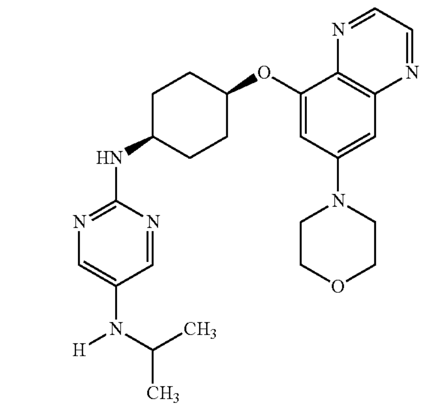
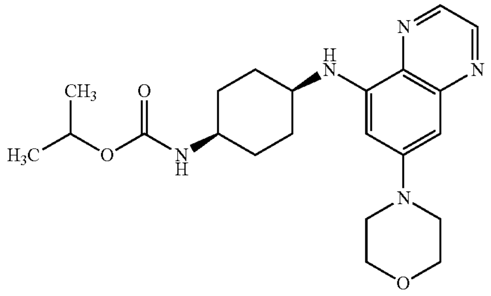
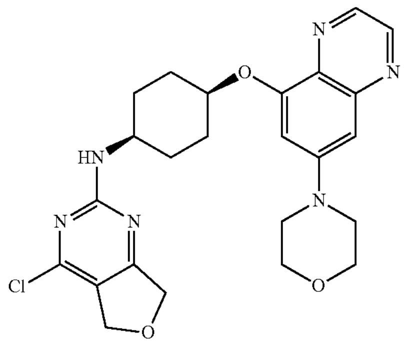
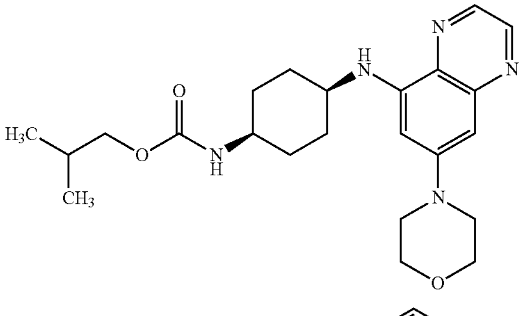
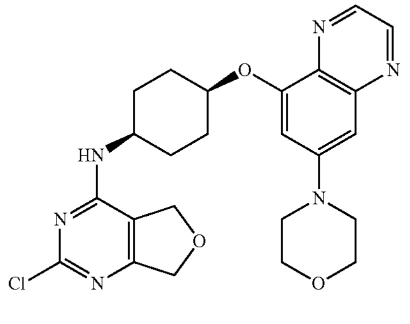

-continued
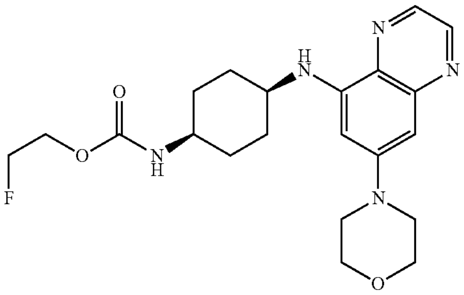
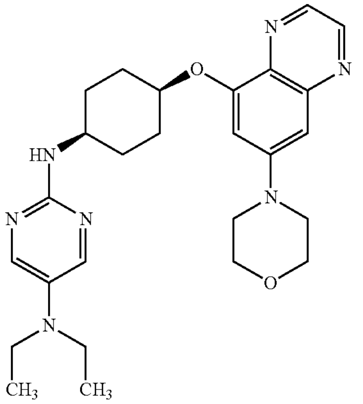
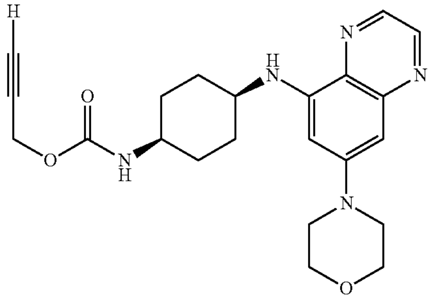
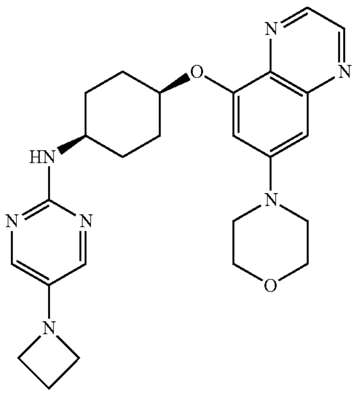
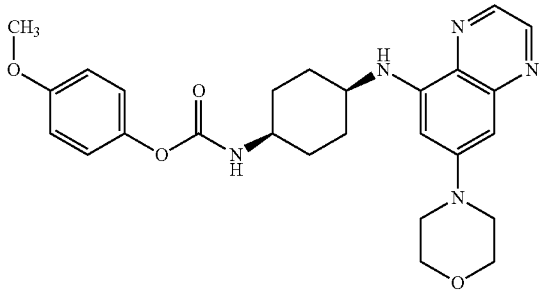
-continued
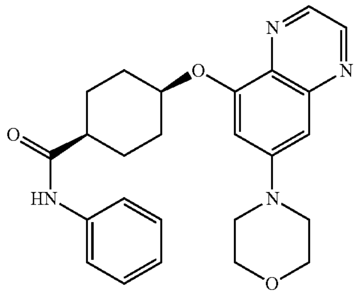
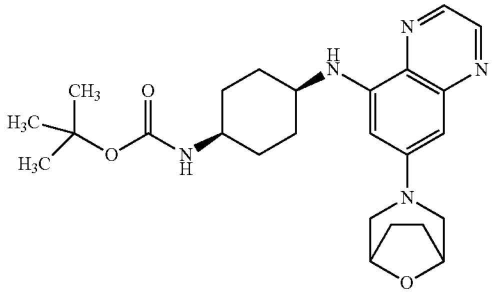
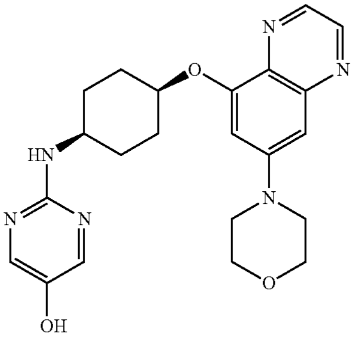
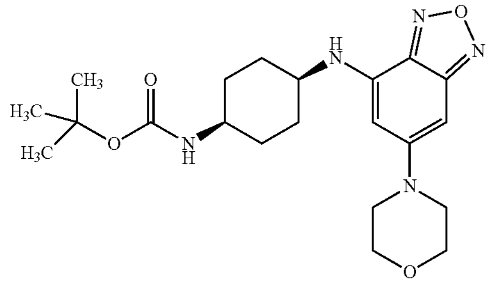
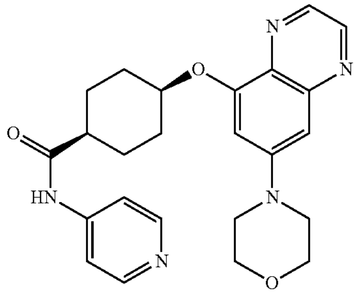

-continued
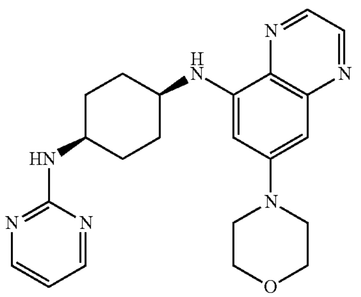
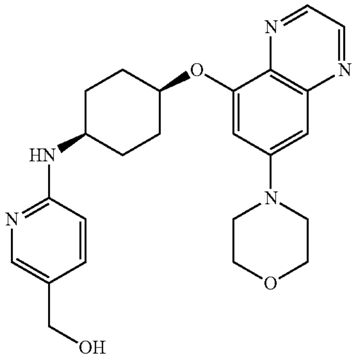
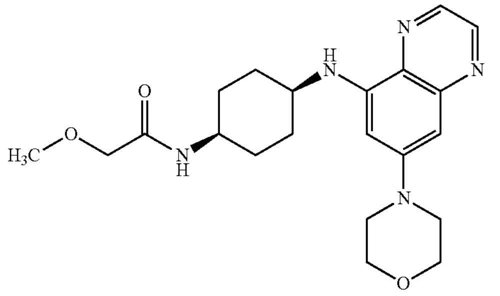
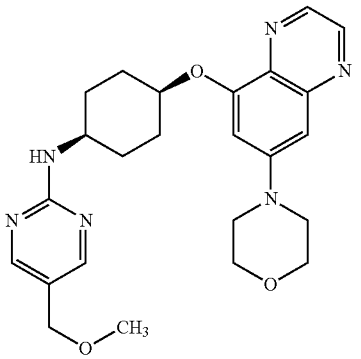
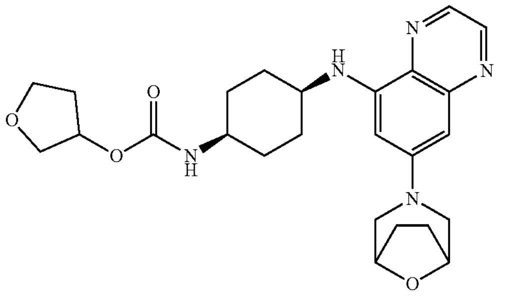
-continued
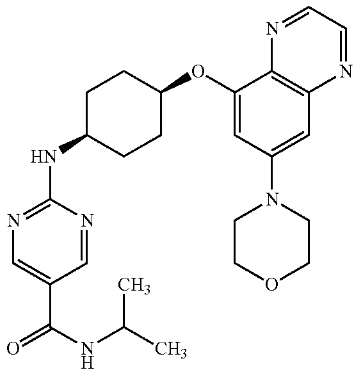
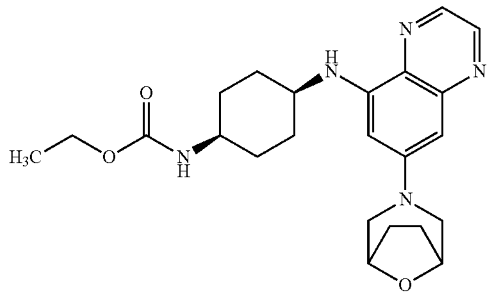
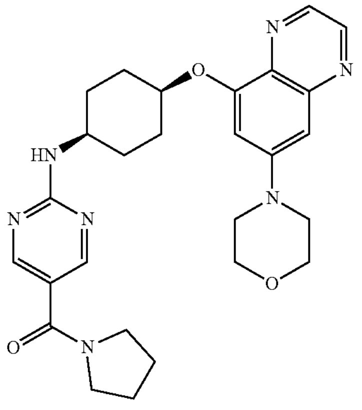
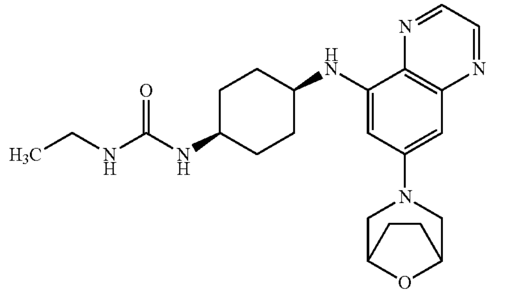
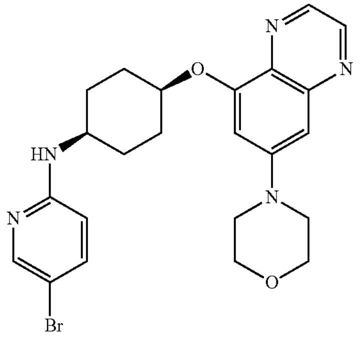

-continued
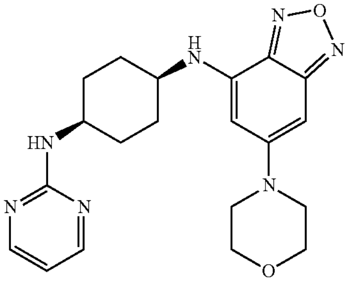
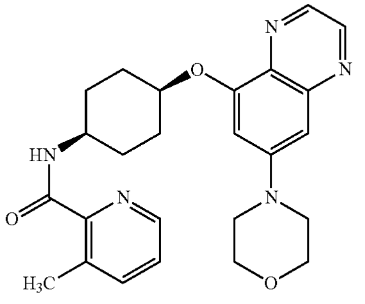
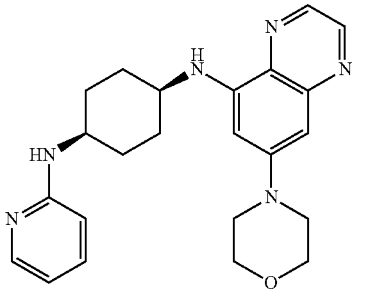
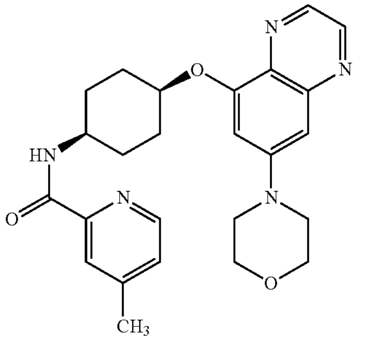
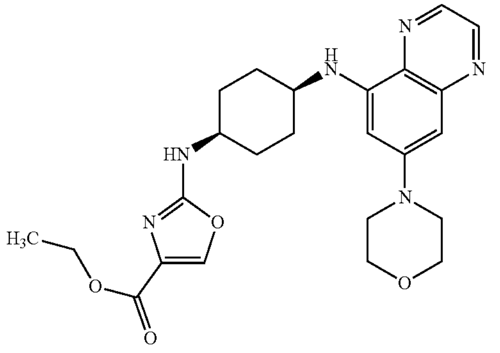
-continued
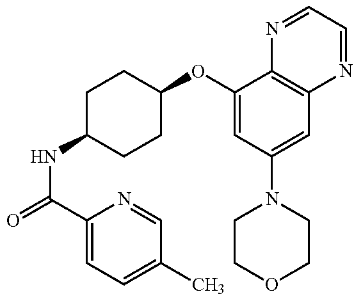
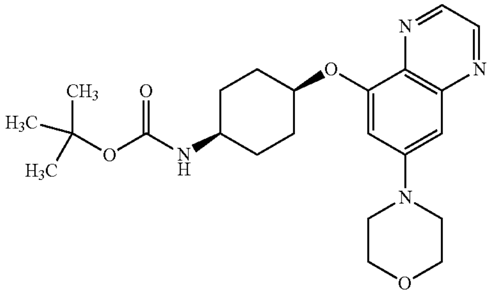
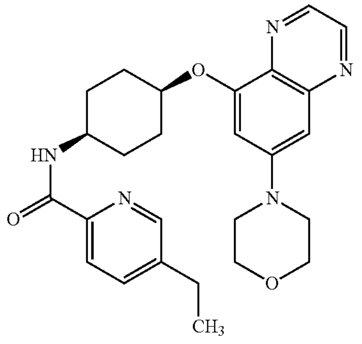
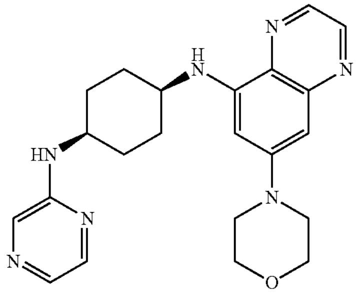
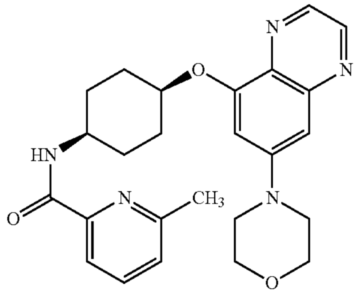

-continued
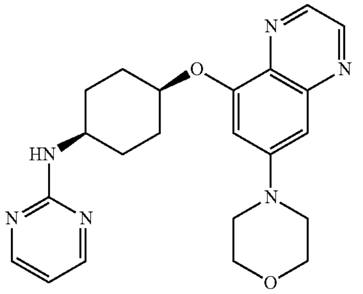
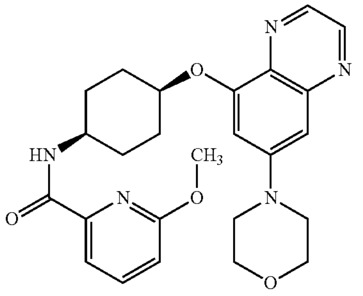
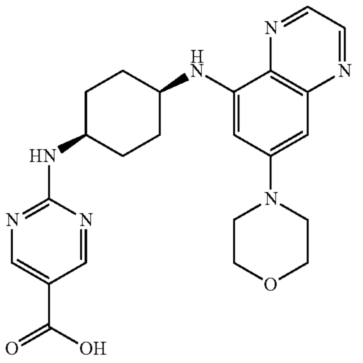
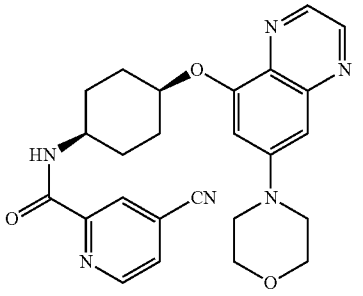
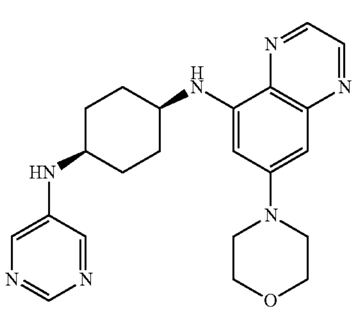
-continued
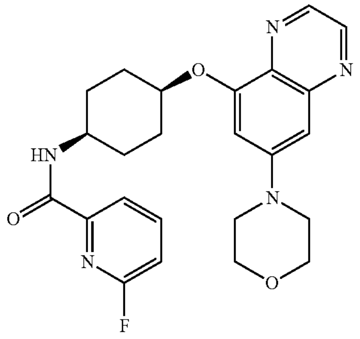
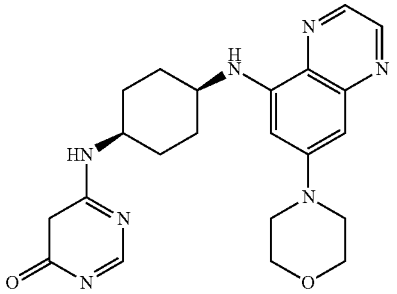
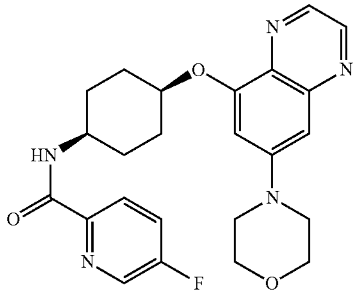
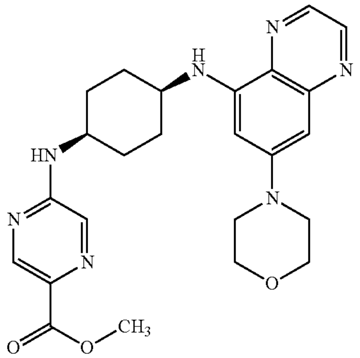
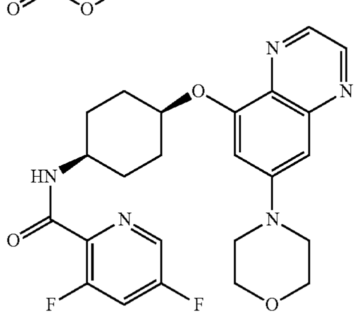

-continued
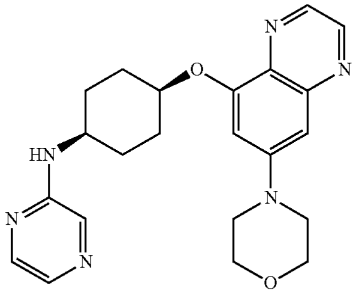
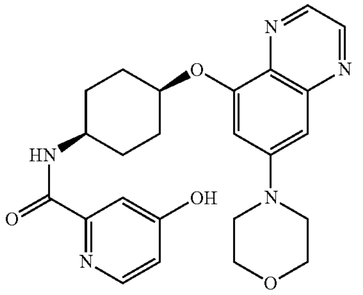
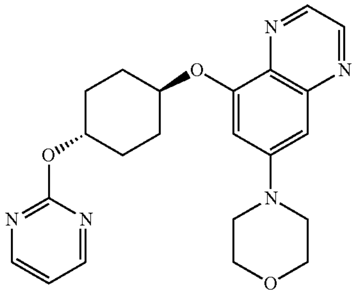
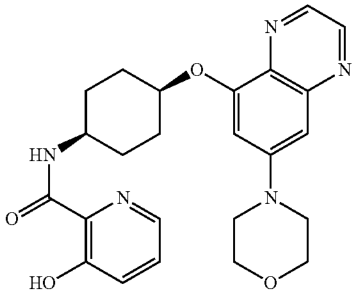
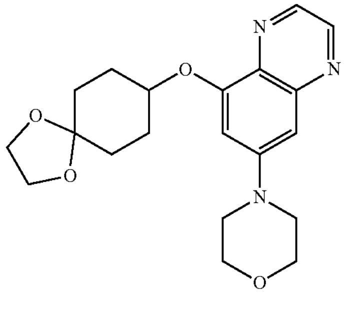
-continued
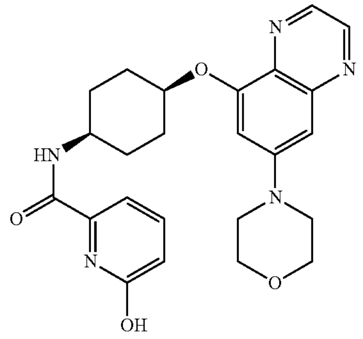
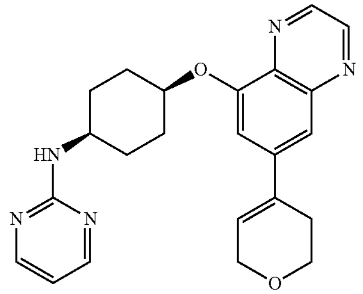
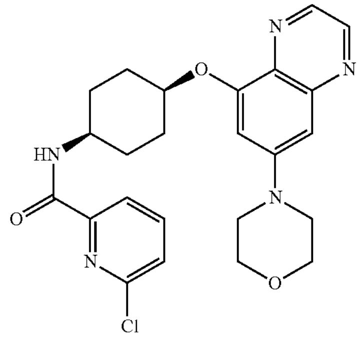
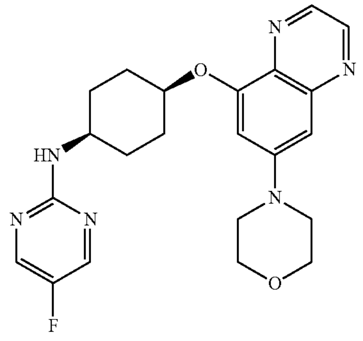
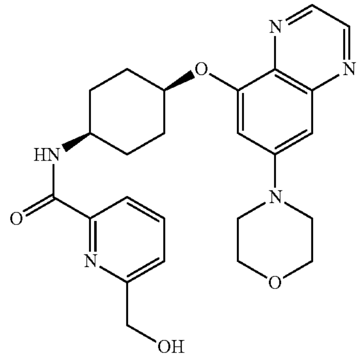

-continued
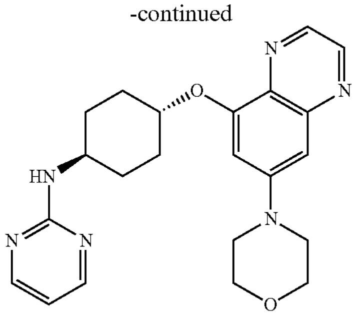
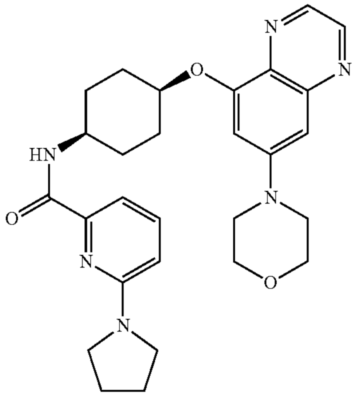
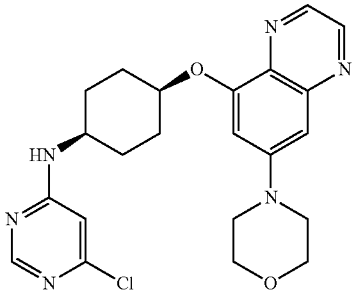
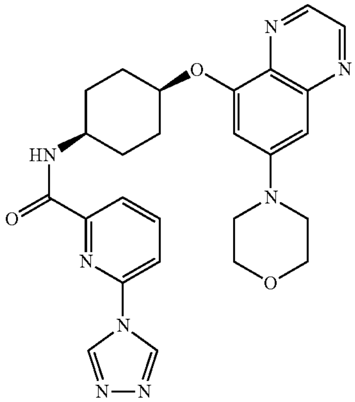
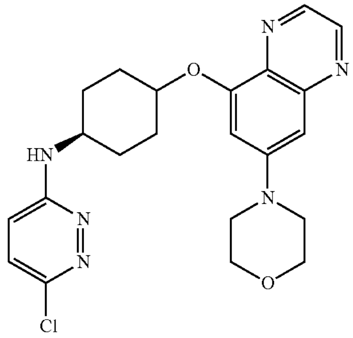
-continued
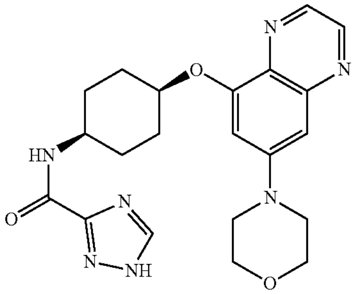
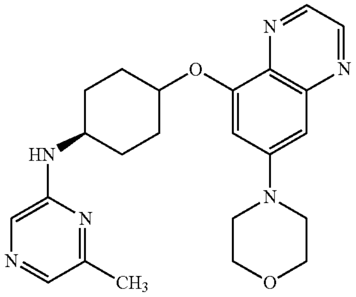
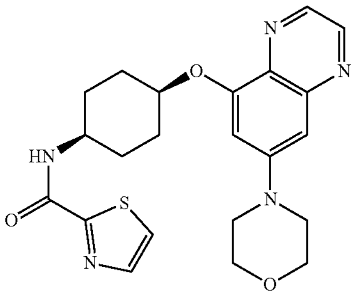
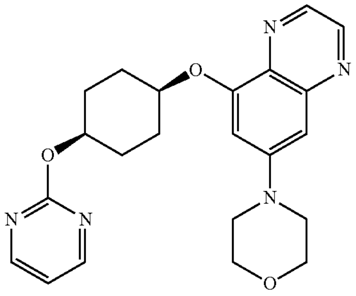
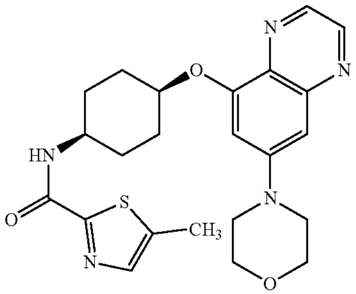

-continued
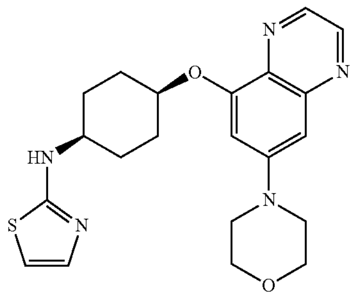
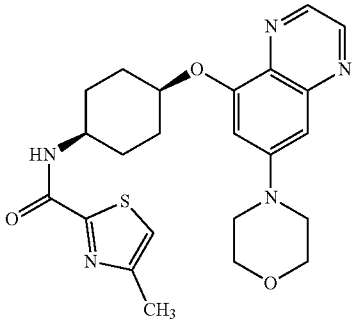
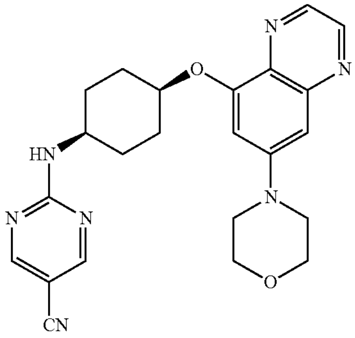
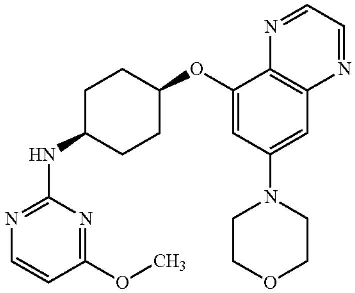
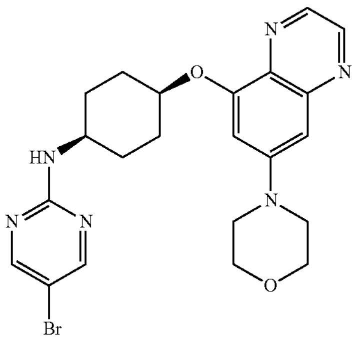
-continued
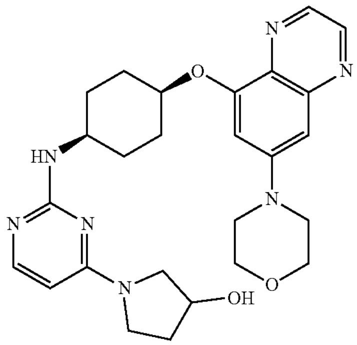
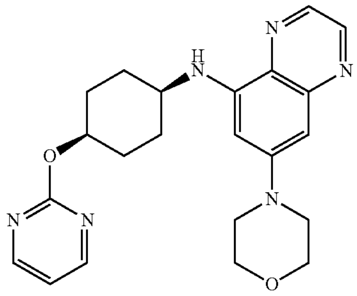
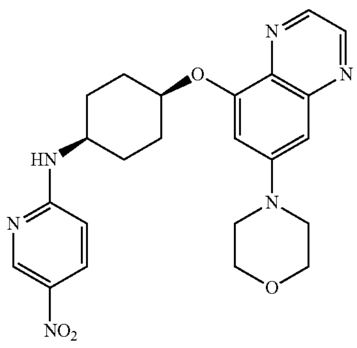
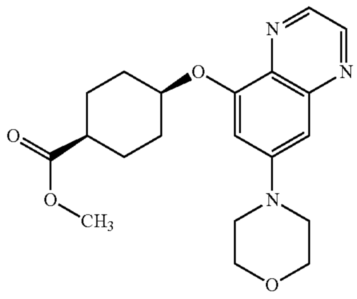
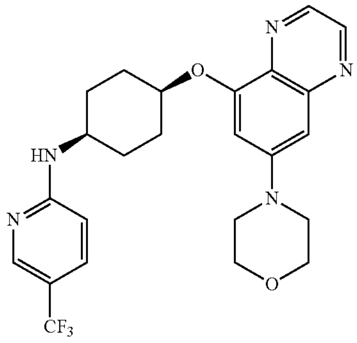

-continued
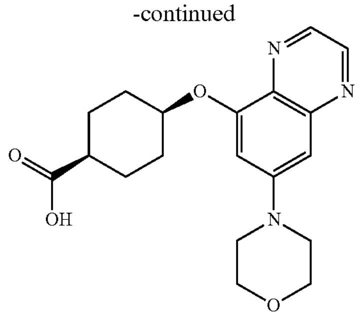
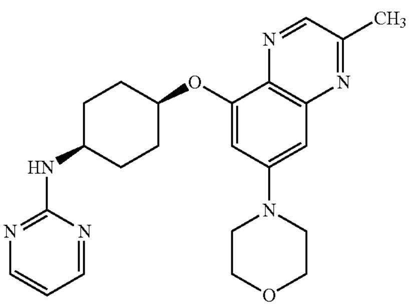
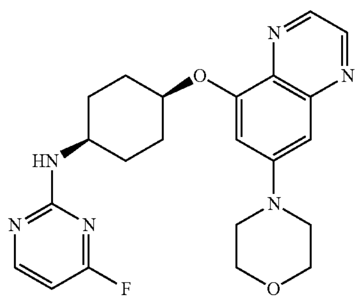
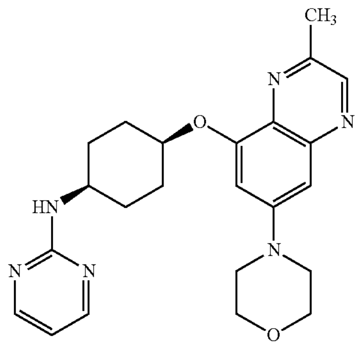
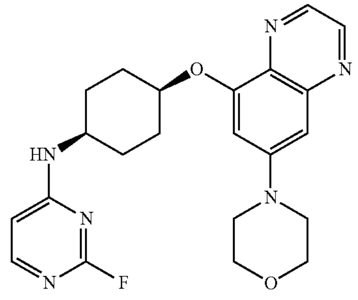
-continued
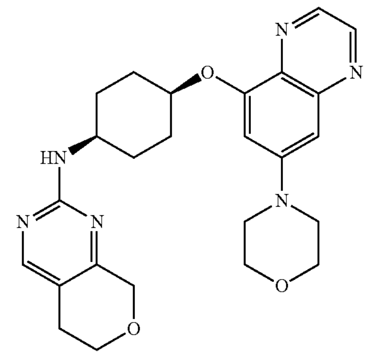
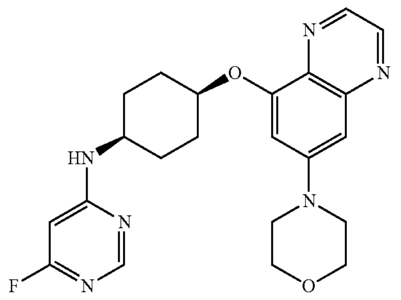
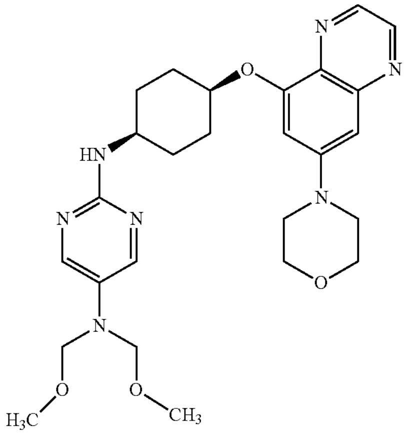
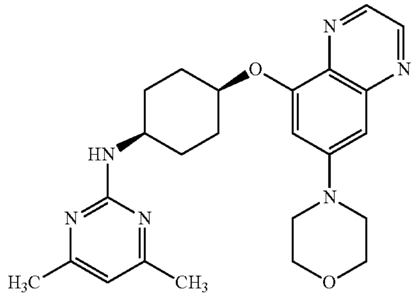

-continued
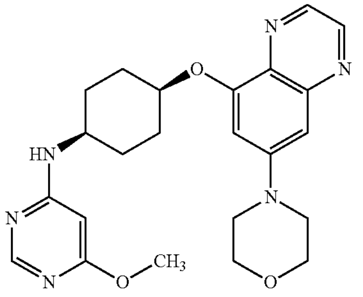
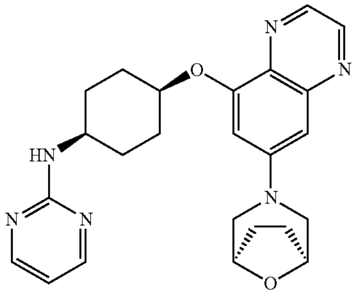
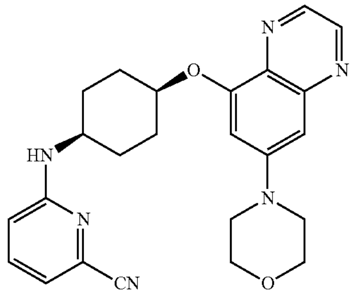
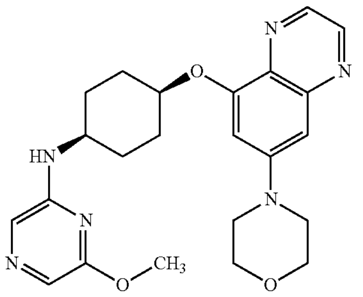
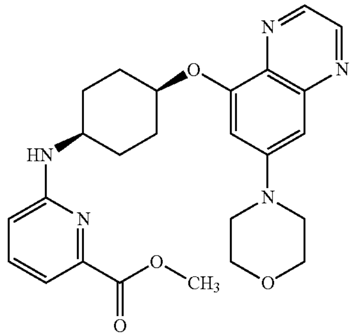
-continued
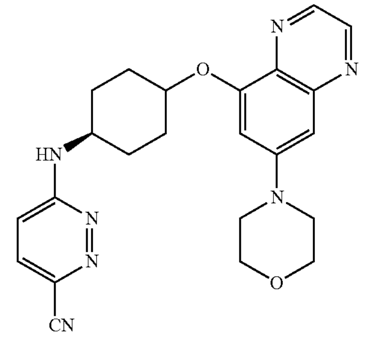
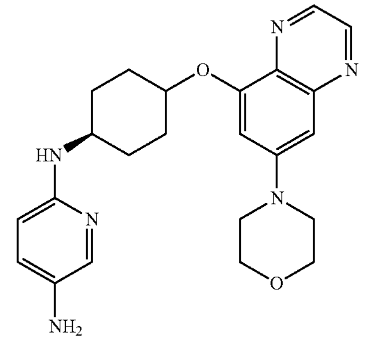
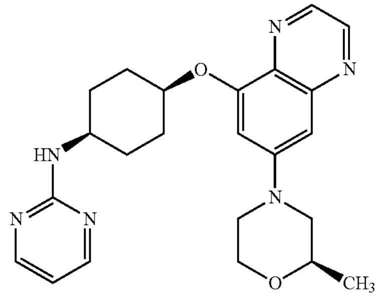
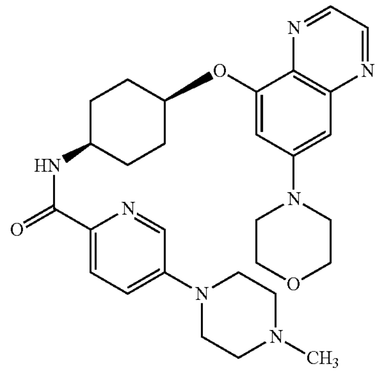
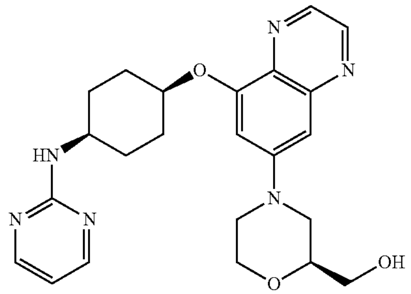

-continued
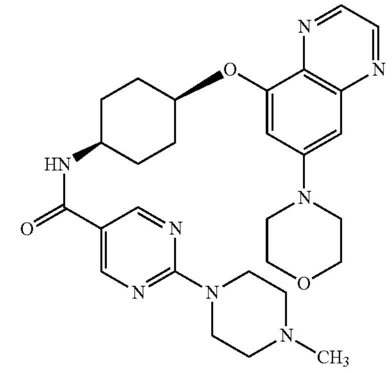
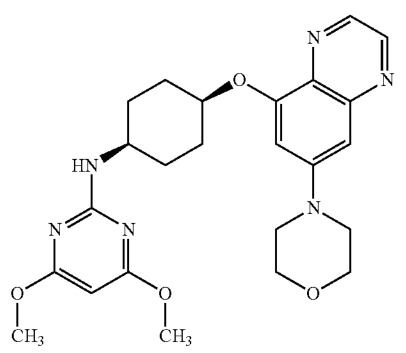
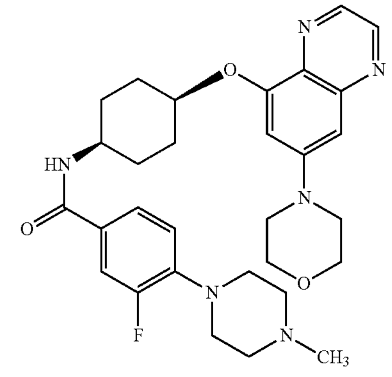
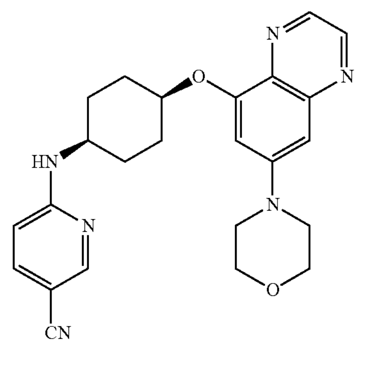
-continued
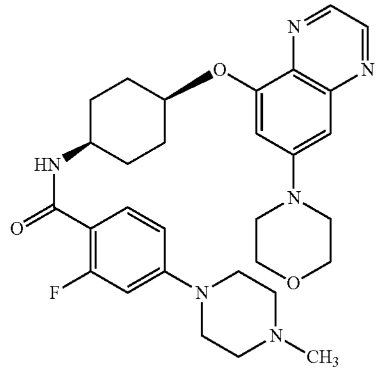
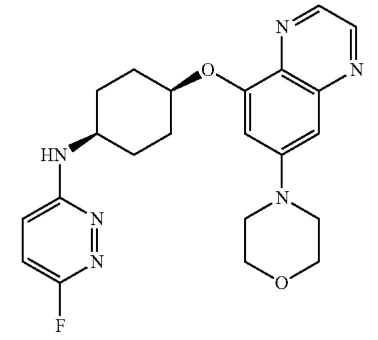
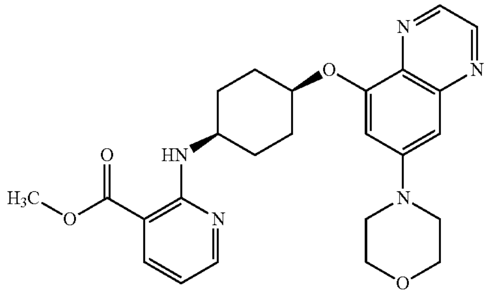
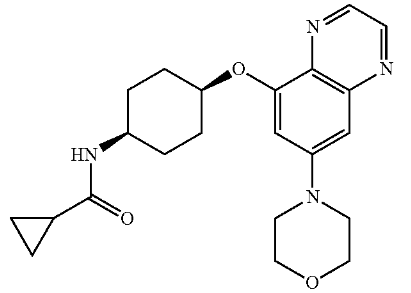
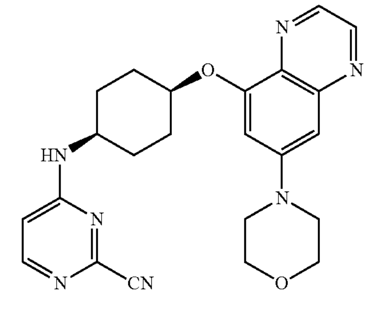

-continued
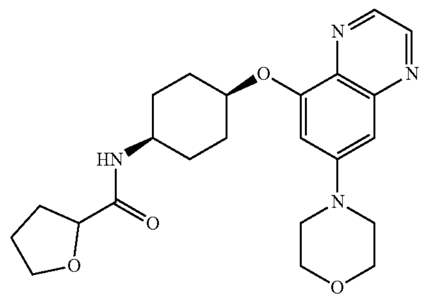
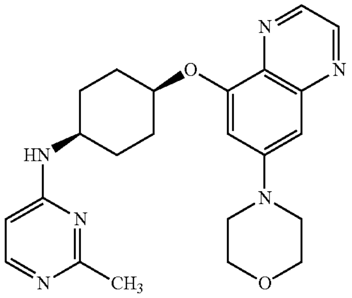
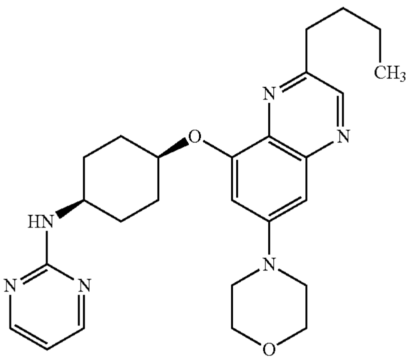
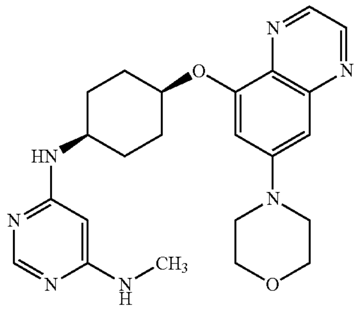
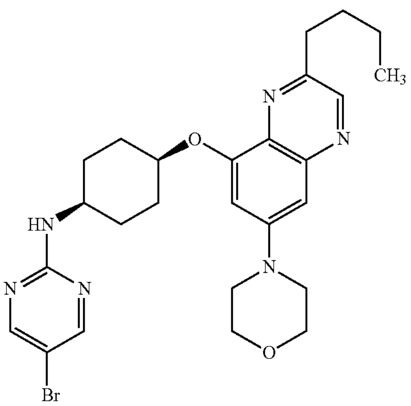
-continued
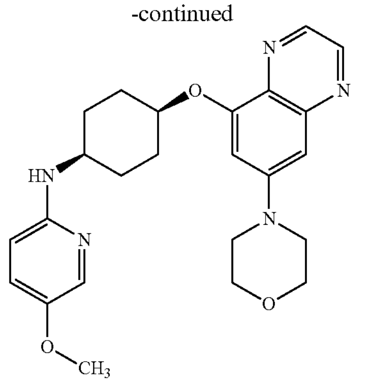
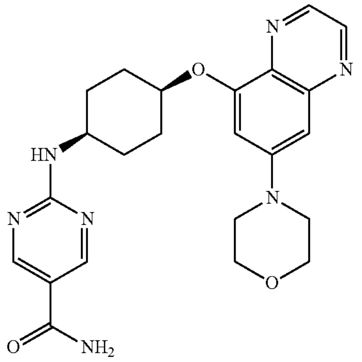
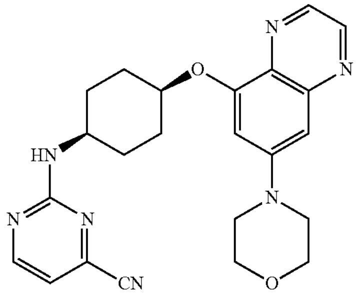
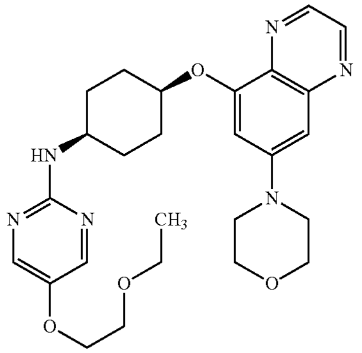
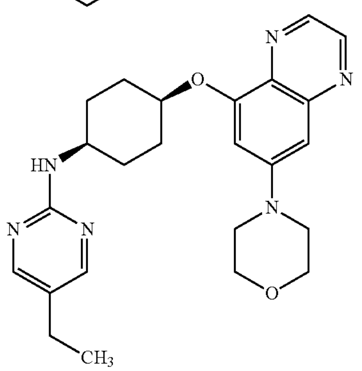

-continued
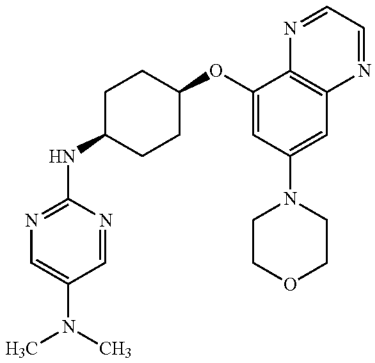
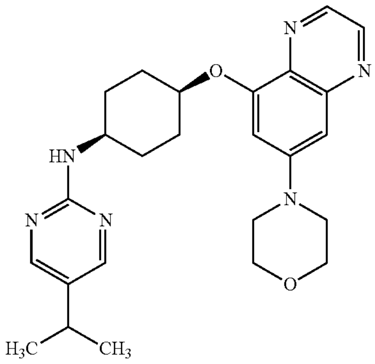
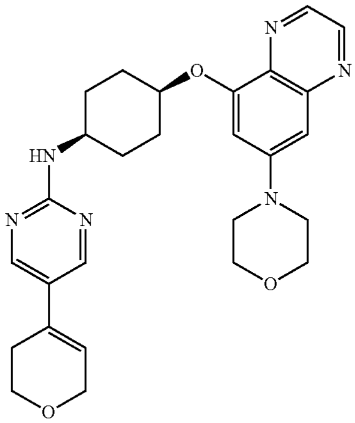
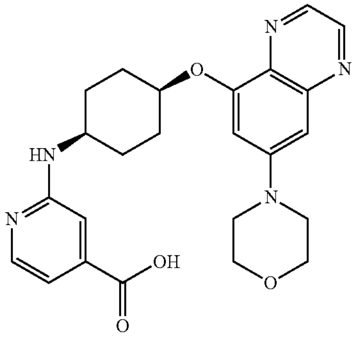
-continued
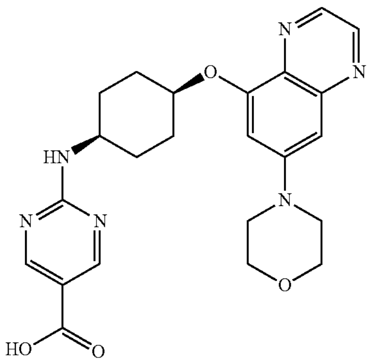
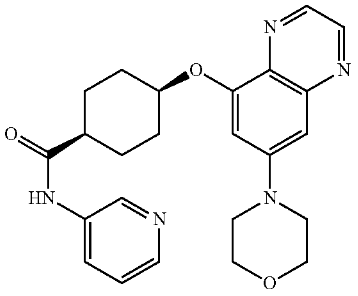
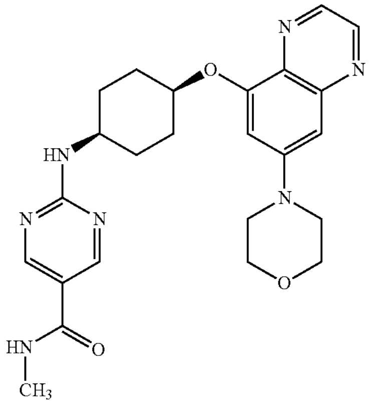
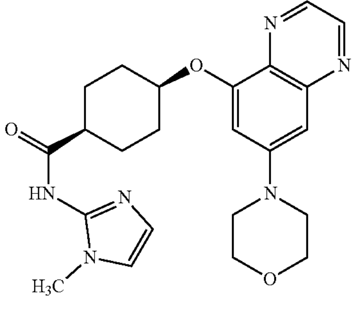

-continued
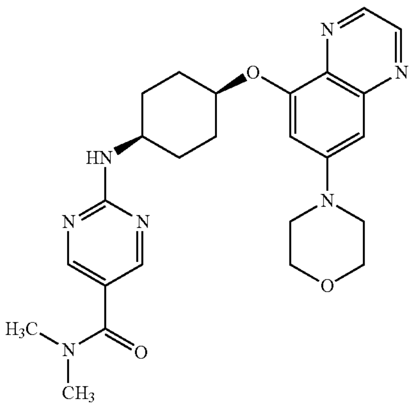
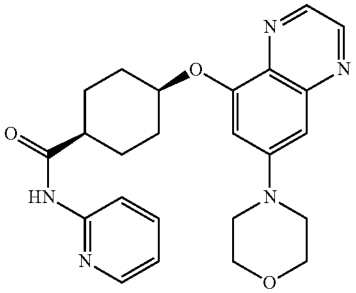
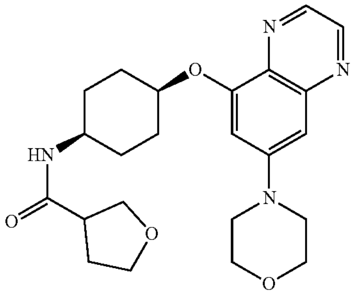
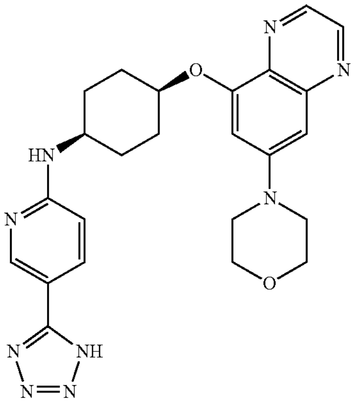
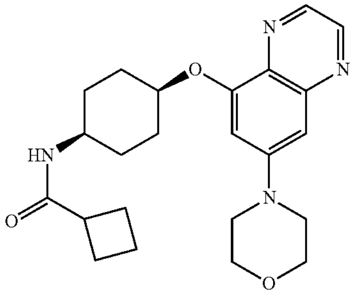
-continued
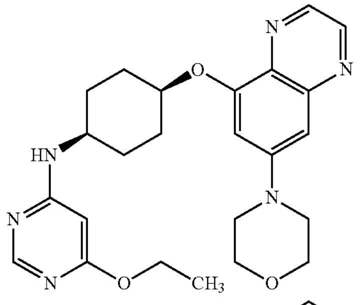
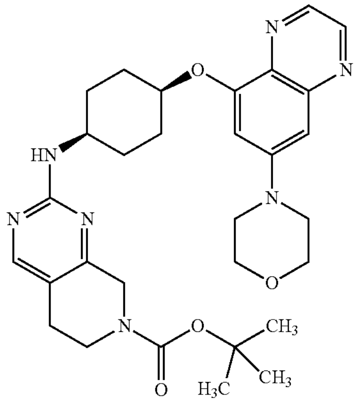
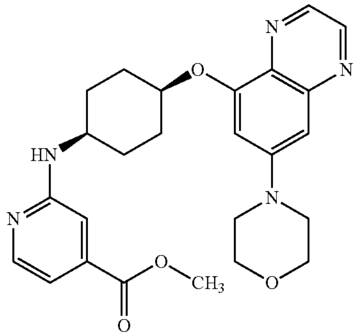
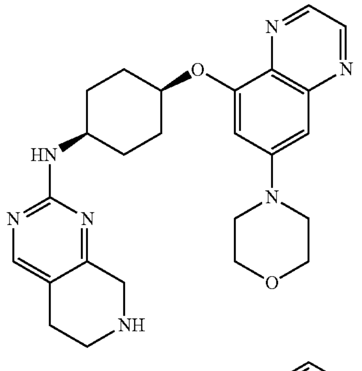
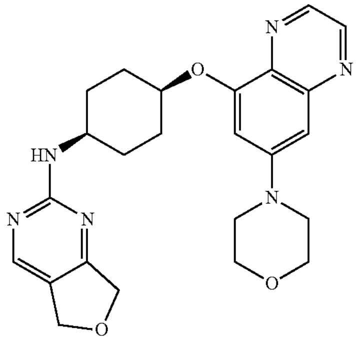

-continued
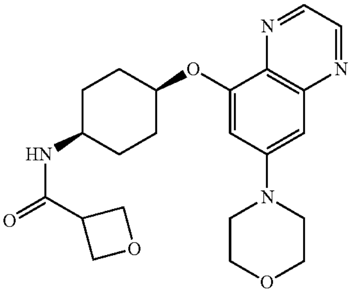
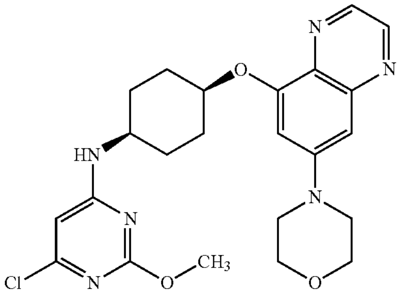
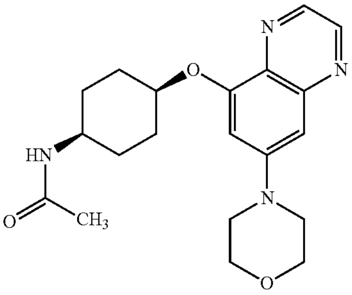
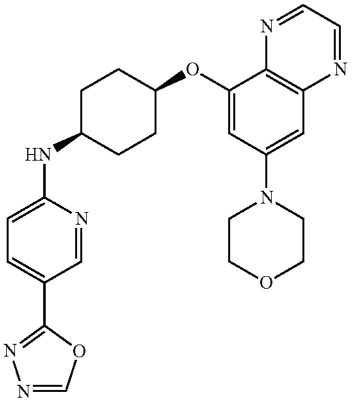
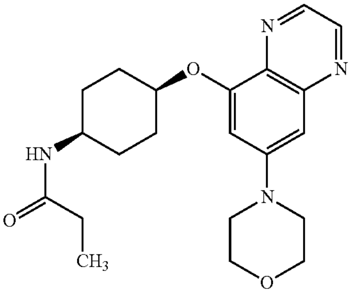
-continued
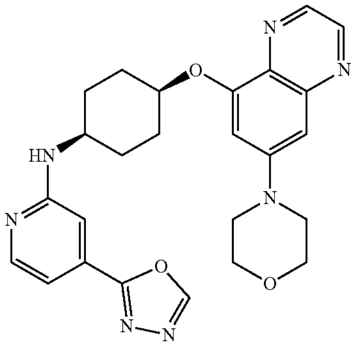
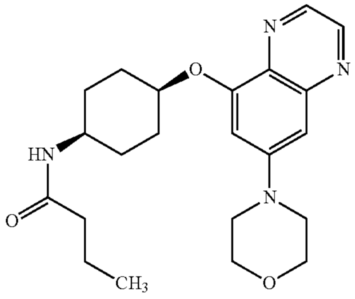
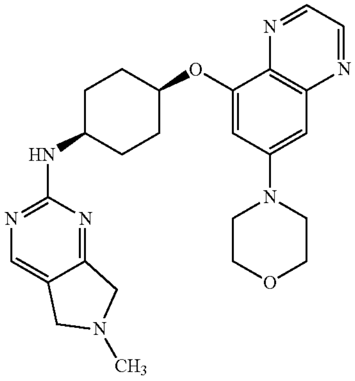
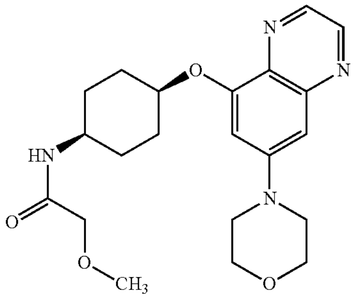
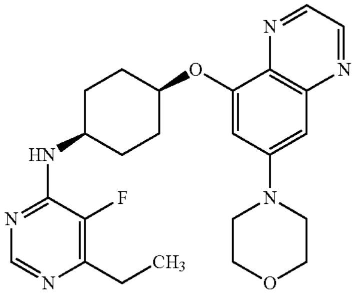

-continued
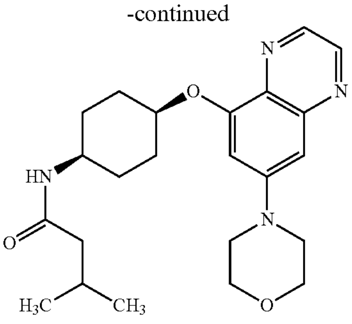
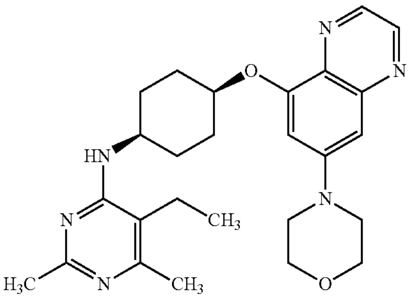
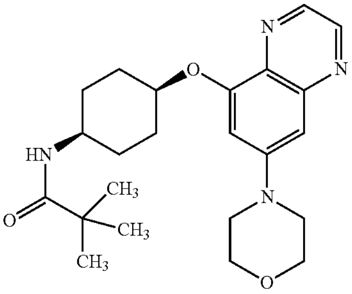
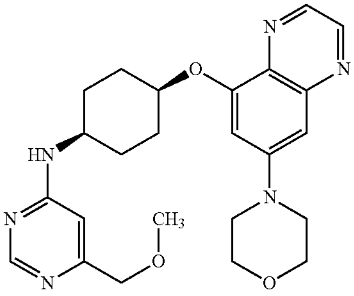
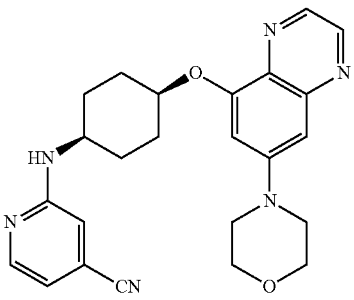
-continued
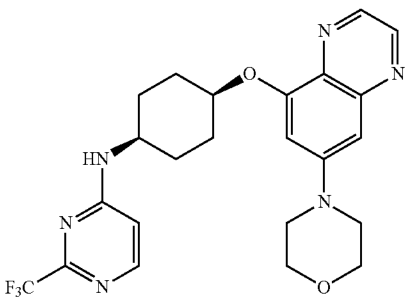
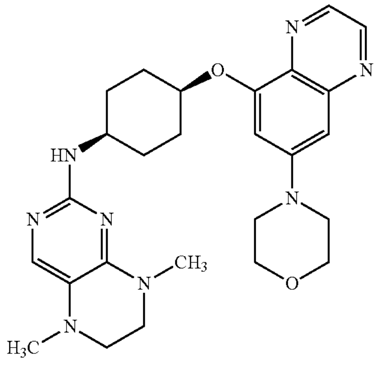
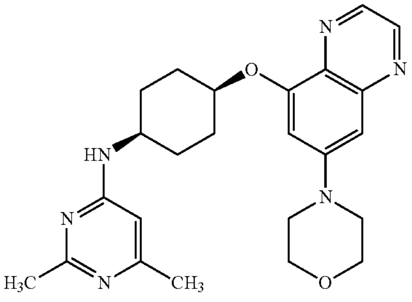
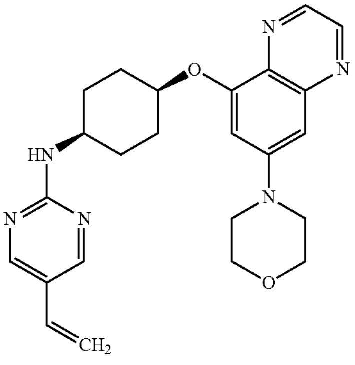

-continued
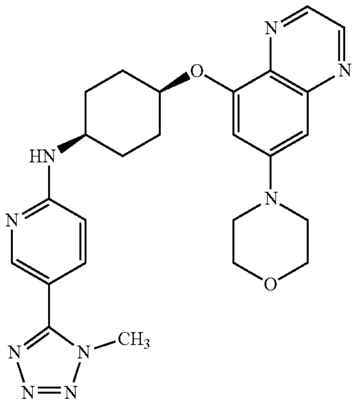
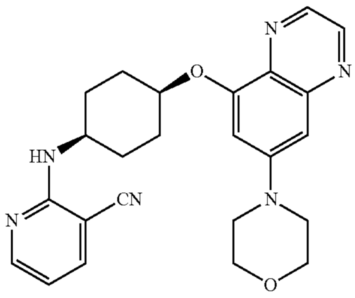
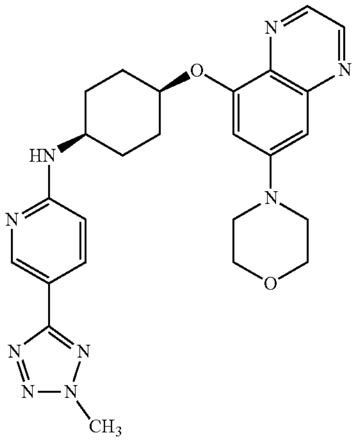
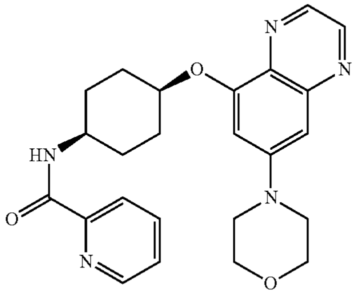
-continued
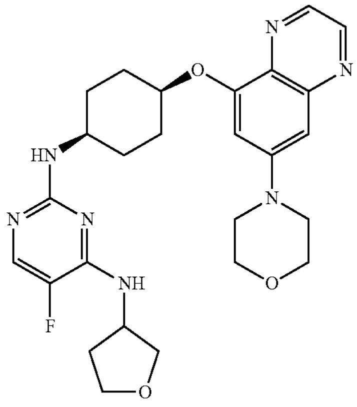
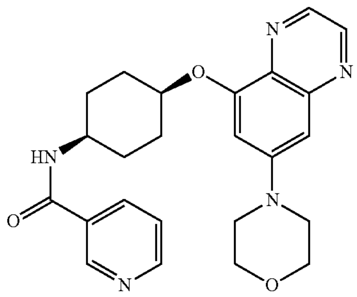
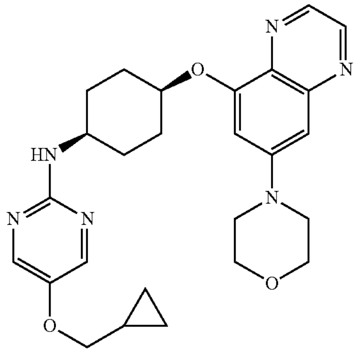
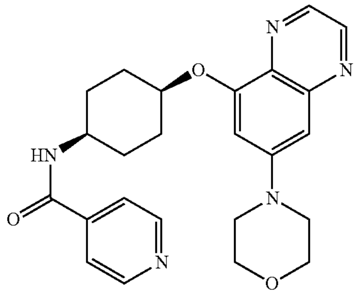
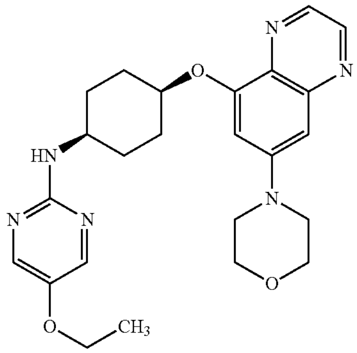

-continued
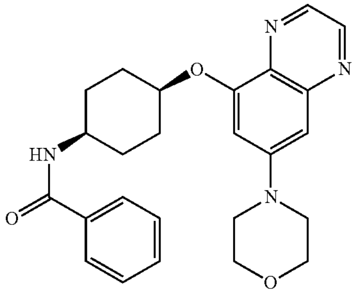
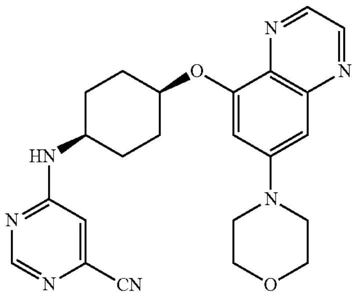
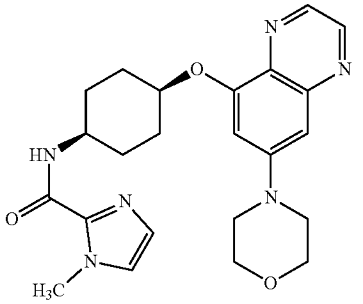
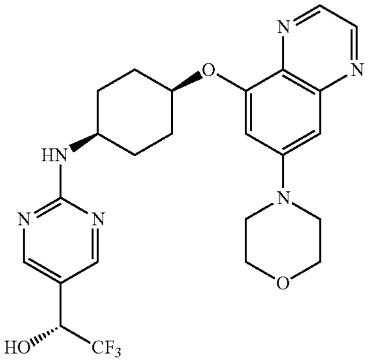
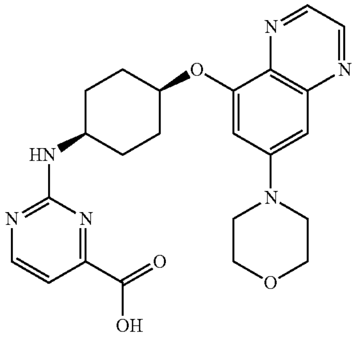
-continued
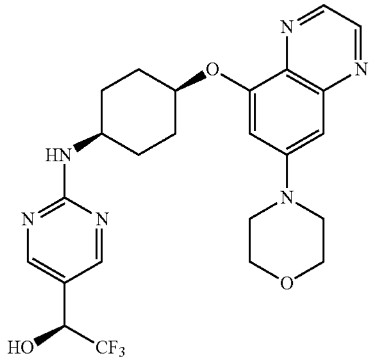
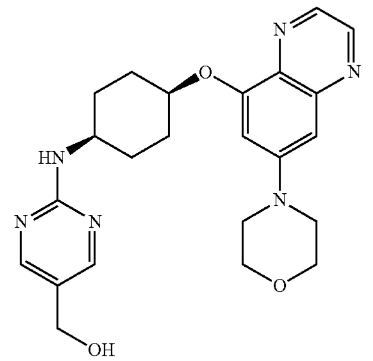
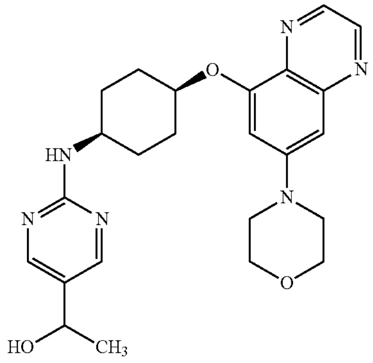
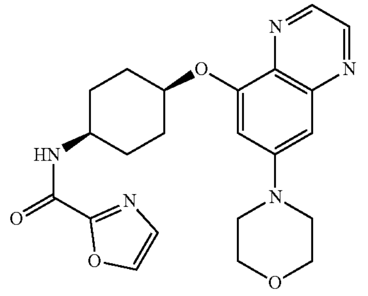
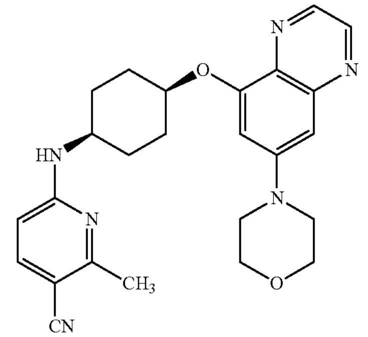

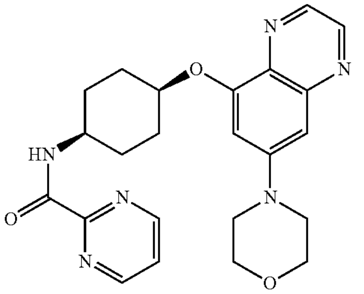
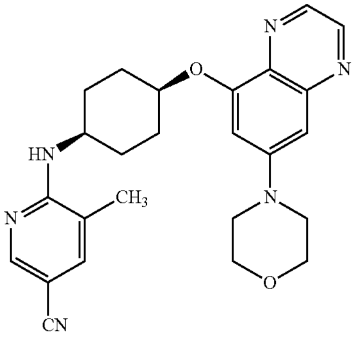
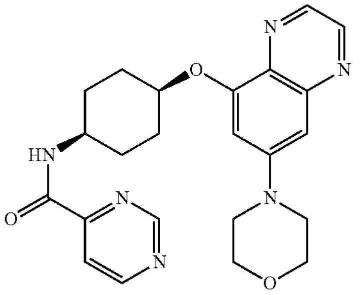
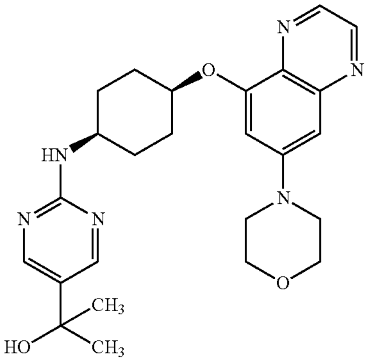
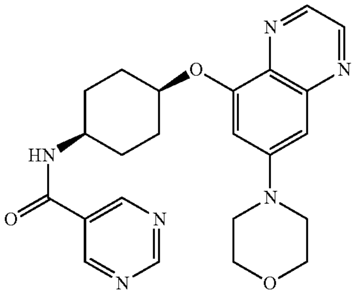
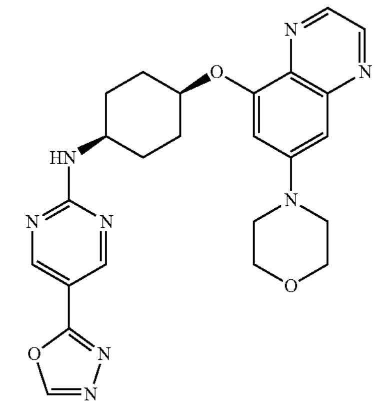
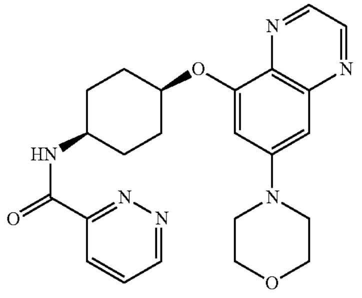
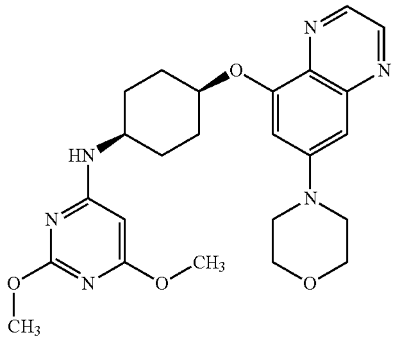
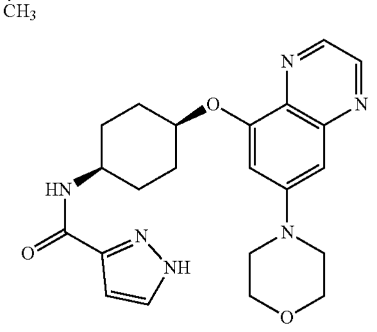
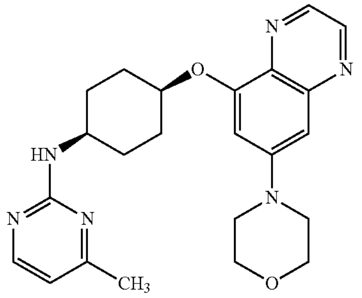

-continued
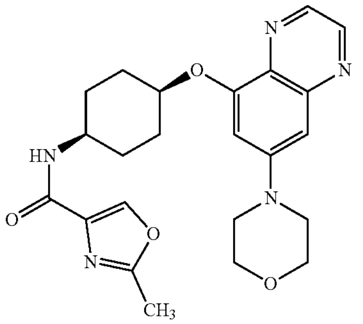
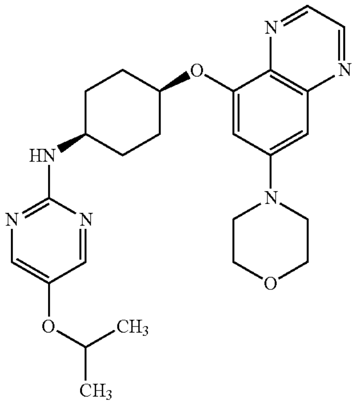
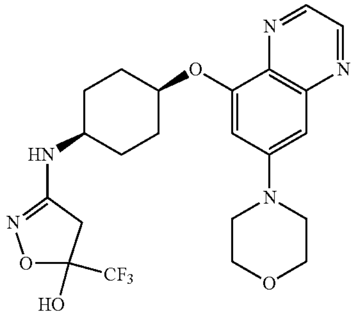
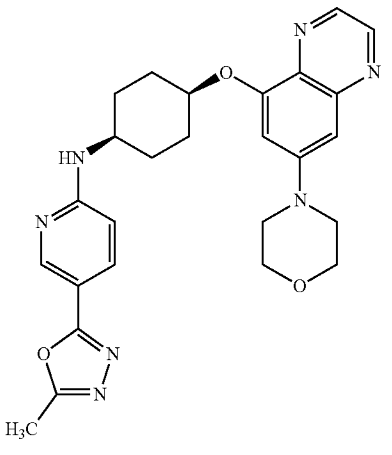
-continued
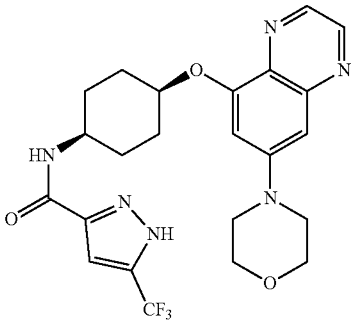
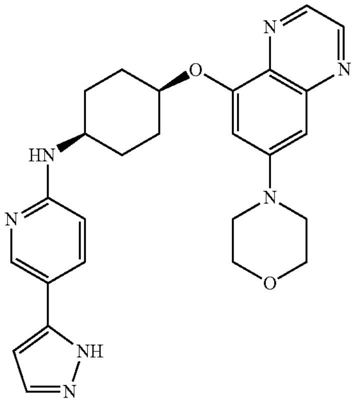
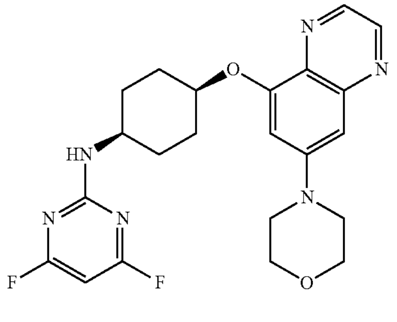
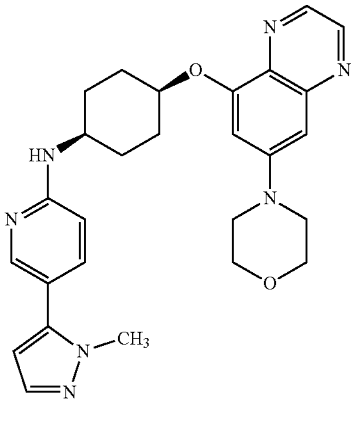

-continued
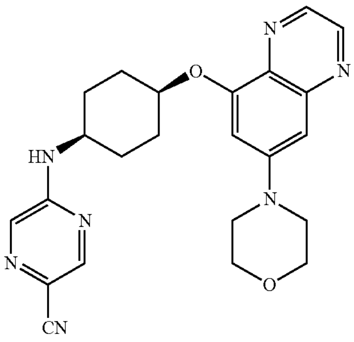
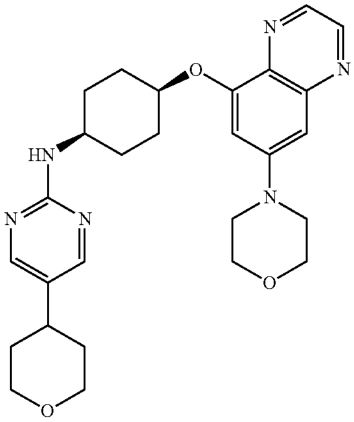
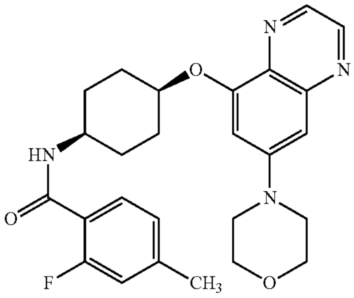
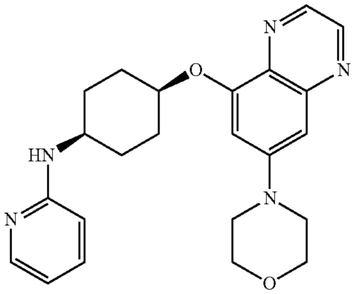
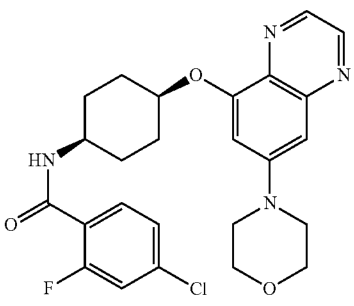
-continued
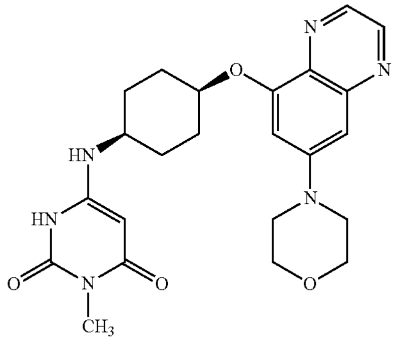
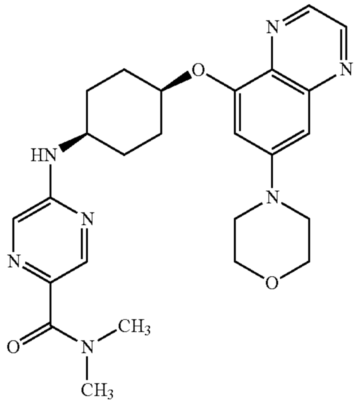
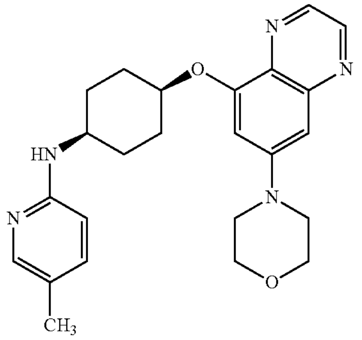
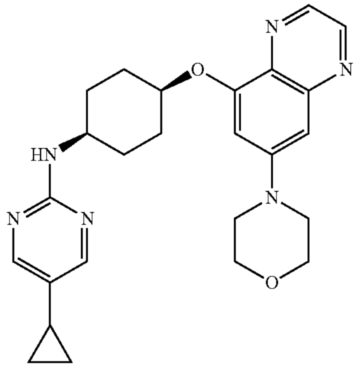

-continued
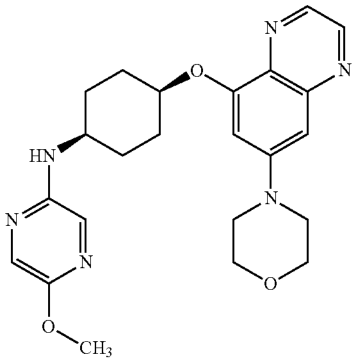
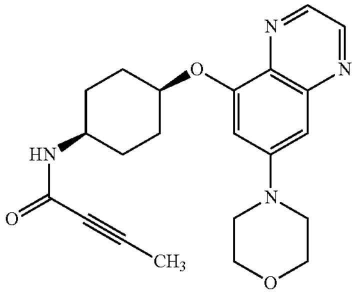
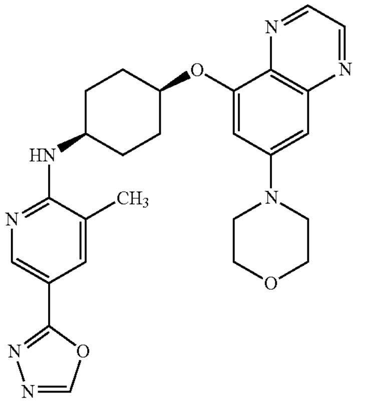
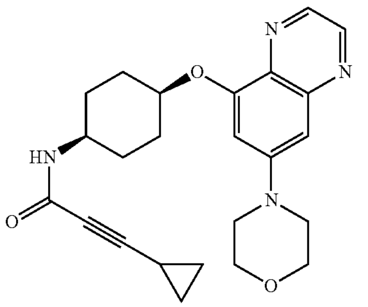
-continued
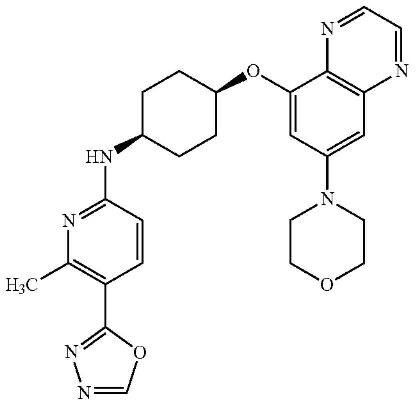
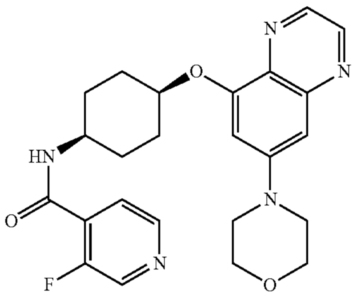
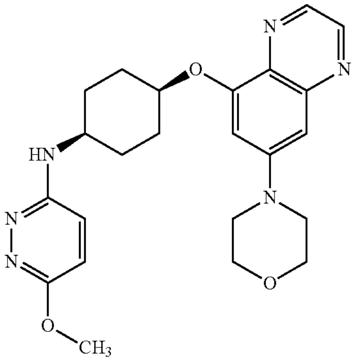
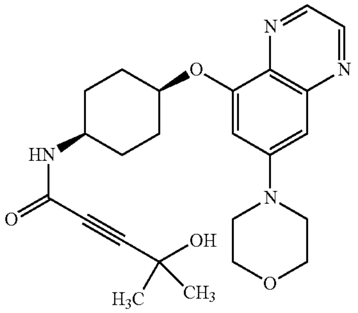

-continued
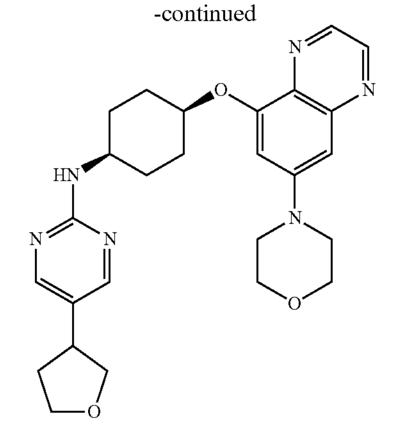
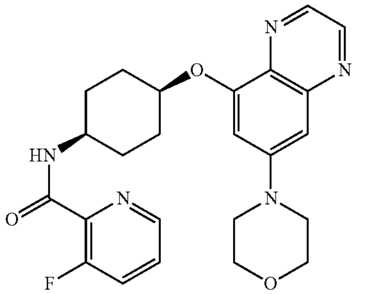
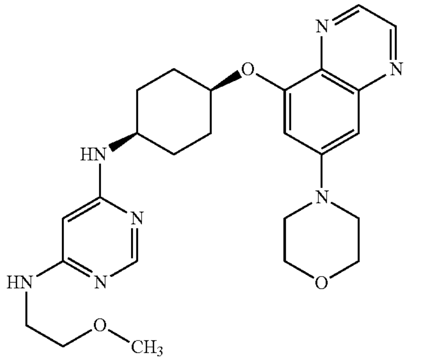
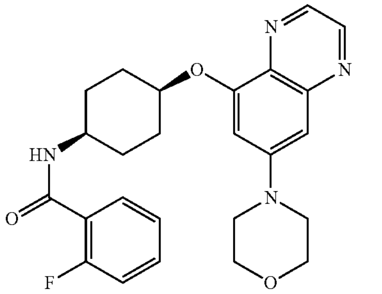
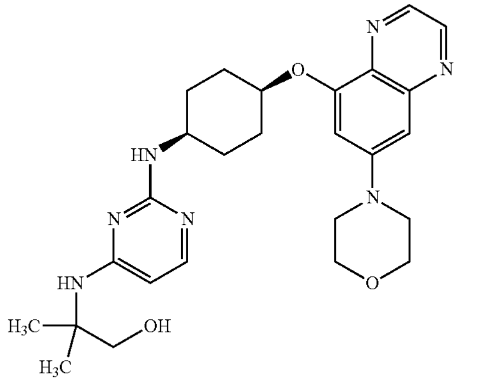
-continued
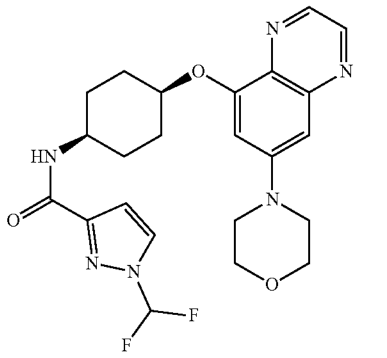
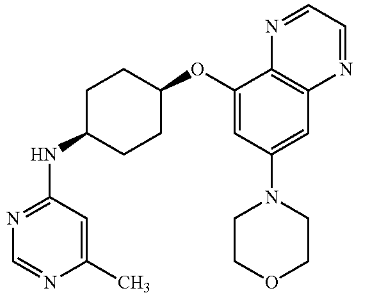
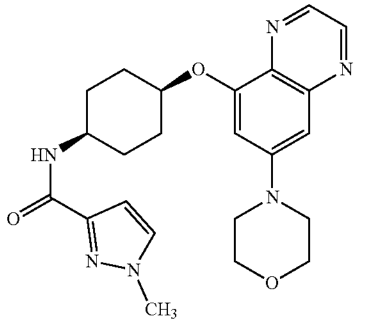
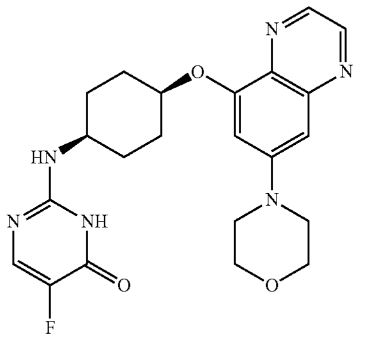
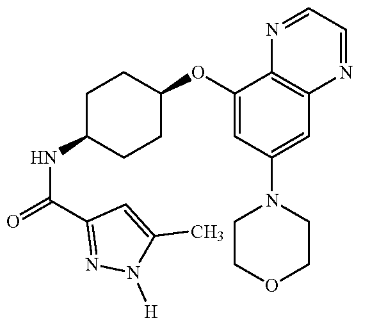

-continued
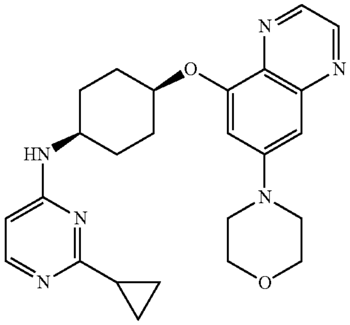
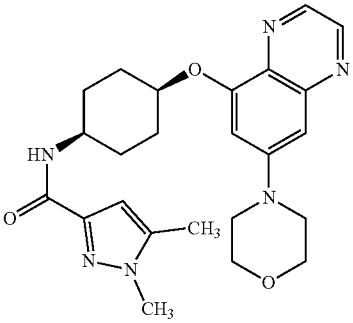
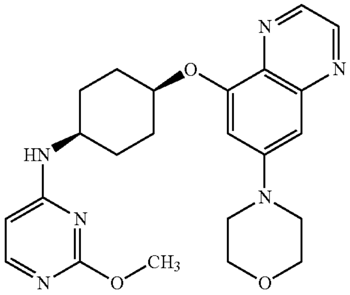
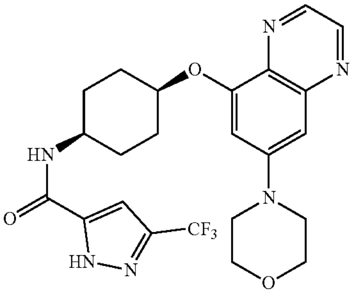
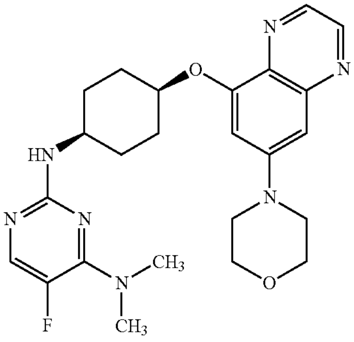
-continued
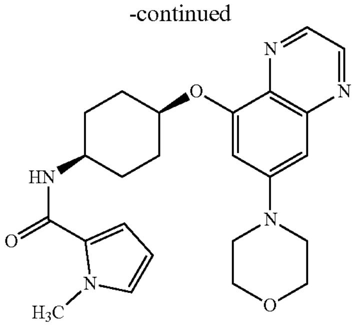
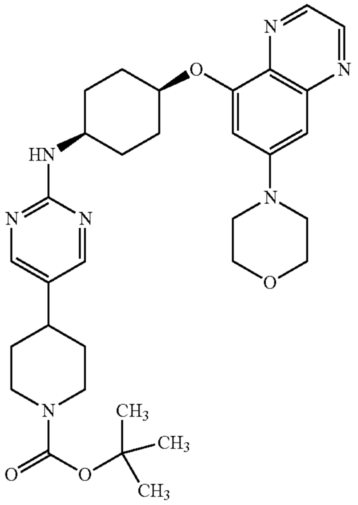
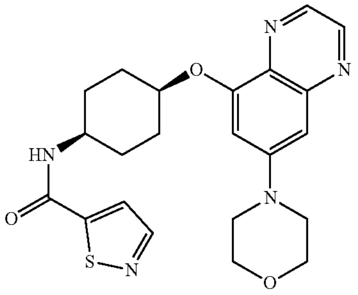
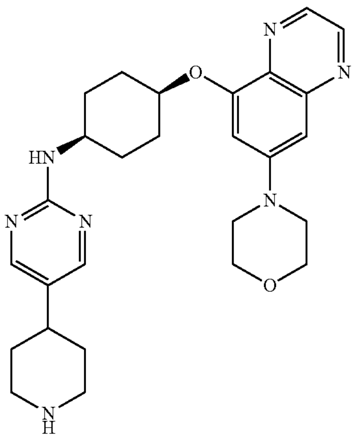

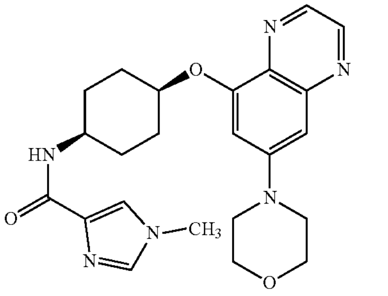
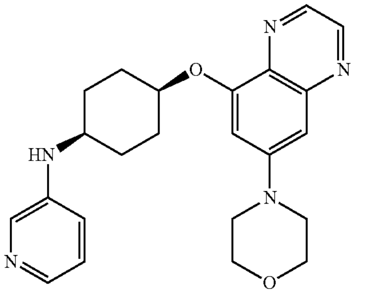
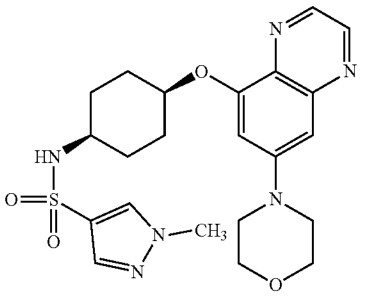
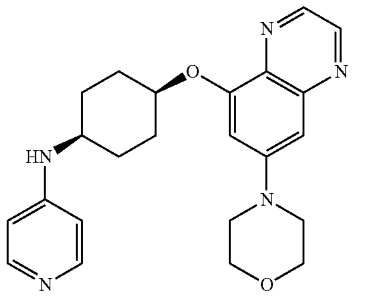
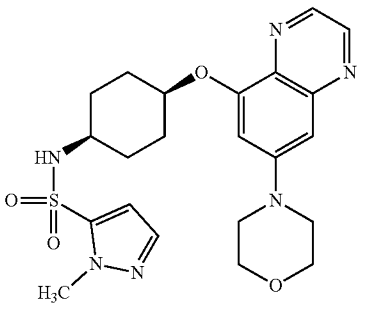
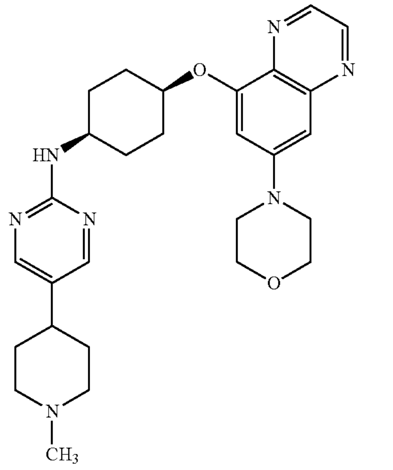
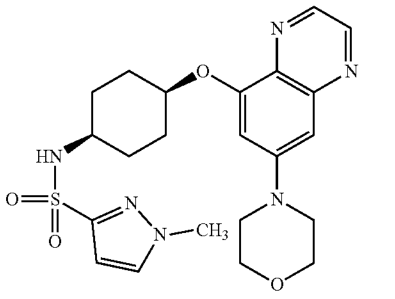
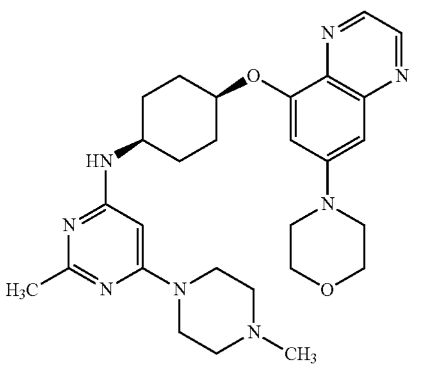
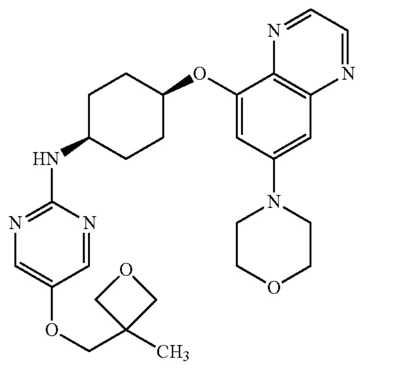

-continued
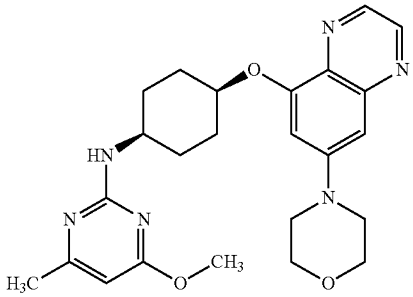
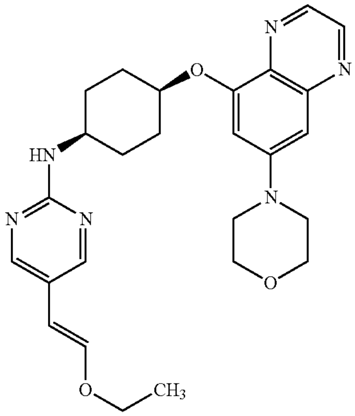
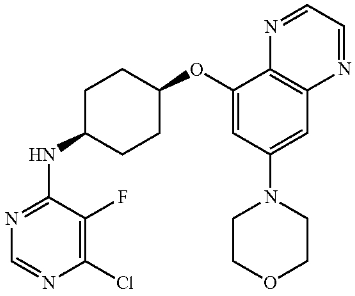
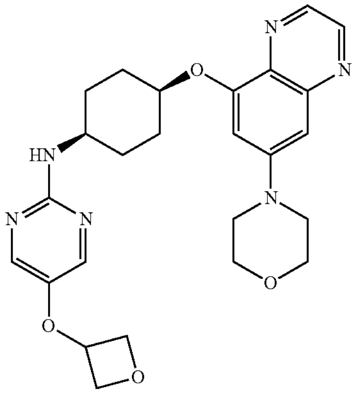
-continued
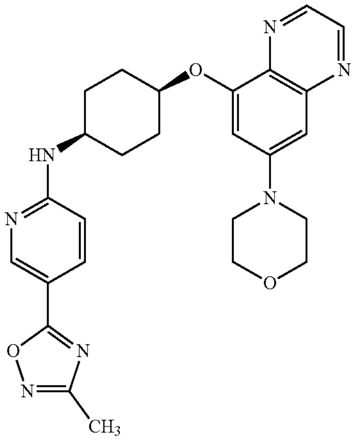
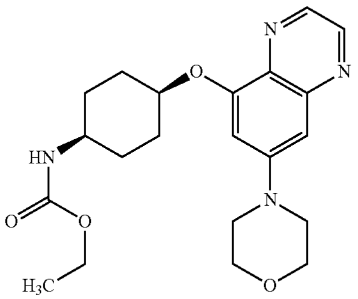
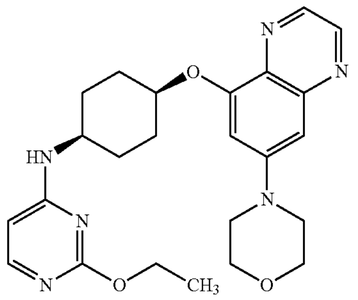
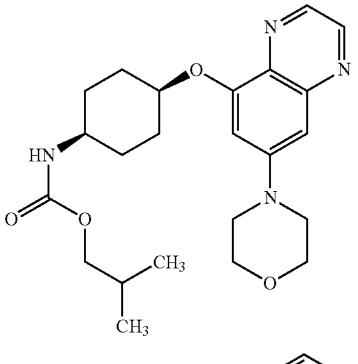
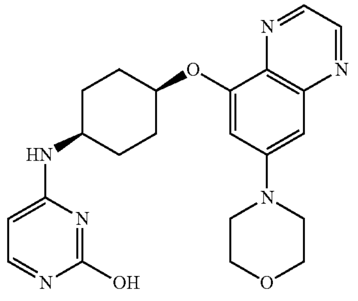

-continued
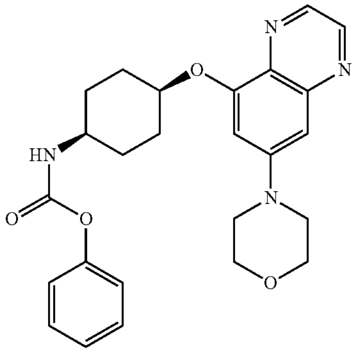
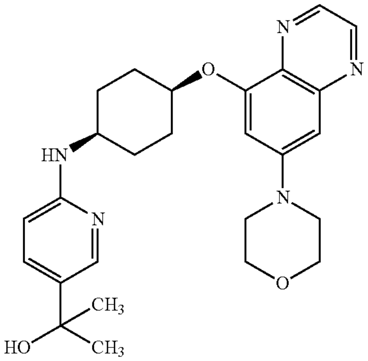
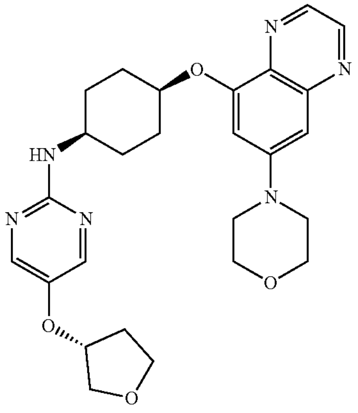
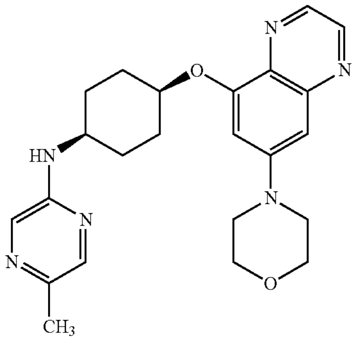
-continued
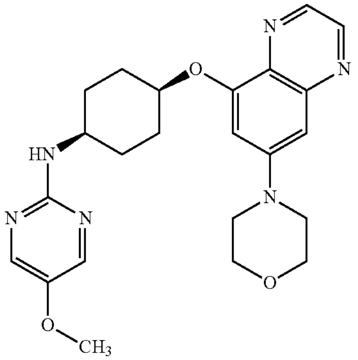
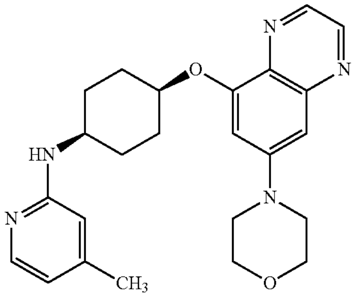
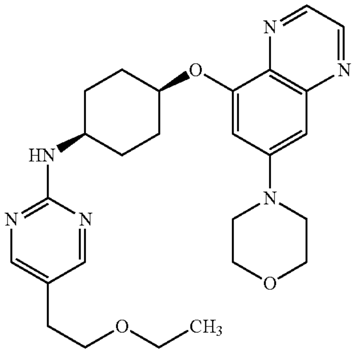
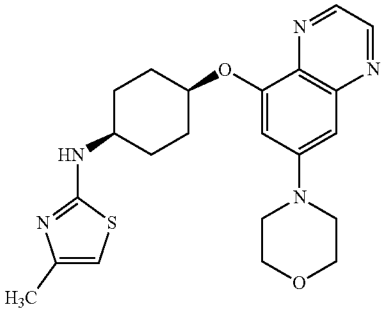
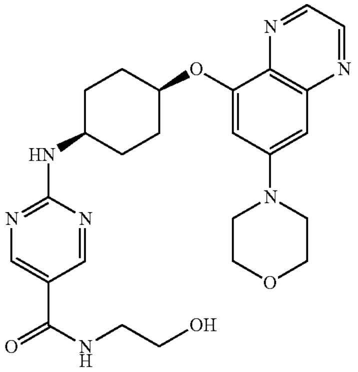

-continued
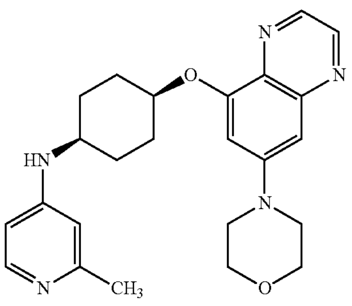
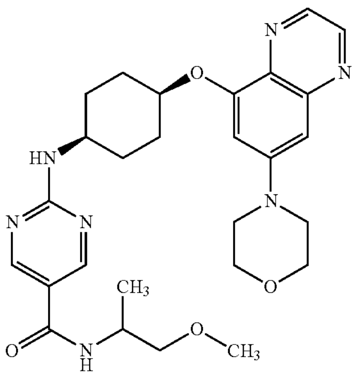
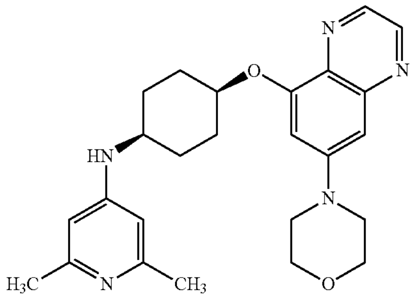
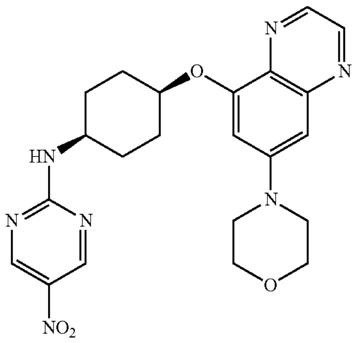
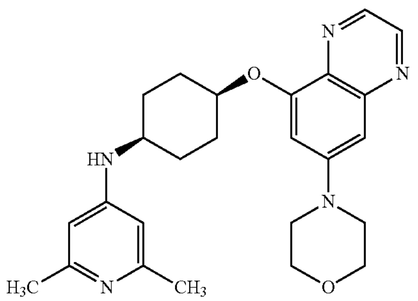
-continued
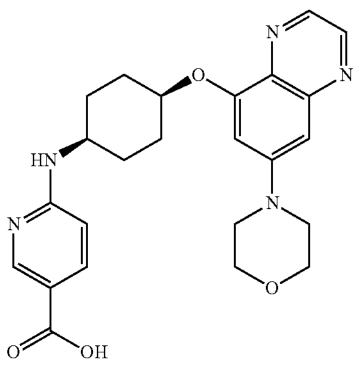
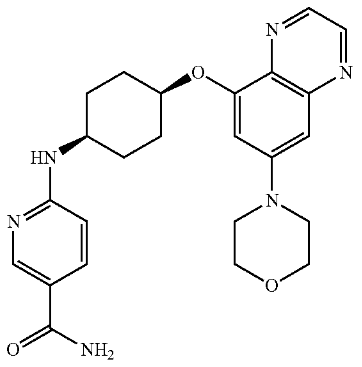
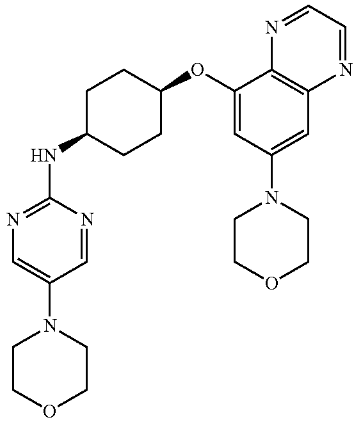
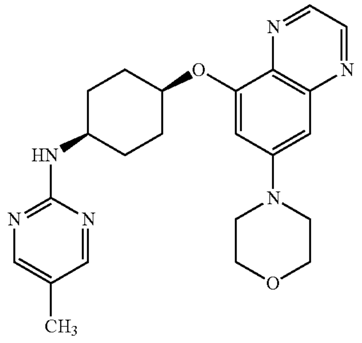
or -continued
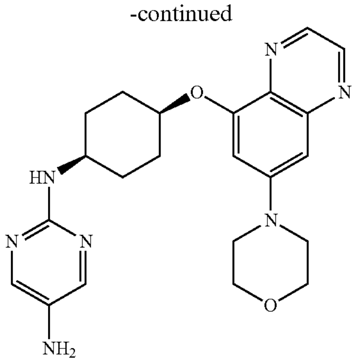
or a pharmaceutically acceptable salt thereof.
* * * * *